US008569281B2

(12) United States Patent
Chan et al.

(10) Patent No.: US 8,569,281 B2
(45) Date of Patent: Oct. 29, 2013

(54) COMPOUNDS AND THEIR ADMINISTRATION FOR TREATING A NEURODEGENERATIVE DISEASE AS WELL AS A METHOD FOR IDENTIFYING A COMPOUND CAPABLE OF INHIBITING A KINASE, SUCH AS LRRK

(75) Inventors: Bryan K. Chan, South San Francisco, CA (US); Huifen Chen, South San Francisco, CA (US); Anthony Estrada, South San Francisco, CA (US); Daniel Shore, South San Francisco, CA (US); Zachary Sweeney, Emeryville, CA (US); Edward Giles McIver, London (GB)

(73) Assignees: Medical Research Council Technology, London (GB); Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/238,840

(22) Filed: Sep. 21, 2011

(65) Prior Publication Data

US 2012/0295883 A1 Nov. 22, 2012

Related U.S. Application Data

(60) Provisional application No. 61/385,522, filed on Sep. 22, 2010.

(51) Int. Cl.

| | |
|---|---|
| *A61K 31/5365* | (2006.01) |
| *A61K 31/00* | (2006.01) |
| *A61K 31/44* | (2006.01) |
| *C07D 498/00* | (2006.01) |
| *C07D 413/00* | (2006.01) |
| *C07D 401/00* | (2006.01) |
| *C07D 471/02* | (2006.01) |

(52) U.S. Cl.
USPC ................. 514/210.08; 514/210.21; 514/303; 544/105; 544/127; 544/333; 544/362; 546/119

(58) Field of Classification Search
USPC .................... 514/210.18, 210.21, 303, 210.8; 546/119; 544/105, 127, 333, 362
See application file for complete search history.

(56) References Cited

FOREIGN PATENT DOCUMENTS

| | | | |
|---|---|---|---|
| WO | 2006/077319 | A1 | 7/2006 |
| WO | 2009/030270 | A1 | 3/2009 |
| WO | 2010/106333 | A1 | 9/2010 |

OTHER PUBLICATIONS

International Search Report and Written Opinion for Application No. PCT/GB2011/051773, dated Oct. 28, 2011.

*Primary Examiner* — Raymond Henley, III
(74) *Attorney, Agent, or Firm* — Nelson Mullins Riley & Scarborough LLP; Cynthia L. Kanik

(57) ABSTRACT

The present invention relates to substituted pyrazolopyridine compounds, and pharmaceutically acceptable salts or esters thereof. The present invention further relates to therapeutic uses of pharmaceutical compositions comprising the substituted pyrazolopyridine compounds, for example, in cancer and neurodegenerative diseases.

9 Claims, 1 Drawing Sheet

Domain structure of LRRK2 and location of mutations that have been linked to Parkinson's disease
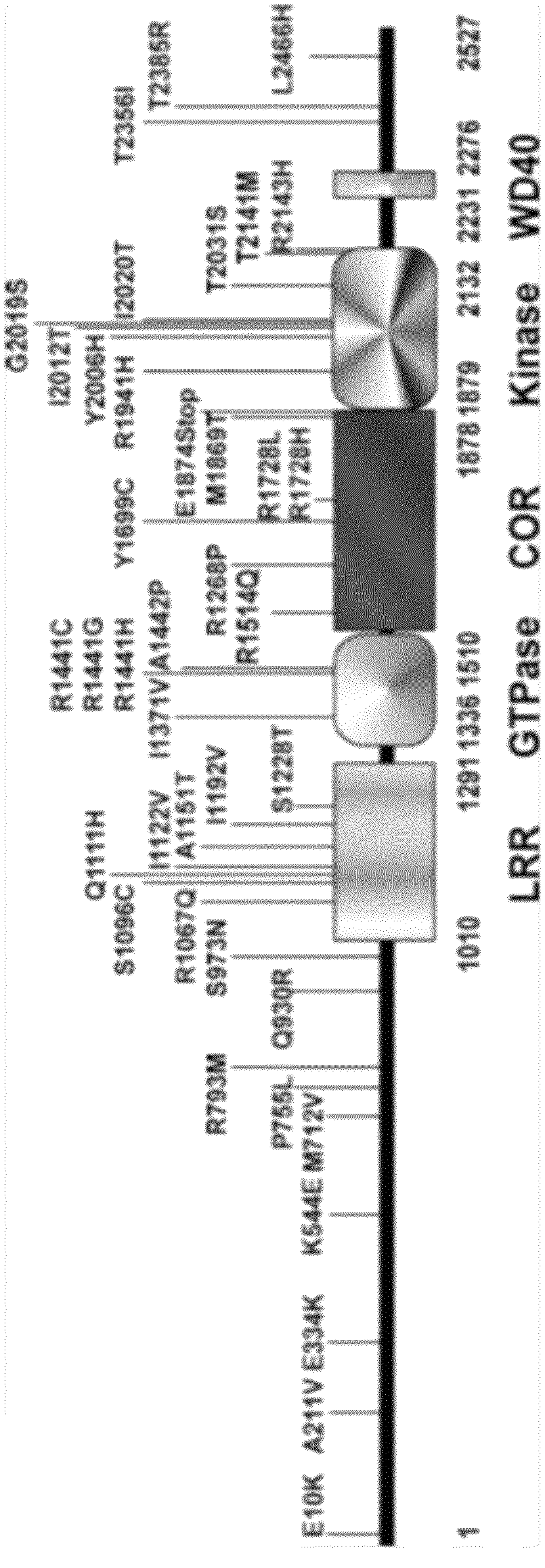

COMPOUNDS AND THEIR ADMINISTRATION FOR TREATING A NEURODEGENERATIVE DISEASE AS WELL AS A METHOD FOR IDENTIFYING A COMPOUND CAPABLE OF INHIBITING A KINASE, SUCH AS LRRK

RELATED APPLICATIONS

This application claims priority to U.S. Provisional Application No. 61/385,522, filed on Sep. 22, 2010 and Great Britain Patent Application No. 1015949.9, filed on Sep. 22, 2010. The contents of the aforementioned applications are hereby incorporated by reference.

FIELD OF THE INVENTION

The present invention relates to pyrazolopyridine compounds that are capable of inhibiting one or more kinases, more particularly, LRRK2. The compounds find applications in the treatment of a variety of disorders, including cancer and neurodegenerative diseases such as Parkinson's disease.

BACKGROUND TO THE INVENTION

There has been much interest raised by the recent discovery that different autosomal dominant point mutations within the gene encoding for LRRK2 predispose humans to develop late-onset PD (OMIM accession number 609007), with a clinical appearance indistinguishable from idiopathic PD [1-3]. The genetic analysis undertaken to date indicates that mutations in LRRK2 are relatively frequent, not only accounting for 5-10% of familial PD, but also being found in a significant proportion of sporadic PD cases [4, 5]. Little is known about how LRRK2 is regulated in cells, what its physiological substrates are and how mutations cause or increase risk of PD.

The domain structure of LRRK2 is shown in FIG. 1, which also depicts the mutations that have thus far been reported in patients with PD. The defining feature of the LRRK2 enzyme is a Leucine Rich Repeat (LRR) motif (residues 1010-1291), a Ras-like small GTPase (residues 1336-1510), a region of high amino acid conservation that has been termed the C-terminal of Ras of complex (COR) domain (residues 1511-1878), a protein kinase catalytic domain (residues 1879-2132) and a C-terminal WD40 motif (2231-2276) [6, 7]. The protein kinase domain of LRRK2 belongs to the tyrosine-like serine/threonine protein kinases and is most similar to the kinase RIP (Receptor Interacting Protein), which play key roles in innate immunity signalling pathways [8]. To date, almost 40 single amino acid substitution mutations have been linked to autosomal-dominant PD and the location of these mutations is illustrated in FIG. 1 ([2, 3]). The most prevalent mutant form of LRRK2 accounting for approximately 6% of familial PD and 3% of sporadic PD cases in Europe, comprises an amino acid substitution of Gly2019 to a Ser residue. Gly2019 is located within the conserved DYG-$Mg^{2+}$-binding motif, in subdomain-VII of the kinase domain [2]. Recent reports suggest that this mutation enhances the autophosphorylation of LRRK2, as well as its ability to phosphorylate myelin basic protein 2-3-fold [9, 10], a finding confirmed by the Applicant [11]. These observations suggest that over-activation of LRRK2 predisposes humans to develop PD, implying that drugs which inhibited LRRK2, could be utilised to halt progression or even perhaps reverse symptoms of some forms of PD.

The study of LRRK2 has been hampered by the difficulty in expressing active recombinant enzyme and by the lack of a robust quantitative assay. In work undertaken by the Applicant, an active recombinant fragment of LRRK2 containing the GTPase-COR and kinase domains encompassing residues 1326-2527 was expressed in 293 cells [11]. The more active G2019S mutant of this LRRK2 fragment was utilised in a KinasE Substrate TRacking and ELucidation (KESTREL) screen in an initial attempt to identify physiological substrates (reviewed in [14]). This led to the identification of a protein termed moesin, which was efficiently phosphorylated by LRRK2 in vitro [11]. Moesin is a member of the Ezrin/Radixin/Moesin (ERM) family of proteins which functions to anchor the actin cytoskeleton to the plasma membrane and plays an important role in regulating membrane structure and organization [15, 16]. It was found that LRRK2 phosphorylated moesin at Thr558 [11], a previously characterised physiologically relevant phosphorylation site [15, 16]. LRRK2 also phosphorylated ezrin and radixin at the equivalent Thr residue. Phosphorylation of ERM proteins at the residue equivalent to Thr558, opens up the structures of these proteins and enables them to interact with actin microfilaments at their C-terminal residues and phosphoinositides and plasma membrane proteins through an N-terminal FERM domain. These findings were utilised to develop a robust and quantitative assay for LRRK2, based upon the phosphorylation of moesin or a short peptide that encompasses the Thr558 residue of moesin which is also efficiently phosphorylated by LRRK2 [11]. These assays were further adapted to develop an improved assay based on the use of the Nictide peptide [17].

The present invention seeks to provide compounds that are capable of inhibiting one or more kinases, more particularly, LRRK, even more preferably LRRK2.

SUMMARY OF THE INVENTION

A first aspect of the invention relates to pyrazolopyridine compounds, and pharmaceutically acceptable salts or esters thereof, as described in the accompanying examples and claims. Further aspects of the invention relate to compounds of formula Ia-Ie, and their pharmaceutically acceptable salts or esters thereof, as described below.

A second aspect of the invention relates to a pharmaceutical composition comprising at least one compound as described above and a pharmaceutically acceptable carrier, diluent or excipient.

A third aspect of the invention relates to a compound as described above for use in medicine.

A fourth aspect of the invention relates to a compound as described above for use in treating a disorder selected from cancer and neurodegenerative diseases such as Parkinson's Disease.

A fifth aspect of the invention relates to the use of a compound as described above in the preparation of a medicament for treating or preventing a disorder selected from cancer and neurodegenerative diseases such as Parkinson's Disease.

A sixth aspect of the invention relates to the use of a compound as described above in the preparation of a medicament for the prevention or treatment of a disorder caused by, associated with or accompanied by any abnormal kinase activity wherein the kinase is preferably LRRK, more preferably LRRK2.

A seventh aspect of the invention relates to a method of treating a mammal having a disease state alleviated by inhibition of a kinase (preferably LRRK, more preferably LRRK2), wherein the method comprises administering to a mammal a therapeutically effective amount of a compound as described above.

An eighth aspect of the invention relates to the use of a compound as described above in an assay for identifying further candidate compounds capable of inhibition of a kinase, preferably LRRK, more preferably LRRK2.

BRIEF DESCRIPTION OF THE FIGURE

FIG. 1 depicts the domain structure of LRRK2 including a Leucine Rich Repeat (LRR) motif (residues 1010-1291), a Ras-like small GTPase (residues 1336-1510), a region of high amino acid conservation that has been termed the C-terminal of Ras of complex (COR) domain (residues 1511-1878), a protein kinase catalytic domain (residues 1879-2132) and a C-terminal WD40 motif (2231-2276). Single amino acid mutations linked to PD are also shown.

DETAILED DESCRIPTION

The present invention relates to pyrazolopyridine compounds that are capable of inhibiting one or more kinases, more particularly LRRK, even more particularly LRRK2. In particular, the invention relates to the specific substituted pyrazolo[4,3-c]pyridine derivatives described in the accompanying examples and claims, and pharmaceutically acceptable salts and esters thereof.

The present invention relates to pyrazolopyridine compounds that are capable of inhibiting one or more kinases, more particularly LRRK, even more particularly LRRK2. Specifically, the invention relates to substituted pyrazolo[4,3-c]pyridine derivatives.

"Alkyl" is defined herein as a straight-chain or branched alkyl radical, preferably $C_{1-6}$ alkyl, for example, methyl, ethyl, propyl, isopropyl, butyl, isobutyl, tert-butyl, pentyl, hexyl.

"Cycloalkyl" is defined herein as a monocyclic alkyl ring, preferably, $C_{3-7}$-cycloalkyl, more preferably $C_{3-6}$-cycloalkyl. Preferred examples include cyclopropyl, cyclobutyl, cyclopentyl, cyclohexyl or cycloheptyl, or a fused bicyclic ring system such as norbornane.

"Halogen" is defined herein as chloro, fluoro, bromo or iodo.

As used herein, the term "aryl" refers to a $C_{6-12}$ aromatic group, which may be benzocondensed, for example, phenyl or naphthyl.

"Heteroaryl" is defined herein as a monocyclic or bicyclic $C_{2-12}$ aromatic ring comprising one or more heteroatoms (that may be the same or different), such as oxygen, nitrogen or sulphur. Examples of suitable heteroaryl groups include thienyl, furanyl, pyrrolyl, pyridinyl, oxazolyl, thiazolyl, imidazolyl, pyrazolyl, isoxazolyl, isothiazolyl, oxadiazolyl, triazolyl, thiadiazolyl etc. and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl etc. and benzo derivatives thereof, such as quinolinyl, isoquinolinyl, cinnolinyl, phthalazinyl, quinazolinyl, quinoxalinyl, naphthyridinyl etc.

"Heterocycloalkyl" refers to a monocyclic or bicyclic aliphatic group containing one or more heteroatoms selected from nitrogen, oxygen and sulphur, which is optionally interrupted by one or more —(CO)— groups in the ring and/or which optionally contains one or more double bonds in the ring. Preferably, the heterocycloalkyl group is a $C_{3-7}$-heterocycloalkyl, more preferably a $C_{3-6}$-heterocycloalkyl. Alternatively, the heterocycloalkyl group is a $C_{4-6}$-heterocycloalkyl, more preferably a $C_{4-6}$-heterocycloalkyl. Preferred heterocycloalkyl groups include, but are not limited to, piperazinyl, piperidinyl, morpholinyl, thiomorpholinyl, pyrrolidinyl, tetrahydrofuranyl and tetrahydropyranyl.

Compounds of Formula Ia

A further aspect of the invention relates to compounds of formula Ia, or a pharmaceutically acceptable salt or ester thereof, Ia

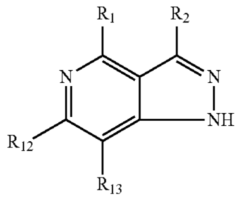

wherein:

$R^1$ is selected from: aryl; heteroaryl; —$NHR^3$; fused aryl-$C_{4-7}$-heterocycloalkyl; —$CONR^4R^5$; —$NHCOR^6$; —$C_{3-7}$-cycloalkyl; —$NR^3R^6$; $OR^3$; OH; $NR^4R^5$; and $C_{1-6}$ alkyl optionally substituted with a substituent selected from $R^{11}$ and a group A; wherein said aryl, heteroaryl, fused aryl-$C_{4-7}$-heterocycloalkyl and $C_{4-7}$-heterocycloalkyl are each optionally substituted with one or more substituents selected from $C_{1-6}$-alkyl, $C_{3-7}$-cycloalkyl, heteroaryl, $C_{4-7}$-heterocycloalkyl, aryl and a group A, and said $C_{1-6}$-alkyl, $C_{3-7}$-cycloalkyl, heteroaryl, $C_{4-7}$-heterocycloalkyl, and aryl substituents are in turn each optionally substituted with one or more groups selected from $R^{11}$ and a group A; $R^2$ is a $C_{3-7}$-cycloalkyl group substituted with one or more substituents selected from $R^{11}$ and A; each $R^3$ is selected from aryl, heteroaryl, $C_{4-7}$-heterocycloalkyl, $C_{3-7}$-cycloalkyl, fused aryl-$C_{4-7}$-heterocycloalkyl and $C_{1-6}$-alkyl, each of which is optionally substituted with one or more substituents selected from $R^{11}$ and A; $R^4$ and $R^5$ are each independently selected from hydrogen, $C_{3-7}$-cycloalkyl, $C_{1-6}$-alkyl-$C_{3-7}$-cycloalkyl, aryl, heteroaryl, $C_{1-6}$-alkyl and a $C_{3-6}$-heterocycloalkyl ring optionally further containing one or more groups selected from oxygen, sulfur, nitrogen and CO, and optionally substituted by one or more $R^{10}$ groups, wherein each $C_{1-6}$-alkyl, heteroaryl and aryl is optionally substituted by one or more substituents selected from $C_{1-6}$-alkyl, halogen, cyano, hydroxyl, aryl, halo-substituted aryl, heteroaryl, —$NR^8R^9$, —$NR^6R^7$, $NR^7(CO)R^6$, —$NR^7COOR^6$, —$NR^7(SO_2)R^6$, —$COOR^6$, —$CONR^8R^9$, $OR^6$, —$SO_2R^6$ and a $C_{3-6}$-heterocycloalkyl ring optionally further containing one or more groups selected from oxygen, sulfur, nitrogen and CO and optionally substituted by one or more or $R^{10}$ groups; or $R^4$ and $R^5$ together with the N to which they are attached form a monocyclic or bicyclic $C_{3-6}$-heterocycloalkyl ring optionally further containing one or more groups selected from oxygen, sulfur, nitrogen and CO, wherein said $C_{3-6}$-heterocycloalkyl ring is saturated or unsaturated and is optionally substituted with one or more groups selected from A, $NR^8R^9$ and $R^{10}$; each $R^6$ is independently selected from $C_{1-6}$-alkyl, $C_{3-7}$ cycloalkyl, $C_{4-7}$-heterocycloalkyl, aryl and heteroaryl, each of which is optionally substituted by one or more substituents selected from $R^{10}$, $R^{11}$ and A; each $R^7$ is selected from hydrogen, $C_{1-6}$-alkyl and $C_{3-7}$-cycloalkyl, wherein said $C_{1-6}$-alkyl is optionally substituted by one or more halogens; each of $R^8$ and $R^9$ is independently selected from hydrogen and $C_{1-6}$-alkyl, wherein said $C_{1-6}$-alkyl group is optionally substituted by one or more halogens; or $R^8$ and $R^9$ together with the N to which they are attached form a monocyclic or bicyclic $C_{3-6}$-heterocycloalkyl ring optionally further containing one or more heteroatoms selected from oxygen and sulfur, wherein said $C_{4-6}$-heterocycloalkyl ring is optionally substituted by one or more $R^{10}$ groups; and each $R^{10}$ is selected from $C_{3-7}$-cycloalkyl, aryl, heteroaryl, O-heteroaryl, aralkyl and $C_{1-6}$-alkyl, each of which is optionally substituted by one or more A groups, wherein where $R^{10}$ is $C_{1-6}$-alkyl and two or more $R^{10}$ groups are attached to the same carbon atom, the $R^{10}$ groups may be linked to form a spiroalkyl group; and each $R^{11}$ is independently selected from $C_{1-6}$-alkyl, $C_{3-7}$-cycloalkyl, $C_{1-6}$ alkyl-$C_{3-7}$-cycloalkyl, $C_{1-6}$-alkyl-heteroaryl, $C_{4-7}$-heterocycloalkyl, aryl and heteroaryl, each of which is optionally substituted with one or more substituents selected from A; and A is selected from halogen, —$NR^4SO_2R^5$, —CN, —$OR^6$, —$NR^4R^5$, —$NR^7R^{11}$, hydroxyl, oxo, —$CF_3$, —$CONR^4R^5$, —$NR^4COR^5$, —$NR^7(CO)NR^4R^5$, —$NO_2$, —$CO_2H$, —$CO_2R^6$, —$SO_2R^6$, —$SO_2NR^4R^5$, —$NR^4COR^5$, —$NR^4COOR^5$, $C_{1-6}$-alkyl, aryl and —$COR^6$; and each of $R^{12}$ and $R^{13}$ is independently selected from hydrogen, halo, $C_{1-6}$-alkyl, $C_{3-7}$-cycloalkyl and cyano, wherein said $C_{1-6}$-alkyl and $C_{3-7}$-cycloalkyl is each optionally substituted with one or more substituents selected from A.

In one preferred embodiment of the invention, $R^1$ is selected from: —$NHR^3$; aryl; heteroaryl; $C_{4-7}$-heterocycloalkyl; fused aryl-$C_{4-7}$-heterocycloalkyl; —$C_{3-7}$-cycloalkyl; —$NR^3R^6$; $OR^3$; $NR^4R^5$; and —$C_{1-6}$alkyl optionally substituted with a substituent selected from $R^{11}$ and a group A; wherein said aryl, heteroaryl, fused aryl-$C_{4-7}$-heterocycloalkyl and $C_{4-7}$-heterocycloalkyl are each optionally substituted with one or more substituents selected from $C_{1-6}$-alkyl, $C_{3-7}$-cycloalkyl, heteroaryl, $C_{4-7}$-heterocycloalkyl, aryl and a group A, and said $C_{1-6}$-alkyl, $C_{3-7}$-cycloalkyl, heteroaryl, $C_{4-7}$-heterocycloalkyl, and aryl substituents are in turn each optionally substituted with one or more groups selected from $R^{11}$ and a group A.

In one preferred embodiment of the invention, $R^1$ is —$NHR^3$ and $R^3$ is selected from: $C_{1-6}$-alkyl, optionally substituted by one or more —$OR^6$, $NR^4COR^5$, heteroaryl, aryl, $C_{4-7}$-heterocycloalkyl, and $C_{3-7}$-cycloalkyl groups, wherein said aryl and heteroaryl groups are each independently optionally further substituted by one or more groups selected from $CF_3$, halogen, $C_{1-6}$-alkyl, —$OR^6$ and —$NR^4R^5$; a phenyl group optionally substituted by one or more substituents selected from —$OR^6$, $NR^4COR^5$, —$CONR^4R^5$, aryl, —$NR^4R^5$, $C_{1-6}$-alkyl-heteroaryl, heteroaryl, halogen, —$SO_2R^6$, CN, $CF_3$, $C_{1-6}$-alkyl, —$SO_2NR^4R^5$, —$NR^4SO_2R^5$, wherein said $C_{1-6}$-alkyl, heteroaryl and aryl groups are each independently optionally further substituted by one or more groups selected from CN, $CF_3$, halogen, $C_{1-6}$-alkyl, —$OR^6$ and —$NR^4R^5$; a heteroaryl group optionally substituted by one or more substituents selected from aryl, $C_{1-6}$-alkyl, and —$NR^4R^5$, wherein said aryl group is optionally further substituted by one or more A groups; a $C_{4-7}$heterocycloalkyl optionally substituted by one or more —$COR^6$ groups; a $C_{3-7}$-cycloalkyl group optionally substituted by one or more halogen or $C_{1-6}$-alkyl groups.

In one preferred embodiment of the invention, $R^1$ is —$NHR^3$, wherein $R^3$ is selected from $C_{1-6}$-alkyl, $C_{3-7}$-cycloalkyl, $C_{4-7}$-heterocycloalkyl and aryl, each of which may be optionally substituted by one or more with one or more substituents selected from $R^{11}$ and A.

In one preferred embodiment of the invention, $R^1$ is —$OR^3$, wherein $R^3$ is selected from $C_{1-6}$-alkyl, $C_{3-7}$-cycloalkyl, $C_{4-7}$-heterocycloalkyl and aryl, each of which may be optionally substituted by one or more with one or more substituents selected from $R^{11}$ and A.

In one preferred embodiment of the invention, $R^1$ is —$OR^3$, wherein $R^3$ is $C_{1-6}$-alkyl, $C_{3-7}$-cycloalkyl or $C_{4-7}$-heterocycloalkyl, each of which may be optionally substituted by one or more A substituents. In one particularly preferred embodiment of the invention, $R^1$ is —O—$C_{3-7}$-cycloalkyl, more preferably, —O-cyclohexyl.

In one preferred embodiment of the invention, $R^1$ is aryl or heteroaryl, each of which may be optionally substituted by one or more with one or more substituents selected from $R^{11}$ and A.

In one preferred embodiment of the invention, $R^1$ is —NH—$C_{3-7}$-cycloalkyl or NH—$C_{4-7}$-heterocycloalkyl, each of which may be optionally substituted by one or more A substituents. Preferably, A is halogen or $C_{1-6}$-alkyl.

In one preferred embodiment of the invention, $R^3$ is cyclohexyl or tetrahydropyranyl, each of which may be optionally substituted by one or more A substituents.

In one preferred embodiment of the invention, $R^1$ is selected from the following:

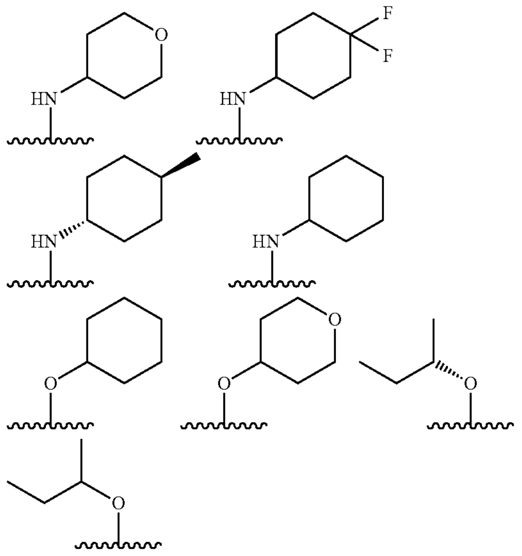

In one preferred embodiment of the invention, $R^1$ is —NH-cyclohexyl.

In one preferred embodiment, $R^2$ is a cyclopropyl group substituted with one or more substituents selected from $R^{11}$ and A.

More preferably, $R^2$ is a cyclopropyl group substituted with a —$CONR^4R^5$ group.

Preferably, $R^4$ and $R^5$ together with the N to which they are attached form a monocyclic or bicyclic $C_{3-6}$-heterocycloalkyl ring optionally further containing one or more groups selected from oxygen, sulfur, nitrogen and CO, wherein said $C_{3-6}$-heterocycloalkyl ring is saturated or unsaturated and is optionally substituted with one or more groups selected from A, $NR^8R^9$ and $R^{10}$. In one preferred embodiment $R^{12}$ and $R^{13}$ are hydrogen.

Compounds of Formula Ib

Another aspect of the invention relates to compounds of formula Ib or a pharmaceutically acceptable salt or ester thereof, Ib

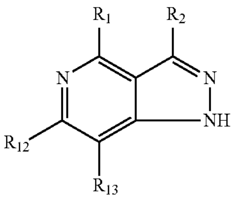

wherein:

$R^1$ is selected from: aryl; heteroaryl; —$NHR^3$; fused aryl-$C_{4-7}$-heterocycloalkyl; —$CONR^4R^5$; —$NHCOR^6$; —$C_{3-7}$-cycloalkyl; —$NR^3R^6$; $OR^3$; OH; $NR^4R^5$; and $C_{1-6}$ alkyl optionally substituted with a substituent selected from $R^{11}$ and a group A; wherein said aryl, heteroaryl, fused aryl-$C_{4-7}$-heterocycloalkyl and $C_{4-7}$-heterocycloalkyl are each optionally substituted with one or more substituents selected from $C_{1-6}$-alkyl, $C_{3-7}$-cycloalkyl, heteroaryl, $C_{4-7}$-heterocycloalkyl, aryl and a group A, and said $C_{1-6}$-alkyl, $C_{3-7}$-cycloalkyl, heteroaryl, $C_{4-7}$-heterocycloalkyl, and aryl substituents are in turn each optionally substituted with one or more groups selected from $R^{11}$ and a group A; $R^2$ is NH-aryl or NH-heteroaryl, wherein said aryl or heteroaryl group is optionally substituted with one or more substituents selected from $R^{11}$ and A; each $R^3$ is selected from aryl, heteroaryl, $C_{4-7}$-heterocycloalkyl, $C_{3-7}$-cycloalkyl, fused aryl-$C_{4-7}$-heterocycloalkyl and $C_{1-6}$-alkyl, each of which is optionally substituted with one or more substituents selected from $R^{11}$ and A; $R^4$ and $R^5$ are each independently selected from hydrogen, $C_{3-7}$-cycloalkyl, $C_{1-6}$-alkyl-$C_{3-7}$-cycloalkyl, aryl, heteroaryl, $C_{1-6}$-alkyl and a $C_{3-6}$-heterocycloalkyl ring optionally further containing one or more groups selected from oxygen, sulfur, nitrogen and CO, and optionally substituted by one or more $R^{10}$ groups, wherein each $C_{1-6}$-alkyl, heteroaryl and aryl is optionally substituted by one or more substituents selected from $C_{1-6}$-alkyl, halogen, cyano, hydroxyl, aryl, halo-substituted aryl, heteroaryl, —$NR^8R^9$, —$NR^6R^7$, $NR^7(CO)R^6$, —$NR^7COOR^6$, —$NR^7(SO_2)R^6$, —$COOR^6$, —$CONR^8R^9$, $OR^6$, —$SO_2R^6$ and a $C_{3-6}$-heterocycloalkyl ring optionally further containing one or more groups selected from oxygen, sulfur, nitrogen and CO and optionally substituted by one or more or $R^{10}$ groups; or $R^4$ and $R^5$ together with the N to which they are attached form a monocyclic or bicyclic $C_{3-6}$-heterocycloalkyl ring optionally further containing one or more groups selected from oxygen, sulfur, nitrogen and CO, wherein said $C_{3-6}$-heterocycloalkyl ring is saturated or unsaturated and is optionally substituted with one or more groups selected from A, $NR^8R^9$ and $R^{10}$; each $R^6$ is independently selected from $C_{1-6}$-alkyl, $C_{3-7}$ cycloalkyl, $C_{4-7}$-heterocycloalkyl, aryl and heteroaryl, each of which is optionally substituted by one or more substituents selected from $R^{10}$, $R^{11}$ and A; each $R^7$ is selected from hydrogen, $C_{1-6}$-alkyl and $C_{3-7}$-cycloalkyl, wherein said $C_{1-6}$-alkyl is optionally substituted by one or more halogens; each of $R^8$ and $R^9$ is independently selected from hydrogen and $C_{1-6}$-alkyl, wherein said $C_{1-6}$-alkyl group is optionally substituted by one or more halogens; or $R^8$ and $R^9$ together with the N to which they are attached form a monocyclic or bicyclic $C_{4-6}$-heterocycloalkyl ring optionally further containing one or more heteroatoms selected from oxygen and sulfur, wherein said $C_{4-6}$-heterocycloalkyl ring is optionally substituted by one or more $R^{10}$ groups; and each $R^{10}$ is selected from $C_{3-7}$-cycloalkyl, aryl, heteroaryl, O-heteroaryl, aralkyl and $C_{1-6}$-alkyl, each of which is optionally substituted by one or more A groups, wherein where $R^{10}$ is $C_{1-6}$-alkyl and two or more $R^{10}$ groups are attached to the same carbon atom, the $R^{10}$ groups may be linked to form a spiroalkyl group; and each $R^{11}$ is independently selected from $C_{1-6}$-alkyl, $C_{3-7}$-cycloalkyl, $C_{1-6}$-alkyl-$C_{3-7}$-cycloalkyl, $C_{1-6}$-alkyl-heteroaryl, $C_{4-7}$-heterocycloalkyl, aryl and heteroaryl, each of which is optionally substituted with one or more substituents selected from A; and A is selected from halogen, —$NR^4SO_2R^5$, —CN, —$OR^6$, —$NR^4R^5$, —$NR^7R^{11}$, hydroxyl, oxo, —$CF_3$, —$CONR^4R^5$, —$NR^4COR^5$, —$NR^7(CO)NR^4R^5$, —$NO_2$, —$CO_2H$, —$CO_2R^6$, —$SO_2R^6$, —$SO_2NR^4R^5$, —$NR^4COR^5$, —$NR^4COOR^5$, $C_{1-6}$-alkyl, aryl and —$COR^6$; and each of $R^{12}$ and $R^{13}$ is independently selected from hydrogen, halo, $C_{1-6}$-alkyl, $C_{3-7}$-cycloalkyl and cyano, wherein said $C_{1-6}$-alkyl and $C_{3-7}$-cycloalkyl is each optionally substituted with one or more substituents selected from A.

In one preferred embodiment, $R^2$ is NH-aryl or NH-heteroaryl, wherein said aryl or heteroaryl group is pyridinyl or pyrazolyl group each of which is optionally substituted by one or more substituents selected from $R^{11}$ and A. More preferably, the pyridinyl or pyrazolyl is optionally substituted by one or more $C_{1-6}$-alkyl or —$OR^6$ groups.

Preferred definitions are as set forth above for formula Ia.

Compounds of Formula Ic

Another aspect of the invention relates to compounds of formula Ic, or a pharmaceutically acceptable salt or ester thereof, Ic

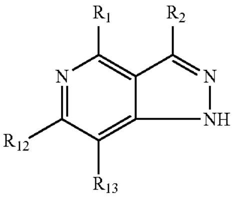

wherein:

$R^1$ is selected from: aryl; heteroaryl; —$NHR^3$; fused aryl-$C_{4-7}$-heterocycloalkyl; —$CONR^4R^5$; —$NHCOR^6$; —$C_{3-7}$-cycloalkyl; —$NR^3R^6$; $OR^3$; OH; $NR^4R^5$; and $C_{1-6}$ alkyl optionally substituted with a substituent selected from $R^{11}$ and a group A; wherein said aryl, heteroaryl, fused aryl-$C_{4-7}$-heterocycloalkyl and $C_{4-7}$-heterocycloalkyl are each optionally substituted with one or more substituents selected from $C_{1-6}$-alkyl, $C_{3-7}$-cycloalkyl, heteroaryl, $C_{4-7}$-heterocycloalkyl, aryl and a group A, and said $C_{1-6}$-alkyl, $C_{3-7}$-cycloalkyl, heteroaryl, $C_{4-7}$-heterocycloalkyl, and aryl substituents are in turn each optionally substituted with one or more groups selected from $R^{11}$ and a group A; $R^2$ is a $C_{2-6}$-alkynyl group optionally substituted with one or more substituents selected from $R^{11}$ and A; each $R^3$ is selected from aryl, heteroaryl, $C_{4-7}$-heterocycloalkyl, $C_{3-7}$-cycloalkyl, fused aryl-$C_{4-7}$-heterocycloalkyl and $C_{1-6}$-alkyl, each of which is optionally substituted with one or more substituents selected from $R^{11}$ and A; $R^4$ and $R^5$ are each independently selected from hydrogen, $C_{3-7}$-cycloalkyl, $C_{1-6}$-alkyl-$C_{3-7}$-cycloalkyl, aryl, heteroaryl, $C_{1-6}$-alkyl and a $C_{3-6}$-heterocycloalkyl ring optionally further containing one or more groups selected from oxygen, sulfur, nitrogen and CO, and optionally substituted by one or more $R^{10}$ groups, wherein each $C_{1-6}$-alkyl, heteroaryl and aryl is optionally substituted by one or more substituents selected from $C_{1-6}$-alkyl, halogen, cyano, hydroxyl, aryl, halo-substituted aryl, heteroaryl, —$NR^8R^9$, —$NR^6R^7$, $NR^7(CO)R^6$, —$NR^7COOR^6$, —$NR^7(SO_2)R^6$, —$COOR^6$, —$CONR^8R^9$, $OR^6$, —$SO_2R^6$ and a $C_{3-6}$-heterocycloalkyl ring optionally further containing one or more groups selected from oxygen, sulfur, nitrogen and CO and optionally substituted by one or more or $R^{10}$ groups; or $R^4$ and $R^5$ together with the N to which they are attached form a monocyclic or bicyclic $C_{3-6}$-heterocycloalkyl ring optionally further containing one or more groups selected from oxygen, sulfur, nitrogen and CO, wherein said $C_{3-6}$-heterocycloalkyl ring is saturated or unsaturated and is optionally substituted with one or more groups selected from A, $NR^8R^9$ and $R^{10}$; each $R^6$ is independently selected from $C_{1-6}$-alkyl, $C_{3-7}$ cycloalkyl, $C_{4-7}$-heterocycloalkyl, aryl and heteroaryl, each of which is optionally substituted by one or more substituents selected from $R^{10}$, $R^{11}$ and A; each $R^7$ is selected from hydrogen, $C_{1-6}$-alkyl and $C_{3-7}$-cycloalkyl, wherein said $C_{1-6}$-alkyl is optionally substituted by one or more halogens; each of $R^8$ and $R^9$ is independently selected from hydrogen and $C_{1-6}$-alkyl, wherein said $C_{1-6}$-alkyl group is optionally substituted by one or more halogens; or $R^8$ and $R^9$ together with the N to which they are attached form a monocyclic or bicyclic $C_{4-6}$-heterocycloalkyl ring optionally further containing one or more heteroatoms selected from oxygen and sulfur, wherein said $C_{4-6}$-heterocycloalkyl ring is optionally substituted by one or more $R^{10}$ groups; and each $R^{10}$ is selected from $C_{3-7}$-cycloalkyl, aryl, heteroaryl, O-heteroaryl, aralkyl and $C_{1-6}$-alkyl, each of which is optionally substituted by one or more A groups, wherein where $R^{10}$ is $C_{1-6}$-alkyl and two or more $R^{10}$ groups are attached to the same carbon atom, the $R^{10}$ groups may be linked to form a spiroalkyl group; and each $R^{11}$ is independently selected from $C_{1-6}$-alkyl, $C_{3-7}$-cycloalkyl, $C_{1-6}$-alkyl-$C_{3-7}$-cycloalkyl, $C_{1-6}$-alkyl-heteroaryl, $C_{4-7}$-heterocycloalkyl, aryl and heteroaryl, each of which is optionally substituted with one or more substituents selected from A; and A is selected from halogen, —$NR^4SO_2R^5$, —CN, —$OR^6$, —$NR^4R^5$, —$NR^7R^{11}$, hydroxyl, oxo, —$CF_3$, —$CONR^4R^5$, —$NR^4COR^5$, —$NR^7(CO)NR^4R^5$, —$NO_2$, —$CO_2H$, —$CO_2R^6$, —$SO_2R^6$, —$SO_2NR^4R^5$, —$NR^4COR^5$, —$NR^4COOR^5$, $C_{1-6}$-alkyl, aryl and —$COR^6$; and each of $R^{12}$ and $R^{13}$ is independently selected from hydrogen, halo, $C_{1-6}$-alkyl, $C_{3-7}$-cycloalkyl and cyano, wherein said $C_{1-6}$-alkyl and $C_{3-7}$-cycloalkyl is each optionally substituted with one or more substituents selected from A.

In one preferred embodiment, $R^2$ is a $C_{2-6}$-alkynyl group optionally substituted with one or more substituents selected from $R^{11}$, where $R^{11}$ is preferably an aryl group optionally substituted by one or more A groups. More preferably, $R^2$ is an ethynyl group optionally substituted by one or more A groups.

Preferred definitions are as set forth above for formula Ia.

Compounds of Formula Id

Another aspect of the invention relates to compounds of formula Id or a pharmaceutically acceptable salt or ester thereof,

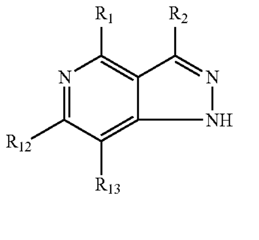

Id wherein:

$R^1$ is selected from: aryl; heteroaryl; —$NHR^3$; fused aryl-$C_{4-7}$-heterocycloalkyl; —$CONR^4R^5$; —$NHCOR^6$; —$C_{3-7}$-cycloalkyl; —$NR^3R^6$; $OR^3$; OH; $NR^4R^5$; and $C_{1-6}$ alkyl optionally substituted with a substituent selected from $R^{11}$ and a group A; wherein said aryl, heteroaryl, fused aryl-$C_{4-7}$-heterocycloalkyl and $C_{4-7}$-heterocycloalkyl are each optionally substituted with one or more substituents selected from $C_{1-6}$-alkyl, $C_{3-7}$-cycloalkyl, heteroaryl, $C_{4-7}$-heterocycloalkyl, aryl and a group A, and said $C_{1-6}$-alkyl, $C_{3-7}$-cycloalkyl, heteroaryl, $C_{4-7}$-heterocycloalkyl, and aryl substituents are in turn each optionally substituted with one or more groups selected from $R^{11}$ and a group A; $R^2$ is O-aryl or O-heteroaryl, wherein said aryl or heteroaryl group is optionally substituted with one or more substituents selected from $R^{11}$ and A; each $R^3$ is selected from aryl, heteroaryl, $C_{4-7}$-heterocycloalkyl, $C_{3-7}$-cycloalkyl, fused aryl-$C_{4-7}$-heterocycloalkyl and $C_{1-6}$-alkyl, each of which is optionally substituted with one or more substituents selected from $R^{11}$ and A; $R^4$ and $R^5$ are each independently selected from hydrogen, $C_{3-7}$-cycloalkyl, $C_{1-6}$-alkyl-$C_{3-7}$-cycloalkyl, aryl, heteroaryl, $C_{1-6}$-alkyl and a $C_{3-6}$-heterocycloalkyl ring optionally further containing one or more groups selected from oxygen, sulfur, nitrogen and CO, and optionally substituted by one or more $R^{10}$ groups, wherein each $C_{1-6}$-alkyl, heteroaryl and aryl is optionally substituted by one or more substituents selected from $C_{1-6}$-alkyl, halogen, cyano, hydroxyl, aryl, halo-substituted aryl, heteroaryl, —$NR^8R^9$, —$NR^6R^7$, $NR^7(CO)R^6$, —$NR^7COOR^6$, —$NR^7(SO_2)R^6$, —$COOR^6$, —$CONR^8R^9$, $OR^6$, —$SO_2R^6$ and a $C_{3-6}$-heterocycloalkyl ring optionally further containing one or more groups selected from oxygen, sulfur, nitrogen and CO and optionally substituted by one or more or $R^{10}$ groups; or $R^4$ and $R^5$ together with the N to which they are attached form a monocyclic or bicyclic $C_{3-6}$-heterocycloalkyl ring optionally further containing one or more groups selected from oxygen, sulfur, nitrogen and CO, wherein said $C_{3-6}$-heterocycloalkyl ring is saturated or unsaturated and is optionally substituted with one or more groups selected from A, $NR^8R^9$ and $R^{10}$; each $R^6$ is independently selected from $C_{1-6}$-alkyl, $C_{3-7}$ cycloalkyl, $C_{4-7}$-heterocycloalkyl, aryl and heteroaryl, each of which is optionally substituted by one or more substituents selected from $R^{10}$, $R^{11}$ and A; each $R^7$ is selected from hydrogen, $C_{1-6}$-alkyl and $C_{3-7}$-cycloalkyl, wherein said $C_{1-6}$-alkyl is optionally substituted by one or more halogens; each of $R^8$ and $R^9$ is independently selected from hydrogen and $C_{1-6}$-alkyl, wherein said $C_{1-6}$-alkyl group is optionally substituted by one or more halogens; or $R^8$ and $R^9$ together with the N to which they are attached form a monocyclic or bicyclic $C_{4-6}$-heterocycloalkyl ring optionally further containing one or more heteroatoms selected from oxygen and sulfur, wherein said $C_{4-6}$-heterocycloalkyl ring is optionally substituted by one or more $R^{10}$ groups; and each $R^{10}$ is selected from $C_{3-7}$-cycloalkyl, aryl, heteroaryl, O-heteroaryl, aralkyl and $C_{1-6}$-alkyl, each of which is optionally substituted by one or more A groups, wherein where $R^{10}$ is $C_{1-6}$-alkyl and two or more $R^{10}$ groups are attached to the same carbon atom, the $R^{10}$ groups may be linked to form a spiroalkyl group; and each $R^{11}$ is independently selected from $C_{1-6}$-alkyl, $C_{3-7}$-cycloalkyl, $C_{1-6}$-alkyl-$C_{3-7}$-cycloalkyl, $C_{1-6}$-alkyl-heteroaryl, $C_{4-7}$-heterocycloalkyl, aryl and heteroaryl, each of which is optionally substituted with one or more substituents selected from A; and A is selected from halogen, —$NR^4SO_2R^5$, —CN, —$OR^6$, —$NR^4R^5$, —$NR^7R^{11}$, hydroxyl, oxo, —$CF_3$, —$CONR^4R^5$, —$NR^4COR^5$, —$NR^7(CO)NR^4R^5$, —$NO_2$, —$CO_2H$, —$CO_2R^6$, —$SO_2R^6$, —$SO_2NR^4R^5$, —$NR^4COR^5$, —$NR^4COOR^5$, $C_{1-6}$-alkyl, aryl and —$COR^6$; and each of $R^{12}$ and $R^{13}$ is independently selected from hydrogen, halo, $C_{1-6}$-alkyl, $C_{3-7}$-cycloalkyl and cyano, wherein said $C_{1-6}$-alkyl and $C_{3-7}$-cycloalkyl each is optionally substituted with one or more substituents selected from A.

In one preferred embodiment, $R^2$ is O-aryl, more preferably O-Ph, wherein said aryl group is optionally substituted with one or more substituents selected from $R^{11}$ and A.

Preferred definitions are as set forth above for formula Ia.

Compounds of Formula Ie

Another aspect of the invention relates to compounds of formula Ie or a pharmaceutically acceptable salt or ester thereof, Ie

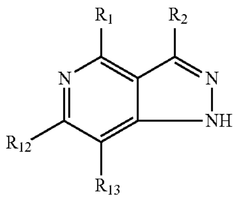

wherein:

$R^1$ is selected from —$NHR^3$ and $OR^3$; $R^2$ is heteroaryl selected from pyrazolyl, pyrrolyl, triazolyl, pyridinyl, benzimidazolyl, indazolyl, pyrazolo[4,3-c]pyridinyl, indolyl or indolinyl, each optionally substituted with one or more substituents selected from $R^{11}$ and A; each $R^3$ is selected from $C_{4-7}$-heterocycloalkyl, $C_{3-7}$-cycloalkyl, and $C_{1-6}$-alkyl, each of which is optionally substituted with one or more substituents selected from $R^{11}$ and A; $R^4$ and $R^5$ are each independently selected from hydrogen, $C_{3-7}$-cycloalkyl, $C_{1-6}$-alkyl-$C_{3-7}$-cycloalkyl, aryl, heteroaryl, $C_{1-6}$-alkyl and a $C_{3-6}$-heterocycloalkyl ring optionally further containing one or more groups selected from oxygen, sulfur, nitrogen and CO, and optionally substituted by one or more $R^{10}$ groups, wherein each $C_{1-6}$-alkyl, heteroaryl and aryl is optionally substituted by one or more substituents selected from $C_{1-6}$-alkyl, halogen, cyano, hydroxyl, aryl, halo-substituted aryl, heteroaryl, —$NR^8R^9$, —$NR^6R^7$, $NR^7(CO)R^6$, —$NR^7COOR^6$, —$NR^7(SO_2)R^6$, —$COOR^6$, —$CONR^8R^9$, $OR^6$, —$SO_2R^6$ and a $C_{3-6}$-heterocycloalkyl ring optionally further containing one or more groups selected from oxygen, sulfur, nitrogen and CO and optionally substituted by one or more or $R^{10}$ groups; or $R^4$ and $R^5$ together with the N to which they are attached form a monocyclic or bicyclic $C_{3-6}$-heterocycloalkyl ring optionally further containing one or more groups selected from oxygen, sulfur, nitrogen and CO, wherein said $C_{3-6}$-heterocycloalkyl ring is saturated or unsaturated and is optionally substituted with one or more groups selected from A, $NR^8R^9$ and $R^{10}$; each $R^6$ is independently selected from $C_{1-6}$-alkyl, $C_{3-7}$ cycloalkyl, $C_{4-7}$-heterocycloalkyl, aryl and heteroaryl, each of which is optionally substituted by one or more substituents selected from $R^{10}$, $R^{11}$ and A; each $R^7$ is selected from hydrogen, $C_{1-6}$-alkyl and $C_{3-7}$-cycloalkyl, wherein said $C_{1-6}$-alkyl is optionally substituted by one or more halogens; each of $R^8$ and $R^9$ is independently selected from hydrogen and $C_{1-6}$-alkyl, wherein said $C_{1-6}$-alkyl group is optionally substituted by one or more halogens; or $R^8$ and $R^9$ together with the N to which they are attached form a monocyclic or bicyclic $C_{4-6}$-heterocycloalkyl ring optionally further containing one or more heteroatoms selected from oxygen and sulfur, wherein said $C_{4-6}$-heterocycloalkyl ring is optionally substituted by one or more $R^{10}$ groups; and each $R^{10}$ is selected from $C_{3-7}$-cycloalkyl, aryl, heteroaryl, O-heteroaryl, aralkyl and $C_{1-6}$-alkyl, each of which is optionally substituted by one or more A groups, wherein where $R^{10}$ is $C_{1-6}$-alkyl and two or more $R^{10}$ groups are attached to the same carbon atom, the $R^{10}$ groups may be linked to form a spiroalkyl group; and each $R^{11}$ is independently selected from $C_{1-6}$-alkyl, $C_{3-7}$-cycloalkyl, $C_{1-6}$-alkyl-$C_{3-7}$-cycloalkyl, $C_{1-6}$-alkyl-heteroaryl, $C_{4-7}$-heterocycloalkyl, aryl and heteroaryl, each of which is optionally substituted with one or more substituents selected from A; and A is selected from halogen, —$NR^4SO_2R^5$, —CN, —$OR^6$, —$NR^4R^5$, —$NR^7R^{11}$, hydroxyl, oxo, —$CF_3$, —$CONR^4R^5$, —$NR^4COR^5$, —$NR^7(CO)NR^4R^5$, —$NO_2$, —$CO_2H$, —$CO_2R^6$, —$SO_2R^6$, —$SO_2NR^4R^5$, —$NR^4COR^5$, —$NR^4COOR^5$, $C_{1-6}$-alkyl, aryl and —$COR^6$; and each of $R^{12}$ and $R^{13}$ is independently selected from hydrogen, halo, $C_{1-6}$-alkyl, $C_{3-7}$-cycloalkyl and cyano, wherein said $C_{1-6}$-alkyl and $C_{3-7}$-cycloalkyl is each optionally substituted with one or more substituents selected from A.

Preferred definitions are as set forth above for formula Ia.

In one preferred embodiment of formula 1e, $R^3$ is tetrahydropyranyl, tetrahydrofuranyl, cyclohexyl, cyclopentyl or $C_{1-6}$-alkyl wherein the cyclohexyl and cyclopentyl each are optionally substituted with halo or $C_{1-6}$-alkyl, and wherein $C_{1-6}$-alkyl is optionally substituted with halo.

In one preferred embodiment of formula 1e, $R^2$ is pyrazolyl, pyrrolyl, triazolyl or pyridinyl, each optionally substituted with one or two substituents selected from $R^{11}$ and A;

In one preferred embodiment of formula 1e, $R^2$ is pyrazolyl, pyrrolyl, triazolyl or pyridinyl, each optionally substituted with one or two substituents selected from —$CONR^4R^5$, $C_{1-6}$-alkyl, $C_{3-7}$-cycloalkyl, $C_{1-6}$-alkyl-$C_{3-7}$-cycloalkyl, —CN, morpholinyl, piperazinyl, pyrrolinyl, piperidinyl, azetidinyl, tetrahydrofuranyl or tetrahydropyranyl, wherein the $C_{3-7}$-cycloalkyl, $C_{1-6}$-alkyl-$C_{3-7}$-cycloalkyl, —CN, morpholinyl, piperazinyl, pyrrolinyl, piperidinyl, azetidinyl, tetrahydrofuranyl or tetrahydropyranyl is each optionally substituted with halo or $C_{1-6}$-alkyl, and wherein the $C_{1-6}$-alkyl, is optionally substituted with halo.

In one preferred embodiment of formula 1e, one of $R^4$ and $R^5$ is hydrogen or $C_{1-6}$-alkyl, and the other is $C_{3-7}$-cycloalkyl, $C_{1-6}$-alkyl-$C_{3-7}$-cycloalkyl, $C_{1-6}$-alkyl, or a $C_{3-6}$-heterocycloalkyl ring optionally further containing one or more groups selected from oxygen, sulfur, nitrogen and CO, wherein each $C_{1-6}$-alkyl, $C_{3-7}$-cycloalkyl, and $C_{1-6}$-alkyl-$C_{3-7}$-cycloalkyl is optionally substituted with halo, or $R^4$ and $R^5$ together with the N to which they are attached form a $C_{3-6}$-heterocycloalkyl ring.

In one preferred embodiment of formula 1e, one of $R^4$ and $R^5$ is hydrogen or $C_{1-6}$-alkyl, and the other is $C_{3-7}$-cycloalkyl, $C_{1-6}$-alkyl-$C_{3-7}$-cycloalkyl, $C_{1-6}$-alkyl, or oxetanyl, wherein each $C_{3-7}$-cycloalkyl, and $C_{1-6}$-alkyl-$C_{3-7}$-cycloalkyl is optionally substituted with halo or $C_{1-6}$-alkyl, and wherein each $C_{1-6}$-alkyl is optionally substituted with halo, or $R^4$ and $R^5$ together with the N to which they are attached form a pyrrolidine or azetidine.

In one preferred embodiment of formula 1e, $R^2$ is pyrazolyl optionally substituted with one or two substituents selected from —$CONR^4R^5$, $C_{1-6}$-alkyl, $C_{3-7}$-cycloalkyl, $C_{1-6}$-alkyl-$C_{3-7}$-cycloalkyl, —CN, morpholinyl, piperazinyl, pyrrolidinyl, piperidinyl, azetidinyl, tetrahydrofuranyl or tetrahydropyranyl, wherein the $C_{3-7}$-cycloalkyl, $C_{1-6}$-alkyl-$C_{3-7}$-cycloalkyl, morpholinyl, piperazinyl, pyrrolidinyl, piperidinyl, azetidinyl, tetrahydrofuranyl or tetrahydropyranyl each is optionally substituted with halo or $C_{1-6}$-alkyl, and wherein the $C_{1-6}$-alkyl is optionally substituted with halo.

In one preferred embodiment of formula 1e, $R^2$ is pyrrolyl optionally substituted with one or two substituents selected from —$CONR^4R^5$, $C_{1-6}$-alkyl, $C_{3-7}$-cycloalkyl, $C_{1-6}$-alkyl-$C_{3-7}$-cycloalkyl, —CN, morpholinyl, piperazinyl, pyrrolidinyl, piperidinyl, azetidinyl, tetrahydrofuranyl or tetrahydropyranyl, wherein the $C_{3-7}$-cycloalkyl, $C_{1-6}$-alkyl-$C_{3-7}$-cycloalkyl, morpholinyl, piperazinyl, pyrrolidinyl, piperidinyl, azetidinyl, tetrahydrofuranyl or tetrahydropyranyl each is optionally substituted with halo or $C_{1-6}$-alkyl, and wherein the $C_{1-6}$-alkyl is optionally substituted with halo.

In one preferred embodiment of formula 1e, $R^2$ is pyridinyl optionally substituted with one or two substituents selected from —$CONR^4R^5$, $C_{1-6}$-alkyl, $C_{3-7}$-cycloalkyl, $C_{1-6}$-alkyl-$C_{3-7}$-cycloalkyl, —CN, morpholinyl, piperazinyl, pyrrolidinyl, piperidinyl, azetidinyl, tetrahydrofuranyl or tetrahydropyranyl, wherein the $C_{3-7}$-cycloalkyl, $C_{1-6}$-alkyl-$C_{3-7}$-cycloalkyl, morpholinyl, piperazinyl, pyrrolidinyl, piperidinyl, azetidinyl, tetrahydrofuranyl or tetrahydropyranyl each is optionally substituted with halo or $C_{1-6}$-alkyl, and wherein the $C_{1-6}$-alkyl is optionally substituted with halo.

In one preferred embodiment of formula 1e, $R^{11}$ is $C_{1-6}$-alkyl, $C_{3-7}$-cycloalkyl, $C_{1-6}$-alkyl-$C_{3-7}$-cycloalkyl, or $C_{4-7}$-heterocycloalkyl, wherein $C_{1-6}$-alkyl is optionally substituted with halo, and wherein each of $C_{3-7}$-cycloalkyl, $C_{1-6}$-alkyl-$C_{3-7}$-cycloalkyl, or $C_{4-7}$-heterocycloalkyl is optionally substituted with $C_{1-6}$-alkyl or halo.

In embodiments of formula 1e wherein $R^{11}$ is $C_{4-7}$-heterocycloalkyl, such $C_{4-7}$-heterocycloalkyl may be morpholinyl, piperidinyl, piperazinyl, pyrrolyl, azetidinyl, tetrahydrofuranyl, tetrahydropyranyl or oxetanyl, each optionally substituted one or more times with $C_{1-6}$-alkyl or halo.

In one preferred embodiment of formula 1e, $R^2$ is selected from

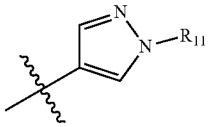

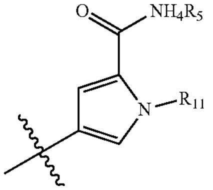

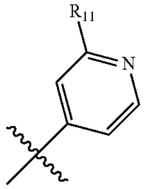

wherein $R^4$, $R^5$ and $R^{11}$ are as defined herein.

In one preferred embodiment of formula 1e, $R^2$ is

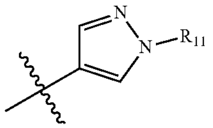

wherein $R^{11}$ is as defined herein.

In one preferred embodiment of formula 1e, $R^2$ is

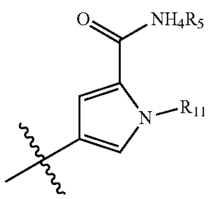

wherein $R^4$, $R^5$ and $R^{11}$ are as defined herein.

In one preferred embodiment of formula 1e, $R^2$ is

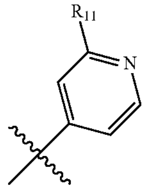

wherein $R^{11}$ is as defined herein.

In one preferred embodiment of formula 1e, $R^{12}$ and $R^{13}$ are hydrogen.

In one preferred embodiment of formula 1e, $R^{12}$ is $C_{1-6}$-alkyl and $R^{13}$ is hydrogen.

Therapeutic Applications

A further aspect of the invention relates to a compound as described above for use in medicine.

Another aspect of the invention relates to a compound as described above for use in treating cancer or a neurodegenerative disorder.

Another aspect relates to the use of a compound as described above in the preparation of a medicament for treating or preventing a neurodegenerative disorder. Preferably, the neurodegenerative disorder is Parkinson's Disease.

Another aspect relates to the use of a compound as described above in the preparation of a medicament for treating or preventing a proliferative disorder, for example, cancer.

Preferably, the compound is administered in an amount sufficient to inhibit one or more kinases, preferably LRRK, even more preferably LRRK2.

Yet another aspect relates to the use of a compound of the invention in the preparation of a medicament for the prevention or treatment of a disorder caused by, associated with or accompanied by any abnormal activity against a biological target, wherein the target is a kinase, more preferably LRRK, even more preferably LRRK2.

Preferably, the disorder is Parkinson's Disease.

Another aspect of the invention relates to a method of treating a protein kinase related disease or disorder. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Yet another aspect of the invention relates to a method of treating a mammal having a disease state alleviated by inhibition of a protein kinase, wherein the method comprises administering to a mammal a therapeutically effective amount of a compound according to the invention.

Preferably, the disease state is alleviated by the inhibition of the protein kinase LRRK, more preferably LRRK2.

Preferably, the mammal is a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing a compound of the present invention and a protein kinase together in such a manner that the compound can affect the enzyme activity of the protein kinase either directly; i.e., by interacting with the protein kinase itself or indirectly; i.e., by interacting with another molecule on which the catalytic activity of the protein kinase is dependent. As used herein, administration can be accomplished either in vitro, i.e. in a test tube, or in vivo, i.e., in cells or tissues of a living organism.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patients condition. (see, e.g., Fingl et al, 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 50-2000 mg/kg/day, commonly from about 100-1000 mg/kg/day, preferably from about 150-700 mg/kg/day and most preferably from about 250-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "kinase related disease or disorder" refers to a disease or disorder characterized by inappropriate kinase activity or over-activity of a kinase as defined herein. Inappropriate activity refers to either; (i) kinase expression in cells which normally do not express said kinase; (ii) increased kinase expression leading to unwanted cell proliferation, differentiation and/or growth; or, (iii) decreased kinase expression leading to unwanted reductions in cell proliferation, differentiation and/or growth. Over-activity of kinase refers to either amplification of the gene encoding a particular kinase or production of a level of kinase activity, which can correlate with a cell proliferation, differentiation and/or growth disorder (that is, as the level of the kinase increases, the severity of one or more of the symptoms of the cellular disorder increases). Over activity can also be the result of ligand independent or constitutive activation as a result of mutations such as deletions of a fragment of a kinase responsible for ligand binding.

Preferred diseases or disorders that the compounds described herein may be useful in preventing, include cancer and neurodegenerative disorders such as Parkinson's Disease.

Thus, the present invention further provides use of compounds as defined herein for the manufacture of medicaments for the treatment of diseases where it is desirable to inhibit LRRK2. Such diseases include Parkinson's Disease.

Pharmaceutical Compostions

For use according to the present invention, the compounds or physiologically acceptable salt, ester or other physiologically functional derivative thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Salts/Esters

The compounds of the invention can be present as salts or esters, in particular pharmaceutically and veterinarily acceptable salts or esters. Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as $(C_1-C_4)$-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as $(C_1-C_4)$-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', 3rd edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}H$, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

In accordance with this invention, an effective amount of a compound of general formula (I) may be administered to inhibit the kinase implicated with a particular condition or disease. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a kinase. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the inhibitory activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

Assay

A further aspect of the invention relates to the use of a compound as described above in an assay for identifying further candidate compounds capable of inhibiting one or more kinases, more preferably LRRK, even more preferably, LRRK2.

Preferably, the assay is a competitive binding assay.

More preferably, the competitive binding assay comprises contacting a compound of the invention with a kinase, preferably LRRK, more preferably LRRK2, and a candidate compound and detecting any change in the interaction between the compound according to the invention and the kinase.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a kinase in the presence of a known substrate of said kinase and detecting any change in the interaction between said kinase and said known substrate.

A further aspect of the invention provides a method of detecting the binding of a ligand to a kinase, said method comprising the steps of:

(i) contacting a ligand with a kinase in the presence of a known substrate of said kinase;

(ii) detecting any change in the interaction between said kinase and said known substrate; and wherein said ligand is a compound of the invention.

One aspect of the invention relates to a process comprising the steps of:

(a) performing an assay method described hereinabove;

(b) identifying one or more ligands capable of binding to a ligand binding domain; and (c) preparing a quantity of said one or more ligands.

Another aspect of the invention provides a process comprising the steps of:

(a) performing an assay method described hereinabove;

(b) identifying one or more ligands capable of binding to a ligand binding domain; and (c) preparing a pharmaceutical composition comprising said one or more ligands.

Another aspect of the invention provides a process comprising the steps of:

(a) performing an assay method described hereinabove;

(b) identifying one or more ligands capable of binding to a ligand binding domain;

(c) modifying said one or more ligands capable of binding to a ligand binding domain;

(d) performing the assay method described hereinabove;

(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for use in the treatment of one or more disorders [insert list of disorders].

The above methods may be used to screen for a ligand useful as an inhibitor of one or more kinases.

Compounds of general formula (I) are useful both as laboratory tools and as therapeutic agents. In the laboratory certain compounds of the invention are useful in establishing whether a known or newly discovered kinase contributes a critical or at least significant biochemical function during the establishment or progression of a disease state, a process commonly referred to as 'target validation'.

Synthesis

The invention also relates to a process for preparing compounds of the invention. Compounds of the invention may be prepared using the general methodology described below, with further reference to the accompanying examples.

More specifically, the compounds may be prepared by converting a compound of formula II into a compound of formula I:

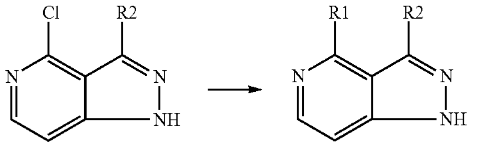

II I

Preferably, the process further comprises the step of preparing said compound of formula II by treating a compound of formula III with hydrazine monohydrate:

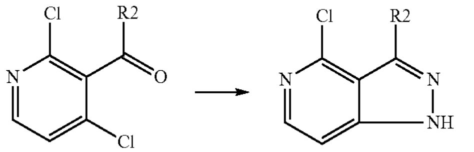

III II

Preferably, the process further comprises the step of preparing said compound of formula III by treating a compound of formula IV with an oxidizing agent:

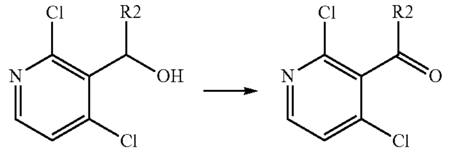

IV III

Preferably, the process further comprises the step of preparing said compound of formula IV by treating a compound of formula V with $R^2$—Mg—Cl:

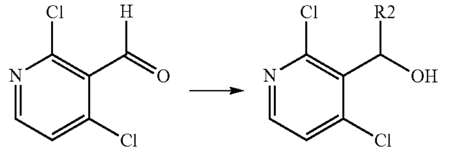

V IV

Preferably, $R^1$ is —$NHR^3$, and the process comprises reacting a compound of formula II with an amine of formula $NH_2R^3$.

In another preferred embodiment of the invention, $R^1$ is an NH-containing $C_{4-7}$-heterocycloalkyl or an NH-containing fused aryl-$C_{4-7}$-heterocycloalkyl, and the process comprises reacting a compound of formula II with the NH-group of said $C_{4-7}$-heterocycloalkyl or fused aryl-$C_{4-7}$-heterocycloalkyl.

In another preferred embodiment of the invention, $R^1$ is selected from aryl, heteroaryl, $C_{4-7}$-heterocycloalkyl, fused aryl-$C_{4-7}$-heterocycloalkyl, —$C_{3-7}$ cycloalkyl and —$C_{1-6}$ alkyl, and said process comprises reacting a compound of formula II with X—$R^1$, where X is a 4,4,5,5-tetramethyl-1,3,2-dioxaborolan-2-yl group, in the presence of a coupling agent.

Preferably, the coupling agent is palladium diphenylphosphinoferrocene dichloride.

A process for preparing compounds of the invention is shown below in Scheme 1.

Scheme 1

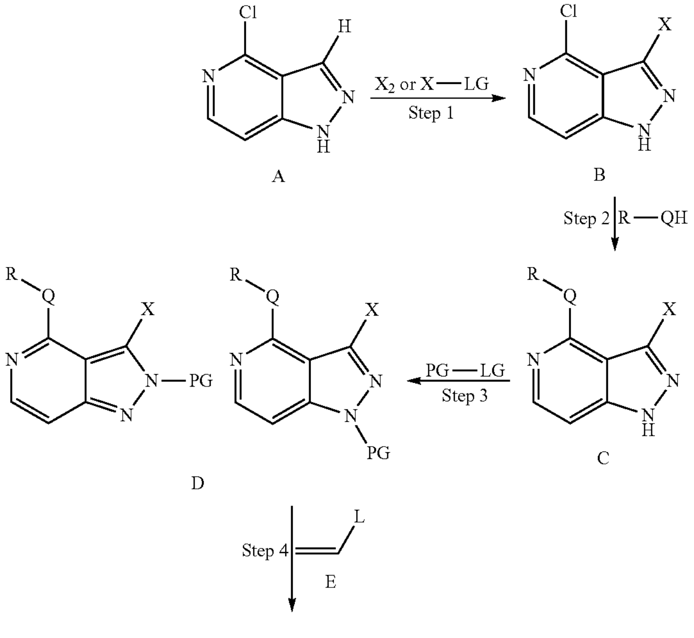

-continued

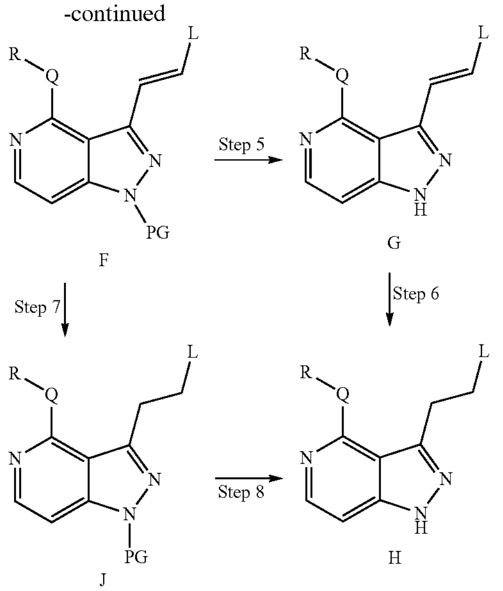

Step 1 describes the conversion of formula A into formula B, wherein X is a halogen, preferably bromine or iodine and LG is a leaving group such as succinimide. The reaction is carried out in the presence of a suitable halogenating agent, such as iodine or N-bromosuccinimide, optionally in the presence of a base, such as potassium hydroxide in a suitable solvent. Typical conditions (X═I), 1 eq. of formula A, 2 eq. of $I_2$, 3.7 eq of KOH in dioxane at 75° C. for 4 h; (X═Br), 1 eq. of formula A, 1 eq. of N-bromosuccinimide in acetonitrile at reflux for 3 h.

Step 2 describes the conversion of formula B into formula C, wherein X is a halogen, RQH can either be a primary or secondary amine, or an alcohol. The group R can optionally contain a functional group which can be manipulated at later stages in the synthetic process using standard conditions known to the skilled person. The reaction involves nucleophilic displacement of the chloro group in formula B with a an amino group in a suitable solvent, optionally in the presence a Bronsted acid. This reaction generally requires heating, either thermally or with the use of microwave irradiation. Where RQH is an alcohol, the alcohol is deprotonated with a suitable base to the corresponding alkoxide followed by subsequent nucleophilic displacement of the chloro group in formula B. Typical conditions (RQH=primary or secondary aliphatic amino group), 2.5 eq. of amine, 1 eq. of formula B in n-butanol, heated to 190° C. in the microwave for 20 min; (RQH=primary or secondary aromatic amino group), 2 eq. of amine, 1 eq of formula B, 3 eq of conc. HCl(aq) in n-butanol, heated to 190° C. in the microwave for 45 min; (RQH=alcohol), 4 eq. of alcohol is treated with 3.5 eq. of sodium hydride in dioxane at room temperature for 2 h prior to addition of 1 eq of formula B and subsequent heating in the microwave at 180° C. for 1.5 h.

Step 3 describes the conversion of formula C into formula D, wherein PG is defined as a protecting group, including but not limited to tert-butoxycarbonyl-; benzyloxycarbonyl-; benzyl-; 4-methoxybenzyl-; 2,4-dimethoxybenzyl- or trityl-; LG is defined as a leaving group, such as a halogen or tert-butylcarbonate. The reaction involves capping of the indazole NH with a protecting group. It will be appreciated by the skilled person, that that many protecting groups can be used for this purpose (see Greene, Theodora W. and Wuts, Peter G. M. Greene's Protective Groups in Organic Synthesis. 4th Ed. (2006)). The skilled person will also appreciate that it is possible to introduce the protecting group either at N1 or N2, and the ratio may change depending on the nature of PG or the precise reaction conditions deployed. The reaction conditions will depend on the nature of the protecting group. Typical conditions (PG=4-methoxybenzyl): 1 eq of 4-methoxybenxyl chloride; 1 eq of formula C, 2 eq of potassium hydroxide is stirred in DMF at room temperature overnight.

Step 4 involves the conversion of formula D to formula F, wherein L is a group, such as but not limited to, aryl, substituted aryl, heteroaryl, substituted heteroaryl, an ester or an amide; X is a halogen, but preferably an iodine. The linker L can optionally contain a functional group which can be manipulated at later stages in the synthetic process using standard conditions known to the skilled person. The reaction involves a cross coupling of a substituted vinyl derivative (formula E) with formula D in the presence of a suitable transition metal catalyst and a suitable base, preferably triethylamine and optionally additional additives, such as tetrabutyl ammonium iodide. This type of transformation is often known as a "Heck Reaction" to those skilled in the art. Typical conditions: 1 eq. of formula D, 10 eq. of formula E, 2 eq. of tetrabutylammonium iodide, 0.2 eq. of $Pd(dppf)Cl_2$ in DMF:Water:triethylamine (6.25:1:1) is heated to 70° C. overnight.

Step 5 involves the conversion of formula F into formula G, wherein Q, PG, and L are as defined earlier. The reaction involved removal of the protecting group from the indazole and the precise conditions will vary depending the nature of the protecting group (Greene, Theodora W. and Wuts, Peter G. M. Greene's Protective Groups in Organic Synthesis. 4th Ed. (2006). Typical conditions (QR is a substituted amino group and PG is 4-methoxybenzyl): Formula F is treated with trifluoroacetic acid at 70° C. overnight.

Step 6 involves the conversion of formula G into formula H, wherein PG, L, PG, RQ- are as defined earlier. The reaction involves hydrogenation of the double bond to the corresponding saturated compound with a hydrogen source in the presence of a suitable transition metal catalyst in a suitable solvent. It may be necessary or desirable to add a Bronsted acid (such as HCl, or acetic acid) to facilitate this reaction. The person skilled in the art will appreciate that a number of different metal catalysts can be used for this type of reaction and that it may be necessary or desirable to carry out these reactions under pressure. Typical conditions: formula G is treated with platinum oxide in glacial acetic acid under an atmosphere of hydrogen.

Step 7 involves the conversion of formula F into formula J, wherein PG, L, PG, RQ- are as defined earlier. The reaction involves hydrogenation of the double bond to the corresponding saturated compound with a hydrogen source in the presence of a suitable transition metal catalyst, such as palladium on carbon or platinum oxide in a suitable solvent, such as ethanol, ethyl acetate or dioxane. It may be necessary or desirable to add a Bronsted acid (such as HCl, or acetic acid) to facilitate this reaction. The person skilled in the art will appreciate that a number of different metal catalysts can be used for this type of reaction and that it may be necessary or desirable to carry out these reactions under pressure. Typical conditions: formula F is treated with 10% palladium on carbon in ethyl acetate under an atmosphere of hydrogen at room temperature overnight.

Step 8 involves the conversion of formula J to formula H, wherein PG, L, PG, RQ- are as defined earlier. The reaction involves removal of the protecting group from the indazole, and the precise conditions will depend on the nature of the protecting group (Greene, Theodora W. and Wuts, Peter G. M. Greene's Protective Groups in Organic Synthesis. 4th Ed. (2006).

Typical conditions (QR is a substituted amino group and PG is 4-methoxybenzyl): Formula F is treated with trifluoroacetic acid at 70° C. overnight.

Step 9

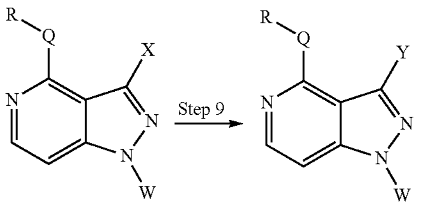

K L describes the conversion of formula K into formula L wherein X and RQ are as defined previously, W can be either hydrogen or a protecting group, such as but not limited to 4-methoxybenzyl or trityl; Y can be aryl, substituted aryl, heteroaryl or substituted heteroaryl. The person skilled in the art will appreciate that where W is a protecting group, this can be removed at a later stage using standard conditions (Greene, Theodora W. and Wuts, Peter G. M. Greene's Protective Groups in Organic Synthesis. 4th Ed. (2006). The reaction involves cross-coupling of the halide in formula K with a boronic acid or boronic ester in the presence of a transition metal catalyst in a suitable solvent. The reactions are typically carried out at elevated temperatures with either thermal or microwave heating. An inorganic base (such as sodium carbonate) is generally added to the reaction mixture. Transformations of this type are known as "Suzuki Couplings" to those skilled in the art. Typical conditions: 1 eq. of formula K, 0.09 eq. of $Pd(dppf)_2Cl_2$, 1.5 eq. of the boronic acid (or boronic ester), 3.5 eq. of 2M aqueous sodium carbonate in dioxane at 90° C. for 18 h.

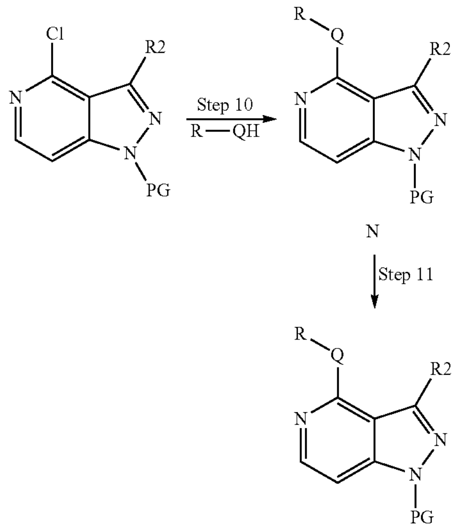

P

Steps 10-11

Step 10 describes the conversion of formula M into formula N, wherein R2 and RQH are as defined earlier and PG is a protecting group such as but not limited to 4-methoxybenzyl or trityl. Where RQH is a primary or secondary amine, the reaction involves nucleophilic displacement of the chloro group in formula M with the amine. The reaction can be either carried out with or without solvent (such as but not limited to n-butanol or N-methylpyrrolidone), optionally in the presence of a Bronsted acid (such as but not limited to HCl) or an organic base (such as but not limited to N,N-diisopropylethylamine). This reaction generally requires heating, either thermally or with the use of microwave irradiation.

Alternatively, the reaction can be carried out by treatment of formula M with a primary or secondary amine in the presence or a transition metal catalyst, in the presence of a base in a suitable solvent. Typical conditions: 1.4 equivalents of amine, 1 equivalent of formula M, 1 equivalent of cesium carbonate, 0.06 equivalents of palladium(II) acetate and 0.08 equivalents of 2,2'-bis(diphenylphosphino)-1,1'-binaphthyl (BINAP) is heated to 90° C. in 1,4-dioxane overnight.

Where RQH is an alcohol, the alcohol is deprotonated with a suitable base to the corresponding alkoxide followed by subsequent nucleophilic displacement of the chloro group in formula M. Alternatively, the reaction can be carried out by treatment of formula M with a primary or secondary alcohol in the presence or a transition metal catalyst, in the presence of a base in a suitable solvent.

Typical conditions (nucleophilic displacement): 2 eq. of alcohol is treated with 1.5 eq. of sodium hydride in dioxane at room temperature for 3 h prior to addition of 1 eq of formula B and subsequent heating in the microwave at 180° C. for 1.5 h. Typical conditions (transition metal catalyzed): 2 equivalents of alcohol, 1 equivalent of formula M, 3 equivalents of sodium tert-butoxide, 0.06 equivalents of palladium(II) acetate and 0.08 equivalents of 2,2'-bis(diphenylphosphino)-1,1'-binaphthyl (BINAP) is heated to 100° C. in toluene overnight.

Step 11 involves the conversion of formula N to formula P, wherein R2, PG, RQ- are as defined earlier. The reaction involves removal of the protecting group from the indazole, and the precise conditions will depend on the nature of the protecting group (Greene, Theodora W. and Wuts, Peter G. M.

Greene's Protective Groups in Organic Synthesis. 4th Ed. (2006). Typical conditions (QR is a substituted amino group and PG is 4-methoxybenzyl): Formula N is treated with trifluoroacetic acid (neat) at 70° C. overnight. Typical conditions (QR is an alkoxy group and PG is trityl): Formula N is treated with trifluoroacetic acid:DCM (1:10) for 18 h at room temperature. The invention is further described by way of the following non-limiting examples.

EXAMPLES

Materials and Methods

In Vitro LRRK2 Assay

This assay was used to determine a compound's potency in inhibiting activity of LRRK2 by determining, $Ki_{app}$, $IC_{50}$, or percent inhibition values. In a polypropylene plate, LRRK2, fluorescently-labeled peptide substrate, ATP and test compound were incubated together. Using a LabChip 3000 (Caliper Life Sciences), after the reaction the substrate was separated by capillary electrophoresis into two populations: phosphorylated and unphosphorylated. The relative amounts of each were quantitated by fluorescence intensity. LRRK2 Ki was determined according to the equation:

$$Y=V0*(1-((x+Ki*(1+S/Km)+Et)/(2*Et)-(((x+Ki*(1+S/Km)+Et)^{\wedge}2-(4*Et*x))^{\wedge}0.5)/(2*Et))).$$

Ki values in Table 4 and elsewhere herein are shown in μM.

Assay conditions and materials used were as follows:

Final Assay Conditions:

LRRK2 G2019S in 5 mM $MgCl_2$: 5.2 nM (Invitrogen lot #567054A)

LRRK2 G2019S in 1 mM $MnCl_2$: 11 nM (Invitrogen lot #567054A)

LRRK2 Wild type in 5 mM $MgCl_2$: 15 nM (Invitrogen lot #500607F)

LRRK2 I2020T in 5 mM $MgCl_2$: 25 nM (Invitrogen lot #43594)

Substrate: 1 μM

ATP: 130 μM

Kinase reaction time: 2 hours

Temperature: ambient

Total volume: 20 μl $ATP^{app}$ Kms:

G2019S in 5 mM $MgCl_2$: 130 μM

G2019S in 1 mM $MnCl_2$: 1 μM

Wild type in 5 mM $MgCl_2$: 80 μM

I2020T in 5 mM $MgCl_2$: 14 μM

Materials:

Solid Support: Black 50 μL volume polypropylene 384 well plate (MatriCal cat #MP101-1-PP)

Kinase: LRRK2 G2019S (Invitrogen cat #PV4882).

LRRK2 Wild type (Invitrogen cat #PV4874).

Substrate: 5FAM-GAGRLGRDKYKT:RQIRQ-$CONH_2$

Non-binding plate: 384 well clear V-bottom polypropylene plates (Greiner cat #781280).

ATP: 10 mM ATP (Cell Signaling cat #9804).

Triton X-100: Triton X-100.

Brij-35: Brij-35 (Pierce cat #20150).

Coating Reagent #3: Coating Reagent #3 (Caliper).

DMSO: DMSO (Sigma cat #34869-100 ML).

Complete Reaction Buffer: $H_2O$/25 mM Tris, pH 8.0/5 mM $MgCl_2$/2 mM DTT/0.01% Triton X-100.

Stop Solution: $H_2O$/100 mM HEPES, pH 7.2/0.015% Brij-35/0.2% Coating Reagent #3/20 mM EDTA.

Separation Buffer: $H_2O$/100 mM HEPES, pH 7.2/0.015% Brij-35/0.1% Coating Reagent #3/1:200 Coating Reagent #8/10 mM EDTA/5% DMSO.

Compound Plate Preparation:

For serial dilutions, 34.6 μl DMSO was added to columns 3-24. For the assay controls, 37.5 μl DMSO was added to columns 1 and 2 of rows A and P. a, d and 50 μl 25 μM G-028831 (Staurosporine) was added to columns 1 and 2, row B. For the samples: to start at 100 μM, 37.5 μl DMSO was to columns 1 and 2, then 12.5 μl 10 mM compound; to start at 10 μM, 78 μl DMSO was added to columns 1 & 2, then 2 μl 10 mM compound; and to start at 1 μM, 25 μM compound (2 μl 10 mM cmpd+798 μl DMSO) was added to empty columns 1 and 2. A Precision instrument was used to perform 1:3.16 serial dilutions ("PLK_BM_serial_halflog").

ATP Preparation:

ATP was diluted to 282.1 μM in Complete Kinase Buffer (final concentration was 130 μM).

Total and Blank Preparation:

In Complete Reaction Buffer, substrate was diluted to 4 μM. Equal volumes of Complete Reaction Buffer and 4 μM substrate were combined to obtain the blank. Equal volumes of Complete Reaction Buffer and 4 μM substrate were combined and to the combined solution was added 2× final LRRK2 concentration.

Assay Procedure:

To a 50 μl polypropylene plate, 5 μl/well buffer/substrate was added by hand to Blank wells. A Biomek FX was used to start the kinase reaction ("PLK SAR 23 ATP"). The following were added to the appropriate wells:

2 μl compound+23 μl ATP;

5 μl/well compound/ATP in Assay Plate;

5 μl/well kinase/substrate in Assay Plate;

The plate was incubated for 2 hours in the dark. Biomek FX was used to stop the kinase reaction ("PLK Stop"), and 10 μl/well Stop solution was added to the Assay Plate. Results were read on the LabChip 3000.

Lab Chip 3000 Protocol:

The LabChip 3000 was run using the job "LRRK2 IC50" with the following job settings:

Pressure: −1.4 psi

Downstream voltage: −500 V

Upstream voltage: −2350 V

Post sample buffer sip time: 75 seconds

Post dye buffer sip time: 75 seconds

Final delay time: 200 seconds

Parkinson's Disease Animal Model

Parkinson's disease can be replicated in mice and in primates by administration of 1-methyl-4-phenyul tetrahydropyridine (MPTP), a selective nigrostriatal dopaminergic neurotoxin that produces a loss of striatal dopamine (DA) nerve terminal markers. Compounds of the invention may be evaluated for effectiveness in treatment of Parkinson's disease using MPTP induced neurodegeneration following generally the protocol described by Saporito et al., *J. Pharmacology* (1999) Vol. 288, pp. 421-427.

Briefly, MPTP is dissolved in PBS at concentrations of 2-4 mg/ml, and mice (male C57 weighing 20-25 g) are given a subcutaneous injection of 20 to 40 mg/kg. Compounds of the invention are solubilized with polyethylene glycol hydroxystearate and dissolved in PBS. Mice are administered 10 ml/kg of compound solution by subcutaneous injection 4 to 6 h before MPTP administration, and then daily for 7 days. On the day of the last injection, mice are sacrificed and the midbrain blocked and postfixed in paraformaldehyde. Striata are dissected free, weighed, and stored at −70° C.

The striata thus collected are evaluated for content of dopamine and its metabolites dihydroxyphenylacetic acid and homovanillic acid, by HPLC with electrochemical detection as described by Sonsalla et al., *J. Pharmacol. Exp. Ther.* (1987) Vol. 242, pp. 850-857. The striata may also be evaluated using the tyrosine hydroxylase assay of Okunu et al., *Anal Biochem* (1987) Vol. 129, pp. 405-411 by measuring $^{14}CO_2$ evolution associated with tyrosine hydroxylase-mediated conversion of labeled tyrosine to L-dopa. The striata may further be evaluated using the Monoamine oxidase-B assay as described by White et al., *Life Sci.* (1984), Vol. 35, pp. 827-833, and by monitoring dopamine uptake as described by Saporito et al., (1992) Vol. 260, pp. 1400-1409.

General Procedures for Synthesis of Compounds

Liquid Chromatography-Mass Spectrometry

Method A—LC-MS was performed on an Agilent 1200 Series HPLC coupled to an Agilent 6110 single-pole mass spectrometer using a Sunfire column (3.5 μm, 4.6×50 mm) held at 5% acetonitrile for 0.2 minute, followed by a linear gradient of 5-95% acetonitrile/water within 1.6 minutes and then held at 95% for 1.2 minutes (with 0.01% trifluoroacetic acid in each mobile phase).

Method B—LC-MS was performed on an Agilent 1200 Series HPLC coupled to an Agilent 6110 single-pole mass spectrometer using a Sunfire column (3.5 μm, 4.6×50 mm) held at 5% acetonitrile for 0.2 minute, followed by a linear gradient of 5-95% acetonitrile/water within 1.6 minutes and then held at 95% for 1.2 minutes (with 0.01% ammonia in the water mobile phase).

Method C—LC-MS was performed on an Agilent 1200 Series HPLC coupled to an Agilent 6110 single-pole mass spectrometer using a Xbridge column (3.5 μm, 4.6×50 mm) held at 5% acetonitrile for 0.2 minute, followed by a linear gradient of 5-95% acetonitrile/water within 1.6 minutes and then held at 95% for 1.2 minutes (with 10 mM $NH_4HCO_3$ in the water mobile phase).

Method D—LC-MS was performed on an Agilent 1200 Series HPLC coupled to an Agilent 6110 single-pole mass spectrometer using a Sunfire column (3.5 μm, 4.6×50 mm) held at 5% acetonitrile for 0.2 minute, followed by a linear gradient of 5-95% acetonitrile/water within 8 minutes and then held at 95% for 1.8 minutes (with 0.01% trifluoroacetic acid in each mobile phase).

Method E—LC-MS was performed on an Agilent 1200 Series HPLC coupled to an Agilent 6110 single-pole mass spectrometer using a Sunfire column (3.5 μm, 4.6×50 mm) held at 5% acetonitrile for 0.2 minute, followed by a linear gradient of 5-95% acetonitrile/water within 8 minutes and then held at 95% for 1.8 minutes (with 0.01% ammonia in the water mobile phase).

Method F—LC-MS was performed on an Agilent 1200 Series HPLC coupled to an Agilent 6110 single-pole mass spectrometer using a Xbridge column (3.5 μm, 4.6×50 mm) held at 5% acetonitrile for 0.2 minute, followed by a linear gradient of 5-95% acetonitrile/water within 8 minutes and then held at 95% for 1.8 minutes (with 10 mM $NH_4HCO_3$ in the water mobile phase).

Method G—LC-MS was performed on an Agilent 1200 Series LC coupled to an Agilent 6140 quadrupole mass spectrometer using an Agilent SD-C18 column (1.8 μm, 2.1×30 mm) with a linear gradient of 3-95% acetonitrile/water (with 0.05% trifluoroacetic acid in each mobile phase) within 8.5 minutes and held at 95% for 2.5 minutes.

Method H—LC-MS was performed on a Waters Acquity HPLC coupled to a Waters SQ mass spectrometer using an Acquity HPLC BEH C18 column (1.7 μm, 2.1×30 mm) with a linear gradient of 5-95% acetonitrile/water (with 0.1% formic acid in each mobile phase) within 1.4 minute and held at 95% for 0.3 minute.

Method I—Preparative high pressure liquid chromatography was carried out using apparatus made by Agilent. The apparatus is constructed such that the chromatography is monitored by a multi-wavelength UV detector (G1365B manufactured by Agilent) and an MM-ES+APCI mass spectrometer (G-1956A, manufactured by Agilent) connected in series, and if the appropriate criteria are met the sample is collected by an automated fraction collector (G1364B manufactured by Agilent). Collection can be triggered by any combination of UV or mass spectrometry or can be based on time. Typical conditions for the separation process are as follows: The gradient is run over a 10 minute period (gradient at start: 10% methanol and 90% water, gradient at finish: 100% methanol and 0% water; as buffer: either 0.1% trifluoroacetic acid is added to the water (low pH buffer), or ammonium bicarbonate (10 mmol/l) and 35% ammonium hydroxide (1.6 ml/l) is added to the water (high pH buffer). It will be appreciated by those skilled in the art that it may be necessary or desirable to modify the conditions for each specific compound, for example by changing the solvent composition at the start or at the end, modifying the solvents or buffers, changing the run time, changing the flow rate and/or the chromatography column.

Flash Chromatography

Flash chromatography refers to silica gel chromatography and carried out using an SP4 or an Isolara 4 MPLC system (manufactured by Biotage); pre-packed silica gel cartridges (supplied by Biotage); or using conventional glass column chromatography.

Analytical Methods $^1H$ Nuclear magnetic resonance (NMR) spectroscopy was carried out using an ECX400 spectrometer (manufactured by JEOL) or a Bruker instrument operating at 400 or 500 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad. Where thin layer chromatography (TLC) has been used it refers to silica gel TLC using silica gel MK6F 60 Å plates, $R_f$ is the distance traveled by the compound divided by the distance traveled by the solvent on a TLC plate. Flash chromatography refers to silica gel chromatography and is carried out using an SP4 or an Isolara 4 MPLC system (manufactured by Biotage); pre-packed silica gel cartridges (supplied by Biotage); or using conventional glass column chromatography.

Compound Preparation

Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques. Where reactions are carried out using microwave irradiation, the microwave used is an Initiator 60 supplied by Biotage. The actual power supplied varies during the course of the reaction in order to maintain a constant temperature.

Compounds made in the following examples are summarized in Table 1 below, which shows affinity values for LRRK2 (Ki, micromolar) for representative compounds together with LC retention time (minutes) and Mass Spec m/z values (molecular weight).

TABLE 1

| | Name | Structure | Ki (μM) | LC-MS Method | Retn Time | m/z |
|---|---|---|---|---|---|---|
| 1 | (R)-1-(3-phenylpiperidin-1-yl)-3-(4-(tetrahydro-2H-pyran-4-ylamino)-1H-pyrazolo[4,3-c]pyridin-3-yl)propan-1-one | 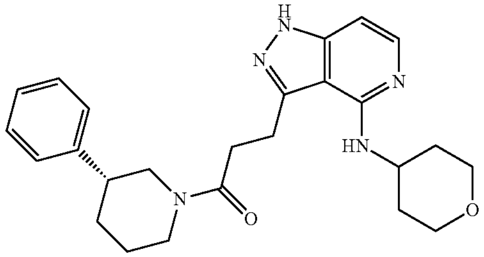 [SMILES: O=C(CCc1n[nH]c2ccnc(NC3CCOCC3)c12)N1CCC[C@H](c2ccccc2)C1] | | I | | 434 |
| 2 | (S)-1-(3-methylpiperidin-1-yl)-3-(4-(tetrahydro-2H-pyran-4-ylamino)-1H-pyrazolo[4,3-c]pyridin-3-yl)propan-1-one | 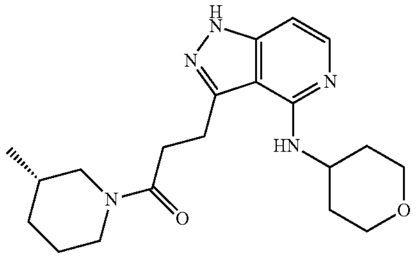 [SMILES: C[C@H]1CCCN(C(=O)CCc2n[nH]c3ccnc(NC4CCOCC4)c23)C1] | 0.034 | I | 1.39 | 372 |
| 3 | 1-(3,4-dimethylpiperazin-1-yl)-3-(4-(tetrahydro-2H-pyran-4-ylamino)-1H-pyrazolo[4,3-c]pyridin-3-yl)propan-1-one | 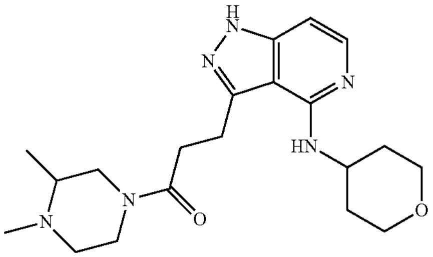 [SMILES: CC1CN(C(=O)CCc2n[nH]c3ccnc(NC4CCOCC4)c23)CCN1C] | | I | 1.07 | 387 |
| 4 | (S)-1-(3-methylpyrrolidin-1-yl)-3-(4-(tetrahydro-2H-pyran-4-ylamino)-1H-pyrazolo[4,3-c]pyridin-3-yl)propan-1-one | 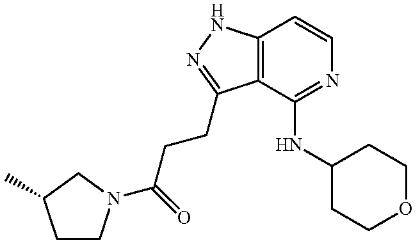 [SMILES: C[C@H]1CCN(C(=O)CCc2n[nH]c3ccnc(NC4CCOCC4)c23)C1] | | I | 1.27 | 358 |
| 5 | (E)-methyl 3-(4-(tetrahydro-2H-pyran-4-ylamino)-1H-pyrazolo[4,3-c]pyridin-3-yl)acrylate | 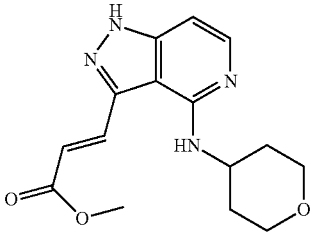 [SMILES: COC(=O)/C=C/c1n[nH]c2ccnc(NC3CCOCC3)c12] | | I | | 303 |
| 6 | (R)-3-(4-(cyclohexyloxy)-1H-pyrazolo[4,3-c]pyridin-3-yl)-1-(3-phenylpiperidin-1-yl)propan-1-one | 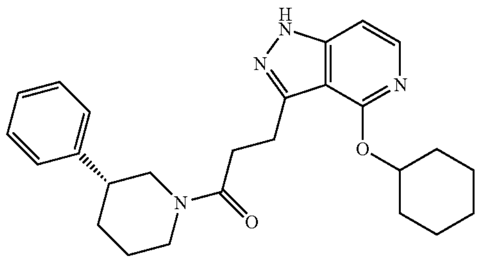 [SMILES: O=C(CCc1n[nH]c2ccnc(OC3CCCCC3)c12)N1CCC[C@H](c2ccccc2)C1] | 0.014 | I | | 433 |

TABLE 1-continued

| | Name | Structure | Ki (μM) | LC-MS Method | LC-MS Retn Time | LC-MS m/z |
|---|---|---|---|---|---|---|
| 7 | 3-(4-(cyclohexylamino)-1H-pyrazolo[4,3-c]pyridin-3-yl)-1-(4-methylpiperazin-1-yl)propan-1-one | 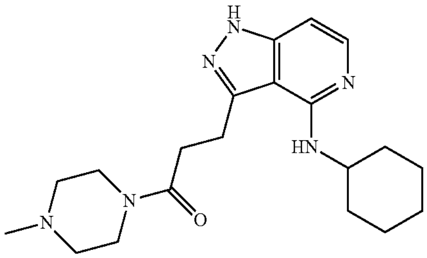 [SMILES: CN1CCN(C(=O)CCc2n[nH]c3ccnc(NC4CCCCC4)c23)CC1] | | I | | 447 |
| 8 | 3-(4-(cyclohexylamino)-1H-pyrazolo[4,3-c]pyridin-3-yl)-1-(4-cyclopropylpiperazin-1-yl)propan-1-one | 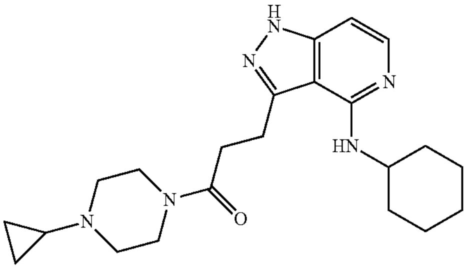 [SMILES: O=C(CCc1n[nH]c2ccnc(NC3CCCCC3)c12)N1CCN(C2CC2)CC1] | 0.017 | I | | 473 |
| 9 | 3-(2-morpholinopyridin-4-yl)-N-(tetrahydro-2H-pyran-4-yl)-1H-pyrazolo[4,3-c]pyridin-4-amine | 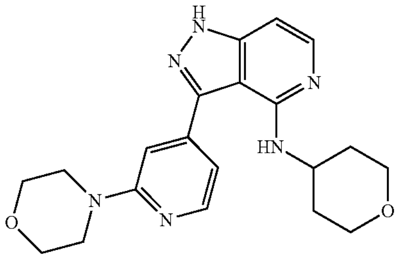 [SMILES: c1cc(-c2n[nH]c3ccnc(NC4CCOCC4)c23)cc(N2CCOCC2)n1] | 0.027 | I | | 381 |
| 10 | 4-(4-(4-(tetrahydro-2H-pyran-4-yloxy)-1H-pyrazolo[4,3-c]pyridin-3-yl)pyridin-2-yl) morpholine | 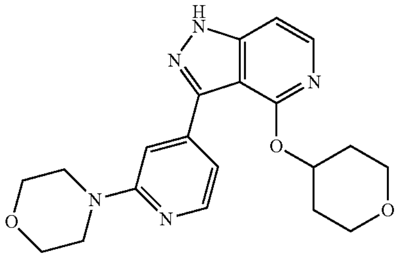 | | I | | 382 |
| 11 | 3-(3-morpholinophenyl)-N-(tetrahydro-2H-pyran-4-yl)-1H-pyrazolo[4,3-c] pyridin-4-amine | 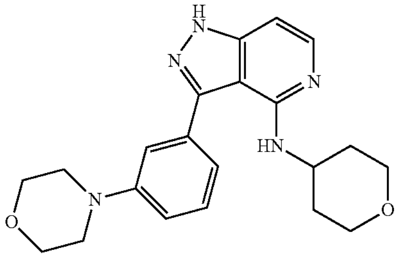 [SMILES: c1cc(-c2n[nH]c3ccnc(NC4CCOCC4)c23)cc(N2CCOCC2)c1] | | I | | 380 |

TABLE 1-continued

| | Name | Structure | Ki (µM) | LC-MS Method | LC-MS Retn Time | LC-MS m/z |
|---|---|---|---|---|---|---|
| 12 | 4-(3-(4-(tetrahydro-2H-pyran-4-yloxy)-1H-pyrazolo[4,3-c]pyridin-3-yl)phenyl)morpholine | 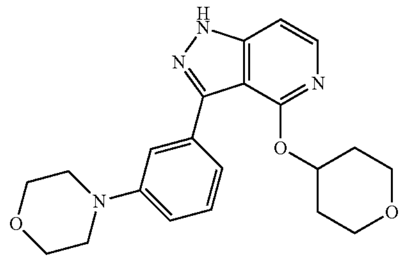 | | I | | 381 |
| 13 | 3-(2-(4-methylpiperazin-1-yl)pyridin-4-yl)-N-(tetrahydro-2H-pyran-4-yl)-1H-pyrazolo[4,3-c] pyridin-4-amine | 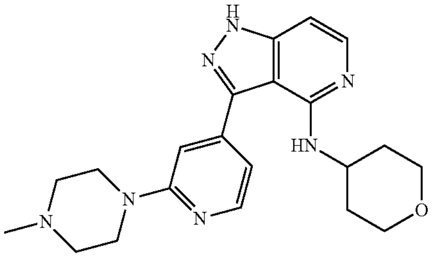 [SMILES: CN1CCN(c2cc(-c3n[nH]c4ccnc(NC5CCOCC5)c34)ccn2)CC1] | | I | | 394 |
| 14 | 3-(2-(4-methylpiperazin-1-yl)pyridin-4-yl)-4-(tetrahydro-2H-pyran-4-yloxy)-1H-pyrazolo [4,3-c]pyridine | 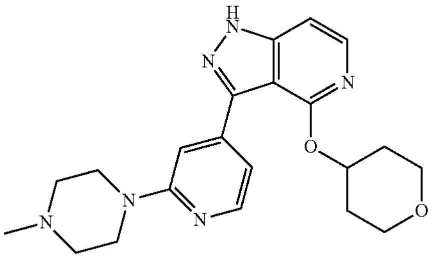 [SMILES: CN1CCN(c2cc(-c3n[nH]c4ccnc(OC5CCOCC5)c34)ccn2)CC1] | 0.006 | I | | 395 |
| 15 | ((R)-3-phenylpiperidin-1-yl)(2-(4-(tetrahydro-2H-pyran-4-yloxy)-1H-pyrazolo[4,3-c]pyridin-3-yl)cyclopropyl) methanone | 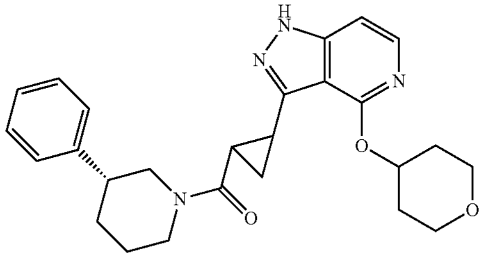 [SMILES: O=C(C1CC1c1n[nH]c2ccnc(OC3CCOCC3)c12)N1CCC[C@H](c2ccccc2)C1] | | I | | 447 |
| 16 | ((S)-3-methylpyrrolidin-1-yl)(2-(4-(tetrahydro-2H-pyran-4-yloxy)-1H-pyrazolo[4,3-c]pyridin-3-yl)cyclopropyl) methanone | 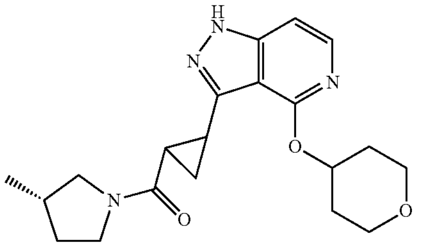 [SMILES: C[C@H]1CCN(C(=O)C2CC2c2n[nH]c3ccnc(OC4CCOCC4)c23)C1] | | I | 1.36 | 371 |

TABLE 1-continued

| | Name | Structure | Ki (μM) | LC-MS Method | LC-MS Retn Time | LC-MS m/z |
|---|---|---|---|---|---|---|
| 17 | morpholino(2-(4-(tetrahydro-2H-pyran-4-yloxy)-1H-pyrazolo[4,3-c]pyridin-3-yl)cyclopropyl) methanone | 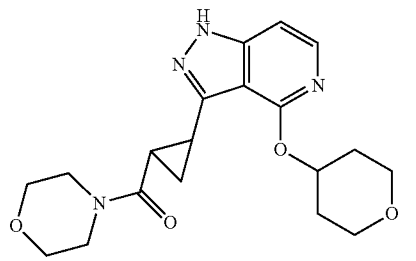 [SMILES: O=C(C1CC1c1n[nH]c2ccnc(OC3CCOCC3)c12)N1CCOCC1] | | I | 1.17 | 373 |
| 18 | (4-methylpiperazin-1-yl)(2-(4-(tetrahydro-2H-pyran-4-yloxy)-1H-pyrazolo[4,3-c]pyridin-3-yl)cyclopropyl) methanone | 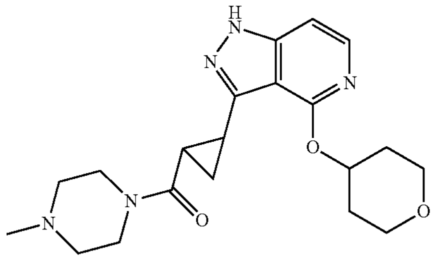 [SMILES: CN1CCN(C(=O)C2CC2c2n[nH]c3ccnc(OC4CCOCC4)c23)CC1] | | I | 1.13 | 386 |
| 19 | 3-cyclopropyl-N-(tetrahydro-2H-pyran-4-yl)-1H-pyrazolo[4,3-c]pyridin-4-amine | 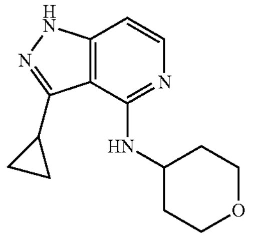 [SMILES: c1cc2[nH]nc(C3CC3)c2c(NC2CCOCC2)n1] | | I | | 259 |
| 20 | 3-cyclohexyl-N-(tetrahydro-2H-pyran-4-yl)-1H-pyrazolo[4,3-c]pyridin-4-amine | 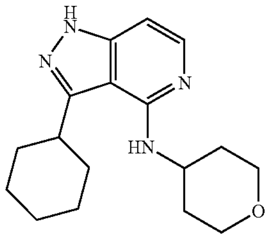 [SMILES: c1cc2[nH]nc(C3CCCCC3)c2c(NC2CCOCC2)n1] | | I | | 301 |
| 21 | 3-isopropyl-N-(tetrahydro-2H-pyran-4-yl)-1H-pyrazolo[4,3-c]pyridin-4-amine | 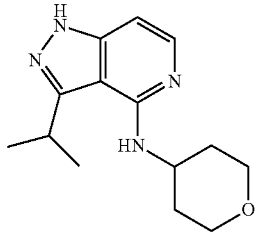 [SMILES: CC(C)c1n[nH]c2ccnc(NC3CCOCC3)c12] | | I | | 261 |
| 22 | N,3-dicyclohexyl-1H-pyrazolo[4,3-c]pyridin-4-amine | 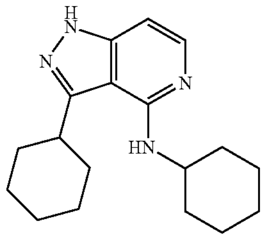 [SMILES: c1cc2[nH]nc(C3CCCCC3)c2c(NC2CCCCC2)n1] | | I | | 299 |

TABLE 1-continued

| | Name | Structure | Ki (μM) | LC-MS Method | LC-MS Retn Time | LC-MS m/z |
|---|---|---|---|---|---|---|
| 23 | N-cyclohexyl-3-isopropyl-1H-pyrazolo[4,3-c]pyridin-4-amine | 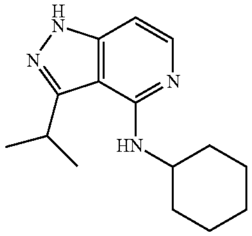 [SMILES: CC(C)c1n[nH]c2ccnc(NC3CCCCC3)c12] | | I | | 259 |
| 24 | 3-cyclopropyl-4-isopropoxy-1H-pyrazolo[4,3-c]pyridine | 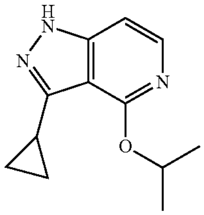 [SMILES: CC(C)Oc1nccc2[nH]nc(C3CC3)c12] | | I | | 218 |
| 25 | 4-isopropoxy-3-isopropyl-1H-pyrazolo[4,3-c]pyridine | 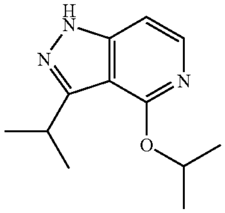 [SMILES: CC(C)Oc1nccc2[nH]nc(C(C)C)c12] | | I | | 220 |
| 26 | 4-(cyclohexyloxy)-3-cyclopropyl-1H-pyrazolo[4,3-c]pyridine | 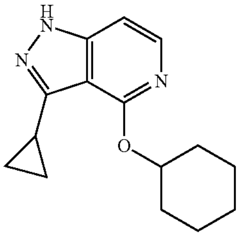 [SMILES: c1cc2[nH]nc(C3CC3)c2c(OC2CCCCC2)n1] | 0.024 | I | | 258 |
| 27 | 4-(cyclohexyloxy)-3-isopropyl-1H-pyrazolo[4,3-c]pyridine | 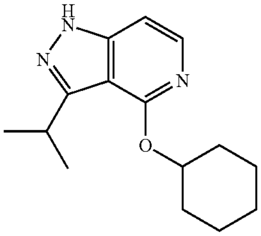 [SMILES: CC(C)c1n[nH]c2ccnc(OC3CCCCC3)c12] | | I | | 260 |
| 28 | 3-cyclopropyl-4-(tetrahydro-2H-pyran-4-yloxy)-1H-pyrazolo[4,3-c]pyridine | 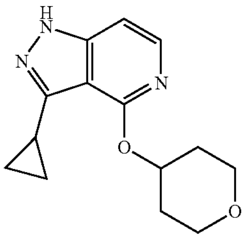 [SMILES: c1cc2[nH]nc(C3CC3)c2c(OC2CCOCC2)n1] | 0.035 | I | | 260 |

TABLE 1-continued

| | Name | Structure | Ki (μM) | LC-MS Method | LC-MS Retn Time | LC-MS m/z |
|---|---|---|---|---|---|---|
| 29 | (S)-4-sec-butoxy-3-cyclopropyl-1H-pyrazolo[4,3-c]pyridine | 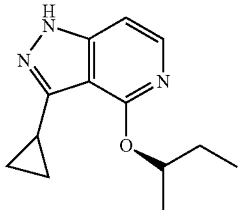 | 0.078 | I | | 232 |
| 30 | (S)-4-sec-butoxy-3-isopropyl-1H-pyrazolo[4,3-c]pyridine | 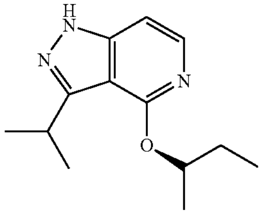 | | I | | 234 |
| 31 | 3-methyl-4-(tetrahydrofuran-3-yloxy)-1H-pyrazolo[4,3-c]pyridine | 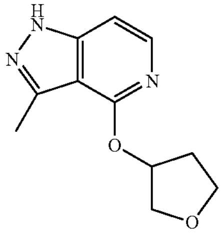 [SMILES: Cc1n[nH]c2ccnc(OC3CCOC3)c12] | 0.158 | I | | 220 |
| 32 | 3-cyclobutyl-N-cyclohexyl-1H-pyrazolo[4,3-c]pyridin-4-amine | 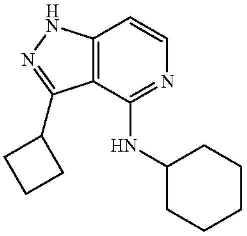 [SMILES: c1cc2[nH]nc(C3CCC3)c2c(NC2CCCCC2)n1] | | I | | 271 |
| 33 | 4-(cyclohexyloxy)-3-(pyrimidin-5-yl)-1H-pyrazolo[4,3-c]pyridine | 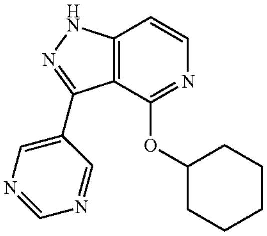 [SMILES: c1ncc(-c2n[nH]c3ccnc(OC4CCCCC4)c23)cn1] | | I | | 296 |
| 34 | 4-(cyclohexyloxy)-3-(1-methyl-1H-pyrazol-5-yl)-1H-pyrazolo[4,3-c]pyridine | 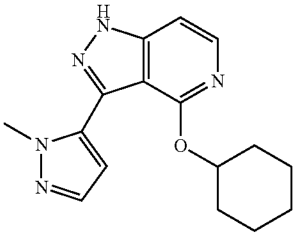 [SMILES: Cn1nccc1-c1n[nH]c2ccnc(OC3CCCCC3)c12] | | I | | 298 |

TABLE 1-continued

| | Name | Structure | Ki (μM) | LC-MS Method | LC-MS Retn Time | LC-MS m/z |
|---|---|---|---|---|---|---|
| 35 | 3-(furan-3-yl)-4-(tetrahydro-2H-pyran-4-yloxy)-1H-pyrazolo[4,3-c]pyridine | 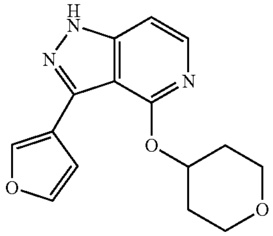 [SMILES: c1cc2[nH]nc(-c3ccoc3)c2c(OC2CCOCC2)n1] | | I | | 286 |
| 36 | 3-(1-isopropyl-1H-pyrazol-5-yl)-4-(tetrahydro-2H-pyran-4-yloxy)-1H-pyrazolo[4,3-c]pyridine | 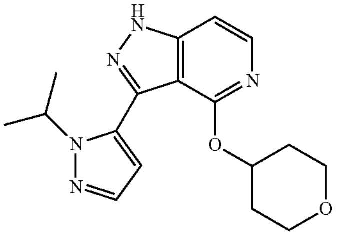 [SMILES: CC(C)n1nccc1-c1n[nH]c2ccnc(OC3CCOCC3)c12] | | I | | 328 |
| 37 | 3-(furan-2-yl)-4-(tetrahydro-2H-pyran-4-yloxy)-1H-pyrazolo[4,3-c]pyridine | 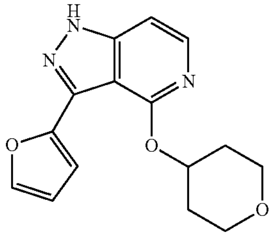 [SMILES: c1coc(-c2n[nH]c3ccnc(OC4CCOCC4)c23)c1] | 0.132 | I | | 286 |
| 38 | 3-(1,3-dimethyl-1H-pyrazol-4-yl)-4-(tetrahydro-2H-pyran-4-yloxy)-1H-pyrazolo[4,3-c]pyridine | 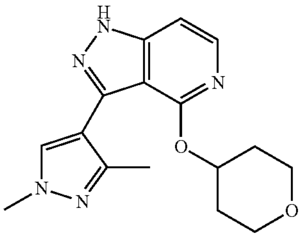 [SMILES: Cc1nn(C)cc1-c1n[nH]c2ccnc(OC3CCOCC3)c12] | | I | | 314 |
| 39 | 3-(1-cyclopentyl-1H-pyrazol-4-yl)-4-(tetrahydro-2H-pyran-4-yloxy)-1H-pyrazolo[4,3-c]pyridine | 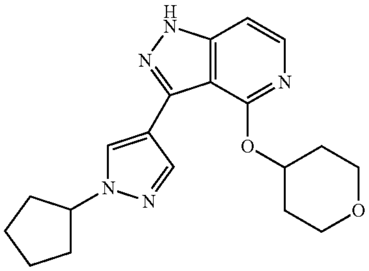 [SMILES: c1cc2[nH]nc(-c3cnn(C4CCCC4)c3)c2c(OC2CCOCC2)n1] | 0.006 | I | | 354 |
| 40 | 3-(1-isobutyl-1H-pyrazol-4-yl)-4-(tetrahydro-2H-pyran-4-yloxy)-1H-pyrazolo[4,3-c]pyridine | 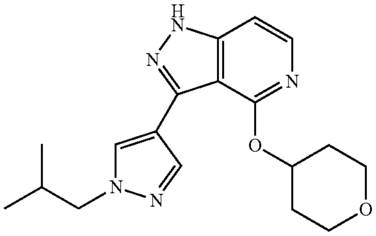 [SMILES: CC(C)Cn1cc(-c2n[nH]c3ccnc(OC4CCOCC4)c23)cn1] | | I | | 342 |

TABLE 1-continued

| | Name | Structure | Ki (μM) | LC-MS Method | LC-MS Retn Time | LC-MS m/z |
|---|---|---|---|---|---|---|
| 41 | 3-(1-(cyclobutylmethyl)-1H-pyrazol-4-yl)-4-(cyclohexyloxy)-1H-pyrazolo[4,3-c]pyridine | 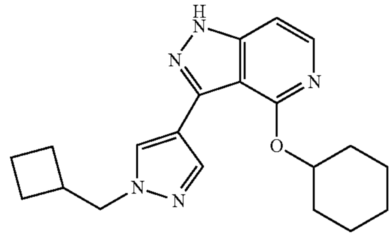 [SMILES: c1cc2[nH]nc(-c3cnn(CC4CCC4)c3)c2c(OC2CCCCC2)n1] | 0.055 | I | | 352 |
| 42 | 3-(1-(2-methoxyethyl)-1H-pyrazol-4-yl)-N-(tetrahydro-2H-pyran-4-yl)-1H-pyrazolo[4,3-c] pyridin-4-amine | 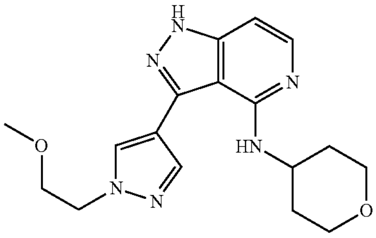 [SMILES: COCCn1cc(-c2n[nH]c3ccnc(NC4CCOCC4)c23)cn1] | | I | | 343 |
| 43 | 3-(1-ethyl-1H-pyrazol-4-yl)-N-(tetrahydro-2H-pyran-4-yl)-1H-pyrazolo[4,3-c]pyridin-4-amine | 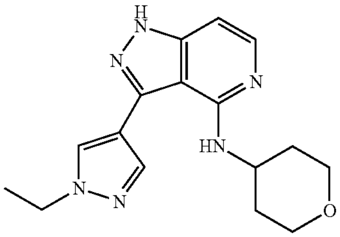 [SMILES: CCn1cc(-c2n[nH]c3ccnc(NC4CCOCC4)c23)cn1] | | I | 1.12 | 313 |
| 44 | 3-(1-propyl-1H-pyrazol-4-yl)-N-(tetrahydro-2H-pyran-4-yl)-1H-pyrazolo[4,3-c]pyridin-4-amine | 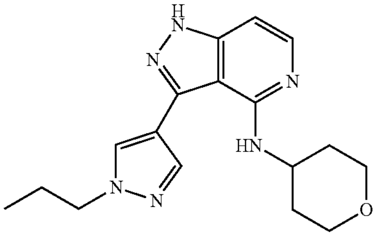 [SMILES: CCCn1cc(-c2n[nH]c3ccnc(NC4CCOCC4)c23)cn1] | | I | 1.23 | 327 |
| 45 | 3-(1-(cyclopentylmethyl)-1H-pyrazol-4-yl)-N-(tetrahydro-2H-pyran-4-yl)-1H-pyrazolo[4,3-c]pyridin-4-amine | 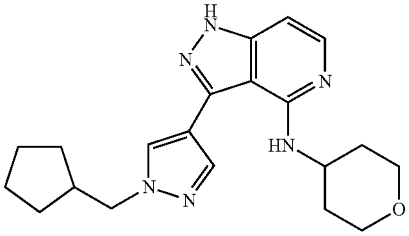 [SMILES: c1cc2[nH]nc(-c3cnn(CC4CCCC4)c3)c2c(NC2CCOCC2)n1] | | I | 1.51 | 367 |
| 46 | 3-(1-(cyclobutylmethyl)-1H-pyrazol-4-yl)-N-(tetrahydro-2H-pyran-4-yl)-1H-pyrazolo[4,3-c]pyridin-4-amine | 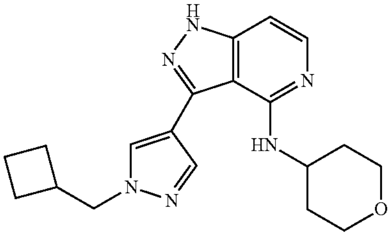 | | I | 1.69 | 353 |

TABLE 1-continued

| | Name | Structure | Ki (μM) | LC-MS Method | LC-MS Retn Time | LC-MS m/z |
|---|---|---|---|---|---|---|
| 47 | 3-(1-cyclopentyl-1H-pyrazol-4-yl)-N-(tetrahydro-2H-pyran-4-yl)-1H-pyrazolo[4,3-c]pyridin-4-amine | 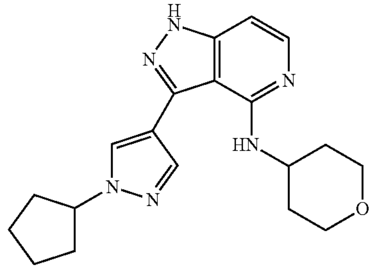 [SMILES: c1cc2[nH]nc(-c3cnn(C4CCCC4)c3)c2c(NC2CCOCC2)n1] | | I | | 353 |
| 48 | 3-(1-isobutyl-1H-pyrazol-4-yl)-N-(tetrahydro-2H-pyran-4-yl)-1H-pyrazolo[4,3-c]pyridin-4-amine | 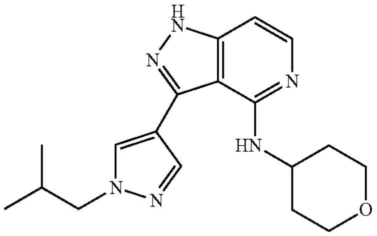 [SMILES: CC(C)Cn1cc(-c2n[nH]c3ccnc(NC4CCOCC4)c23)cn1] | | I | | 341 |
| 49 | 3-(1-(1-methylpiperidin-4-yl)-1H-pyrazol-4-yl)-N-(tetrahydro-2H-pyran-4-yl)-1H-pyrazolo[4,3-c]pyridin-4-amine | 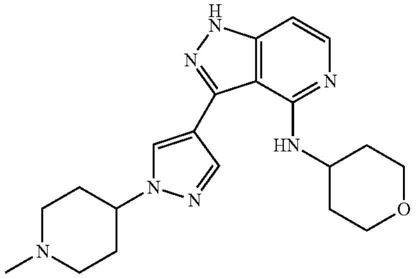 [SMILES: CN1CCC(n2cc(-c3n[nH]c4ccnc(NC5CCOCC5)c34)cn2)CC1] | | I | | 382 |
| 50 | N-(2-(4-(cyclohexyloxy)-1H-pyrazolo[4,3-c]pyridin-3-yl)ethyl)cyclohexane-carboxamide | 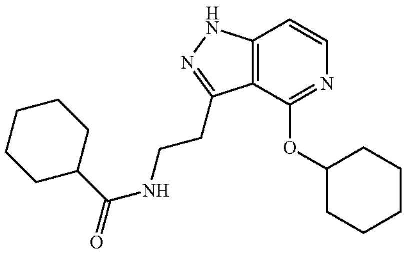 [SMILES: O=C(NCCc1n[nH]c2ccnc(OC3CCCCC3)c12)C1CCCCC1] | | I | | 371 |
| 51 | 4-(cyclohexyloxy)-3-ethyl-1H-pyrazolo[4,3-c]pyridine | 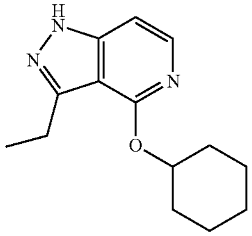 [SMILES: CCc1n[nH]c2ccnc(OC3CCCCC3)c12] | | I | | 246 |

TABLE 1-continued

| | Name | Structure | Ki (μM) | LC-MS Method | LC-MS Retn Time | LC-MS m/z |
|---|---|---|---|---|---|---|
| 52 | (E)-4-(cyclohexyloxy)-3-(2-(1-methyl-1H-pyrazol-4-yl)vinyl)-1H-pyrazolo[4,3-c]pyridine | 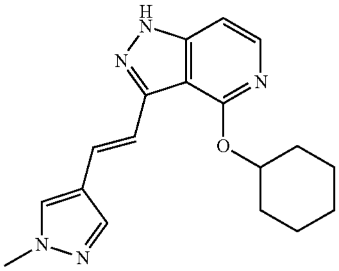 [SMILES: Cn1cc(/C=C/c2n[nH]c3ccnc(OC4CCCCC4)c23)cn1] | 0.0003 | I | | 324 |
| 53 | 4-(4-isopropoxy-1H-pyrazolo[4,3-c]pyridin-3-yl)-1-isopropyl-N-methyl-1H-pyrrole-2-carboxamide | 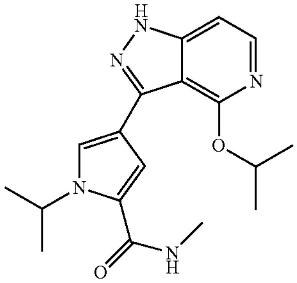 [SMILES: CNC(=O)c1cc(-c2n[nH]c3ccnc(OC(C)C)c23)cn1C(C)C] | | | | |
| 54 | 4-(4-isopropoxy-1H-pyrazolo[4,3-c]pyridin-3-yl)-1-isopropyl-N,N-dimethyl-1H-pyrrole-2-carboxamide | 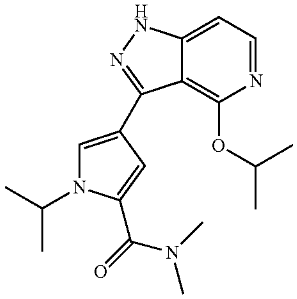 [SMILES: CC(C)Oc1nccc2[nH]nc(-c3cc(C(=O)N(C)C)n(C(C)C)c3)c12] | 0.018 | D | 1.66 | 356 |
| 55 | azetidin-1-yl(4-(4-isopropoxy-1H-pyrazolo[4,3-c]pyridin-3-yl)-1-isopropyl-1H-pyrrol-2-yl)methanone | 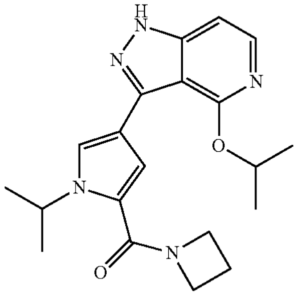 [SMILES: CC(C)Oc1nccc2[nH]nc(-c3cc(C(=O)N4CCC4)n(C(C)C)c3)c12] | | F | 5.30 | 368 |
| 56 | (4-(4-isopropoxy-1H-pyrazolo[4,3-c]pyridin-3-yl)-1-isopropyl-1H-pyrrol-2-yl)(piperidin-1-yl)methanone | 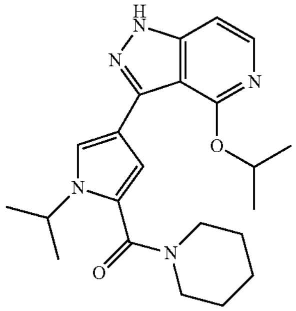 [SMILES: CC(C)Oc1nccc2[nH]nc(-c3cc(C(=O)N4CCCCC4)n(C(C)C)c3)c12] | 0.019 | D | 5.49 | 396 |

TABLE 1-continued

| | Name | Structure | Ki (μM) | LC-MS Method | LC-MS Retn Time | LC-MS m/z |
|---|---|---|---|---|---|---|
| 57 | (4-(4-isopropoxy-1H-pyrazolo[4,3-c]pyridin-3-yl)-1-isopropyl-1H-pyrrol-2-yl)(morpholino) methanone | 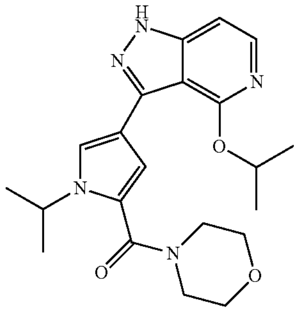 [SMILES: CC(C)Oc1nccc2[nH]nc(-c3cc(C(=O)N4CCOCC4)n(C(C)C)c3)c12] | 0.019 | D | 1.66 | 398 |
| 58 | N-cyclopropyl-4-(4-isopropoxy-1H-pyrazolo[4,3-c]pyridin-3-yl)-1-isopropyl-1H-pyrrole-2-carboxamide | 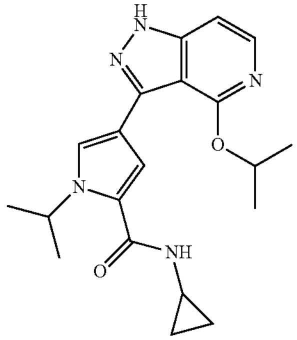 [SMILES: CC(C)Oc1nccc2[nH]nc(-c3cc(C(=O)NC4CC4)n(C(C)C)c3)c12] | | D | 5.09 | 368 |
| 59 | 4-(4-isopropoxy-1H-pyrazolo[4,3-c]pyridin-3-yl)-1-isopropyl-N-(oxetan-3-yl)-1H-pyrrole-2-carboxamide | 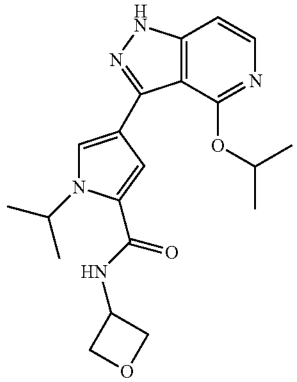 [SMILES: CC(C)Oc1nccc2[nH]nc(-c3cc(C(=O)NC4COC4)n(C(C)C)c3)c12] | 0.0024 | D | 3.68 | 384 |
| 60 | 1-isopropyl-4-(4-methoxy-1H-pyrazolo[4,3-c]pyridin-3-yl)-N-methyl-1H-pyrrole-2-carboxamide | 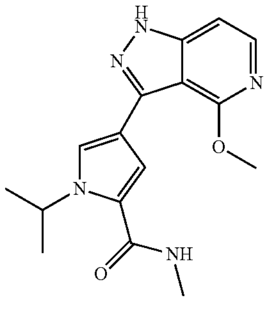 [SMILES: CNC(=O)c1cc(-c2n[nH]c3ccnc(OC)c23)cn1C(C)C] | | E | 4.31 | 314 |

TABLE 1-continued

| | Name | Structure | Ki (μM) | LC-MS Method | LC-MS Retn Time | LC-MS m/z |
|---|---|---|---|---|---|---|
| 61 | 1-isopropyl-4-(4-methoxy-1H-pyrazolo[4,3-c]pyridin-3-yl)-N,N-dimethyl-1H-pyrrole-2-carboxamide | 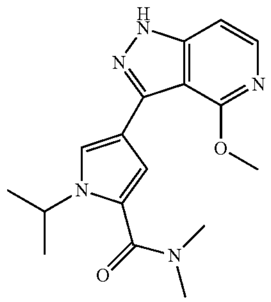 [SMILES: COc1nccc2[nH]nc(-c3cc(C(=O)N(C)C)n(C(C)C)c3)c12] | 0.077 | E | 4.39 | 328 |
| 62 | (1-isopropyl-4-(4-methoxy-1H-pyrazolo[4,3-c]pyridin-3-yl)-1H-pyrrol-2-yl)(morpholino) methanone | 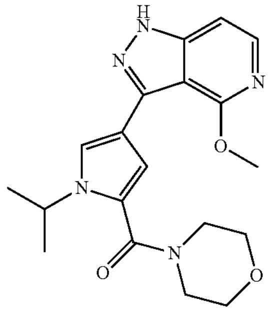 [SMILES: COc1nccc2[nH]nc(-c3cc(C(=O)N4CCOCC4)n(C(C)C)c3)c12] | | E | 4.41 | 370 |
| 63 | N-cyclopropyl-1-isopropyl-4-(4-methoxy-1H-pyrazolo[4,3-c]pyridin-3-yl)-1H-pyrrole-2-carboxamide | 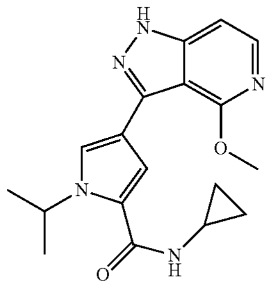 [SMILES: COc1nccc2[nH]nc(-c3cc(C(=O)NC4CC4)n(C(C)C)c3)c12] | | E | 4.67 | 340 |
| 64 | 1-isopropyl-4-(4-methoxy-1H-pyrazolo[4,3-c]pyridin-3-yl)-N-(oxetan-3-yl)-1H-pyrrole-2-carboxamide | 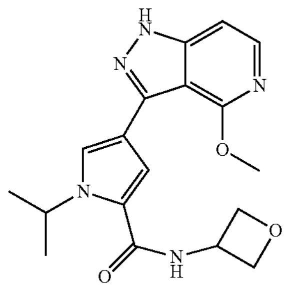 [SMILES: COc1nccc2[nH]nc(-c3cc(C(=O)NC4COC4)n(C(C)C)c3)c12] | 0.014 | D | 3.08 | 356 |
| 65 | (1-isopropyl-4-(4-(tetrahydro-2H-pyran-4-yloxy)-1H-pyrazolo[4,3-c]pyridin-3-yl)-1H-pyrrol-2-yl)(morpholino) methanone | 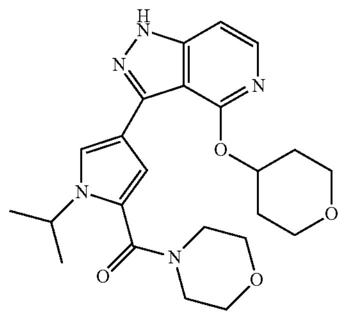 [SMILES: CC(C)n1cc(-c2n[nH]c3ccnc(OC4CCOCC4)c23)cc1C(=O)N1CCOCC1] | 0.039 | D | 4.40 | 440.1 |

TABLE 1-continued

| | Name | Structure | Ki (μM) | LC-MS Method | LC-MS Retn Time | LC-MS m/z |
|---|---|---|---|---|---|---|
| 66 | 1-isopropyl-N,N-dimethyl-4-(4-(tetrahydro-2H-pyran-4-yloxy)-1H-pyrazolo[4,3-c]pyridin-3-yl)-1H-pyrrole-2-carboxamide | 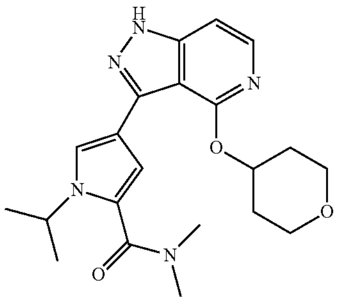 [SMILES: CC(C)n1cc(-c2n[nH]c3ccnc(OC4CCOCC4)c23)cc1C(=O)N(C)C] | 0.045 | D | 4.38 | 398.1 |
| 67 | N-cyclobutyl-1-isopropyl-4-(4-(tetrahydro-2H-pyran-4-yloxy)-1H-pyrazolo[4,3-c]pyridin-3-yl)-1H-pyrrole-2-carboxamide | 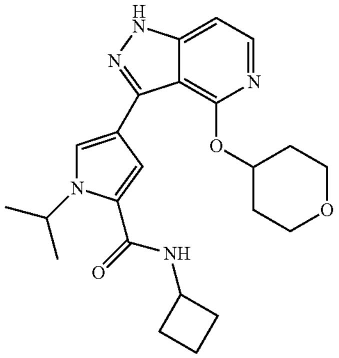 [SMILES: CC(C)n1cc(-c2n[nH]c3ccnc(OC4CCOCC4)c23)cc1C(=O)NC1CCC1] | | D | 5.23 | 424.2 |
| 68 | (1-isopropyl-4-(4-(tetrahydro-2H-pyran-4-yloxy)-1H-pyrazolo[4,3-c]pyridin-3-yl)-1H-pyrrol-2-yl)(pyrrolidin-1-yl) methanone | 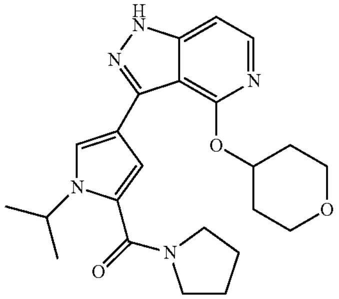 [SMILES: CC(C)n1cc(-c2n[nH]c3ccnc(OC4CCOCC4)c23)cc1C(=O)N1CCCC1] | | D | 4.75 | 424.2 |
| 69 | N-cyclopropyl-1-isopropyl-4-(4-(tetrahydro-2H-pyran-4-yloxy)-1H-pyrazolo[4,3-c]pyridin-3-yl)-1H-pyrrole-2-carboxamide | 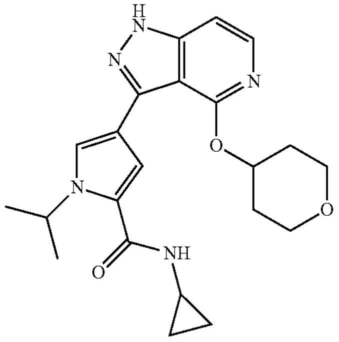 [SMILES: CC(C)n1cc(-c2n[nH]c3ccnc(OC4CCOCC4)c23)cc1C(=O)NC1CC1] | | D | 4.69 | 410.1 |

TABLE 1-continued

| | Name | Structure | Ki (μM) | LC-MS Method | Retn Time | m/z |
|---|---|---|---|---|---|---|
| 70 | 1-isopropyl-N-(oxetan-3-yl)-4-(4-(tetrahydro-2H-pyran-4-yloxy)-1H-pyrazolo[4,3-c]pyridin-3-yl)-1H-pyrrole-2-carboxamide | 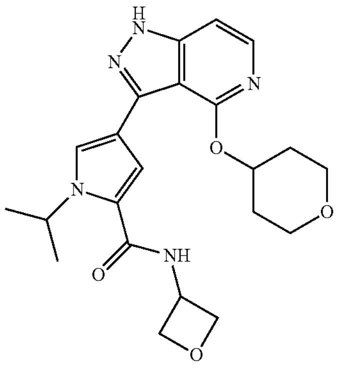 [SMILES: CC(C)n1cc(-c2n[nH]c3ccnc(OC4CCOCC4)c23)cc1C(=O)NC1COC1] | 0.003 | F | 4.45 | 426.3 |
| 71 | isopropyl 1-isopropyl-4-(4-methoxy-1H-pyrazolo[4,3-c]pyridin-3-yl)-1H-pyrrole-2-carboxylate | 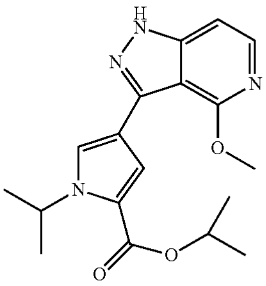 [SMILES: COc1nccc2[nH]nc(-c3cc(C(=O)OC(C)C)n(C(C)C)c3)c12] | | E | 6.14 | 343 |
| 72 | N,N-dimethyl-4-(4-(tetrahydro-2H-pyran-4-yloxy)-1H-pyrazolo[4,3-c]pyridin-3-yl) picolinamide | 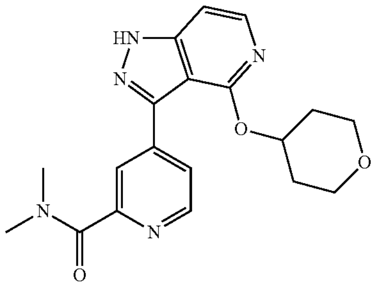 [SMILES: CN(C)C(=O)c1cc(-c2n[nH]c3ccnc(OC4CCOCC4)c23)ccn1] | | E | 3.62 | 368 |
| 73 | morpholino(4-(4-(tetrahydro-2H-pyran-4-yloxy)-1H-pyrazolo[4,3-c]pyridin-3-yl)pyridin-2-yl)methanone | 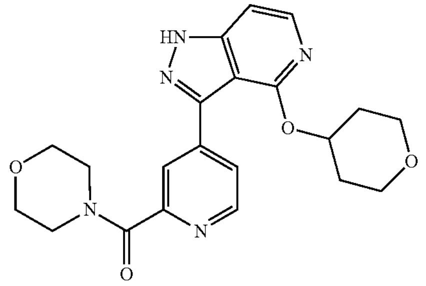 [SMILES: O=C(c1cc(-c2n[nH]c3ccnc(OC4CCOCC4)c23)ccn1)N1CCOCC1] | 0.221 | D | 3.77 | 410 |
| 74 | 4-(4-(4-(2,2,2-trifluoroethoxy)-1H-pyrazolo[4,3-c]pyridin-3-yl)pyridin-2-yl)morpholine | 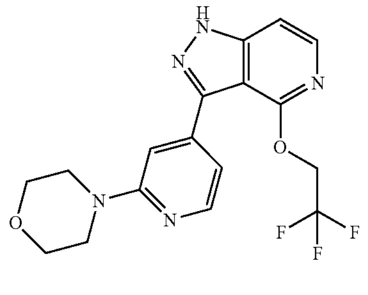 [SMILES: FC(F)(F)COc1nccc2[nH]nc(-c3ccnc(N4CCOCC4)c3)c12] | 0.031 | F | 5.28 | 380 |

TABLE 1-continued

| | | | | LC-MS | | |
|---|---|---|---|---|---|---|
| | Name | Structure | Ki (μM) | Method | Retn Time | m/z |
| 75 | 4-(4-(4-ethoxy-1H-pyrazolo[4,3-c]pyridin-3-yl)pyridin-2-yl)morpholine | 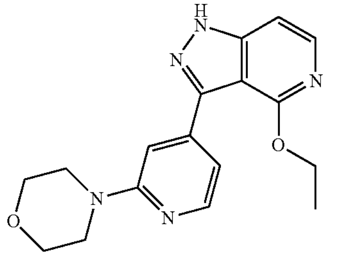 | | D | 5.78 | 340.7 |
| 76 | 3-(1-isopropyl-1H-pyrazol-4-yl)-4-(2,2,2-trifluoroethoxy)-1H-pyrazolo[4,3-c]pyridine | 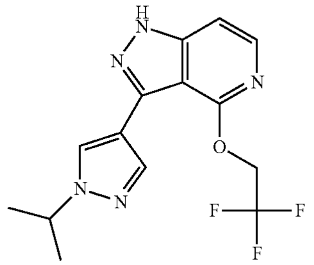 [SMILES: CC(C)n1cc(-c2n[nH]c3ccnc(OCC(F)(F)F)c23)cn1] | 0.026 | D | 5.78 | 326 |
| 77 | 3-(1-isopropyl-1H-pyrazol-4-yl)-4-(tetrahydro-2H-pyran-3-yloxy)-1H-pyrazolo[4,3-c]pyridine | 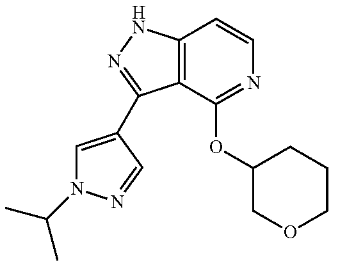 [SMILES: CC(C)n1cc(-c2n[nH]c3ccnc(OC4CCCOC4)c23)cn1] | | F | 5.46 | 300 |
| 78 | 3-(1-isopropyl-1H-pyrazol-4-yl)-4-(1,1,1-trifluoropropan-2-yloxy)-1H-pyrazolo[4,3-c] pyridine | 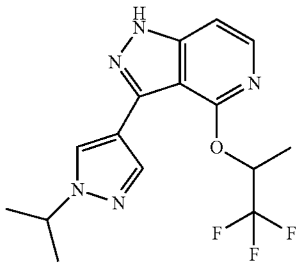 [SMILES: CC(C)n1cc(-c2n[nH]c3ccnc(OC(C)C(F)(F)F)c23)cn1] | 0.013 | F | 5.78 | 340.7 |
| 79 | 4-ethoxy-3-(1-isopropyl-1H-pyrazol-4-yl)-1H-pyrazolo[4,3-c]pyridine | 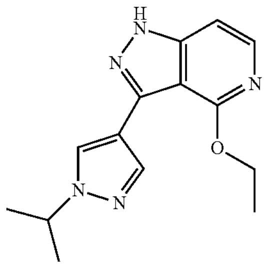 [SMILES: CCOc1nccc2[nH]nc(-c3cnn(C(C)C)c3)c12] | | D | 4.27 | 272.7 |

TABLE 1-continued

| | Name | Structure | Ki (μM) | LC-MS Method | Retn Time | m/z |
|---|---|---|---|---|---|---|
| 80 | 4-(4-(4-methoxy-1H-pyrazolo[4,3-c]pyridin-3-yl)pyridin-2-yl)-2,6-dimethylmorpholine | 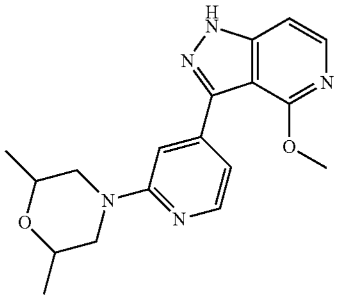 | | G | 3.38 | 340.1 |
| 81 | 3-(1-isopropyl-1H-pyrazol-4-yl)-4-(2-methylcyclopentyloxy)-1H-pyrazolo[4,3-c] pyridine | 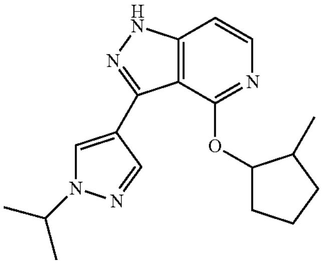 [SMILES: CC1CCCC1Oc1nccc2[nH]nc(-c3cnn(C(C)C)c3)c12] | | F | 6.1 | 326 |
| 82 | 3-(1-ethyl-1H-pyrazol-4-yl)-4-isopropoxy-1H-pyrazolo[4,3-c]pyridine | 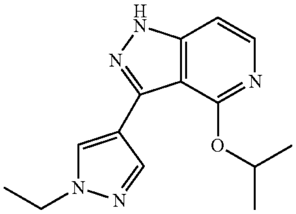 [SMILES: CCn1cc(-c2n[nH]c3ccnc(OC(C)C)c23)cn1] | | G | 4.312 | |
| 83 | 3-(1-sec-butyl-1H-pyrazol-4-yl)-4-isopropoxy-1H-pyrazolo[4,3-c]pyridine | 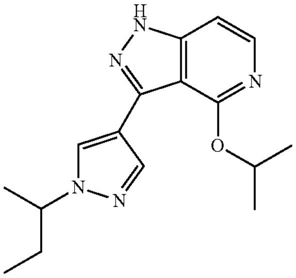 [SMILES: CCC(C)n1cc(-c2n[nH]c3ccnc(OC(C)C)c23)cn1] | | D | 5.14 | 300 |
| 84 | 4-(4-(4-(tetrahydro-2H-pyran-4-yloxy)-1H-pyrazolo[4,3-c]pyridin-3-yl)pyrimidin-2-yl) morpholine | 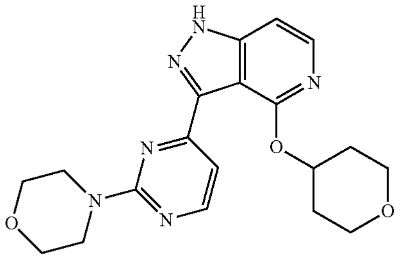 | 0.065 | G | 3.52 | 383.1 |

TABLE 1-continued

| | Name | Structure | Ki (μM) | LC-MS Method | LC-MS Retn Time | LC-MS m/z |
|---|---|---|---|---|---|---|
| 85 | 4-(6-(4-(tetrahydro-2H-pyran-4-yloxy)-1H-pyrazolo[4,3-c]pyridin-3-yl)pyridin-2-yl) morpholine | 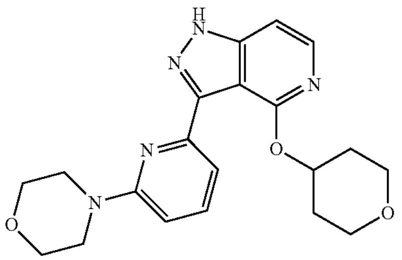 [SMILES: c1cc(-c2n[nH]c3ccnc(OC4CCOCC4)c23)nc(N2CCOCC2)c1] | | C | 1.78 | 382 |
| 86 | 4-methoxy-3-(1-(oxetan-3-yl)-1H-pyrazol-4-yl)-1H-pyrazolo[4,3-c]pyridine | 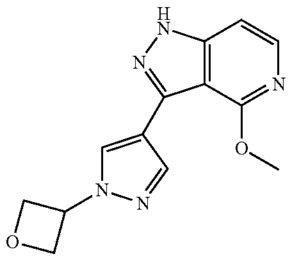 [SMILES: COc1nccc2[nH]nc(-c3cnn(C4COC4)c3)c12] | 0.031 | G | 2.85 | 272.1 |
| 87 | 3-(1-(cyclobutylmethyl)-1H-pyrazol-4-yl)-4-methoxy-1H-pyrazolo[4,3-c]pyridine | 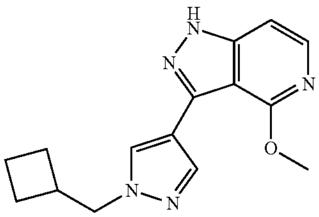 [SMILES: COc1nccc2[nH]nc(-c3cnn(CC4CCC4)c3)c12] | | G | 3.72 | 284.1 |
| 88 | 4-methoxy-3-(1-(2,2,2-trifluoroethyl)-1H-pyrazol-4-yl)-1H-pyrazolo[4,3-c]pyridine | 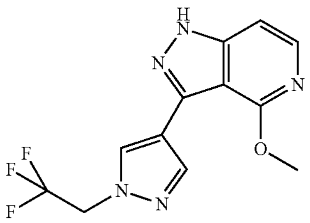 [SMILES: COc1nccc2[nH]nc(-c3cnn(CC(F)(F)F)c3)c12] | 0.025 | G | 3.40 | 298.0 |
| 89 | 4-methoxy-3-(1-((3-methyloxetan-3-yl)methyl)-1H-pyrazol-4-yl)-1H-pyrazolo[4,3-c] pyridine | 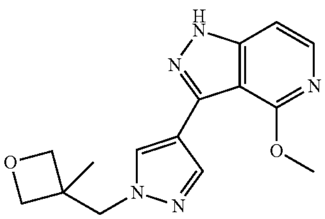 [SMILES: COc1nccc2[nH]nc(-c3cnn(CC4(C)COC4)c3)c12] | 0.108 | G | 2.54 | 300.0 |
| 90 | 3-(1-(cyclopropylmethyl)-1H-pyrazol-4-yl)-4-methoxy-1H-pyrazolo[4,3-c]pyridine | 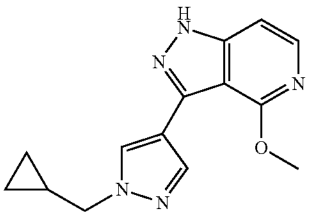 [SMILES: COc1nccc2[nH]nc(-c3cnn(CC4CC4)c3)c12] | | G | 3.42 | 270.0 |

TABLE 1-continued

| | Name | Structure | Ki (μM) | LC-MS | | |
|---|---|---|---|---|---|---|
| | | | | Method | Retn Time | m/z |
| 91 | 3-(1-((2,2-difluorocyclopropyl)-methyl)-1H-pyrazol-4-yl)-4-methoxy-1H-pyrazolo[4,3-c]pyridine | 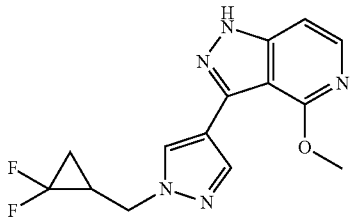 [SMILES: COc1nccc2[nH]nc(-c3cnn(CC4CC4(F)F)c3)c12] | | G | 3.49 | 306.0 |
| 92 | 3-(1-(cyclopropylmethyl)-1H-pyrazol-4-yl)-4-(tetrahydro-2H-pyran-4-yloxy)-1H-pyrazolo[4,3-c]pyridine | 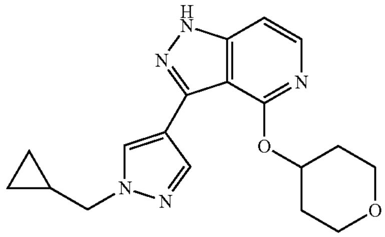 [SMILES: c1cc2[nH]nc(-c3cnn(CC4CC4)c3)c2c(OC2CCOCC2)n1] | | G | 3.63 | 340.1 |
| 93 | 3-(1-((tetrahydro-2H-pyran-4-yl)methyl)-1H-pyrazol-4-yl)-4-(tetrahydro-2H-pyran-4-yloxy)-1H-pyrazolo[4,3-c]pyridine | 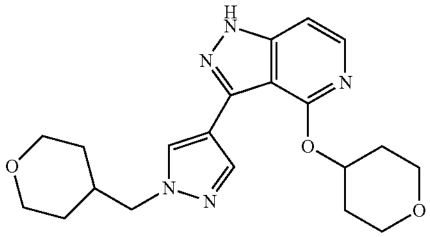 [SMILES: c1cc2[nH]nc(-c3cnn(CC4CCOCC4)c3)c2c(OC2CCOCC2)n1] | 0.011 | G | 3.44 | 384.1 |
| 94 | 3-(1-((3-methyloxetan-3-yl)methyl)-1H-pyrazol-4-yl)-4-(tetrahydro-2H-pyran-4-yloxy)-1H-pyrazolo[4,3-c]pyridine | 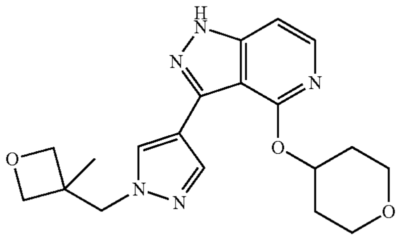 [SMILES: CC1(Cn2cc(-c3n[nH]c4ccnc(OC5CCOCC5)c34)cn2)COC1] | | B | 2.85 | 370.1 |
| 95 | 3-(1-((2,2-difluorocyclopropyl)methyl)-1H-pyrazol-4-yl)-4-(tetrahydro-2H-pyran-4-yloxy)-1H-pyrazolo[4,3-c]pyridine | 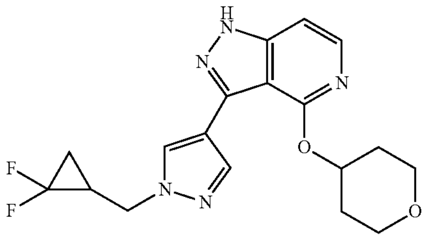 [SMILES: FC1(F)CC1Cn1cc(-c2n[nH]c3ccnc(OC4CCOCC4)c23)cn1] | | G | 3.72 | 376.1 |
| 96 | 4-(tetrahydro-2H-pyran-4-yloxy)-3-(1-(2,2,2-trifluoroethyl)-1H-pyrazol-4-yl)-1H-pyrazolo[4,3-c]pyridine | 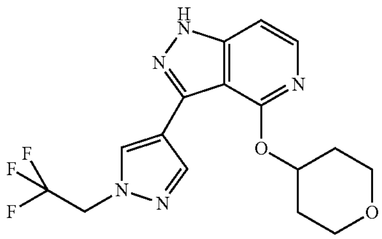 [SMILES: FC(F)(F)Cn1cc(-c2n[nH]c3ccnc(OC4CCOCC4)c23)cn1] | 0.006 | G | 3.69 | 368.1 |

TABLE 1-continued

| | Name | Structure | Ki (μM) | LC-MS Method | LC-MS Retn Time | LC-MS m/z |
|---|---|---|---|---|---|---|
| 97 | 3-(1-(tetrahydro-2H-pyran-4-yl)-1H-pyrazol-4-yl)-4-(tetrahydro-2H-pyran-4-yloxy)-1H-pyrazolo[4,3-c]pyridine | 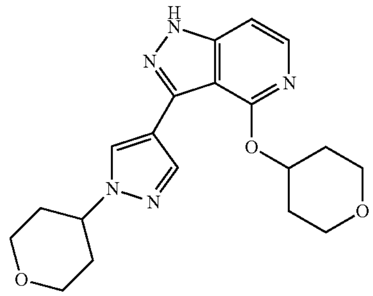 [SMILES: c1cc2[nH]nc(-c3cnn(C4CCOCC4)c3)c2c(OC2CCOCC2)n1] | | G | 3.09 | 300.1 |
| 98 | 4-(tetrahydro-2H-pyran-4-yloxy)-3-(1-(tetrahydrofuran-3-yl)-1H-pyrazol-4-yl)-1H-pyrazolo[4,3-c]pyridine | 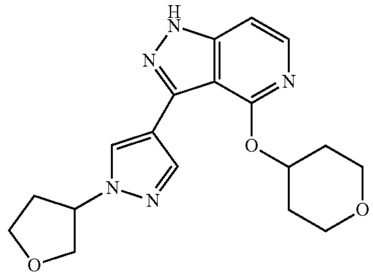 [SMILES: c1cc2[nH]nc(-c3cnn(C4CCOC4)c3)c2c(OC2CCOCC2)n1] | 0.005 | G | 3.31 | 356.1 |
| 99 | 3-(1H-pyrazol-5-yl)-4-(tetrahydro-2H-pyran-4-yloxy)-1H-pyrazolo[4,3-c]pyridine | 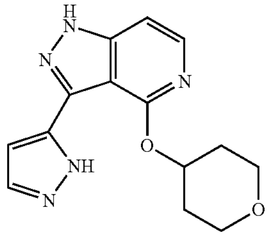 [SMILES: c1cc(-c2n[nH]c3ccnc(OC4CCOCC4)c23)[nH]n1] | | G | 2.99 | 286.0 |
| 100 | 3-(2,6-dimethylpyridin-4-yl)-4-(tetrahydro-2H-pyran-4-yloxy)-1H-pyrazolo[4,3-c]pyridine | 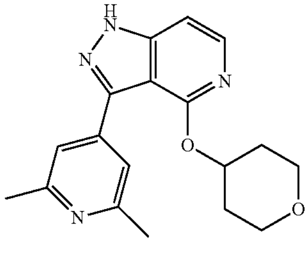 [SMILES: Cc1cc(-c2n[nH]c3ccnc(OC4CCOCC4)c23)cc(C)n1] | 0.005 | G | 3.13 | 325.1 |
| 101 | 3-(2-methoxypyridin-4-yl)-4-(tetrahydro-2H-pyran-4-yloxy)-1H-pyrazolo[4,3-c]pyridine | 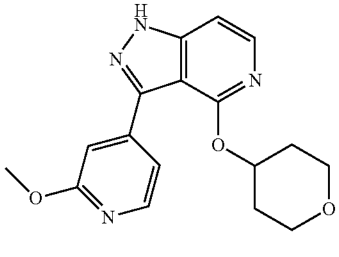 [SMILES: COc1cc(-c2n[nH]c3ccnc(OC4CCOCC4)c23)ccn1] | 0.022 | G | 3.63 | 327.1 |

TABLE 1-continued

| | Name | Structure | Ki (μM) | LC-MS Method | LC-MS Retn Time | LC-MS m/z |
|---|---|---|---|---|---|---|
| 102 | 4-(4-(4-(tetrahydro-2H-pyran-4-yloxy)-1H-pyrazolo[4,3-c]pyridin-3-yl)pyridin-2-yl)morpholine | 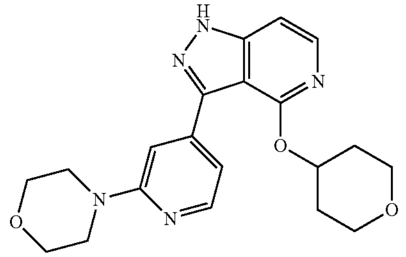 [SMILES: c1cc(-c2n[nH]c3ccnc(OC4CCOCC4)c23)cc(N2CCOCC2)n1] | | G | 3.15 | 382.1 |
| 103 | 4-(3-fluoro-4-(4-(tetrahydro-2H-pyran-4-yloxy)-1H-pyrazolo[4,3-c]pyridin-3-yl)pyridin-2-yl)morpholine | 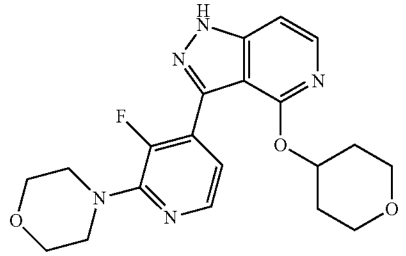 [SMILES: Fc1c(-c2n[nH]c3ccnc(OC4CCOCC4)c23)ccnc1N1CCOCC1] | 0.046 | G | 3.66 | 400.1 |
| 104 | 4-methoxy-3-(pyridin-4-yl)-1H-pyrazolo[4,3-c]pyridine | 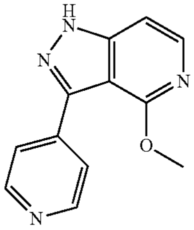 [SMILES: COc1nccc2[nH]nc(-c3ccncc3)c12] | | G | 2.56 | 227.1 |
| 105 | 4-(3-fluoro-4-(4-methoxy-1H-pyrazolo[4,3-c]pyridin-3-yl)pyridin-2-yl)morpholine | 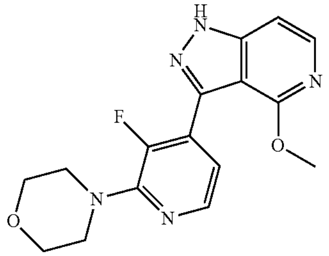 [SMILES: COc1nccc2[nH]nc(-c3ccnc(N4CCOCC4)c3F)c12] | | G | 3.66 | 330.1 |
| 106 | 4-methoxy-3-(2-methoxypyridin-4-yl)-1H-pyrazolo[4,3-c]pyridine | 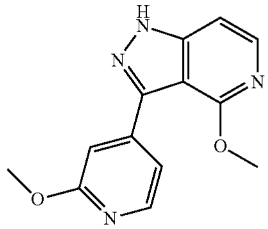 | 0.080 | G | 2.99 | 312.0 |
| 107 | 4-(4-(4-methoxy-1H-pyrazolo[4,3-c]pyridin-3-yl)pyridin-2-yl)-morpholine | 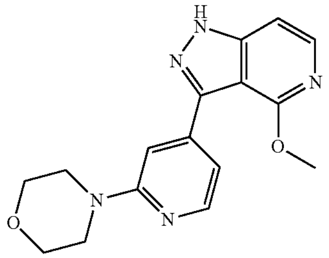 [SMILES: COc1nccc2[nH]nc(-c3ccnc(N4CCOCC4)c3)c12] | 0.029 | G | 2.99 | 312.0 |

TABLE 1-continued

| | | | | LC-MS | | |
|---|---|---|---|---|---|---|
| | Name | Structure | Ki (μM) | Method | Retn Time | m/z |
| 108 | 4-methoxy-3-(2-(trifluoromethyl)pyridin-4-yl)-1H-pyrazolo[4,3-c]pyridine | 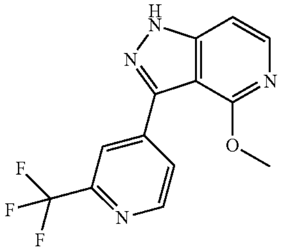 [SMILES: COc1nccc2[nH]nc(-c3ccnc(C(F)(F)F)c3)c12] | 0.075 | G | 3.54 | 373.1 |
| 109 | (2-chloro-4-(4-methoxy-1H-pyrazolo[4,3-c]pyridin-3-yl)phenyl)(morpholino)methanone | 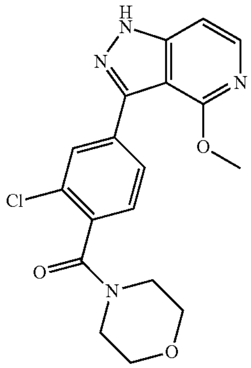 [SMILES: COc1nccc2[nH]nc(-c3ccc(C(=O)N4CCOCC4)c(Cl)c3)c12] | 0.209 | G | 3.54 | 373.1 |
| 110 | 3-(2-(pyrrolidin-1-yl)pyridin-4-yl)-4-(tetrahydro-2H-pyran-4-yloxy)-1H-pyrazolo[4,3-c]pyridine | 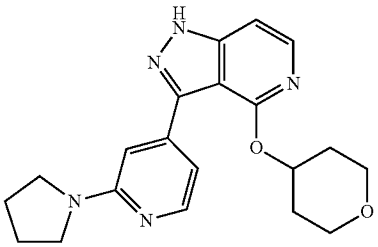 [SMILES: c1cc(-c2n[nH]c3ccnc(OC4CCOCC4)c23)cc(N2CCCC2)n1] | 0.003 | G | 3.36 | 366.1 |
| 111 | 3-(2-(3-methylpiperidin-1-yl)pyridin-4-yl)-4-(tetrahydro-2H-pyran-4-yloxy)-1H-pyrazolo[4,3-c]pyridine | 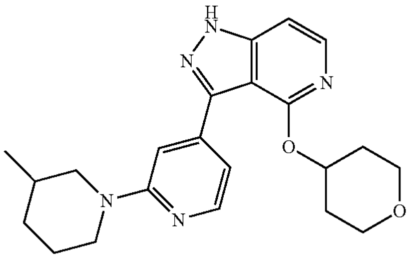 [SMILES: CC1CCCN(c2cc(-c3n[nH]c4ccnc(OC5CCOCC5)c34)ccn2)C1] | 0.006 | G | 3.70 | 394.2 |
| 112 | (1S,4S)-5-(4-(4-(tetrahydro-2H-pyran-4-yloxy)-1H-pyrazolo[4,3-c]pyridin-3-yl)pyridin-2-yl)-2-oxa-5-azabicyclo[2.2.1]heptane | 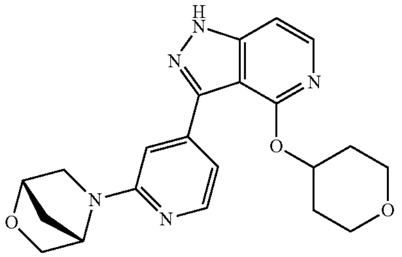 [SMILES: c1cc(-c2n[nH]c3ccnc(OC4CCOCC4)c23)cc(N2C[C@@H]3C[C@H]2CO3)n1] | | G | 3.32 | 408.1 |

TABLE 1-continued

| | Name | Structure | Ki (μM) | LC-MS Method | LC-MS Retn Time | LC-MS m/z |
|---|---|---|---|---|---|---|
| 113 | N-(oxetan-3-yl)-4-(4-(tetrahydro-2H-pyran-4-yloxy)-1H-pyrazolo[4,3-c]pyridin-3-yl)pyridin-2-amine | 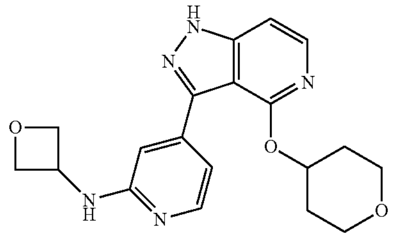 [SMILES: c1cc(-c2n[nH]c3ccnc(OC4CCOCC4)c23)cc(NC2COC2)n1] | 0.136 | G | 2.93 | 368.1 |
| 114 | 3-(2-(azetidin-1-yl)pyridin-4-yl)-4-(tetrahydro-2H-pyran-4-yloxy)-1H-pyrazolo[4,3-c]pyridine | 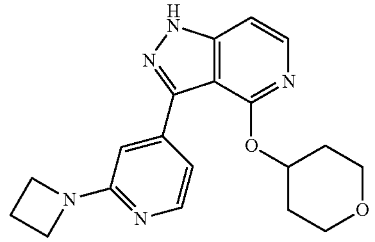 [SMILES: c1cc(-c2n[nH]c3ccnc(OC4CCOCC4)c23)cc(N2CCC2)n1] | 0.009 | G | 3.24 | 352.1 |
| 115 | (1R,5S)-8-(4-(4-(tetrahydro-2H-pyran-4-yloxy)-1H-pyrazolo[4,3-c]pyridin-3-yl)pyridin-2-yl)-3-oxa-8-azabicyclo[3.2.1]octane | 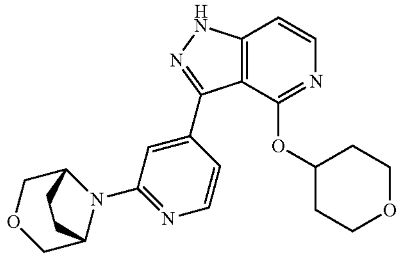 [SMILES: c1cc(-c2n[nH]c3ccnc(OC4CCOCC4)c23)cc(N2[C@@H]3CC[C@H]2COC3)n1] | | G | 3.32 | 408.1 |
| 116 | 3-(2-(1-methyl-1H-pyrazol-4-yl)pyridin-4-yl)-4-(tetrahydro-2H-pyran-4-yloxy)-1H-pyrazolo[4,3-c]pyridine | 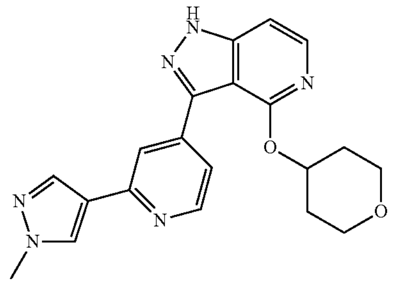 [SMILES: Cn1cc(-c2cc(-c3n[nH]c4ccnc(OC5CCOCC5)c34)ccn2)cn1] | 0.010 | G | 3.25 | 377.1 |
| 117 | (1R,5S)-8-(4-(4-methoxy-1H-pyrazolo[4,3-c]pyridin-3-yl)pyridin-2-yl)-3-oxa-8-azabicyclo[3.2.1]octane | 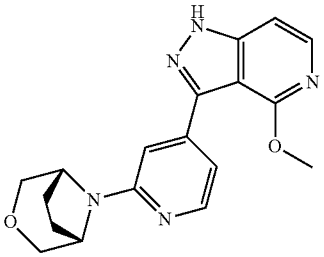 [SMILES: COc1nccc2[nH]nc(-c3ccnc(N4[C@@H]5CC[C@H]4COC5)c3)c12] | 0.08 | G | 3.19 | 338.1 |

TABLE 1-continued

| | Name | Structure | Ki (μM) | LC-MS Method | LC-MS Retn Time | LC-MS m/z |
|---|---|---|---|---|---|---|
| 118 | (1S,4S)-5-(4-(4-methoxy-1H-pyrazolo[4,3-c]pyridin-3-yl)pyridin-2-yl)-2-oxa-5-azabicyclo[2.2.1]heptane | 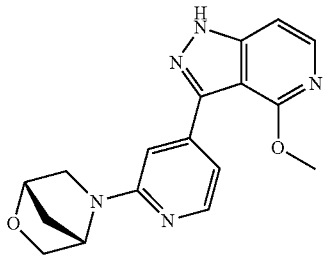 [SMILES: COc1nccc2[nH]nc(-c3ccnc(N4C[C@@H]5C[C@H]4CO5)c3)c12] | 0.051 | G | 2.94 | 324.1 |
| 119 | 4-methoxy-3-(2-(pyrrolidin-1-yl)pyridin-4-yl)-1H-pyrazolo[4,3-c] pyridine | 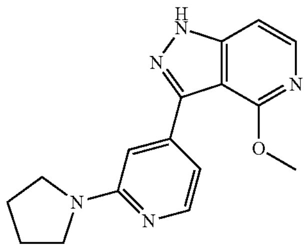 [SMILES: COc1nccc2[nH]nc(-c3ccnc(N4CCCC4)c3)c12] | 0.026 | G | 3.25 | 296.1 |
| 120 | 3-(2-(3,5-dimethylpiperidin-1-yl)pyridin-4-yl)-4-methoxy-1H-pyrazolo[4,3-c]pyridine | 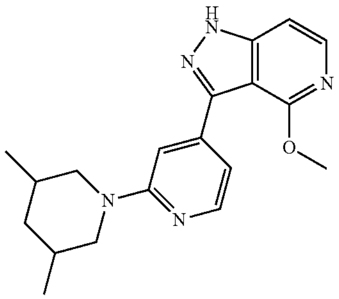 | | G | 3.38 | 340.1 |
| 121 | 4-methoxy-3-(2-(1-methyl-1H-pyrazol-4-yl)pyridin-4-yl)-1H-pyrazolo[4,3-c]pyridine | 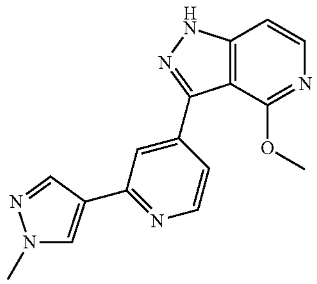 | 0.042 | G | 3.06 | 307.0 |
| 122 | 3-(1-isopropyl-1H-benzo[d]imidazol-5-yl)-4-(tetrahydro-2H-pyran-4-yloxy)-1H-pyrazolo[4,3-c]pyridine | 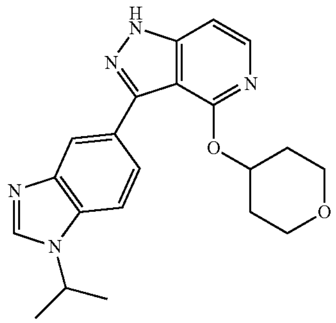 [SMILES: CC(C)n1cnc2cc(-c3n[nH]c4ccnc(OC5CCOCC5)c34)ccc21] | | G | 3.82 | 378 |

TABLE 1-continued

| | Name | Structure | Ki (μM) | LC-MS Method | LC-MS Retn Time | LC-MS m/z |
|---|---|---|---|---|---|---|
| 123 | 3-(1-isopropyl-1H-benzo[d]imidazol-6-yl)-4-(tetrahydro-2H-pyran-4-yloxy)-1H-pyrazolo[4,3-c]pyridine | 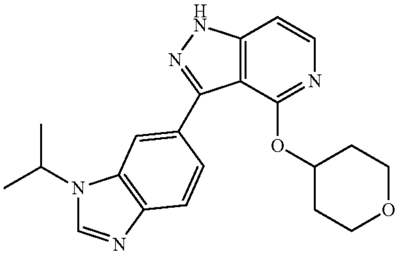 [SMILES: CC(C)n1cnc2ccc(-c3n[nH]c4ccnc(OC5CCOCC5)c34)cc21] | 0.020 | G | 4.11 | 378 |
| 124 | 3-(1-(oxetan-3-yl)-1H-benzo[d]imidazol-5-yl)-4-(tetrahydro-2H-pyran-4-yloxy)-1H-pyrazolo[4,3-c]pyridine | 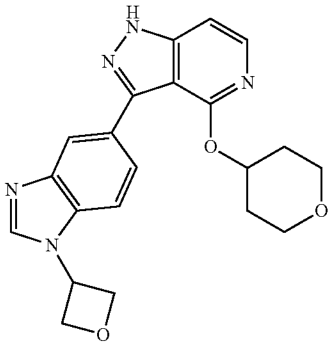 [SMILES: c1cc2[nH]nc(-c3ccc4c(c3)ncn4C3COC3)c2c(OC2CCOCC2)n1] | 0.019 | G | 2.95 | 392.1 |
| 125 | 3-(1-(oxetan-3-yl)-1H-benzo[d]imidazol-6-yl)-4-(tetrahydro-2H-pyran-4-yloxy)-1H-pyrazolo[4,3-c]pyridine | 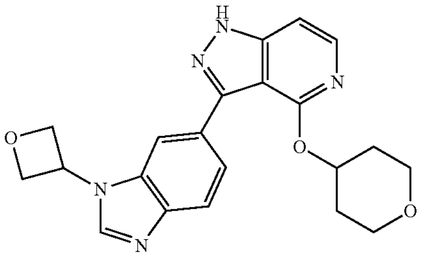 [SMILES: c1cc2[nH]nc(-c3ccc4ncn(C5COC5)c4c3)c2c(OC2CCOCC2)n1] | 0.056 | G | 3.00 | 392.1 |
| 126 | 3-(1-((2,2-difluorocyclopropyl)meth-yl)-1H-benzo[d]imidazol-5-yl)-4-(tetrahydro-2H-pyran-4-yloxy)-1H-pyrazolo[4,3-c]pyridine | 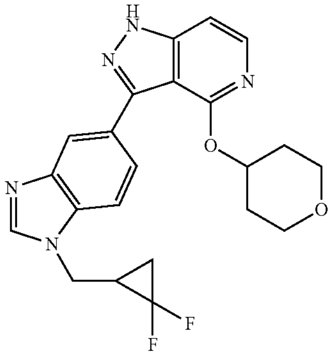 [SMILES: FC1(F)CC1Cn1cnc2cc(-c3n[nH]c4ccnc(OC5CCOCC5)c34)ccc21] | | G | 3.34 | 426.1 |
| 127 | 3-(1-((2,2-difluorocyclopropyl)meth-yl)-1H-benzo[d]imidazol-6-yl)-4-(tetrahydro-2H-pyran-4-yloxy)-1H-pyrazolo[4,3-c]pyridine | 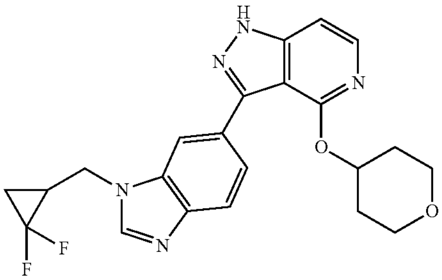 [SMILES: FC1(F)CC1Cn1cnc2ccc(-c3n[nH]c4ccnc(OC5CCOCC5)c34)cc21] | 0.023 | G | 3.42 | 426.1 |

TABLE 1-continued

| | Name | Structure | Ki (μM) | LC-MS Method | Retn Time | m/z |
|---|---|---|---|---|---|---|
| 128 | 4-(tetrahydro-2H-pyran-4-yloxy)-3-(1-(tetrahydrofuran-3-yl)-1H-benzo[d]imidazol-6-yl)-1H-pyrazolo[4,3-c]pyridine | 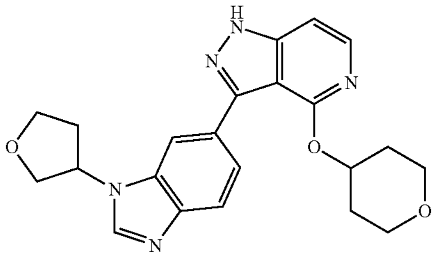 [SMILES: c1cc2[nH]nc(-c3ccc4ncn(C5CCOC5)c4c3)c2c(OC2CCOCC2)n1] | 0.034 | G | 3.05 | 406.1 |
| 129 | 4-(tetrahydro-2H-pyran-4-yloxy)-3-(1-(tetrahydrofuran-3-yl)-1H-benzo[d]imidazol-5-yl)-1H-pyrazolo[4,3-c]pyridine | 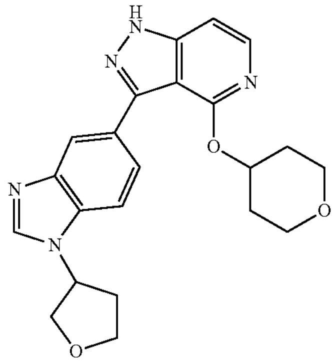 [SMILES: c1cc2[nH]nc(-c3ccc4c(c3)ncn4C3CCOC3)c2c(OC2CCOCC2)n1] | 0.010 | G | 3.05 | 406.1 |
| 130 | 3-(3-isopropyl-1H-1,2,4-triazol-5-yl)-4-(tetrahydro-2H-pyran-4-yloxy)-1H-pyrazolo[4,3-c]pyridine | 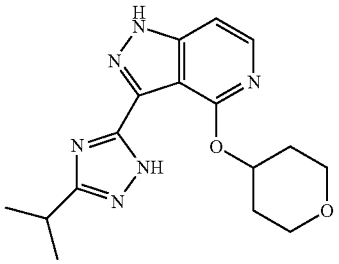 [SMILES: CC(C)c1n[nH]c(-c2n[nH]c3ccnc(OC4CCOCC4)c23)n1] | | G | 2.93 | 329.1 |
| 131 | 3-(1-(cyclobutylmethyl)-1H-pyrazol-4-yl)-4-(tetrahydro-2H-pyran-4-yloxy)-1H-pyrazolo[4,3-c]pyridine | 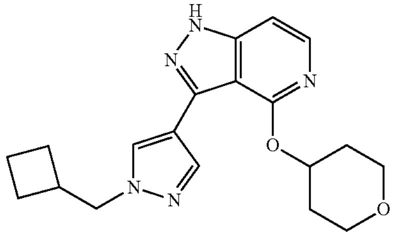 [SMILES: c1cc2[nH]nc(-c3cnn(CC4CCC4)c3)c2c(OC2CCOCC2)n1] | | G | 8.96 | 354.0 |
| 132 | 3-((2-chlorophenyl)ethynyl)-4-(tetrahydro-2H-pyran-4-yloxy)-1H-pyrazolo[4,3-c]pyridine | 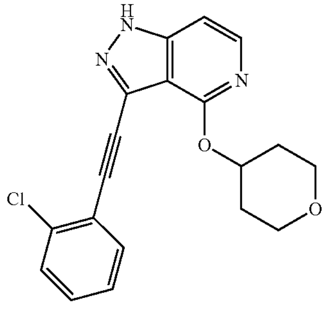 [SMILES: Clc1ccccc1C#Cc1n[nH]c2ccnc(OC3CCOCC3)c12] | 0.005 | G | 4.72 | 354.0 |

TABLE 1-continued

| | Name | Structure | Ki (μM) | LC-MS Method | Retn Time | m/z |
| --- | --- | --- | --- | --- | --- | --- |
| 133 | morpholino(4-(4-(tetrahydro-2H-pyran-4-yloxy)-1H-pyrazolo[4,3-c]pyridin-3-yl) phenyl)methanone | 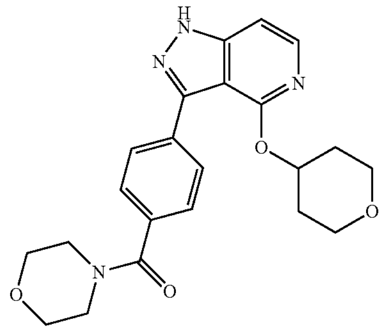 [SMILES: O=C(c1ccc(-c2n[nH]c3ccnc(OC4CCOCC4)c23)cc1)N1CCOCC1] | 0.076 | G | 3.42 | 409.1 |
| 134 | morpholino(3-(4-(tetrahydro-2H-pyran-4-yloxy)-1H-pyrazolo[4,3-c]pyridin-3-yl) phenyl)methanone | 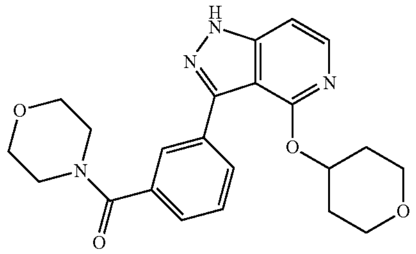 [SMILES: O=C(c1cccc(-c2n[nH]c3ccnc(OC4CCOCC4)c23)c1)N1CCOCC1] | | G | 3.44 | 409.0 |
| 135 | 2-fluoro-N,N-dimethyl-4-(4-(tetrahydro-2H-pyran-4-yloxy)-1H-pyrazolo[4,3-c]pyridin-3-yl) benzamide | 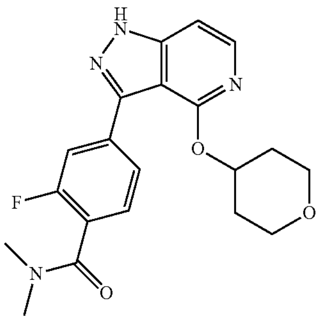 [SMILES: CN(C)C(=O)c1ccc(-c2n[nH]c3ccnc(OC4CCOCC4)c23)cc1F] | 0.104 | G | 3.68 | 385.0 |
| 136 | 3-(1-methyl-1H-indazol-6-yl)-4-(tetrahydro-2H-pyran-4-yloxy)-1H-pyrazolo[4,3-c]pyridine | 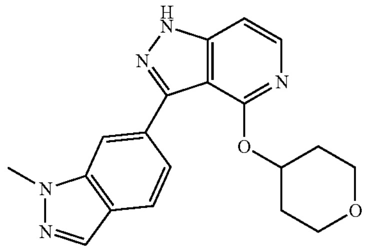 [SMILES: Cn1ncc2ccc(-c3n[nH]c4ccnc(OC5CCOCC5)c34)cc21] | | G | 3.68 | 350.0 |
| 137 | 3-(1H-indazol-5-yl)-4-(tetrahydro-2H-pyran-4-yloxy)-1H-pyrazolo[4,3-c]pyridine | 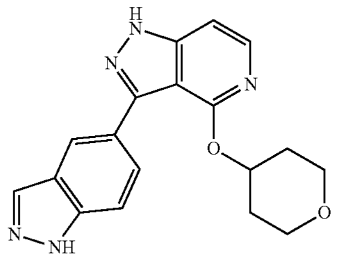 [SMILES: c1cc2[nH]nc(-c3ccc4[nH]ncc4c3)c2c(OC2CCOCC2)n1] | | G | 3.25 | 336.1 |

TABLE 1-continued

| | | | | LC-MS | | |
|---|---|---|---|---|---|---|
| | Name | Structure | Ki (μM) | Method | Retn Time | m/z |
| 138 | 3-(1H-indazol-6-yl)-4-(tetrahydro-2H-pyran-4-yloxy)-1H-pyrazolo[4,3-c]pyridine | 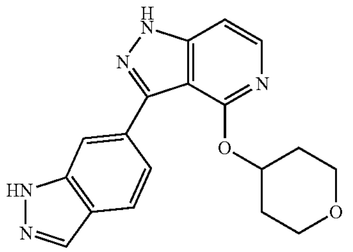 [SMILES: c1cc2[nH]nc(-c3ccc4cn[nH]c4c3)c2c(OC2CCOCC2)n1] | 0.013 | G | 3.25 | 336 |
| 139 | 3-(1H-benzo[d]imidazol-6-yl)-4-(tetrahydro-2H-pyran-4-yloxy)-1H-pyrazolo[4,3-c]pyridine | 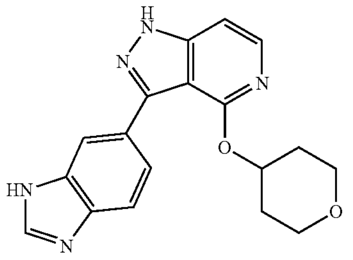 [SMILES: c1cc2[nH]nc(-c3ccc4nc[nH]c4c3)c2c(OC2CCOCC2)n1] | 0.014 | G | 2.90 | 336.1 |
| 140 | 3-(1-methyl-1H-indazol-5-yl)-4-(tetrahydro-2H-pyran-4-yloxy)-1H-pyrazolo[4,3-c]pyridine | 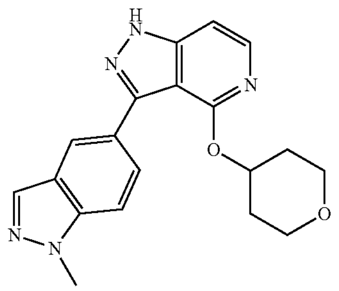 [SMILES: Cn1ncc2cc(-c3n[nH]c4ccnc(OC5CCOCC5)c34)ccc21] | 0.013 | G | 3.57 | 350.1 |
| 141 | 3-(2-methyl-2H-indazol-5-yl)-4-(tetrahydro-2H-pyran-4-yloxy)-1H-pyrazolo[4,3-c]pyridine | 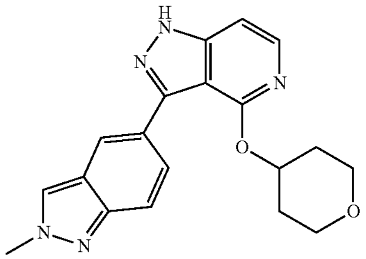 [SMILES: Cn1cc2cc(-c3n[nH]c4ccnc(OC5CCOCC5)c34)ccc2n1] | | G | 3.32 | 350.1 |
| 142 | 3-(1-isopropyl-1H-indazol-6-yl)-4-(tetrahydro-2H-pyran-4-yloxy)-1H-pyrazolo[4,3-c]pyridine | 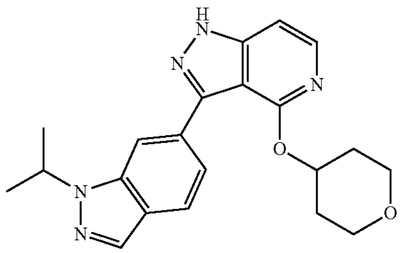 [SMILES: CC(C)n1ncc2ccc(-c3n[nH]c4ccnc(OC5CCOCC5)c34)cc21] | | G | 4.11 | 378.1 |

TABLE 1-continued

| | Name | Structure | Ki (μM) | LC-MS Method | LC-MS Retn Time | LC-MS m/z |
|---|---|---|---|---|---|---|
| 143 | 3-(2-isopropyl-2H-indazol-6-yl)-4-(tetrahydro-2H-pyran-4-yloxy)-1H-pyrazolo[4,3-c]pyridine | 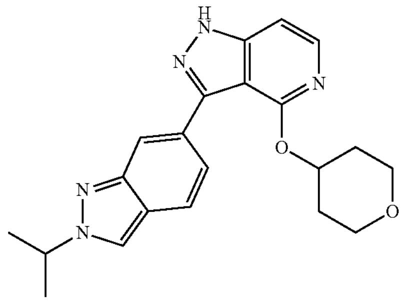 [SMILES: CC(C)n1cc2ccc(-c3n[nH]c4ccnc(OC5CCOCC5)c34)cc2n1] | 0.032 | G | 3.82 | 378.1 |
| 144 | 3-(1-methyl-1H-benzo[d]imidazol-6-yl)-4-(tetrahydro-2H-pyran-4-yloxy)-1H-pyrazolo[4,3-c]pyridine | 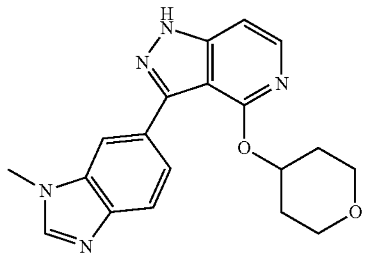 [SMILES: Cn1cnc2ccc(-c3n[nH]c4ccnc(OC5CCOCC5)c34)cc21] | | G | 2.96 | 350.0 |
| 145 | 3-(1-methyl-1H-benzo[d]imidazol-5-yl)-4-(tetrahydro-2H-pyran-4-yloxy)-1H-pyrazolo[4,3-c]pyridine | 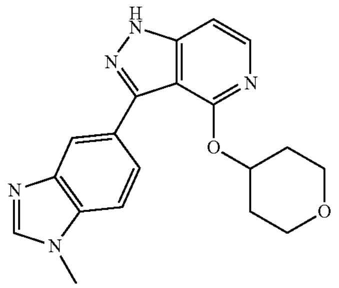 [SMILES: Cn1cnc2cc(-c3n[nH]c4ccnc(OC5CCOCC5)c34)ccc21] | 0.036 | G | 2.97 | 350.0 |
| 146 | 4-(tetrahydro-2H-pyran-4-yloxy)-3-(1-(tetrahydrofuran-3-yl)-1H-pyrazol-4-yl)-1H-pyrazolo[4,3-c]pyridine | 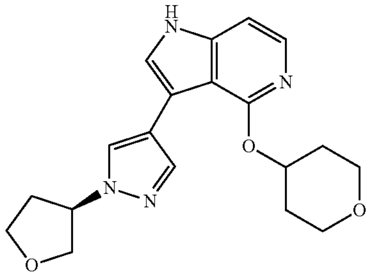 [SMILES: c1cc2[nH]cc(-c3cnn([C@@H]4CCOC4)c3)c2c(OC2CCOCC2)n1] | 0.005 | G | 3.31 | 356.1 |
| 147 | 4-(tetrahydro-2H-pyran-4-yloxy)-3-(1-(tetrahydrofuran-3-yl)-1H-pyrazol-4-yl)-1H-pyrazolo[4,3-c]pyridine | 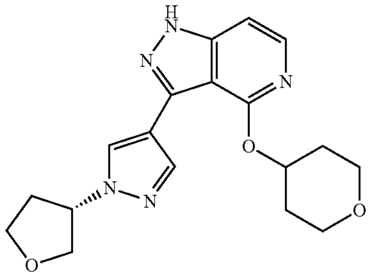 | 0.003 | G | 3.31 | 356.1 |

TABLE 1-continued

| | Name | Structure | Ki (μM) | LC-MS Method | LC-MS Retn Time | LC-MS m/z |
|---|---|---|---|---|---|---|
| 148 | 4-(cyclohexyloxy)-6-cyclopropyl-3-methyl-1H-pyrazolo[4,3-c]pyridine | 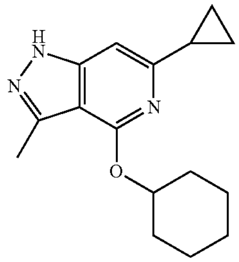 [SMILES: Cc1n[nH]c2cc(C3CC3)nc(OC3CCCCC3)c12] | 0.271 | G | 5.44 | 272.1 |
| 149 | 5-(4-(tetrahydro-2H-pyran-4-yloxy)-1H-pyrazolo[4,3-c]pyridin-3-yl)quinoline | 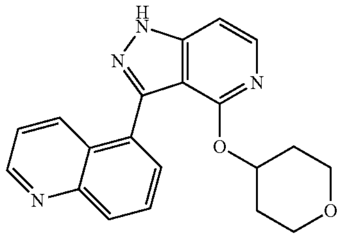 [SMILES: c1cc(-c2n[nH]c3ccnc(OC4CCOCC4)c23)c2cccnc2c1] | | G | 2.98 | 347.1 |
| 150 | 3-(4-(tetrahydro-2H-pyran-4-yloxy)-1H-pyrazolo[4,3-c]pyridin-3-yl)quinoline | 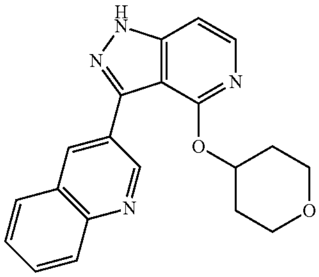 [SMILES: c1ccc2ncc(-c3n[nH]c4ccnc(OC5CCOCC5)c34)cc2c1] | 0.012 | G | 3.47 | 347.1 |
| 151 | 2-(3-(4-(tetrahydro-2H-pyran-4-yloxy)-1H-pyrazolo[4,3-c]pyridin-3-yl)phenyl)acetonitrile | 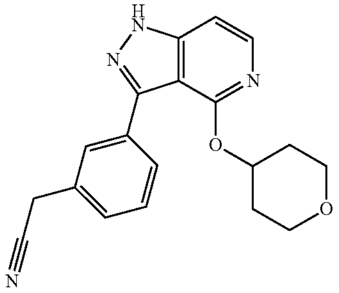 [SMILES: N#CCc1cccc(-c2n[nH]c3ccnc(OC4CCOCC4)c23)c1] | 0.017 | G | 3.74 | 335.1 |
| 152 | N-(2-(dimethylamino)ethyl)-3-(4-(tetrahydro-2H-pyran-4-yloxy)-1H-pyrazolo[4,3-c]pyridin-3-yl)benzamide | 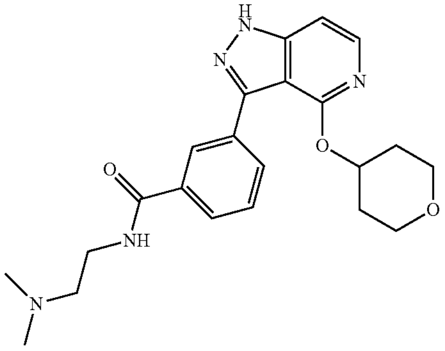 [SMILES: CN(C)CCNC(=O)c1cccc(-c2n[nH]c3ccnc(OC4CCOCC4)c23)c1] | | G | 3.03 | 410.2 |

TABLE 1-continued

| | Name | Structure | Ki (μM) | LC-MS Method | LC-MS Retn Time | LC-MS m/z |
|---|---|---|---|---|---|---|
| 153 | N,N-dimethyl-3-(4-(tetrahydro-2H-pyran-4-yloxy)-1H-pyrazolo[4,3-c]pyridin-3-yl)aniline | 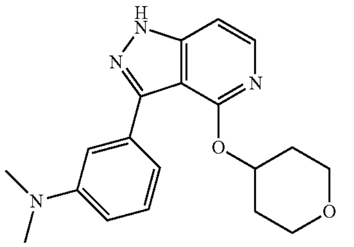 [SMILES: CN(C)c1cccc(-c2n[nH]c3ccnc(OC4CCOCC4)c23)c1] | 0.050 | G | 3.13 | 339.1 |
| 154 | N-isopropyl-3-(4-(tetrahydro-2H-pyran-4-yloxy)-1H-pyrazolo[4,3-c]pyridin-3-yl)benzamide | 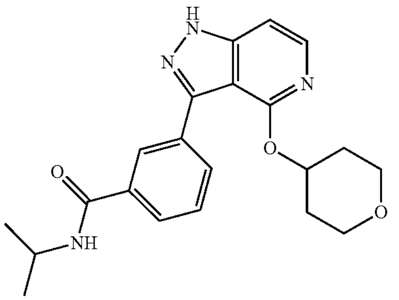 [SMILES: CC(C)NC(=O)c1cccc(-c2n[nH]c3ccnc(OC4CCOCC4)c23)c1] | 0.0784 | G | 3.66 | 381.1 |
| 155 | N-cyclopropyl-3-(4-(tetrahydro-2H-pyran-4-yloxy)-1H-pyrazolo[4,3-c]pyridin-3-yl)benzamide | 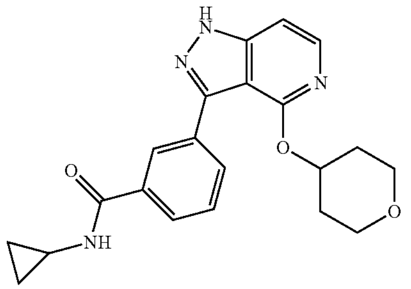 [SMILES: O=C(NC1CC1)c1cccc(-c2n[nH]c3ccnc(OC4CCOCC4)c23)c1] | 0.027 | G | 3.49 | 379.1 |
| 156 | 5-(4-(tetrahydro-2H-pyran-4-yloxy)-1H-pyrazolo[4,3-c]pyridin-3-yl)nicotinonitrile | 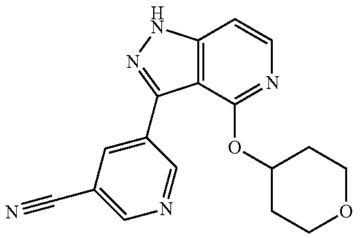 [SMILES: N#Cc1cncc(-c2n[nH]c3ccnc(OC4CCOCC4)c23)c1] | 0.172 | G | 3.69 | 322.1 |
| 157 | 3-(1-methylindolin-4-yl)-4-(tetrahydro-2H-pyran-4-yloxy)-1H-pyrazolo[4,3-c]pyridine | 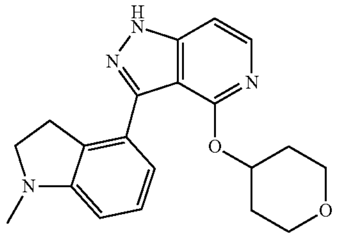 [SMILES: CN1CCc2c(-c3n[nH]c4ccnc(OC5CCOCC5)c34)cccc21] | 0.495 | G | 3.22 | 351.1 |

TABLE 1-continued

| | Name | Structure | Ki (μM) | LC-MS Method | Retn Time | m/z |
|---|---|---|---|---|---|---|
| 158 | 3-(1H-indol-4-yl)-4-(tetrahydro-2H-pyran-4-yloxy)-1H-pyrazolo[4,3-c]pyridine | 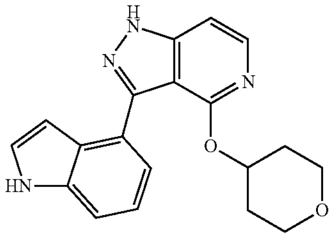 [SMILES: c1cc(-c2n[nH]c3ccnc(OC4CCOCC4)c23)c2cc[nH]c2c1] | 0.448 | G | 3.39 | 355.1 |
| 159 | 3-(1H-pyrrolo[2,3-b]pyridin-5-yl)-4-(tetrahydro-2H-pyran-4-yloxy)-1H-pyrazolo[4,3-c]pyridine | 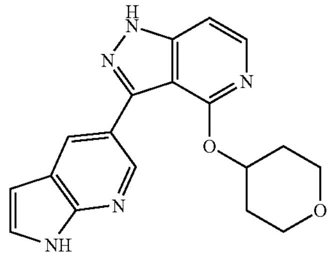 [SMILES: c1cc2[nH]nc(-c3cnc4[nH]ccc4c3)c2c(OC2CCOCC2)n1] | | G | 3.26 | 366.1 |
| 160 | N-methyl-3-(4-(tetrahydro-2H-pyran-4-yloxy)-1H-pyrazolo[4,3-c]pyridin-3-yl)benzamide | 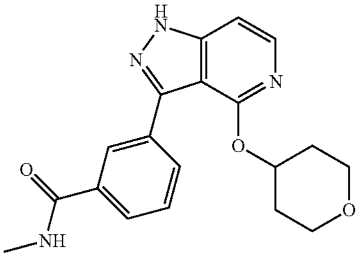 [SMILES: CNC(=O)c1cccc(-c2n[nH]c3ccnc(OC4CCOCC4)c23)c1] | 0.025 | G | 3.25 | 353.1 |
| 161 | 4-(3-(4-(tetrahydro-2H-pyran-4-yloxy)-1H-pyrazolo[4,3-c]pyridin-3-yl)benzyl)morpholine | 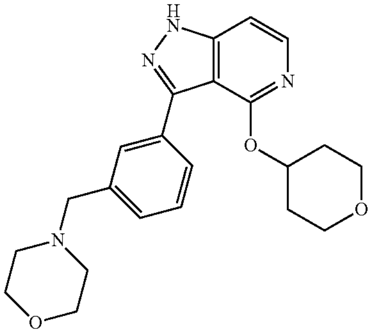 [SMILES: c1cc(CN2CCOCC2)cc(-c2n[nH]c3ccnc(OC4CCOCC4)c23)c1] | 0.107 | G | 3.0 | 395.1 |
| 162 | N-(2-methoxypyridin-4-yl)-4-(tetrahydro-2H-pyran-4-yloxy)-1H-pyrazolo[4,3-c]pyridin-3-amine | 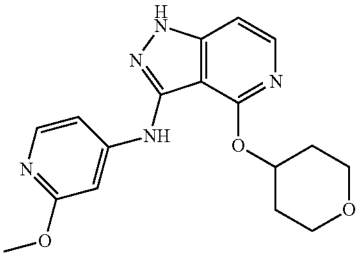 [SMILES: COc1cc(Nc2n[nH]c3ccnc(OC4CCOCC4)c23)ccn1] | 0.040 | G | 2.68 | 312.1 |

TABLE 1-continued

| | Name | Structure | Ki (μM) | LC-MS Method | LC-MS Retn Time | LC-MS m/z |
|---|---|---|---|---|---|---|
| 163 | N-(pyridin-4-yl)-4-(tetrahydro-2H-pyran-4-yloxy)-1H-pyrazolo[4,3-c]pyridin-3-amine | 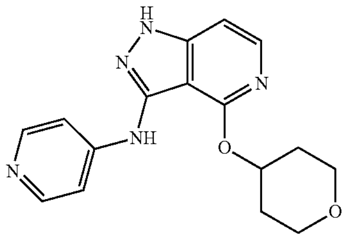 [SMILES: c1cc(Nc2n[nH]c3ccnc(OC4CCOCC4)c23)ccn1] | 0.165 | G | 2.68 | 312.1 |
| 164 | N-(1-isopropyl-1H-pyrazol-4-yl)-4-(tetrahydro-2H-pyran-4-yloxy)-1H-pyrazolo[4,3-c]pyridin-3-amine | 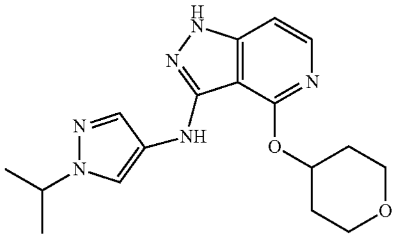 [SMILES: CC(C)n1cc(Nc2n[nH]c3ccnc(OC4CCOCC4)c23)cn1] | 0.030 | G | 3.30 | 343.1 |
| 165 | 3-(3-(methylsulfonyl)phenyl)-4-(tetrahydro-2H-pyran-4-yloxy)-1H-pyrazolo[4,3-c]pyridine | 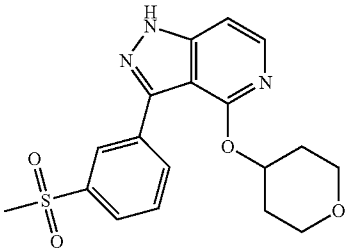 [SMILES: CS(=O)(=O)c1cccc(-c2n[nH]c3ccnc(OC4CCOCC4)c23)c1] | 0.029 | G | 3.53 | 290.0 |
| 166 | 3-(4-(methylsulfonyl)phenyl)-4-(tetrahydro-2H-pyran-4-yloxy)-1H-pyrazolo[4,3-c]pyridine | 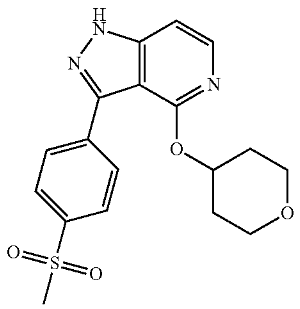 [SMILES: CS(=O)(=O)c1ccc(-c2n[nH]c3ccnc(OC4CCOCC4)c23)cc1] | | G | 3.54 | 290.0 |
| 167 | 4-methoxy-3-(3-(methylsulfonyl)phenyl)-1H-pyrazolo[4,3-c]pyridine | 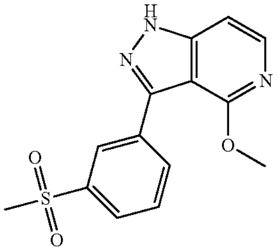 | 0.045 | G | 3.32 | 304 |

TABLE 1-continued

| | Name | Structure | Ki (μM) | LC-MS Method | LC-MS Retn Time | LC-MS m/z |
|---|---|---|---|---|---|---|
| 168 | 3-(5-isopropyl-4H-1,2,4-triazol-3-yl)-N-(tetrahydro-2H-pyran-4-yl)-1H-pyrazolo[4,3-c] pyridin-4-amine | 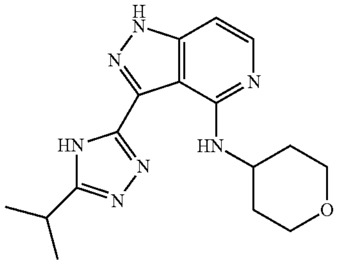 [SMILES: CC(C)c1nnc(-c2n[nH]c3ccnc(NC4CCOCC4)c23)[nH]1] | 0.007 | G | 3.03 | 328.1 |
| 169 | N-(1-methyl-1H-pyrazol-4-yl)-4-(tetrahydro-2H-pyran-4-yloxy)-1H-pyrazolo[4,3-c]pyridin-3-amine | 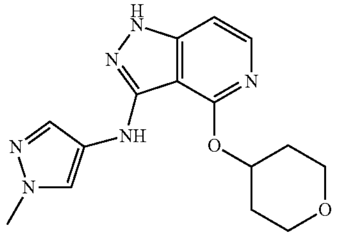 [SMILES: Cn1cc(Nc2n[nH]c3ccnc(OC4CCOCC4)c23)cn1] | | G | 2.88 | 315.1 |
| 170 | 3-phenoxy-N-(tetrahydro-2H-pyran-4-yl)-1H-pyrazolo[4,3-c] pyridin-4-amine | 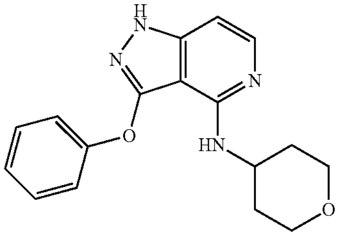 [SMILES: c1ccc(Oc2n[nH]c3ccnc(NC4CCOCC4)c23)cc1] | | G | 3.26 | 311.1 |
| 171 | N-methyl-3-(6-methyl-4-(tetrahydro-2H-pyran-4-yloxy)-1H-pyrazolo[4,3-c]pyridin-3-yl)benzamide | 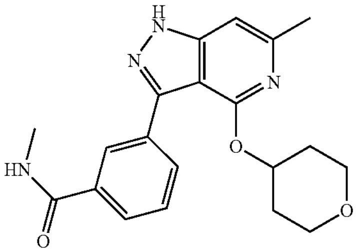 [SMILES: CNC(=O)c1cccc(-c2n[nH]c3cc(C)nc(OC4CCOCC4)c23)c1] | 0.154 | | | |
| 172 | 4-(4-(6-methyl-4-(tetrahydro-2H-pyran-4-yloxy)-1H-pyrazolo[4,3-c]pyridin-3-yl)pyridin-2-yl)morpholine | 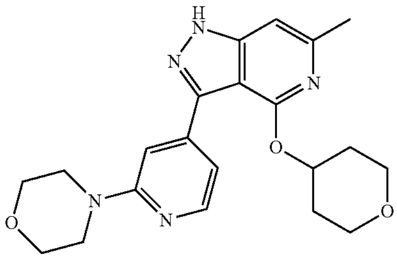 [SMILES: Cc1cc2[nH]nc(-c3ccnc(N4CCOCC4)c3)c2c(OC2CCOCC2)n1] | 0.035 | | | |

TABLE 1-continued

| | Name | Structure | Ki (μM) | LC-MS Method | LC-MS Retn Time | LC-MS m/z |
|---|---|---|---|---|---|---|
| 173 | 4-methoxy-3-(4-(methylsulfonyl)phenyl)-1H-pyrazolo[4,3-c] pyridine | 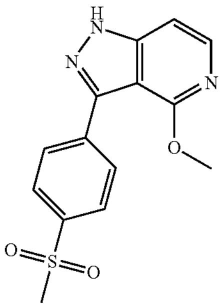 [SMILES: COc1nccc2[nH]nc(-c3ccc(S(C)(=O)=O)cc3)c12] | 0.09 | | | |
| 174 | 4-(4-(tetrahydro-2H-pyran-4-yloxy)-1H-pyrazolo[4,3-c]pyridin-3-yl)picolinonitrile | 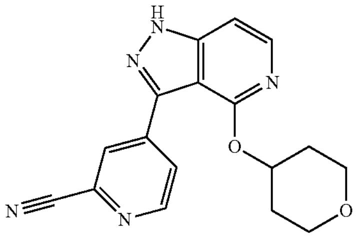 [SMILES: N#Cc1cc(-c2n[nH]c3ccnc(OC4CCOCC4)c23)ccn1] | 0.13 | | | |
| 175 | 1-methyl-4-(4-(tetrahydro-2H-pyran-4-yloxy)-1H-pyrazolo[4,3-c]pyridin-3-yl)pyridin-2(1H)-one | 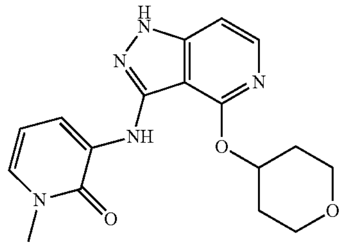 [SMILES: Cn1cccc(Nc2n[nH]c3ccnc(OC4CCOCC4)c23)c1=O] | 0.007 | | | |
| 176 | 3-(1-isopropyl-1H-pyrazol-4-yl)-4-(tetrahydro-2H-pyran-4-yloxy)-1H-pyrazolo[4,3-c]pyridine | 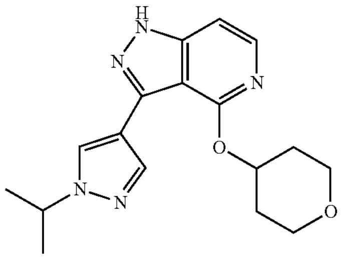 [SMILES: CC(C)n1cc(-c2n[nH]c3ccnc(OC4CCOCC4)c23)cn1] | | | | |
| 177 | 4-(4-(4-(1,1,1-trifluoropropan-2-yloxy)-1H-pyrazolo[4,3-c]pyridin-3-yl)pyridin-2-yl)morpholine | 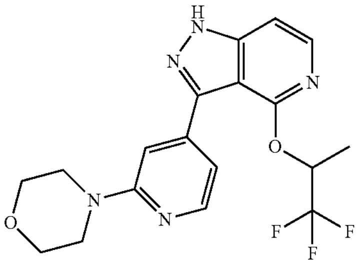 [SMILES: CC(Oc1nccc2[nH]nc(-c3ccnc(N4CCOCC4)c3)c12)C(F)(F)F] | 0.016 | | | |

TABLE 1-continued

| | Name | Structure | Ki (μM) | LC-MS Method | Retn Time | m/z |
|---|---|---|---|---|---|---|
| 178 | 4-(4-(4-(2-methoxyethoxy)-1H-pyrazolo[4,3-c]pyridin-3-yl)pyridin-2-yl) morpholine | 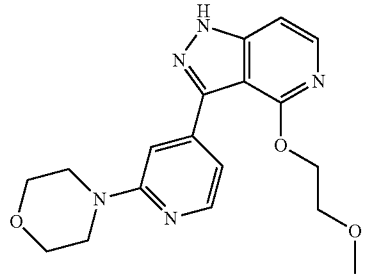 [SMILES: COCCOc1nccc2[nH]nc(-c3ccnc(N4CCOCC4)c3)c12] | 0.023 | | | |
| 179 | 3-(2-(3-(2-morpholinopyridin-4-yl)-1H-pyrazolo[4,3-c]pyridin-4-yloxy) ethyl)oxazolidin-2-one | 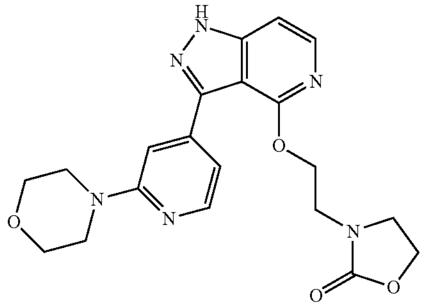 [SMILES: O=C1OCCN1CCOc1nccc2[nH]nc(-c3ccnc(N4CCOCC4)c3)c12] | 0.354 | | | |
| 180 | 4-sec-butoxy-3-(1-isopropyl-1H-pyrazol-4-yl)-1H-pyrazolo[4,3-c] pyridine | 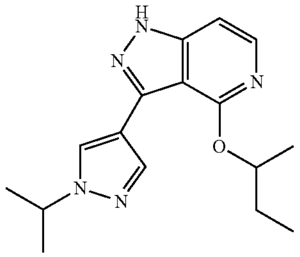 [SMILES: CCC(C)Oc1nccc2[nH]nc(-c3cnn(C(C)C)c3)c12] | | | | |
| 181 | 4-isobutoxy-3-(1-isopropyl-1H-pyrazol-4-yl)-1H-pyrazolo[4,3-c] pyridine | 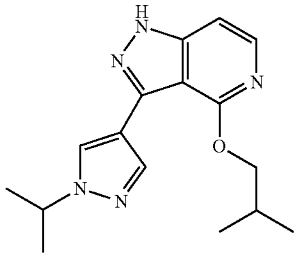 [SMILES: CC(C)COc1nccc2[nH]nc(-c3cnn(C(C)C)c3)c12] | | | | |
| 182 | 3-(2-(3-(1-isopropyl-1H-pyrazol-4-yl)-1H-pyrazolo[4,3-c]pyridin-4-yloxy)ethyl)oxazolidin-2-one | 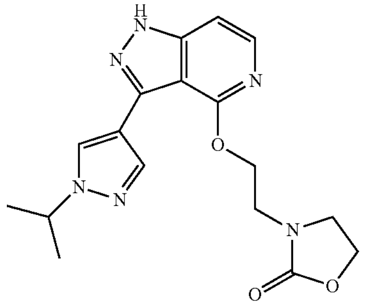 [SMILES: CC(C)n1cc(-c2n[nH]c3ccnc(OCCN4CCOC4=O)c23)cn1] | 0.323 | | | |

TABLE 1-continued

| | Name | Structure | Ki (μM) | LC-MS Method | LC-MS Retn Time | LC-MS m/z |
|---|---|---|---|---|---|---|
| 183 | 4-isopropoxy-3-(1-(tetrahydrofuran-3-yl)-1H-pyrazol-4-yl)-1H-pyrazolo[4,3-c]pyridine | 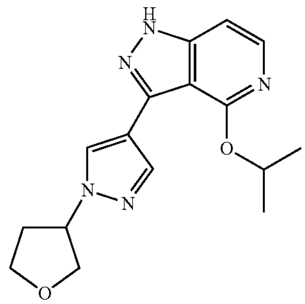 [SMILES: CC(C)Oc1nccc2[nH]nc(-c3cnn(C4CCOC4)c3)c12] | | | | |
| 184 | 4-methoxy-3-(1-(tetrahydro-2H-pyran-4-yl)-1H-pyrazol-4-yl)-1H-pyrazolo[4,3-c]pyridine | 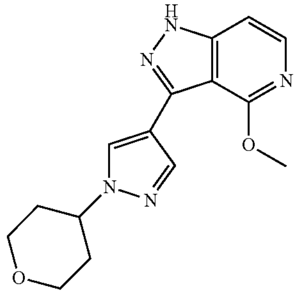 [SMILES: COc1nccc2[nH]nc(-c3cnn(C4CCOCC4)c3)c12] | 0.033 | | | |
| 185 | methyl 4-(tetrahydro-2H-pyran-4-ylamino)-1H-pyrazolo[4,3-c]pyridine-3-carboxylate | 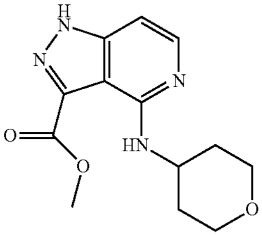 [SMILES: COC(=O)c1n[nH]c2ccnc(NC3CCOCC3)c12] | 0.100 | | | |
| 186 | 3-(1-(tetrahydro-2H-pyran-4-yl)-1H-pyrazol-4-yl)-4-(tetrahydro-2H-pyran-4-yloxy)-1H-pyrazolo[4,3-c]pyridine | 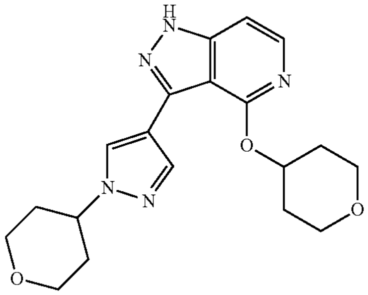 [SMILES: c1cc2[nH]nc(-c3cnn(C4CCOCC4)c3)c2c(OC2CCOCC2)n1] | 0.013 | | | |
| 187 | N-isopropyl-4-(tetrahydro-2H-pyran-4-ylamino)-1H-pyrazolo[4,3-c]pyridine-3-carboxamide | 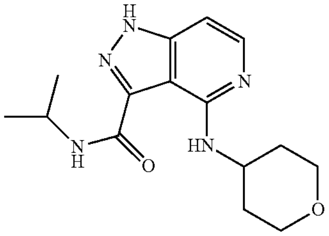 [SMILES: CC(C)NC(=O)c1n[nH]c2ccnc(NC3CCOCC3)c12] | | | | |

TABLE 1-continued

| | Name | Structure | Ki (μM) | LC-MS Method | LC-MS Retn Time | LC-MS m/z |
|---|---|---|---|---|---|---|
| 188 | 3-methyl-N-(tetrahydro-2H-pyran-4-yl)-1H-pyrazolo[4,3-c]pyridin-4-amine | 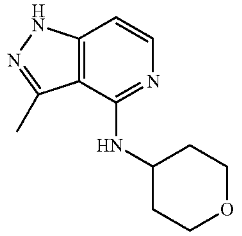 [SMILES: Cc1n[nH]c2ccnc(NC3CCOCC3)c12] | 0.130 | | | |
| 189 | 1-isopropyl-N-methyl-4-(4-(tetrahydro-2H-pyran-4-yloxy)-1H-pyrazolo[4,3-c]pyridin-3-yl)-1H-pyrrole-2-carboxamide | 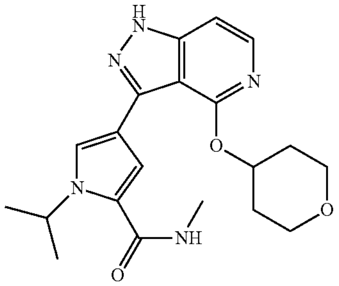 [SMILES: CNC(=O)c1cc(-c2n[nH]c3ccnc(OC4CCOCC4)c23)cn1C(C)C] | | | | |
| 190 | 4-(4-(4-(tetrahydrofuran-3-yloxy)-1H-pyrazolo[4,3-c]pyridin-3-yl)pyridin-2-yl)morpholine | 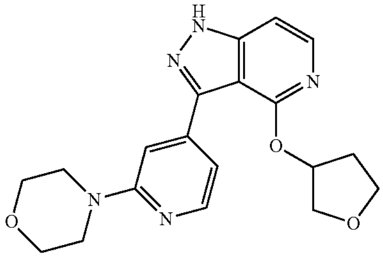 [SMILES: c1cc(-c2n[nH]c3ccnc(OC4CCOC4)c23)cc(N2CCOCC2)n1] | 0.013 | | | |
| 191 | 4-(4-(4-sec-butoxy-1H-pyrazolo[4,3-c]pyridin-3-yl)pyridin-2-yl) morpholine | 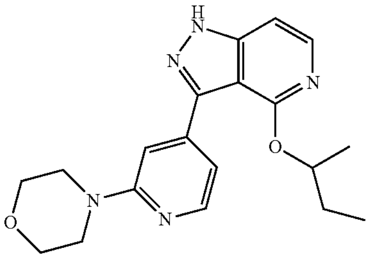 [SMILES: CCC(C)Oc1nccc2[nH]nc(-c3ccnc(N4CCOCC4)c3)c12] | | | | |
| 192 | 4-(4-(4-isobutoxy-1H-pyrazolo[4,3-c]pyridin-3-yl)pyridin-2-yl) morpholine | 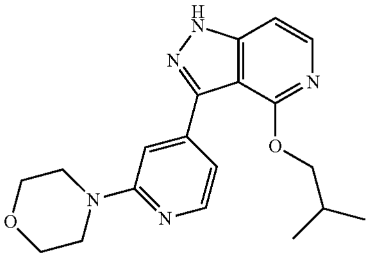 [SMILES: CC(C)COc1nccc2[nH]nc(-c3ccnc(N4CCOCC4)c3)c12] | | | | |

TABLE 1-continued

| | Name | Structure | Ki (μM) | LC-MS Method | LC-MS Retn Time | LC-MS m/z |
|---|---|---|---|---|---|---|
| 193 | 4-(4-(4-(tetrahydro-2H-pyran-3-yloxy)-1H-pyrazolo[4,3-c]pyridin-3-yl)pyridin-2-yl) morpholine | 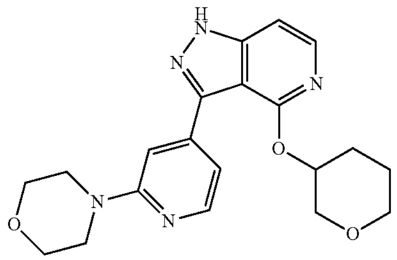 [SMILES: c1cc(-c2n[nH]c3ccnc(OC4CCCOC4)c23)cc(N2CCOCC2)n1] | | | | |
| 194 | 4-isopropoxy-3-(1-isopropyl-1H-pyrazol-4-yl)-1H-pyrazolo[4,3-c] pyridine | 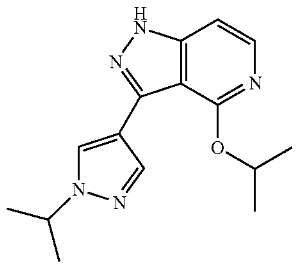 [SMILES: CC(C)Oc1nccc2[nH]nc(-c3cnn(C(C)C)c3)c12] | | | | |
| 195 | 4-isopropoxy-3-(1-(tetrahydro-2H-pyran-4-yl)-1H-pyrazol-4-yl)-1H-pyrazolo[4,3-c]pyridine | 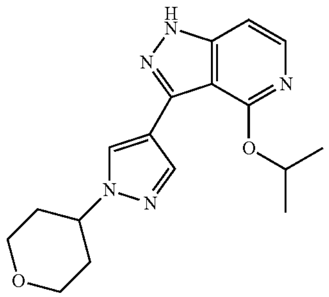 [SMILES: CC(C)Oc1nccc2[nH]nc(-c3cnn(C4CCOCC4)c3)c12] | | | | |
| 196 | 4-(cyclopentyloxy)-3-methyl-1H-pyrazolo[4,3-c]pyridine | 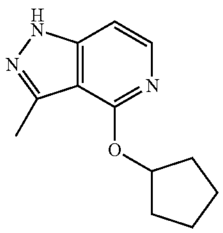 [SMILES: Cc1n[nH]c2ccnc(OC3CCCC3)c12] | 0.858 | | | |
| 197 | 3-(2,3'-bipyridin-4-yl)-4-(tetrahydro-2H-pyran-4-yloxy)-1H-pyrazolo[4,3-c]pyridine | 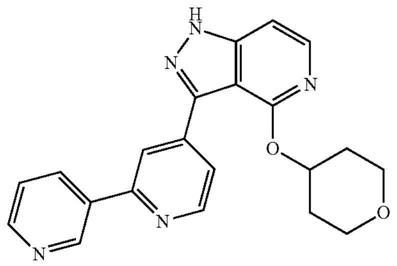 [SMILES: c1cncc(-c2cc(-c3n[nH]c4ccnc(OC5CCOCC5)c34)ccn2)c1] | 0.021 | | | |

TABLE 1-continued

| | Name | Structure | Ki (μM) | LC-MS Method | LC-MS Retn Time | LC-MS m/z |
|---|---|---|---|---|---|---|
| 198 | 3-(2,4'-bipyridin-4-yl)-4-(tetrahydro-2H-pyran-4-yloxy)-1H-pyrazolo[4,3-c]pyridine | 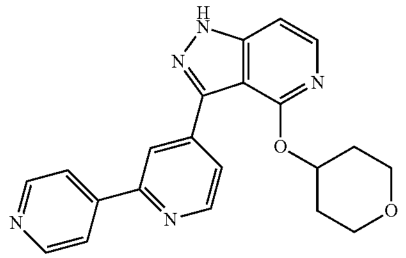 [SMILES: c1cc(-c2cc(-c3n[nH]c4ccnc(OC5CCOCC5)c34)ccn2)ccn1] | 0.026 | | | |
| 199 | 3-(2-(pyrimidin-5-yl)pyridin-4-yl)-4-(tetrahydro-2H-pyran-4-yloxy)-1H-pyrazolo[4,3-c]pyridine | 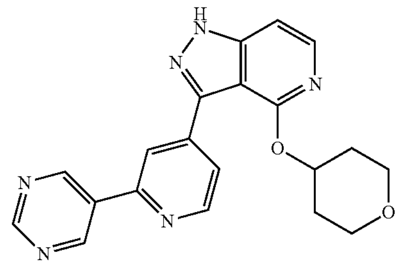 | 0.046 | | | |
| 200 | 3-(2'-methyl-2,3'-bipyridin-4-yl)-4-(tetrahydro-2H-pyran-4-yloxy)-1H-pyrazolo[4,3-c]pyridine | 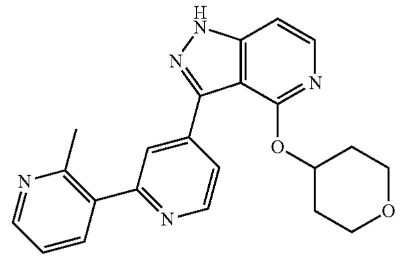 [SMILES: Cc1ncccc1-c1cc(-c2n[nH]c3ccnc(OC4CCOCC4)c23)ccn1] | | | | |
| 201 | 3-(4-(4-(tetrahydro-2H-pyran-4-yloxy)-1H-pyrazolo[4,3-c]pyridin-3-yl)pyridin-2-yl) benzonitrile | 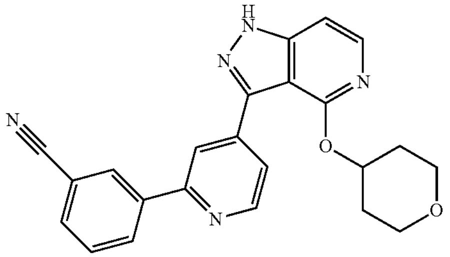 [SMILES: N#Cc1cccc(-c2cc(-c3n[nH]c4ccnc(OC5CCOCC5)c34)ccn2)c1] | 0.009 | | | |
| 202 | 4-(4-(4-(tetrahydro-2H-pyran-4-yloxy)-1H-pyrazolo[4,3-c]pyridin-3-yl)pyridin-2-yl) benzonitrile | 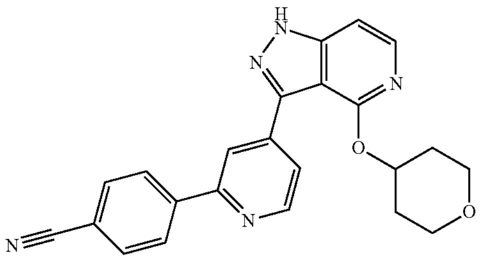 [SMILES: N#Cc1ccc(-c2cc(-c3n[nH]c4ccnc(OC5CCOCC5)c34)ccn2)cc1] | 0.025 | | | |

TABLE 1-continued

| | | | | LC-MS | | |
|---|---|---|---|---|---|---|
| | Name | Structure | Ki (μM) | Method | Retn Time | m/z |
| 203 | N,N-dimethyl-3-(4-(4-(tetrahydro-2H-pyran-4-yloxy)-1H-pyrazolo[4,3-c]pyridin-3-yl)pyridin-2-yl)benzamide | 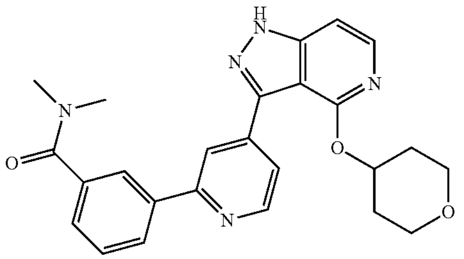 [SMILES: CN(C)C(=O)c1cccc(-c2cc(-c3n[nH]c4ccnc(OC5CCOCC5)c34)ccn2)c1] | 0.018 | | | |
| 204 | 3-(2-(1H-pyrazol-4-yl)pyridin-4-yl)-4-(tetrahydro-2H-pyran-4-yloxy)-1H-pyrazolo[4,3-c]pyridine | 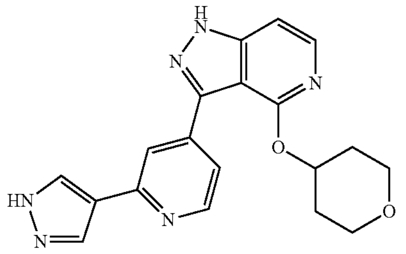 [SMILES: c1cc(-c2n[nH]c3ccnc(OC4CCOCC4)c23)cc(-c2cn[nH]c2)n1] | 0.012 | | | |
| 205 | 3-(2-(3,5-dimethyl-1H-pyrazol-4-yl)pyridin-4-yl)-4-(tetrahydro-2H-pyran-4-yloxy)-1H-pyrazolo[4,3-c]pyridine | 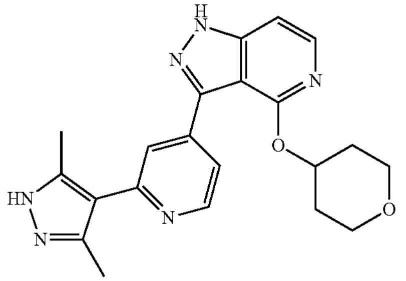 [SMILES: Cc1n[nH]c(C)c1-c1cc(-c2n[nH]c3ccnc(OC4CCOCC4)c23)ccn1] | | | | |
| 206 | N-(2-(4-(4-(tetrahydro-2H-pyran-4-yloxy)-1H-pyrazolo[4,3-c]pyridin-3-yl)pyridin-2-yl) phenyl)acetamide | 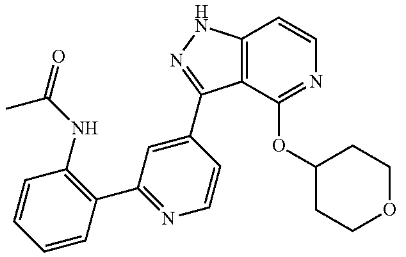 [SMILES: CC(=O)Nc1ccccc1-c1cc(-c2n[nH]c3ccnc(OC4CCOCC4)c23)ccn1] | 0.066 | | | |
| 207 | N-(4-(4-(tetrahydro-2H-pyran-4-yloxy)-1H-pyrazolo[4,3-c]pyridin-3-yl)-2,3'-bipyridin-6'-yl)acetamide | 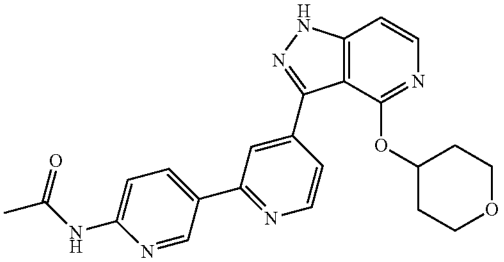 [SMILES: CC(=O)Nc1ccc(-c2cc(-c3n[nH]c4ccnc(OC5CCOCC5)c34)ccn2)cn1] | 0.021 | | | |

TABLE 1-continued

| | Name | Structure | Ki (μM) | LC-MS Method | LC-MS Retn Time | LC-MS m/z |
|---|---|---|---|---|---|---|
| 208 | 3-(2-(1-isobutyl-1H-pyrazol-4-yl)pyridin-4-yl)-4-(tetrahydro-2H-pyran-4-yloxy)-1H-pyrazolo[4,3-c]pyridine | 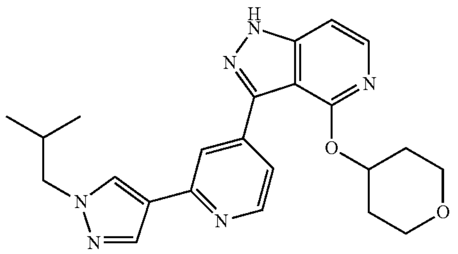 [SMILES: CC(C)Cn1cc(-c2cc(-c3n[nH]c4ccnc(OC5CCOCC5)c34)ccn2)cn1] | | | | |
| 209 | N-(3-(4-(4-(tetrahydro-2H-pyran-4-yloxy)-1H-pyrazolo[4,3-c]pyridin-3-yl)pyridin-2-yl)phenyl)acetamide | 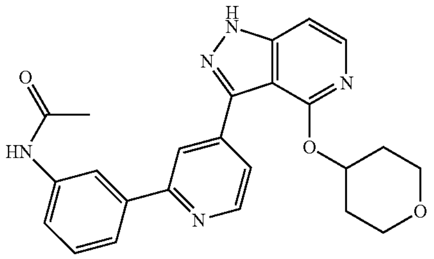 [SMILES: CC(=O)Nc1cccc(-c2cc(-c3n[nH]c4ccnc(OC5CCOCC5)c34)ccn2)c1] | 0.010 | | | |
| 210 | N-(4-(4-(4-(tetrahydro-2H-pyran-4-yloxy)-1H-pyrazolo[4,3-c]pyridin-3-yl)pyridin-2-yl)phenyl)acetamide | 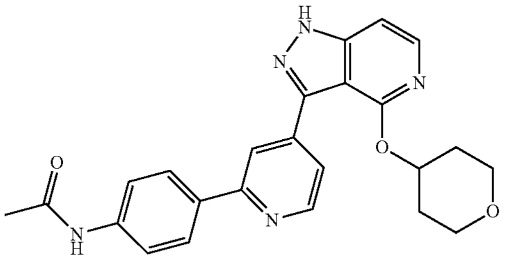 [SMILES: CC(=O)Nc1ccc(-c2cc(-c3n[nH]c4ccnc(OC5CCOCC5)c34)ccn2)cc1] | 0.011 | | | |
| 211 | N-methyl-3-(4-(4-(tetrahydro-2H-pyran-4-yloxy)-1H-pyrazolo[4,3-c]pyridin-3-yl)pyridin-2-yl)benzamide | 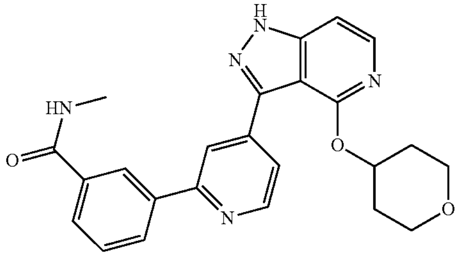 [SMILES: CNC(=O)c1cccc(-c2cc(-c3n[nH]c4ccnc(OC5CCOCC5)c34)ccn2)c1] | 0.015 | | | |
| 212 | N,N-dimethyl-4-(4-(4-(tetrahydro-2H-pyran-4-yloxy)-1H-pyrazolo[4,3-c]pyridin-3-yl)pyridin-2-yl)benzamide | 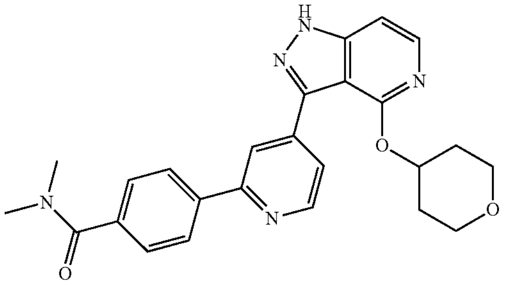 [SMILES: CN(C)C(=O)c1ccc(-c2cc(-c3n[nH]c4ccnc(OC5CCOCC5)c34)ccn2)cc1] | 0.009 | | | |

TABLE 1-continued

| | Name | Structure | Ki (μM) | LC-MS Method | LC-MS Retn Time | LC-MS m/z |
|---|---|---|---|---|---|---|
| 213 | 3-(2-(1-ethyl-1H-pyrazol-4-yl)pyridin-4-yl)-4-(tetrahydro-2H-pyran-4-yloxy)-1H-pyrazolo[4,3-c]pyridine | 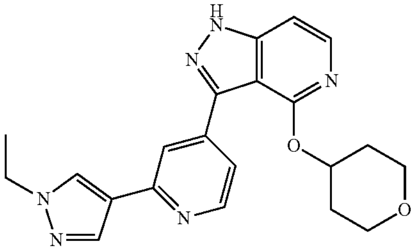 [SMILES: CCn1cc(-c2cc(-c3n[nH]c4ccnc(OC5CCOCC5)c34)ccn2)cn1] | 0.012 | | | |
| 214 | 4-(4-Isopropoxy-1H-pyrazolo[4,3-c]pyridin-3-yl)-1-isopropyl-1H-pyrrole-2-carboxylic acid ethylamide | 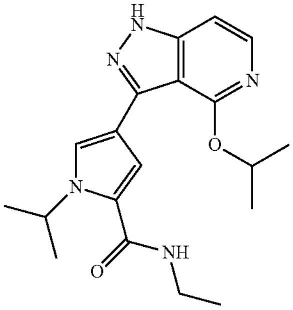 [SMILES: CCNC(=O)c1cc(-c2n[nH]c3ccnc(OC(C)C)c23)cn1C(C)C] | | | | |
| 215 | 4-(4-Isopropoxy-1H-pyrazolo[4,3-c]pyridin-3-yl)-1-isopropyl-1H-pyrrole-2-carboxylic acid cyclobutylamide | 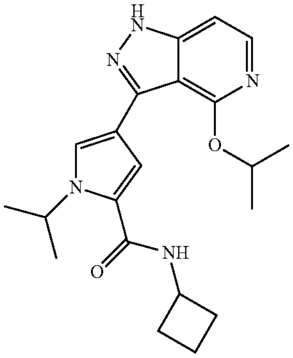 [SMILES: CC(C)Oc1nccc2[nH]nc(-c3cc(C(=O)NC4CCC4)n(C(C)C)c3)c12] | | | | |
| 216 | [4-(4-Isopropoxy-1H-pyrazolo[4,3-c]pyridin-3-yl)-1-isopropyl-1H-pyrrol-2-yl]-pyrrolidin-1-yl-methanone | 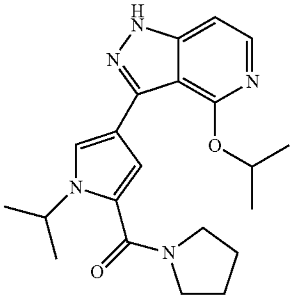 [SMILES: CC(C)Oc1nccc2[nH]nc(-c3cc(C(=O)N4CCCC4)n(C(C)C)c3)c12] | 0.006 | | | |

TABLE 1-continued

| | Name | Structure | Ki (μM) | LC-MS Method | LC-MS Retn Time | LC-MS m/z |
|---|---|---|---|---|---|---|
| 217 | 1-Isopropyl-4-[4-(tetrahydro-pyran-4-yloxy)-1H-pyrazolo[4,3-c]pyridin-3-yl]-1H-pyrrole-2-carboxylic acid ethylamide | 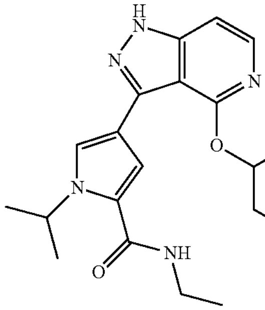 | | | | |
| 218 | Azetidin-1-yl-{1-isopropyl-4-[4-(tetrahydro-pyran-4-yloxy)-1H-pyrazolo[4,3-c]pyridin-3-yl]-1H-pyrrol-2-yl}-methanone | 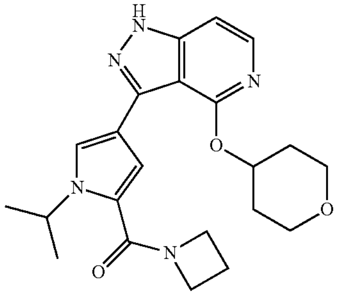 [SMILES: CC(C)n1cc(-c2n[nH]c3ccnc(OC4CCOCC4)c23)cc1C(=O)N1CCC1] | 0.008 | | | |
| 219 | [4-(4-Isopropoxy-1H-pyrazolo[4,3-c]pyridin-3-yl)-pyridin-2-yl]-morpholin-4-yl-methanone | 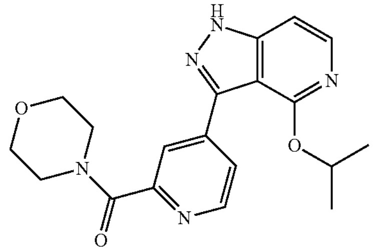 [SMILES: CC(C)Oc1nccc2[nH]nc(-c3ccnc(C(=O)N4CCOCC4)c3)c12] | | | | |
| 220 | [4-(4-Isopropoxy-1H-pyrazolo[4,3-c]pyridin-3-yl)-pyridin-2-yl]-(1S,4S)-2-oxa-5-aza-bicyclo[2.2.1]hept-5-yl-methanone | 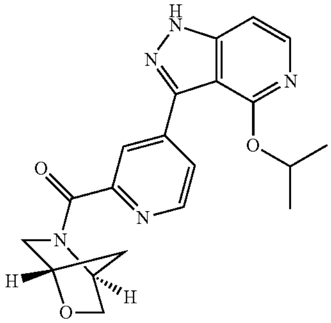 [SMILES: CC(C)Oc1nccc2[nH]nc(-c3ccnc(C(=O)N4C[C@@H]5C[C@H]4CO5)c3)c12] | 0.384 | | | |
| 221 | Pyrrolidin-1-yl-{4-[4-(tetrahydro-pyran-4-yloxy)-1H-pyrazolo[4,3-c]pyridin-3-yl]-pyridin-2-yl}-methanone | 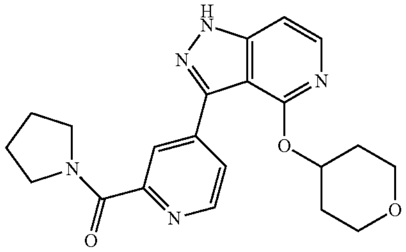 [SMILES: O=C(c1cc(-c2n[nH]c3ccnc(OC4CCOCC4)c23)ccn1)N1CCCC1] | 0.757 | | | |

TABLE 1-continued

| | Name | Structure | Ki (μM) | LC-MS Method | LC-MS Retn Time | LC-MS m/z |
|---|---|---|---|---|---|---|
| 222 | (1S,4S)-2-Oxa-5-aza-bicyclo[2.2.1]hept-5-yl-{4-[4-(tetrahydro-pyran-4-yloxy)-1H-pyrazolo[4,3-c]pyridin-3-yl]-pyridin-2-yl}-methanone | 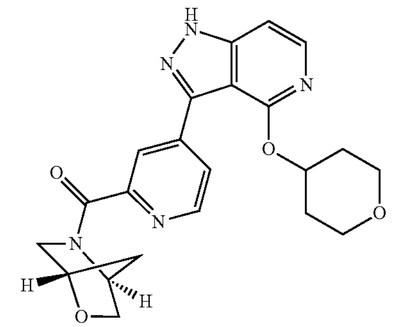 [SMILES: O=C(c1cc(-c2n[nH]c3ccnc(OC4CCOCC4)c23)ccn1)N1C[C@@H]2C[C@H]1CO2] | | | | |
| 223 | 4-(2-Methyl-cyclopentyloxy)-3-(2-morpholin-4-yl-pyridin-4-yl)-1H-pyrazolo[4,3-c]pyridine | 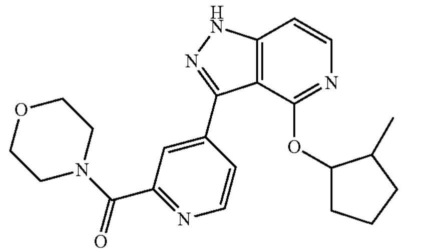 [SMILES: CC1CCCC1Oc1nccc2[nH]nc(-c3ccnc(C(=O)N4CCOCC4)c3)c12] | | | | |
| 224 | 3-(1-Isopropyl-1H-pyrazol-4-yl)-4-(tetrahydro-furan-3-yloxy)-1H-pyrazolo[4,3-c]pyridine | 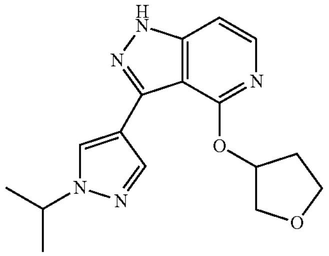 [SMILES: CC(C)n1cc(-c2n[nH]c3ccnc(OC4CCOC4)c23)cn1] | 0.007 | | | |
| 225 | 3-(2-morpholinopyridin-4-yl)-4-(tetrahydro-2H-pyran-4-yloxy)-1H-pyrazolo[4,3-c]pyridine-6-carbonitrile | 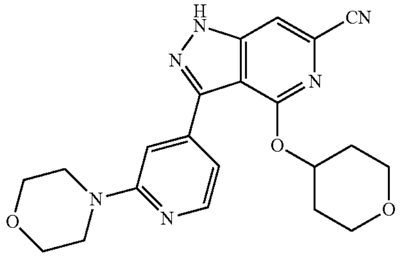 [SMILES: N#Cc1cc2[nH]nc(-c3ccnc(N4CCOCC4)c3)c2c(OC2CCOCC2)n1] | | | | |
| 226 | 4-(4-(6-chloro-4-(tetrahydro-2H-pyran-4-yloxy)-1H-pyrazolo[4,3-c]pyridin-3-yl)pyridin-2-yl)morpholine | 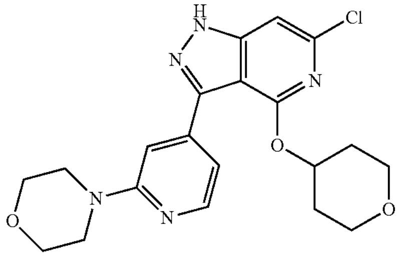 | | | | |

TABLE 1-continued

| | Name | Structure | Ki (μM) | LC-MS Method | LC-MS Retn Time | LC-MS m/z |
|---|---|---|---|---|---|---|
| 227 | 4-(4-(7-fluoro-4-(tetrahydro-2H-pyran-4-yloxy)-1H-pyrazolo[4,3-c]pyridin-3-yl)pyridin-2-yl)morpholine | 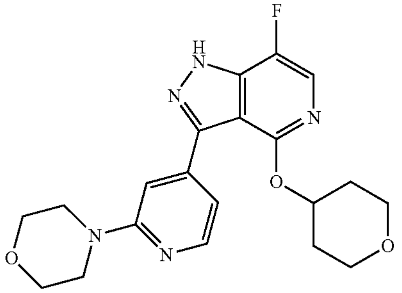 [SMILES: Fc1cnc(OC2CCOCC2)c2c(-c3ccnc(N4CCOCC4)c3)n[nH]c12] | | | | |
| 228 | 3-(1-isopropyl-1H-pyrazol-4-yl)-4-(tetrahydro-2H-pyran-4-yloxy)-1H-pyrazolo[4,3-c]pyridine-6-carbonitrile | 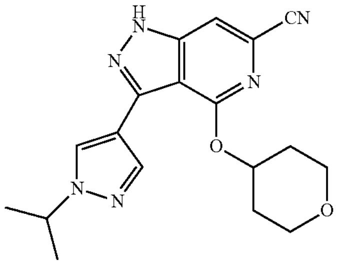 [SMILES: CC(C)n1cc(-c2n[nH]c3cc(C#N)nc(OC4CCOCC4)c23)cn1] | | | | |
| 229 | 6-chloro-3-(1-isopropyl-1H-pyrazol-4-yl)-4-(tetrahydro-2H-pyran-4-yloxy)-1H-pyrazolo[4,3-c]pyridine | 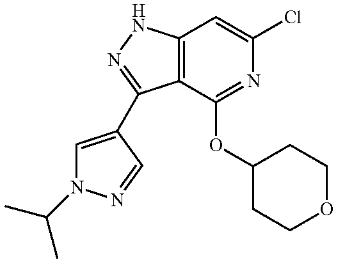 [SMILES: CC(C)n1cc(-c2n[nH]c3cc(Cl)nc(OC4CCOCC4)c23)cn1] | | | | |
| 230 | 7-fluoro-3-(1-isopropyl-1H-pyrazol-4-yl)-4-(tetrahydro-2H-pyran-4-yloxy)-1H-pyrazolo[4,3-c]pyridine | 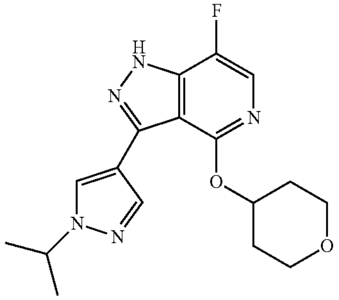 [SMILES: CC(C)n1cc(-c2n[nH]c3c(F)cnc(OC4CCOCC4)c23)cn1] | | | | |
| 231 | 3-(1-isobutyl-1H-pyrazol-4-yl)-4-(tetrahydro-2H-pyran-4-yloxy)-1H-pyrazolo[4,3-c]pyridine-6-carbonitrile | 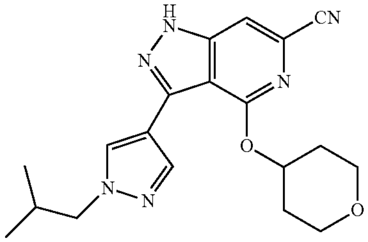 [SMILES: CC(C)Cn1cc(-c2n[nH]c3cc(C#N)nc(OC4CCOCC4)c23)cn1] | | | | |

TABLE 1-continued

| | Name | Structure | Ki (μM) | LC-MS Method | LC-MS Retn Time | LC-MS m/z |
|---|---|---|---|---|---|---|
| 232 | 6-chloro-3-(1-isobutyl-1H-pyrazol-4-yl)-4-(tetrahydro-2H-pyran-4-yloxy)-1H-pyrazolo[4,3-c]pyridine | 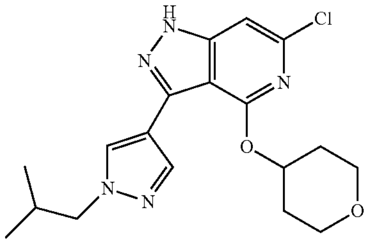 [SMILES: CC(C)Cn1cc(-c2n[nH]c3cc(Cl)nc(OC4CCOCC4)c23)cn1] | | | | |
| 233 | 7-fluoro-3-(1-isobutyl-1H-pyrazol-4-yl)-4-(tetrahydro-2H-pyran-4-yloxy)-1H-pyrazolo[4,3-c]pyridine | 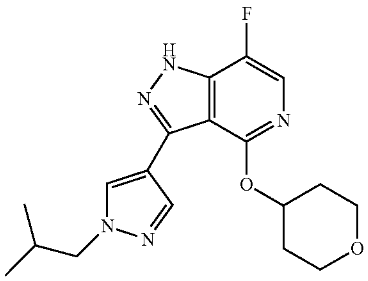 [SMILES: CC(C)Cn1cc(-c2n[nH]c3c(F)cnc(OC4CCOCC4)c23)cn1] | | | | |
| 234 | 4-methoxy-3-(1-(tetrahydrofuran-3-yl)-1H-pyrazol-4-yl)-1H-pyrazolo[4,3-c]pyridine | 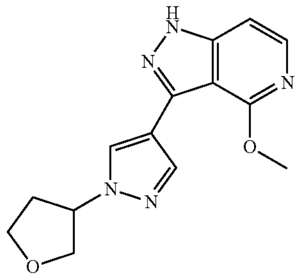 [SMILES: COc1nccc2[nH]nc(-c3cnn(C4CCOC4)c3)c12] | 0.023 | | | |
| 235 | 3-(4-methoxy-6-methyl-1H-pyrazolo[4,3-c]pyridin-3-yl)-N-methylbenzamide | 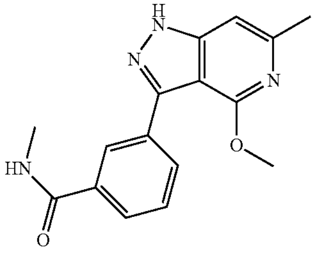 [SMILES: CNC(=O)c1cccc(-c2n[nH]c3cc(C)nc(OC)c23)c1] | 0.199 | | | |
| 236 | 4-(4-(4-methoxy-6-methyl-1H-pyrazolo[4,3-c]pyridin-3-yl)pyridin-2-yl)morpholine | 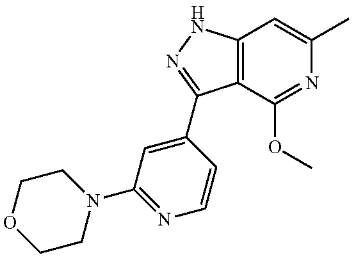 [SMILES: COc1nc(C)cc2[nH]nc(-c3ccnc(N4CCOCC4)c3)c12] | | | | |

TABLE 1-continued

| | Name | Structure | Ki (μM) | LC-MS Method | LC-MS Retn Time | LC-MS m/z |
|---|---|---|---|---|---|---|
| 237 | 3-(1-isopropyl-1H-pyrazol-4-yl)-4-(3-methoxypropoxy)-1H-pyrazolo[4,3-c]pyridine | 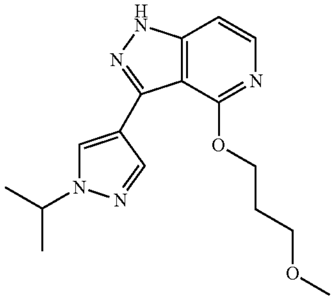 [SMILES: COCCCOc1nccc2[nH]nc(-c3cnn(C(C)C)c3)c12] | | | | |
| 238 | (2S,6R)-4-(4-(4-methoxy-1H-pyrazolo[4,3-c]pyridin-3-yl)pyridin-2-yl)-2,6-dimethylmorpholine | 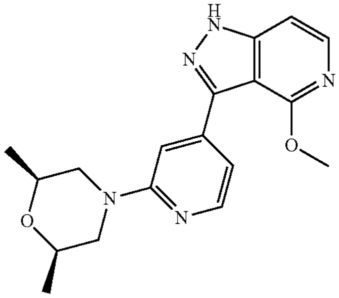 | 0.025 | | | |
| 239 | 3-(5-cyclopropyl-4H-1,2,4-triazol-3-yl)-N-(tetrahydro-2H-pyran-4-yl)-1H-pyrazolo[4,3-c]pyridin-4-amine | 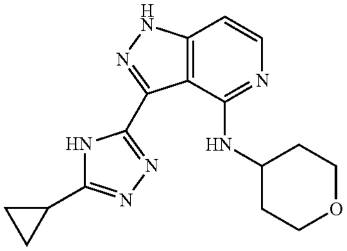 [SMILES: c1cc2[nH]nc(-c3nnc(C4CC4)[nH]3)c2c(NC2CCOCC2)n1] | | | | |

Abbreviations
DCM=Dichloromethane
DMF=N,N-Dimethylformamide
THF=Tetrahydrofuran
MeOH=Methanol
TFA=Trifluoroacetic acid
Xantphos=4,5-Bis(diphenylphosphino)-9,9-dimethylxanthene
HATU=N,N,N',N'-Tetramethyl-O-(7-azabenzotriazol-1-yl)uronium-hexafluorophospate
EDCI=1,3-Propanediamine, N3-(ethylcarbonimidoyl)-N1,N1-dimethyl-, hydrochloride
DCC=1,3-Dicyclohexylcarbodiimide
$Pd_2(dba)_3$=tris(dibenzylideneacetone)dipalladium(0)
TEA=Triethylamine
rm=Reaction mixture
rt=Room temperature
AcOH=Acetic acid
IPA=Isopropanol
DIPEA=N,N-diisopropylethylamine
TBSMSCl=Tertiarybutyldimethylsilyl chloride
MeCN=Acetonitrile
$NH_3$=Ammonia
EtOH=Ethanol
EtOAc=Ethyl Acetate
LCMS=Mass spectrometry directed high pressure liquid chromatography
UV=Ultraviolet
SCX=Strong cation exchange
TPAP=Tetrapropylammonium perruthenate
DMSO=Dimethylsulphoxide
BINAP=2,2'-bis(diphenylphosphino)-1,1'-binaphthyl
XPhos=2-Dicyclohexylphosphino-2',4',6'-triisopropylbiphenyl Intermediate 1

2,4-Dichloro-pyridine-3-carbaldehyde

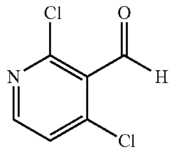

To a solution of n-butyllithium (1.6 M in hexane, 64 ml, 101 mmol) in THF (150 ml) at −78° C. was added diisopropylamine (14.3 ml, 101 mmol) dropwise. The reaction mixture was allowed to warm to 0° C. over 1 h, and then cooled down to −78° C. 2,4-Dichloropyridine (11 ml, 101 mmol) was added dropwise and the solution was stirred at −78° C. for 2.5 h. N-Formylpiperidine (11.2 ml, 101 mmol) was then added dropwise and the mixture stirred at −78° C. for a further 1.5 h. The solution was quenched at −78° C. with saturated $NH_4Cl$ (aq) and then allowed to warm to room temperature. The reaction mixture was diluted with ethyl acetate and washed with 1M HCl (aq), the organic phase was separated, washed with saturated $NaHCO_3$ (aq), dried ($MgSO_4$) and evaporated to dryness. The crude residue was purified by flash chromatography, eluting with 0 to 20% ethyl acetate/petroleum ether gradient to give a yellow solid (9.7 g, 54%). $^1H$ NMR (400 MHz, DMSO-$d_6$) δ ppm 7.78 (d, J=5.04 Hz, 1H), 8.56 (d, J=5.50 Hz, 1H), 10.31 (s, 1H). $R_f$(20% ethyl acetate in petroleum ether)=0.70.

Intermediate 2

4-Chloro-1H-pyrazolo[4,3-c]pyridine

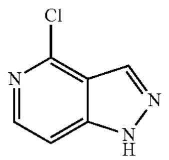

To a solution of Intermediate 1 (1.7 g, 9.7 mmol) in dimethoxyethane (12 ml) at room temperature was added hydrazine monohydrate (1.2 ml, 38.6 mmol) and the resulting mixture was stirred at 75° C. overnight. The mixture was then concentrated to dryness and the crude residue was purified by flash chromatography, eluting with 20 to 100% ethyl acetate/petroleum ether gradient to give a white solid (0.82 g, 56%). $^1H$ NMR (400 MHz, DMSO-$d_6$) δ ppm 7.60 (d, J=6.9 Hz, 1 H), 8.14 (d, J=6.0 Hz, 1 H), 8.32 (s, 1 H); m/z (ES+APCI)$^+$: 154 $[M+H]^+$.

Intermediate 3

4-Chloro-3-iodo-1H-pyrazolo[4,3-c]pyridine

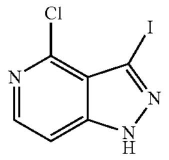

To a mixture of Intermediate 2 (5.8 g, 38 mmol) and KOH (8 g, 142 mmol) in dioxane (100 ml) at room temperature was added iodine (19 g, 76 mmol). The reaction mixture was stirred at 75° C. for 4 h, and then allowed to cool to room temperature. The solution was diluted with saturated $Na_2S_2O_3$ (aq), and the resulting precipitate was filtered and dried to give a yellow solid (4.1 g). The filtrate was left standing for 3 days and filtration of the resulting precipitate yielded a further 2.35 g of the product. Combined yield (6.45 g, 61%). 1H NMR (400 MHz, DMSO-d6) δ ppm 7.64 (d, J=6.0 Hz, 1 H), 8.11 (d, J=6.0 Hz, 1 H); m/z (ES+APCI)+: 280 [M+H]+.

Intermediate 4

4-Chloro-3-iodo-1-(4-methoxy-benzyl)-1H-pyrazolo[4,3-c]pyridine

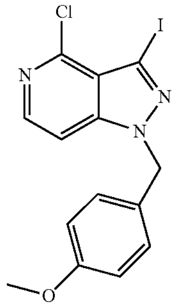 [SMILES: COc1ccc(Cn2nc(I)c3c(Cl)nccc32)cc1]

To a mixture of Intermediate 3 (1 g, 3.6 mmol) and KOH (0.3 mg, 5.4 mmol) in DMF (10 ml) at room temperature was added 4-methoxybenzyl chloride (0.5 ml, 3.6 mmol). The resulting mixture was stirred at room temperature for 2.5 h, and then evaporated to dryness. The crude residue was dissolved in EtOAc and washed with water. The organic phase was dried and purified by flash chromatography, eluting with 0 to 30% ethyl acetate/petroleum ether gradient to give a 9:1 mixture of regioisomers as a solid (1.3 g, 93%). Major regioisomer: $^1H$ NMR (400 MHz, DMSO-$d_6$) δ ppm 3.72 (s, 3 H), 5.62 (s, 2 H), 6.85-6.94 (m, 2 H), 7.20-7.27 (m, 2 H), 7.95 (d, J=6.0 Hz, 1 H), 8.20 (d, J=6.0 Hz, 1 H); m/z (ES+APCI)$^+$: 400 $[M+H]^+$.

Intermediate 5

3-Iodo-1-(4-methoxybenzyl)-N-(tetrahydro-2H-pyran-4-yl)-1H-pyrazolo[4,3-c]pyridin-4-amine

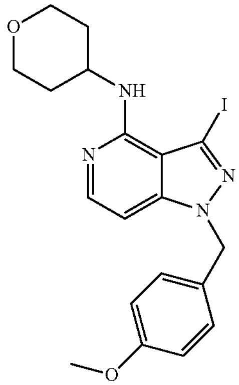 [SMILES: COc1ccc(Cn2nc(I)c3c(NC4CCOCC4)nccc32)cc1]

To a solution of Intermediate 4 (5 g, 12.5 mmol) in 1-butanol (25 ml) at room temperature was added 4-aminotetrahydropyran (5 g, 50 mmol). The resulting mixture was transferred into two 20 ml microwave vials and then irradiated at 180° C. for 1 h in a Biotage I-60 microwave reactor. The mixture was then evaporated to dryness and the crude residue was purified by flash chromatography gradient elution from 0-20% methanol in ethyl acetate to give a white solid (5.36 g, 92%) $^1$H NMR (400 MHz, DMSO-$d_6$) δ ppm 1.46-1.60 (m, 2 H), 1.95-2.09 (m, 2 H), 3.43-3.60 (m, 2 H), 3.70 (s, 3 H), 3.87 (m, 2 H), 4.21-4.32 (m, 1 H), 5.45 (s, 2 H), 5.97 (d, J=7.3 Hz, 1 H), 6.84-6.93 (m, 2 H), 6.99 (d, J=6.4 Hz, 1 H), 7.15-7.26 (m, 2 H), 7.78 (d, J=6.4 Hz, 1 H); m/z (ES+APCI)$^+$: 465 $[M+H]^+$.

Intermediate 6

Methyl (2E)-3-[1-(4-methoxybenzyl)-4-(tetrahydro-2H-pyran-4-ylamino)-1H-pyrazolo[4,3-c]pyridin-3-yl]prop-2-enoate

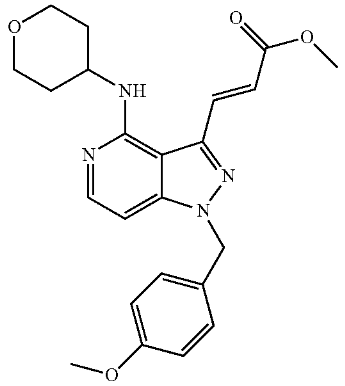 [SMILES: COC(=O)/C=C/c1nn(Cc2ccc(OC)cc2)c2ccnc(NC3CCOCC3)c12]

To a mixture of Intermediate 5 (0.6 g, 1.3 mmol), tetrabutylammonium iodide (0.95 g, 2.6 mmol), DMF (15 ml), water (2.4 ml) and triethylamine (2.4 ml) at room temperature was added methyl acrylate (1.16 ml, 13 mmol) followed by Pd(dppf)$Cl_2$ (0.21 g, 0.26 mmol) respectively. The resulting mixture was heated at 70° C. overnight and then evaporated to dryness. The crude residue was purified by flash chromatography, to give a brown solid (0.39 g, 71%). $^1$H NMR (400 MHz, DMSO-$d_6$) δ ppm 1.49-1.73 (m, 2 H), 1.89 (m, 2 H), 3.35-3.47 (m, 2 H), 3.70 (s, 3 H), 3.75 (s, 3 H), 3.89 (m, 2 H), 4.04-4.43 (m, 1 H), 5.50 (s, 2 H), 6.46 (d, J=7.3 Hz, 1 H), 6.68 (d, J=15.6 Hz, 1 H), 6.85-6.90 (m, 2 H), 6.96 (d, J=6.4 Hz, 1 H), 7.20-7.25 (m, 2 H), 7.81 (d, J=6.4 Hz, 1 H), 8.09 (d, J=15.6 Hz, 1 H); m/z (ES+APCI)$^+$: 423 $[M+H]^+$.

Intermediate 7

Methyl 3-[1-(4-methoxybenzyl)-4-(tetrahydro-2H-pyran-4-ylamino)-1H-pyrazolo[4,3-c]pyridin-3-yl]propanoate

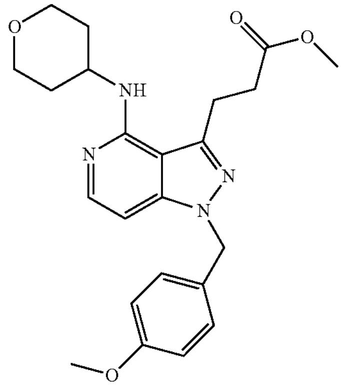 [SMILES: COC(=O)CCc1nn(Cc2ccc(OC)cc2)c2ccnc(NC3CCOCC3)c12]

To a solution of Intermediate 6 (0.39 g, 0.92 mmol) in 1:1 ethyl acetate/ethanol (10 ml) at room temperature was added 10% Pd/C (80 mg). The resulting mixture was stirred under an atmosphere of hydrogen at room temperature overnight. A further 50 mg of 10% Pd/C was added and the mixture stirred for a further 24 h. The reaction mixture was then filtered through Celite™ and evaporated to give a brown oil (0.31 mg, 80%). $^1$H NMR (400 MHz, DMSO-$d_6$) δ ppm 1.56-1.74 (m, 2 H), 1.90 (m, 2 H), 2.78 (t, J=7.1 Hz, 2 H), 3.30 (t, J=7.1 Hz, 2 H), 3.42 (m, 2 H), 3.58 (s, 3 H), 3.69 (s, 3 H), 3.85-3.93 (m, 2 H), 4.20-4.30 (m, 1 H), 5.34 (s, 2 H), 5.83 (d, J=7.8 Hz, 1 H), 6.78-6.88 (m, 3 H), 7.10-7.16 (m, 2 H), 7.70 (d, J=6.4 Hz, 1 H); m/z (ES+APCI)$^+$: 425 $[M+H]^+$.

Intermediate 8

Methyl 3-[4-(tetrahydro-2H-pyran-4-ylamino)-1H-pyrazolo[4,3-c]pyridin-3-yl]propanoate

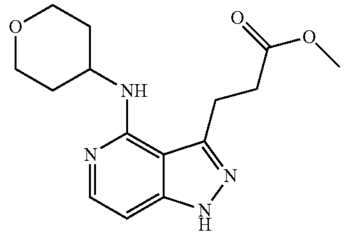 [SMILES: COC(=O)CCc1n[nH]c2ccnc(NC3CCOCC3)c12]

A solution of Intermediate 7 (0.31 g, 0.73 mmol) in TFA (3 ml) was stirred at 70° C. overnight. The reaction mixture was cooled to room temperature and then evaporated. The crude residue was re-dissolved in 10% MeOH/EtOAc and eluted through an SCX cartridge, eluting first with 10% MeOH/EtOAc, followed by 2 M $NH_3$ in methanol to yield a brown gum (220 mg, 99%). $^1$H NMR (400 MHz, DMSO-$d_6$) δ ppm 1.59-1.70 (m, 2 H), 1.89-1.95 (m, 2 H), 2.79 (t, J=7.1 Hz, 2 H), 3.27-3.33 (m, 2 H), 3.37-3.48 (m, 2 H), 3.58 (s, 3 H), 3.86-3.92 (m, 2 H), 4.21-4.30 (m, 1 H), 5.75-5.81 (m, 1 H), 6.61 (d, J=6.0 Hz, 1 H), 7.68 (d, J=6.0 Hz, 1 H); m/z (ES+APCI)$^+$: 305 $[M+H]^+$.

Intermediate 9

3-[4-(Tetrahydro-2H-pyran-4-ylamino)-1H-pyrazolo[4,3-c]pyridin-3-yl]propanoic acid

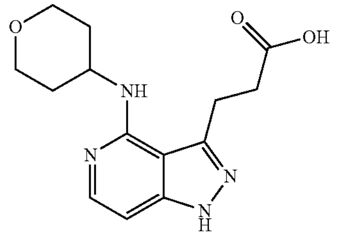 [SMILES: O=C(O)CCc1n[nH]c2ccnc(NC3CCOCC3)c12]

To a stirring solution of Intermediate 8 (0.22 g, 0.72 mmol) in methanol (3 ml) at room temperature was added 2M aqueous NaOH (0.9 ml, 1.8 mmol). The resulting mixture was stirred at room temperature overnight. Acetic acid (85 μl, 1.45 mmol) was then added, and the resulting mixture was evaporated in the Genevac to give a gum (225 mg). $^1$H NMR (400 MHz, DMSO-$d_6$) δ ppm 1.55-1.73 (m, 2 H), 1.86-2.06 (m, 2 H), 2.29-2.43 (m, 2 H), 2.95-3.16 (m, 2 H), 3.29-3.56 (m, 2

H), 3.75-3.99 (m, 2 H), 4.06-4.29 (m, 1 H), 6.40-6.74 (m, 1 H), 7.41-7.75 (m, 1 H), 7.79-7.98 (m, 1 H); m/z (ES+APCI)$^+$: 291 [M+H]$^+$.

Intermediate 10

4-Chloro-3-iodo-1-trityl-1H-pyrazolo[4,3-c]pyridine

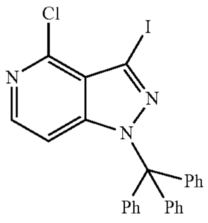 [SMILES: Clc1nccc2c1c(I)nn2C(c1ccccc1)(c1ccccc1)c1ccccc1]

NaH (60% dispersion, 108 mg, 2.69 mmol) was added to a solution of Intermediate 3 (500 mg, 1.79 mmol) in DMF (2 ml) at 0° C. and the mixture was stirred at this temperature for 30 min. Trityl chloride (550 mg, 1.97 mmol) was then added and stirring continued at room temperature for 19 h. Water was added, and the white precipitate was filtered and washed with water. The residue was then dissolved in DCM, washed with water, followed by brine, dried ($MgSO_4$) and solvents evaporated to give a white solid (900 mg, 96%). 1H NMR (400 MHz, DMSO-d6) δ ppm 6.33 (d, J=7.8 Hz, 1 H), 7.15-7.19 (m, 5 H), 7.31-7.46 (m, 10 H), 7.91 (d, J=6.4 Hz, 1 H); Rf=0.52 (1:1, petroleum ether:ethyl acetate).

Intermediate 11

4-(Cyclohexyloxy)-3-iodo-1-trityl-1H-pyrazolo[4,3-c]pyridine

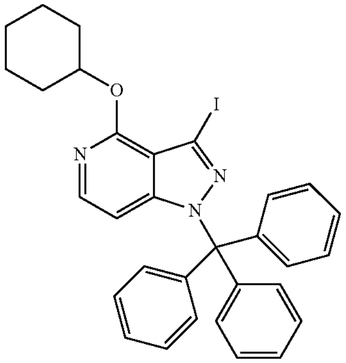 [SMILES: Ic1nn(C(c2ccccc2)(c2ccccc2)c2ccccc2)c2ccnc(OC3CCCCC3)c12]

Sodium hydride (60% dispersion, 287 mg, 7.2 mmol) was added slowly to a solution of cyclohexanol (998 μl, 9.6 mmol) in dioxane (15 ml) at room temperature. The resulting suspension was stirred at room temperature for 1 h, then Intermediate 10 (2.5 g, 4.8 mmol) was added. The mixture was irradiated at 180° C. for 1.5 h in a Biotage I-60 microwave reactor and then evaporated to dryness. The crude residue was partitioned between DCM and water. The organic phase was dried ($MgSO_4$), evaporated. The crude residue was triturated with MeOH and filtered to yield a white solid after drying (2.5 g, 89%) $^1$H NMR (400 MHz, DMSO-$d_6$) δ ppm 1.37-1.58 (m, 4 H), 1.61-1.77 (m, 2 H), 1.86 (br. s., 4 H), 5.26-5.35 (m, 1 H), 5.79 (d, J=6.0 Hz, 1 H), 7.07-7.22 (m, 6 H), 7.22-7.43 (m, 9 H), 7.54 (d, J=6.4 Hz, 1 H); m/z (ES+APCI)$^+$: 586 [M+H]$^+$.

Intermediate 12

Methyl (2E)-3-[4-(cyclohexyloxy)-1-trityl-1H-pyrazolo[4,3-c]pyridin-3-yl]prop-2-enoate

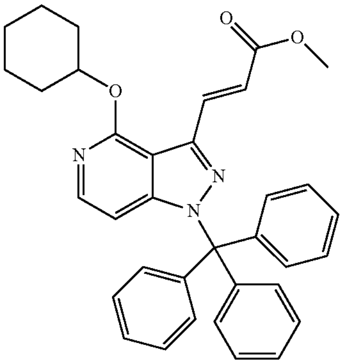 [SMILES: COC(=O)/C=C/c1nn(C(c2ccccc2)(c2ccccc2)c2ccccc2)c2ccnc(OC3CCCCC3)c12]

To a mixture of Intermediate 11 0.5 g, 0.85 mmol), tetrabutylammonium iodide (0.63 g, 1.71 mmol), DMF (12.5 ml), water (2 ml), triethylamine (2 ml) at room temperature was added methyl acrylate (770 μl, 8.55 mmol) and Pd(dppf)$Cl_2$ (0.14 g, 0.17 mmol) respectively. The resulting mixture was heated at 105° C. overnight and then evaporated to dryness. The crude residue was purified by flash chromatography, eluting with 0 to 5% ethyl acetate/petroleum ether gradient to give a white solid (0.2 g, 44%) $^1$H NMR (400 MHz, DMSO-$d_6$) δ ppm 1.36-1.58 (m, 4 H), 1.58-1.71 (m, 2 H), 1.71-1.83 (m, 2 H), 1.91-2.02 (m, 2 H), 3.73 (s, 3 H), 5.25-5.33 (m, 1 H), 5.78 (d, J=6.0 Hz, 1 H), 6.75 (d, J=16.0 Hz, 1 H), 7.07-7.18 (m, 6 H), 7.27-7.41 (m, 9 H), 7.59 (d, J=6.4 Hz, 1 H), 7.97 (d, J=16.0 Hz, 1 H); m/z (ES+APCI)$^+$: 544 [M+H]$^+$.

Intermediate 13

Methyl (2E)-3-[4-(cyclohexyloxy)-1H-pyrazolo[4,3-c]pyridin-3-yl]prop-2-enoate

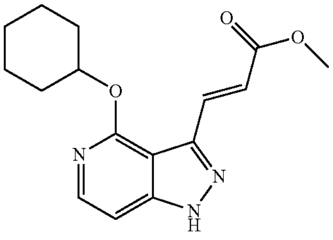 [SMILES: COC(=O)/C=C/c1n[nH]c2ccnc(OC3CCCCC3)c12]

A solution of Intermediate 12 (0.2 g, 0.37 mmol) in 10% TFA/DCM (0.4/3.6 ml) was stirred at room temperature overnight. The reaction mixture was evaporated and the crude residue was re-dissolved in 10% MeOH/EtOAc and eluted through an SCX cartridge, eluting first with 10% MeOH/EtOAc, followed by 2M $NH_3$ in methanol. The crude mixture was evaporated and purified by flash chromatography, eluting with 10 to 50% ethyl acetate/petroleum ether gradient to give a white solid (50 mg, 45%) $^1$H NMR (400 MHz, DMSO-$d_6$) δ ppm 1.35-1.56 (m, 4 H), 1.56-1.70 (m, 2 H), 1.70-1.82 (m, 2 H), 1.94-2.03 (m, 2 H), 3.75 (s, 3 H), 5.34 (t, J=3.9 Hz, 1 H), 6.99 (d, J=16.0 Hz, 1 H), 7.13 (d, J=6.0 Hz, 1 H), 7.89 (d, J=6.0 Hz, 1 H), 8.01 (d, J=16.0 Hz, 1 H); m/z (ES+APCI)$^+$: 302 [M+H]$^+$.

Intermediate 14

Methyl 3-[4-(cyclohexyloxy)-1H-pyrazolo[4,3-c]pyridin-3-yl]propanoate

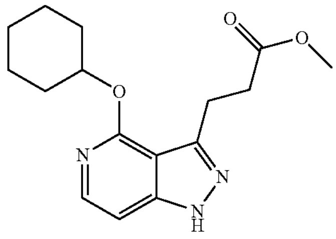 [SMILES: COC(=O)CCc1n[nH]c2ccnc(OC3CCCCC3)c12]

To a solution of Intermediate 13 (45 mg, 0.15 mmol) in 1:1 ethyl acetate/ethanol (3 ml) at room temperature was added 10% Pd/C (15 mg). The resulting mixture was stirred under an atmosphere of hydrogen at room temperature overnight. The reaction mixture was then filtered through Celite™ and evaporated to give a brown gum (38 mg, 84%) $^1$H NMR (400 MHz, DMSO-d$_6$) δ ppm 1.33-1.56 (m, 4 H), 1.56-1.68 (m, 2 H), 1.68-1.80 (m, 2 H), 1.83-2.00 (m, 2 H), 2.80 (t, J=7.6 Hz, 2 H), 3.22 (t, J=7.8 Hz, 2 H), 3.60 (s, 3 H), 5.23-5.34 (m, 1 H), 6.99 (d, J=6.0 Hz, 1 H), 7.79 (d, J=6.0 Hz, 1 H); m/z (ES+APCI)$^+$: 304 [M+H]$^+$.

Intermediate 15

3-[4-(Cyclohexyloxy)-1H-pyrazolo[4,3-c]pyridin-3-yl]propanoic acid

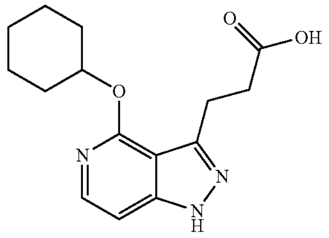 [SMILES: O=C(O)CCc1n[nH]c2ccnc(OC3CCCCC3)c12]

To a stirred solution of Intermediate 14 (38 mg, 0.12 mmol) in methanol (1.5 ml) at room temperature was added 2M NaOH (156 μl, 0.31 mmol). The resulting mixture was stirred at room temperature overnight, and then evaporated. The crude residue was dissolved in water, and acetic acid (15 μl) was then added, and the resulting precipitate was filtered and dried to give a white solid (29 mg, 80%). $^1$H NMR (400 MHz, DMSO-d$_6$) δ ppm 1.33-1.82 (m, 8 H), 1.85-2.17 (m, 2 H), 2.64-2.89 (m, 2 H), 3.07-3.28 (m, 2 H), 4.80-5.63 (m, 1 H), 7.02 (d, J=6.41 Hz, 1 H), 7.82 (d, J=5.95 Hz, 1 H), 12.20 (br. s., 1 H); m/z (ES+APCI)$^+$: 290 [M+H]$^+$.

Intermediate 16

Cyclohexyl-[3-iodo-1-(4-methoxy-benzyl)-1H-pyrazolo[4,3-c]pyridin-4-yl]-amine

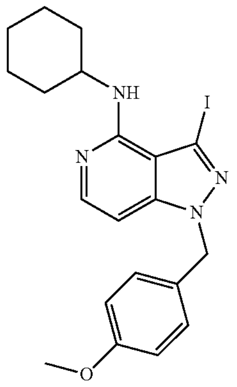 [SMILES: COc1ccc(Cn2nc(I)c3c(NC4CCCCC4)nccc32)cc1]

To a solution of Intermediate 4 (0.95 g, 2.4 mmol) in 1-butanol (5 ml) at room temperature was added cyclohexylamine (1.1 ml, 9.52 mmol). The resulting mixture was irradiated at 190° C. for 1 h in a Biotage I-60 microwave reactor. The reaction mixture was then evaporated to dryness and the crude residue was purified by flash chromatography eluting with 10 to 100% ethyl acetate/petroleum ether gradient to give a white solid (0.87 g, 80%) $^1$H NMR (400 MHz, DMSO-d$_6$) δ ppm 1.24-1.50 (m, 5 H), 1.50-1.63 (m, 1 H), 1.63-1.80 (m, 2 H), 1.86-2.03 (m, 2 H), 3.72 (s, 3 H), 4.02-4.15 (m, 1 H), 5.43 (s, 2 H), 5.95 (d, J=7.3 Hz, 1 H), 6.85-6.90 (m, 2 H), 6.95 (d, J=6.0 Hz, 1 H), 7.15-7.24 (m, 2 H), 7.76 (d, J=6.0 Hz, 1 H); m/z (ES+APCI)$^+$: 463 [M+H]$^+$.

Intermediate 17

4-{(E)-2-[4-Cyclohexylamino-1-(4-methoxy-benzyl)-1H-pyrazolo[4,3-c]pyridin-3-yl]-vinyl}-benzoic acid methyl ester

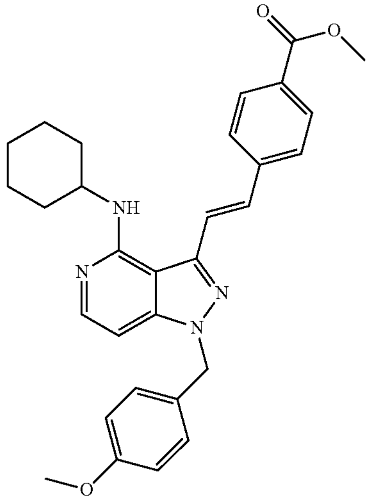 [SMILES: COC(=O)c1ccc(/C=C/c2nn(Cc3ccc(OC)cc3)c3ccnc(NC4CCCCC4)c23)cc1]

To a mixture of Intermediate 16 (0.25 g, 0.54 mmol) and tetrabutylammonium iodide (0.4 g, 1.08 mmol) in DMF/water/triethylamine (5 ml/0.75 ml/0.75 ml) at room temperature was added methyl-4-vinyl benzoate (0.44 g, 2.7 mmol) and [1,1'-bis(diphenylphosphino)ferrocene]palladium(II) chloride (88 mg, 0.11 mmol) respectively. The resulting mixture was heated at 70° C. overnight and then evaporated to dryness. The crude residue was dissolved in EtOAc and washed with water. The organic phase was collected, dried ($MgSO_4$) and then evaporated. The crude residue was purified by flash chromatography, eluting with 10 to 100% ethyl acetate/petroleum ether gradient to give the desired product as a brown solid (190 mg, 70%). $^1$H NMR (400 MHz, DMSO-$d_6$) δ ppm 1.15-1.24 (m, 1 H), 1.27-1.48 (m, 4 H), 1.59-1.65 (m, 1 H), 1.70-1.77 (m, 2 H), 1.94-2.01 (m, 2 H), 3.69 (s, 3 H), 3.86 (s, 3 H), 4.03-4.11 (m, 1 H), 5.47 (s, 2 H), 6.14 (d, J=7.8 Hz, 1 H), 6.85-6.90 (m, 3 H), 7.19-7.23 (m, 2 H), 7.45 (d, J=16.0 Hz, 1 H), 7.73-7.82 (m, 2 H), 7.85 (d, J=8.2 Hz, 2 H), 7.98 (d, J=8.7 Hz, 2 H); m/z (ES+APCI)$^+$: 497 [M+H]$^+$.

Intermediate 18

4-{2-[4-Cyclohexylamino-1-(4-methoxy-benzyl)-1H-pyrazolo[4,3-c]pyridin-3-yl]ethyl}-benzoic acid methyl ester

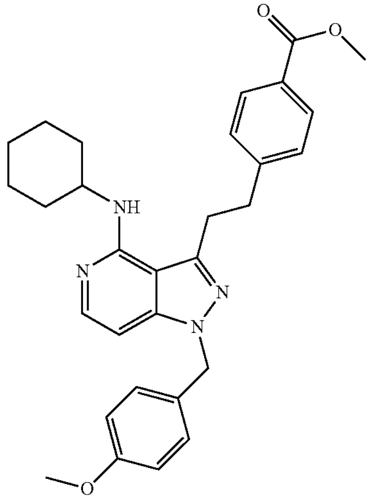 [SMILES: COC(=O)c1ccc(CCc2nn(Cc3ccc(OC)cc3)c3ccnc(NC4CCCCC4)c23)cc1]

To Intermediate 17 (0.19 g, 0.38 mmol) in ethanol (5 ml) at room temperature was added 10% Pd/C (40 mg). The resulting mixture was stirred under an atmosphere of hydrogen at room temperature overnight. A further 40 mg of 10% Pd/C was added and the mixture stirred for a further 24 h. The reaction mixture was then filtered through Celite™ and evaporated to give the product as a brown gum (185 mg, 97%). $^1$H NMR (400 MHz, DMSO-$d_6$) δ ppm 1.12-1.27 (m, 1 H), 1.27-1.42 (m, 4 H), 1.57-1.65 (m, 1 H), 1.66-1.76 (m, 2 H), 1.92-1.99 (m, 2 H), 3.05-3.11 (m, 2 H), 3.34-3.41 (m, 2 H), 3.70 (s, 3 H), 3.83 (s, 3 H), 3.98-4.06 (m, 1 H), 5.32 (s, 2H), 5.61 (d, J=6.4 Hz, 1 H), 6.74 (d, J=6.0 Hz, 1 H), 6.77-6.82 (m, 2 H), 7.01-7.06 (m, 2 H), 7.34-7.38 (m, 2 H), 7.68 (d, J=6.4 Hz, 1 H), 7.82-7.87 (m, 2 H); m/z (ES+APCI)$^+$: 499 [M+H]$^+$.

Intermediate 19

4-[2-(4-Cyclohexylamino-1H-pyrazolo[4,3-c]pyridin-3-yl)-ethyl]-benzoic acid methyl ester

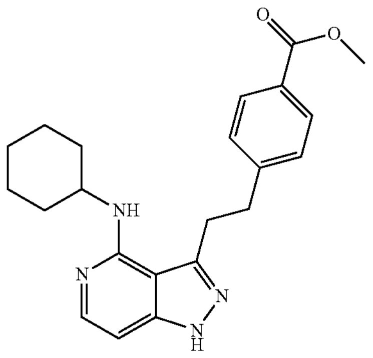 [SMILES: COC(=O)c1ccc(CCc2n[nH]c3ccnc(NC4CCCCC4)c23)cc1]

A solution of Intermediate 18 (0.18 g, 0.37 mmol) in TFA (2 ml) was stirred at 70° C. overnight. The reaction mixture was cooled to room temperature, diluted with DCM, and saturated $Na_2CO_3$ (aq) was added. The organic phase was separated, filtered through a phase separation tube and evaporated. The crude residue was purified by flash chromatography, eluting with 20% ethyl acetate/petroleum ether to 10% 2M $NH_3$ in MeOH in ethyl acetate gradient to give the product as a brown solid (0.12 g, 86%). $^1$H NMR (400 MHz, DMSO-$d_6$) δ ppm 1.13-1.24 (m, 1 H), 1.27-1.41 (m, 4 H), 1.58-1.66 (m, 1 H), 1.67-1.76 (m, 2 H), 1.92-2.01 (m, 2 H), 3.06-3.12 (m, 2 H), 3.34-3.42 (m, 2 H), 3.83 (s, 3 H), 3.99-4.07 (m, 1 H), 5.52 (d, J=7.8 Hz, 1 H), 6.58 (d, J=6.0 Hz, 1 H), 7.42 (d, J=8.2 Hz, 2 H), 7.67 (d, J=6.0 Hz, 1 H), 7.88 (d, J=8.7 Hz, 2 H); m/z (ES+APCI)$^+$: 379 [M+H]$^+$.

Intermediate 20

4-[2-(4-Cyclohexylamino-1H-pyrazolo[4,3-c]pyridin-3-yl)-ethyl]-benzoic acid

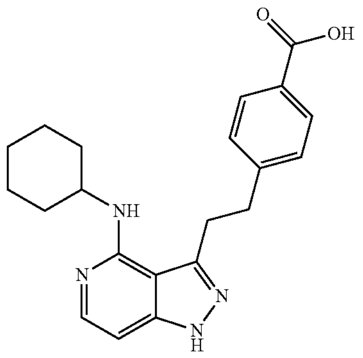 [SMILES: O=C(O)c1ccc(CCc2n[nH]c3ccnc(NC4CCCCC4)c23)cc1]

To a stirred solution of Intermediate 19 (0.1 g, 0.26 mmol) in methanol (2 ml) at room temperature was added 2M NaOH (0.33 ml, 0.66 mmol). The resulting mixture was stirred at 70° C. overnight. Acetic acid (40 μl, 0.66 mmol) was then added, and the resulting precipitate was filtered and dried to give a white solid (35 mg, 36%). $^1$H NMR (400 MHz, DMSO-$d_6$) δ ppm 1.13-1.24 (m, 1 H), 1.27-1.43 (m, 4 H), 1.58-1.65 (m, 1 H), 1.68-1.78 (m, 2 H), 1.93-2.01 (m, 2H), 3.05-3.12 (m, 2 H), 3.36-3.45 (m, 2 H), 3.96-4.05 (m, 1 H), 5.68 (br. s., 1 H), 6.62 (d, J=6.0 Hz, 1 H), 7.36-7.41 (m, 2 H), 7.66 (d, J=6.0 Hz, 1 H), 7.84-7.88 (m, 2 H); m/z (ES+APCI)$^+$: 364 [M+H]$^+$.

Intermediate 21

3-Iodo-4-(tetrahydro-2H-pyran-4-yloxy)-1-trityl-1H-pyrazolo[4,3-c]pyridine

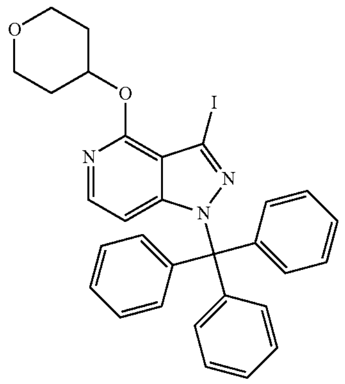 [SMILES: Ic1nn(C(c2ccccc2)(c2ccccc2)c2ccccc2)c2ccnc(OC3CCOCC3)c12]

Two separate 10-20 ml Biotage microwave vials were each charged with a solution of tetrahydro-2H-pyran-4-ol (1.46 ml, 15.4 mmol) in dioxane (10 ml). To each vial was added sodium hydride (60% dispersion in mineral oil, 0.536 g, 13.4 mmol), and the resulting suspension was stirred at room temperature for 3 h, prior to addition of a solution of Intermediate 10 (2 g, 3.83 mmol) in dioxane (2.5 ml), followed by irradiation at 190° C. for 2 h in a Biotage I-60 microwave reactor. The reaction mixtures from each vial were combined, concentrated under reduced pressure, and the residue was partitioned between water (100 ml) and ethyl acetate (100 ml). The layers were separated and the aqueous phase was extracted with ethyl acetate (400 ml) and the combined organic layers were washed with brine, dried ($MgSO_4$) and concentrated. Purification by flash chromatography (gradient elution from 0 to 50% EtOAc in petroleum ether) gave a pale yellow solid (2 g, 44%). $^1H$ NMR (400 MHz, DMSO-$d_6$) δ ppm 1.71-1.80 (m, 2 H), 1.97-2.08 (m, 2 H), 3.56-3.65 (m, 2 H), 3.94-4.02 (m, 2 H), 5.44-5.51 (m, 1 H), 5.79-5.83 (m, 1 H), 7.10-7.15 (m, 6 H), 7.26-7.41 (m, 9 H), 7.54 (d, J=6.9 Hz, 1 H). m/z (ES+APCI)$^+$: 588 [M+H]+

Intermediate 22

1-(4-Methoxybenzyl)-3-[2-(morpholin-4-yl)pyridin-4-yl]-N-(tetrahydro-2H-pyran-4-yl)-1H-pyrazolo[4,3-c]pyridin-4-amine

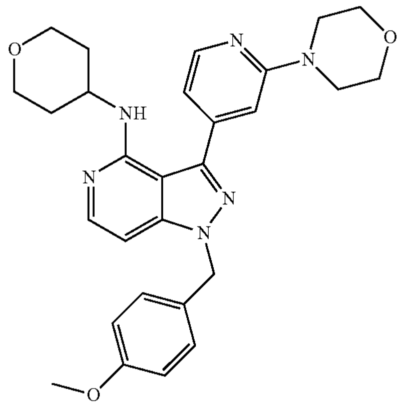 [SMILES: COc1ccc(Cn2nc(-c3ccnc(N4CCOCC4)c3)c3c(NC4CCOCC4)nccc32)cc1]

To a solution of Intermediate 5 (0.1 g, 0.2 mmol) and 2-morpholinopyridine-4-boronic acid pinacol ester (94 mg, 0.32 mmol) in dioxane (2 ml) at room temperature was added bis(diphenylphosphino)ferrocene]palladium(II) chloride (18 mg, 0.02 mmol) followed by 2M sodium carbonate (377 μl, 0.75 mmol). The resulting mixture was degassed and then heated at 90° C. overnight. The reaction mixture was then evaporated to dryness and the crude residue was purified by flash chromatography (gradient elution from 0-10% methanol/ethyl acetate) to give a cream solid (110 mg). $^1H$ NMR (400 MHz, DMSO-$d_6$) δ ppm 1.30-1.49 (m, 2 H), 1.82-1.97 (m, 2 H), 3.35-3.46 (m, 2 H), 3.48-3.60 (m, 4 H), 3.63-3.85 (m, 9 H), 4.14-4.31 (m, 1 H), 5.38 (d, J=7.3 Hz, 1 H), 5.51 (s, 2 H), 6.78-6.91 (m, 2 H), 6.92-7.01 (m, 2 H), 7.05 (s, 1 H), 7.10-7.42 (m, 2 H), 7.83 (d, J=6.0 Hz, 1 H), 8.27 (s, 1 H); m/z (ES+APCI)$^+$: 501 [M+H]$^+$.

Intermediate 23

1-(4-Methoxybenzyl)-3-[3-(morpholin-4-yl)phenyl]-N-(tetrahydro-2H-pyran-4-yl)-1H-pyrazolo[4,3-c]pyridin-4-amine

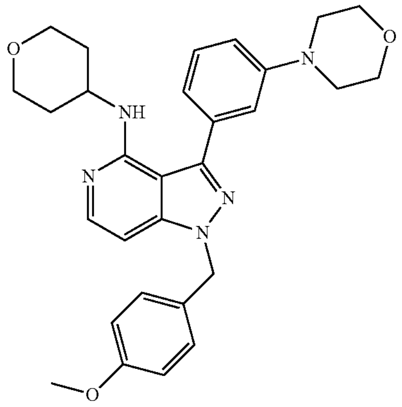 [SMILES: COc1ccc(Cn2nc(-c3cccc(N4CCOCC4)c3)c3c(NC4CCOCC4)nccc32)cc1]

Prepared analogously to Intermediate 22 from Intermediate 5 and 3-morpholinophenylboronic acid pinacol ester to give the desired product as a white solid (120 mg) $^1H$ NMR (400 MHz, DMSO-$d_6$) δ ppm 1.22-1.31 (m, 2 H), 1.90 (d, J=9.2 Hz, 2 H), 3.17-3.22 (m, 4 H), 3.37-3.44 (m, 2 H), 3.69-3.77 (m, 9 H), 3.94 (s, 1 H), 5.17 (d, J=7.3 Hz, 1 H), 5.5 (s, 2 H), 6.86-6.90 (m, 2 H), 6.95 (d, J=6.0 Hz, 1 H), 7.05 (d, J=7.3 Hz, 1 H), 7.09-7.12 (m, 1 H), 7.14-7.16 (m, 1 H), 7.22-7.26 (m, 2 H), 7.39-7.46 (m, 1 H), 7.80 (d, J=6.1 Hz, 1 H); m/z (ES+APCI)$^+$: 500 [M+H]$^+$.

Intermediate 24

1-(4-Methoxybenzyl)-3-[2-(4-methylpiperazin-1-yl)pyridin-4-yl]-N-(tetrahydro-2H-pyran-4-yl)-1H-pyrazolo[4,3-c]pyridin-4-amine

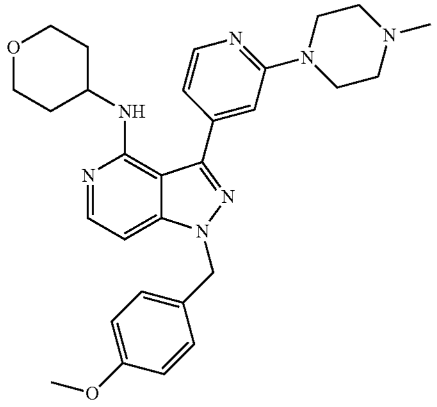 [SMILES: COc1ccc(Cn2nc(-c3ccnc(N4CCN(C)CC4)c3)c3c(NC4CCOCC4)nccc32)cc1]

Prepared analogously to Intermediate 22 from Intermediate 5 and 2-(4-methylpiperazin-1-yl)pyridine-4-boronic acid pinacol ester to give the desired product as an off-white solid (120 mg). $^1$H NMR (400 MHz, DMSO-$d_6$) δ ppm 1.32-1.44 (m, 2 H), 1.86-1.95 (m, 2 H), 2.22 (s, 3 H), 2.31-2.48 (m, 4 H), 3.41 (t, J=10.53 Hz, 2 H), 3.49-3.63 (m, 4 H), 3.70 (s, 3 H), 3.72-3.88 (m, 2 H), 4.17-4.26 (m, 1 H), 5.38 (d, J=6.9 Hz, 1 H), 5.52 (s, 2 H), 6.83-6.99 (m, 4 H), 7.04 (s, 1 H), 7.23 (d, J=8.7 Hz, 2 H), 7.83 (d, J=6.4 Hz, 1 H), 8.24 (d, J=5.0 Hz, 1 H); m/z (ES+APCI)$^+$: 514 [M+H]$^+$.

Intermediate 25

3-[2-(Morpholin-4-yl)pyridin-4-yl]-4-(tetrahydro-2H-pyran-4-yloxy)-1-trityl-1H-pyrazolo[4,3-c]pyridine

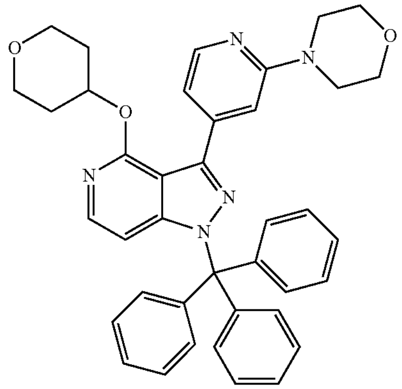 [SMILES: c1ccc(C(c2ccccc2)(c2ccccc2)n2nc(-c3ccnc(N4CCOCC4)c3)c3c(OC4CCOCC4)nccc32)cc1]

Prepared analogously to Intermediate 22 from Intermediate 21 and 2-morpholinopyridine-4-boronic acid pinacol ester to give the desired product as a cream solid (95 mg, 89%) $^1$H NMR (400 MHz, DMSO-$d_6$) δ ppm 1.60-1.70 (m, 2 H), 1.98-2.06 (m, 2 H), 3.42-3.54 (m, 6 H), 3.66-3.79 (m, 6 H), 5.39-5.45 (m, 1 H), 5.89 (d, J=6.4 Hz, 1 H), 7.09-7.14 (m, 1 H), 7.14-7.21 (m, 6 H), 7.23 (s, 1 H), 7.29-7.39 (m, 9 H), 7.61 (d, J=6.4 Hz, 1 H), 8.19 (d, J=6.0 Hz, 1H); m/z (ES+APCI)$^+$: 624 [M+H]$^+$.

Intermediate 26

3-[3-(Morpholin-4-yl)phenyl]-4-(tetrahydro-2H-pyran-4-yloxy)-1-trityl-1H-pyrazolo[4,3-c]pyridine

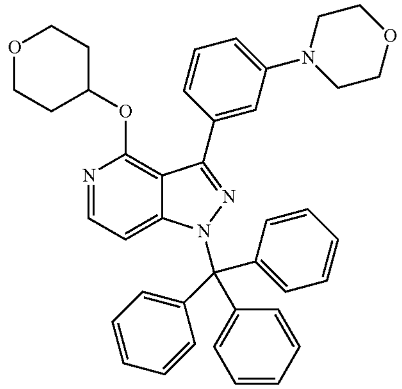 [SMILES: c1ccc(C(c2ccccc2)(c2ccccc2)n2nc(-c3cccc(N4CCOCC4)c3)c3c(OC4CCOCC4)nccc32)cc1]

Prepared analogously to Intermediate 22 from Intermediate 21 and 3-morpholinophenylboronic acid pinacol ester to give the desired product as a gum (120 mg) $^1$H NMR (400 MHz, DMSO-$d_6$) δ ppm 1.60-1.69 (m, 2 H), 1.96-2.03 (m, 2 H), 3.07-3.14 (m, 4 H), 3.44-3.51 (m, 2 H), 3.68-3.77 (m, 6 H), 5.33-5.53 (m, 1 H), 5.86 (d, J=6.4 Hz, 1 H), 6.96-7.00 (m, 1 H), 7.18 (dd, J=8.0, 1.6 Hz, 6 H), 7.26-7.40 (m, 12 H), 7.57 (d, J=6.0 Hz, 1 H); m/z (ES+APCI)$^+$: 623 [M+H]$^+$.

Intermediate 27

3-[2-(4-Methylpiperazin-1-yl)pyridin-4-yl]-4-(tetrahydro-2H-pyran-4-yloxy)-1-trityl-1H-pyrazolo[4,3-c]pyridine

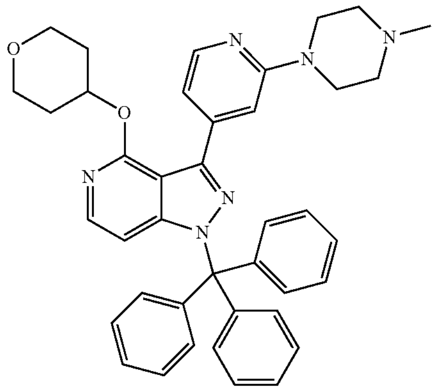 [SMILES: CN1CCN(c2cc(-c3nn(C(c4ccccc4)(c4ccccc4)c4ccccc4)c4ccnc(OC5CCOCC5)c34)ccn2)CC1]

Prepared analogously to Intermediate 22 from Intermediate 21 and 2-(4-methylpiperazin-1-yl)pyridine-4-boronic acid pinacol ester to give the desired product as an off-white foam (110 mg) $^1$H NMR (400 MHz, DMSO-$d_6$) δ ppm 1.62-1.71 (m, 2 H), 1.99-2.07 (m, 2 H), 2.24 (s, 3H), 2.37-2.44 (m, 4 H), 3.45-3.57 (m, 6 H), 3.72-3.79 (m, 2 H), 5.40-5.47 (m, 1 H), 5.90 (d, J=6.0 Hz, 1 H), 7.07-7.09 (m, 1 H), 7.15-7.21 (m, 6 H), 7.25 (s, 1 H), 7.31-7.40 (m, 9 H), 7.62 (d, J=6.4 Hz, 1 H), 8.17 (d, J=4.6 Hz, 1 H); m/z (ES+APCI)$^+$: 637 [M+H]$^+$.

Intermediate 28

Methyl (2E)-3-[4-(tetrahydro-2H-pyran-4-yloxy)-1-trityl-1H-pyrazolo[4,3-c]pyridin-3-yl]prop-2-enoate

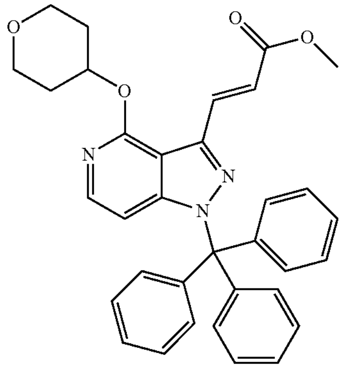 [SMILES: COC(=O)/C=C/c1nn(C(c2ccccc2)(c2ccccc2)c2ccccc2)c2ccnc(OC3CCOCC3)c12]

To a mixture of Intermediate 21 (1.5 g, 2.55 mmol) and tetrabutylammonium iodide (1.9 g, 5.1 mmol) in DMF:water:

triethylamine (37.5 ml:6 ml:6 ml) at room temperature was added methyl acrylate (2.3 ml, 25 mmol) and Pd(dppf)$Cl_2$ (0.42 g, 0.51 mmol) respectively. The resulting mixture was heated at 105° C. overnight and then evaporated to dryness. The crude residue was purified by flash chromatography, eluting with 25 to 60% ethyl acetate/petroleum ether gradient to give a brown solid (0.81 g, 58%) $^1$H NMR (400 MHz, DMSO-$d_6$) δ ppm 1.67-1.82 (m, 2 H), 2.02-2.13 (m, 2 H), 3.47-3.64 (m, 2 H), 3.70-3.81 (m, 3 H), 3.81-3.94 (m, 2H), 5.43-5.50 (m, 1 H), 5.82 (d, J=5.95 Hz, 1 H), 6.77 (d, J=16.03 Hz, 1 H), 7.09-7.18 (m, 6H), 7.27-7.41 (m, 9 H), 7.61 (d, J=5.95 Hz, 1 H), 7.97 (d, J=16.03 Hz, 1 H); m/z (ES+APCI)$^+$: 462 [M+H]$^+$.

Intermediate 29

Methyl 2-[4-(tetrahydro-2H-pyran-4-yloxy)-1-trityl-1H-pyrazolo[4,3-c]pyridin-3-yl]cyclopropanecarboxylate

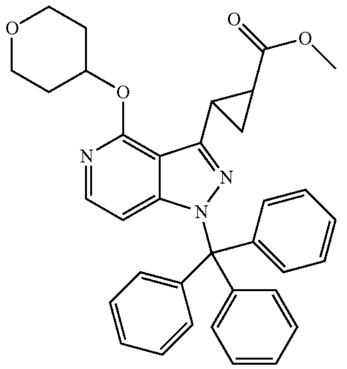 [SMILES: COC(=O)C1CC1c1nn(C(c2ccccc2)(c2ccccc2)c2ccccc2)c2ccnc(OC3CCOCC3)c12]

Sodium hydride (44 mg, 1.1 mmol) was slowly added to a solution of Trimethylsulfoxium iodide (145 mg, 0.66 mmol) in DMSO (3 ml) at room temperature. The resulting mixture was stirred for 5 minutes, then Intermediate 28 (0.3 g, 0.55 mmol) in DMSO (3 ml) was added dropwise and the mixture was stirred at room temperature for a further 2 h. Saturated $NH_4Cl$ (aq) was then added and the reaction mixture was diluted with ethyl acetate and washed with $H_2O$ (×4), dried ($MgSO_4$) and evaporated to dryness. The crude residue was purified by flash chromatography, eluting with 15 to 50% ethyl acetate/petroleum ether gradient to give a white solid (0.14 g, 45%) $^1$H NMR (400 MHz, DMSO-$d_6$) δ ppm 1.45-1.55 (m, 2 H), 1.57-1.80 (m, 2 H), 1.85-1.92 (m, 1 H), 1.94-2.06 (m, 2 H), 2.93-2.98 (m, 1 H), 3.50-3.61 (m, 2 H), 3.64 (s, 3 H), 3.71-3.89 (m, 2 H), 5.38-5.44 (m, 1 H), 5.69 (d, J=6.41 Hz, 1 H), 7.06-7.15 (m, 6 H), 7.27-7.37 (m, 9 H), 7.51 (d, J=6.41 Hz, 1 H); m/z (ES+APCI)$^+$: 560 [M+H]$^+$.

Intermediate 30

2-[4-(Tetrahydro-2H-pyran-4-yloxy)-1-trityl-1H-pyrazolo[4,3-c]pyridin-3-yl]cyclopropanecarboxylic acid

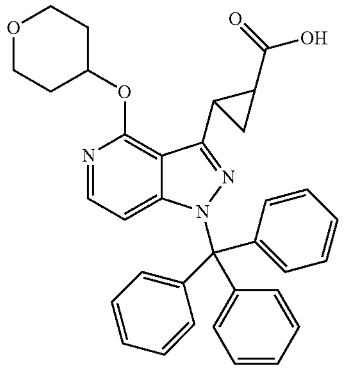 [SMILES: O=C(O)C1CC1c1nn(C(c2ccccc2)(c2ccccc2)c2ccccc2)c2ccnc(OC3CCOCC3)c12]

To a stirred suspension of Intermediate 29 (295 mg, 0.53 mmol) in 1:1 MeOH/THF (3 ml) at room temperature was added 2M NaOH (1.3 ml, 2.64 mmol). The resulting mixture was heated at 70° C. for 4 h, and then evaporated. The crude residue was dissolved in water and then 1M HCl was added dropwise, whereupon precipitation occurred. The resulting precipitate was filtered and dried to give a white solid (255 mg, 89%). $^1$H NMR (400 MHz, DMSO-$d_6$) δ ppm 1.36-1.46 (m, 2 H), 1.60-1.76 (m, 3 H), 1.92-2.04 (m, 2 H), 2.86-2.94 (m, 1 H), 3.48-3.58 (m, 2 H), 3.75-3.86 (m, 2 H), 5.34-5.41 (m, 1 H), 5.66 (d, J=6.41 Hz, 1 H), 7.03-7.13 (m, 6 H), 7.23-7.35 (m, 9 H), 7.48 (d, J=6.41 Hz, 1 H), 12.40 (br. s., 1 H); m/z (ES+APCI)$^+$: 546 [M+H]$^+$.

Intermediate 31

4-Chloro-3-methyl-1H-pyrazolo[4,3-c]pyridine

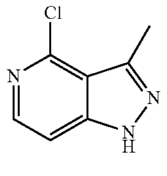

1-(2,4-Dichloro-pyridin-3-yl)-ethanone (6.2 g, 32.6 mmol) in 65% aqueous hydrazine (45 ml) was stirred at rt overnight. The mixture was diluted with EtOAc and water. The organic extract was washed with brine, dried and concentrated to give a white solid. The crude product was purified by flash column chromatography over silica gel (200 g) eluting with 1:1 petroleum ether:EtOAc to give an off-white solid (3.5 g, 64%). $^1$H NMR (400 MHz, DMSO-$d_6$) δ ppm 2.64 (s, 3 H), 7.47 (d, J=5.95 Hz, 1 H), 8.06 (d, J=5.95 Hz, 1 H). m/z (ES+APCI)$^+$: 168/170 [M+H]$^+$.

Intermediate 32

4-Chloro-3-methyl-1-trityl-1H-pyrazolo[4,3-c]pyridine

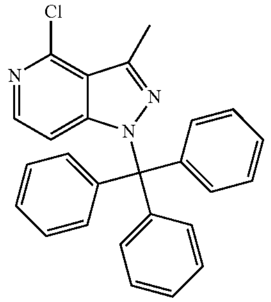 [SMILES: Cc1nn(C(c2ccccc2)(c2ccccc2)c2ccccc2)c2ccnc(Cl)c12]

NaH (60% dispersion, 1.07 g, 27.0 mmol) was added to a solution of Intermediate 31 (3 g, 18.0 mmol) in DMF (50 ml), and the suspension was stirred for 30 minutes at 0° C. Triphenylmethyl chloride (5.51 g, 20.0 mmol) was added and the reaction stirred for 18 h at r.t. The mixture was quenched with water (100 ml) and extracted twice with EtOAc (50 ml). The combined organic layers were washed three times with water (50 ml), then brine (50 ml), dried ($MgSO_4$) and evaporated. Purification by flash chromatography, eluting with 0 to 50% ethyl acetate/petroleum ether gradient to give a pale yellow solid (5.2 g, 71%). m/z $(ES+APCI)^+$: 410 $[M+H]^+$.

Intermediate 33

4-Chloro-3-isopropyl-1H-pyrazolo[4,3-c]pyridine

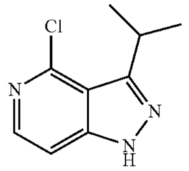

Step 1—1-(2,4-Dichloropyridin-3-yl)-2-methylpropan-1-ol

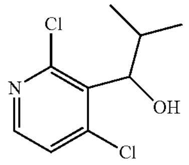

To a solution of Intermediate 1 (30 g, 170 mmol) in dry THF (500 mL) was added 2M isopropyl magnesium chloride in THF (110.7 mL, 221.59 mmol) at −78° C. The reaction mass was allowed to warm to rt over 2 h and then quenched at 0° C. with sat. $NH_4Cl$(aq) (300 mL). The aqueous phase was extracted with EtOAc (2×250 mL), the organic layer was dried over $Na_2SO_4$ and concentrated. The crude compound was purified by column chromatography (silica gel, 100-200 mesh, eluted with 20% EtOAc-pet ether) to afford an off-white solid (12.2 g, 33%). $^1$H NMR (400 MHz, $CDCl_3$) δ ppm 0.77 (d, J=6.8 Hz, 3 H), 1.21 (d, J=6.8 Hz, 3 H), 2.47-2.53 (m, 1 H), 4.98 (d, J=10.4 Hz, 1 H), 7.30 (d, J=5.6 Hz, 1 H), 8.20, (d, J=5.6 Hz, 1 H).

Step 2—1-(2,4-Dichloropyridin-3-yl)-2-methylpropan-1-one

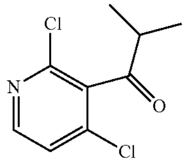

To the solution 1-(2,4-dichloropyridin-3-yl)-2-methylpropan-1-ol (12 g, 54.5 mmol) in dry $CH_2Cl_2$ (150 mL) was added PCC (23.45 g, 109 mmol) at 0° C. and stirred at rt for 16 h. The reaction mixture was concentrated, the residue was purified by column chromatography (silica gel, 100-200 mesh, eluted with 8% EtOAc-pet ether) to afford an off-white solid (9.95 g, 84%). $^1$H NMR (400 MHz, $CDCl_3$) δ ppm 1.26 (d, J=7.8 Hz, 6 H), 3.15-3.23 (m, 1 H), 7.34 (d, J=5.6 Hz, 1 H), 8.34, (d, J=5.2 Hz, 1 H).

Step 3—4-Chloro-3-isopropyl-1H-pyrazolo[4,3-c]pyridine

To a solution of 1-(2,4-dichloropyridin-3-yl)-2-methylpropan-1-one (9.85 g, 45.2 mmol) in 1, 4, dioxane (100 mL) was added $N_2H_4$ (100 mL, 80% solution) at 0° C. and stirred at rt for 16 h. The reaction mass was concentrated in vacuo. The crude compound was washed with $CHCl_3$ (3×100 mL) to afford a white solid (5.35 g, 60%). 1H NMR (400 MHz, DMSO-$d_6$) δ ppm 1.37 (d, J=6.8 Hz, 6 H), 3.62-3.72 (m, 1 H), 7.50 (d, J=6.0 Hz, 1 H), 8.09, (d, J=6.0 Hz, 1 H); m/z $(ES)^+$: 196/198 $[M+H]^+$.

Intermediate 34

4-Chloro-3-cyclohexyl-1H-pyrazolo[4,3-c]pyridine

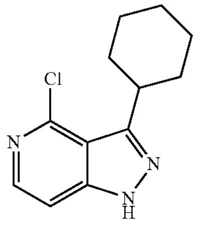 [SMILES: Clc1nccc2[nH]nc(C3CCCCC3)c12]

Prepared analogously to Intermediate 33 to give the title compound as a white solid. 1H NMR (400 MHz, DMSO-$d_6$) δ ppm 1.22-2.08 (m, 10 H), 3.25-3.32 (m, 1 H), 7.51 (d, J=6.0 Hz, 1 H), 8.09, (d, J=6.0 Hz, 1 H); m/z $(ES)^+$: 236/238 $[M+H]^+$.

Intermediate 35

4-Chloro-3-cyclopropyl-1H-pyrazolo[4,3-c]pyridine

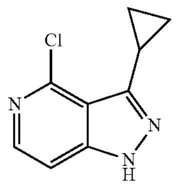 [SMILES: Clc1nccc2[nH]nc(C3CC3)c12]

Prepared analogously to Intermediate 33 to give the title compound as a white solid. $^1$H NMR (400 MHz, DMSO-$d_6$) δ ppm 0.92-1.12 (m, 6 H), 2.45-2.52 (m, 1 H), 7.47 (d, J=6.0 Hz, 1 H), 8.07, (d, J=6.0 Hz, 1 H), 13.35 (br. s, 1 H); m/z (ES)$^+$: 194/196 [M+H]$^+$.

Intermediate 36

4-Chloro-3-cyclobutyl-1H-pyrazolo[4,3-c]pyridine

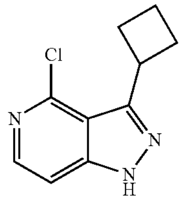 [SMILES: Clc1nccc2[nH]nc(C3CCC3)c12]

Prepared analogously to Intermediate 33 to give the title compound as a white solid. 1H NMR (400 MHz, DMSO-$d_6$) δ ppm 1.81-1.95 (m, 1 H), 2.01-2.17 (m, 1 H), 2.35-2.50 (m, 4 H), 4.05-4.18 (m, 1 H), 7.51 (d, J=5.6 Hz, 1 H), 8.08, (d, J=5.6 Hz, 1 H), 13.35 (br. s, 1 H); m/z (ES)$^+$: 208/210 [M+H]$^+$.

Intermediate 37

4-(Cyclohexyloxy)-3-(1H-pyrazol-4-yl)-1-trityl-1H-pyrazolo[4,3-c]pyridine

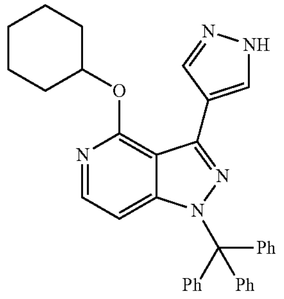 [SMILES: c1ccc(C(c2ccccc2)(c2ccccc2)n2nc(-c3cn[nH]c3)c3c(OC4CCCCC4)nccc32)cc1]

Intermediate 11 (1.86 g, 3.18 mmol), Pd(dppf)$Cl_2$ (260 mg, 0.32 mmol), 2M $Na_2CO_3$ (aq) (5.56 ml, 11.1 mmol) and 4-(4,4,5,5-tetramethyl-1,3,2-dioxaborolan-2-yl)-1H-pyrazole-1-carboxylic acid tert-butyl ester (1.4 g, 4.77 mmol) were combined in dioxane (50 ml), degassed with nitrogen for 15 min and stirred at reflux under nitrogen for 19 h. After concentration under reduced pressure, the crude product was partitioned between DCM and water, extracted with DCM and combined organic extracts washed with brine, dried ($MgSO_4$) and concentrated. Trituration with acetonitrile yielded some of the pure desired product and the remaining crude material was purified by column chromatography eluting with 10% ethyl acetate/petroleum ether to 50% ethyl acetate/petroleum ether. This was combined together with triturated material to give a white solid (512 mg, 31%). $^1$H NMR (400 MHz, DMSO-$d_6$) δ ppm 1.22-1.46 (m, 3 H), 1.49-1.62 (m, 3 H), 1.70-1.80 (m, 2 H), 2.06-2.15 (m, 2 H), 5.15-5.28 (m, 1 H), 5.72 (d, J=6.4 Hz, 1 H), 7.10-7.20 (m, 6 H), 7.28-7.39 (m, 9 H), 7.52 (d, J=6.4 Hz, 1 H), 7.88 (br. s., 1 H), 8.17 (br. s., 1 H); m/z (ES+APCI)$^+$: 526 [M+H]$^+$.

Intermediate 38

1-(4-Methoxybenzyl)-3-(1H-pyrazol-4-yl)-N-(tetrahydro-2H-pyran-4-yl)-1H-pyrazolo[4,3-c]pyridin-4-amine

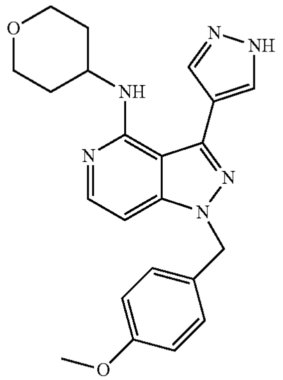 [SMILES: COc1ccc(Cn2nc(-c3cn[nH]c3)c3c(NC4CCOCC4)nccc32)cc1]

Intermediate 5 (2.0 g, 4.31 mmol), Pd(dppf)$Cl_2$ (352 mg, 0.43 mmol), 2M $Na_2CO_3$ (aq), (7.5 ml, 15.1 mmol) and 4-(4,4,5,5-tetramethyl-1,3,2-dioxaborolan-2-yl)-1H-pyrazole-1-carboxylic acid tert-butyl ester (1.9 g, 6.47 mmol) were combined in dioxane (50 ml) and the mixture was degassed with nitrogen for 10 min. The reaction mixture was then stirred at reflux under nitrogen for 18 h. The mixture was concentrated, the crude product partitioned between DCM and water, extracted twice with DCM and the combined organic extracts washed with brine, dried ($MgSO_4$) and solvents removed. Purification by column chromatography eluting with 100% DCM to 10% methanol/DCM yielded the product as a brown oil (1.33 g, 76%). $^1$H NMR (400 MHz, DMSO-$d_6$) δ ppm 1.33-1.44 (m, 2 H), 1.91-2.01 (m, 2 H), 3.38-3.47 (m, 2 H), 3.70 (s, 3 H), 3.77 (m, 2 H), 4.09-4.23 (m, 1 H), 5.30 (d, J=7.3 Hz, 1 H), 5.46 (s, 2 H), 6.85-6.93 (m, 3 H), 7.19-7.24 (m, 2 H), 7.78 (d, J=6.4 Hz, 1 H), 7.82 (d, J=1.4 Hz, 1 H), 8.15 (s, 1 H); m/z (ES+APCI)$^+$: 405 [M+H]$^+$.

Intermediate 39

Tert-butyl-4-{4-[1-(4-methoxybenzyl)-4-(tetrahydro-2H-pyran-4-ylamino)-1H-pyrazolo-[4,3-c]pyridin-3-yl]-1H-pyrazol-1-yl}piperidine-1-carboxylate

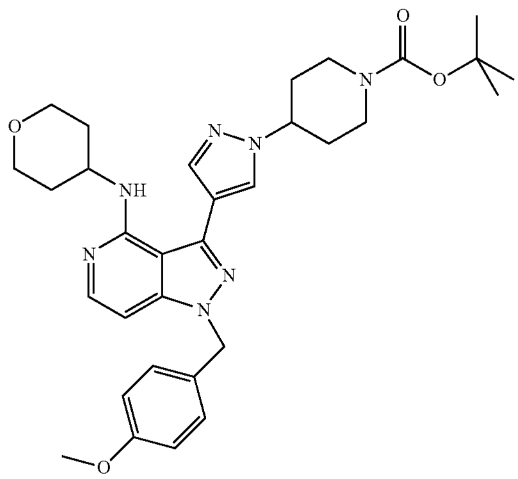 [SMILES: COc1ccc(Cn2nc(-c3cnn(C4CCN(C(=O)OC(C)(C)C)CC4)c3)c3c(NC4CCOCC4)nccc32)cc1]

Intermediate 38 (100 mg, 0.25 mmol) and caesium carbonate (302 mg, 0.50 mmol) were dissolved in DMF (1 ml) and stirred at rt for 30 min. 1-tert-butoxycarbonyl-4-methane-sulfonyloxy-piperidine (104 mg, 0.37 mmol) was added and the solution was heated to 90° C. for 18 h. The reaction mixture was cooled down, partitioned between ethyl acetate and water, extracted ethyl acetate (×2), and the combined organic extracts washed with brine, dried ($MgSO_4$) and concentrated. The crude material was purified by column chromatography (gradient elution from 0-10% methanol/DCM to give a brown oil (121 mg, 83%). $^1$H NMR (400 MHz, DMSO-$d_6$) δ ppm 1.40 (s, 9 H), 1.79-1.99 (m, 5 H), 2.04-2.10 (m, 2 H), 2.97 (br. s, 1 H), 3.38-3.46 (m, 2 H), 3.68 (s, 3 H), 3.77 (dt, J=11.4, 3.7 Hz, 2 H), 4.01-4.19 (m, 4 H), 4.43-4.51 (m, 1 H), 5.30 (d, J=7.3 Hz, 1 H), 5.45 (s, 2 H), 6.80-6.97 (m, 4 H), 7.15-7.27 (m, 2 H), 7.76-7.79 (m, 1 H), 8.20 (s, 1 H); m/z (ES+APCI)$^+$: 588 [M+H]$^+$.

Intermediate 40

4-(Cyclohexyloxy)-3-methyl-1H-pyrazolo[4,3-c]pyridine

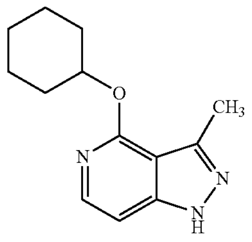 [SMILES: Cc1n[nH]c2ccnc(OC3CCCCC3)c12]

Sodium hydride, 60% in mineral oil (512 mg, 12.80 mmol) was added to a stirred solution of cyclohexanol (1.49 g, 14.88 mol) in dioxane (15 ml) in a sealed microwave vial. The mixture was allowed to stir at rt for 1 hour. A thick mixture formed and the vial was vortexed several times to facilitate stirring. Intermediate 31 (500 mg, 2.98 mmol) was then added. The mixture was stirred at rt for 1 hour and then irradiated in the 1-60 microwave reactor at 190° C. for 1 hour. A further 3 reactions were set up and repeated as above. The combined reaction mixtures were added to ice/water and extracted with ethyl acetate. The organic phase was dried and concentrated to provide an oil. The crude oil was purified by flash column chromatography on silica gel eluting with 3:1 petrol:ethyl acetate to give a white solid (2.18 g, 79%). $^1$H NMR (400 MHz, DMSO-d6) δ ppm 1.36-1.79 (m, 8 H), 1.92 (s, 2 H), 2.54 (s, 3 H), 5.23-5.30 (m, 1 H), 6.96 (d, J=6.0 Hz, 1 H), 7.76 (d, J=6.0 Hz, 1 H).

Intermediate 41

Tert-butyl-4-(cyclohexyloxy)-3-methyl-1H-pyrazolo[4,3-c]pyridine-1-carboxylate

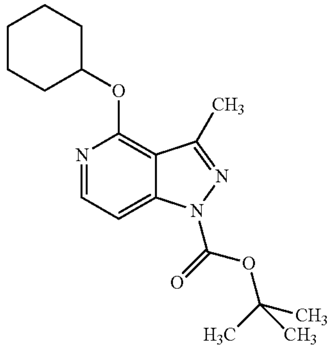 [SMILES: Cc1nn(C(=O)OC(C)(C)C)c2ccnc(OC3CCCCC3)c12]

Di-tert-butyl dicarbonate (2.45 g, 11.22 mmol) was added to a mixture of Intermediate 41 (2.16 g, 9.35 mmol) $Et_3N$ (1.37 mmol, 9.81 mmol) and DMAP (1.14 g, 9.35 mmol) in acetonitrile (60 ml). The reaction mixture was stirred at rt for 1 hour. The mixture was then diluted with ethyl acetate and water. The organic phase was washed with brine, dried and concentrated. The crude product was purified by flash column chromatography on silica eluting with 10:1 petrol:ethyl acetate to give a white solid (2.86 g, 92%). $^1$H NMR (400 MHz, DMSO-d6) δ ppm 1.35-1.78 (m, 17 H), 1.89-1.99 (m, 2 H), 2.56 (s, 3 H), 5.25-5.32 (m, 1 H), 7.48 (d, J=6.0 Hz, 1 H), 8.08 (d, J=6.0 Hz, 1 H). m/z (ES+APCI)+: 332 [M+H]+.

Intermediate 42

Tert-butyl-3-(bromomethyl)-4-(cyclohexyloxy)-1H-pyrazolo[4,3-c]pyridine-1-carboxylate

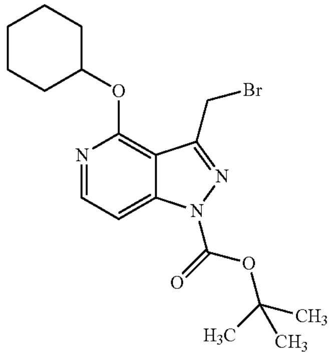 [SMILES: CC(C)(C)OC(=O)n1nc(CBr)c2c(OC3CCCCC3)nccc21]

A mixture of Intermediate 41 (2.35 g, 7.10 mmol), NBS (1.33 g, 7.45 mmol) and dibenzoyl peroxide, 75% (214 mg, 0.710 mmol) in carbon tetrachloride (100 ml) was stirred and heated under reflux overnight. The mixture was allowed to cool to rt and concentrated to dryness. The residue was pre-absorbed onto silica gel and purified by flash column chromatography on silica gel eluting with 10:1 petrol:ethyl acetate to afford a white solid (960 mg, 33%). $^1$H NMR (400 MHz, DMSO-$d_6$) δ ppm 1.37-1.57 (m, 4 H), 1.60-1.86 (m, 13 H), 1.88-2.02 (m, 2 H), 4.89 (s, 2 H), 5.29-5.36 (m, 1 H), 7.50-7.51 (d, J=6.0 Hz, 1 H), 8.16 (d, J=6.0 Hz, 1 H).

Intermediate 43

[4-(Cyclohexyloxy)-1H-pyrazolo[4,3-c]pyridin-3-yl] acetonitrile

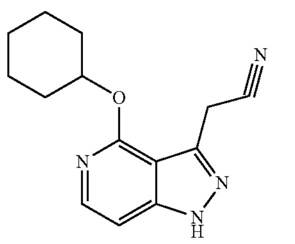 [SMILES: N#CCc1n[nH]c2ccnc(OC3CCCCC3)c12]

A mixture of Intermediate 42 (495 mg, 1.21 mmol) and sodium cyanide (296 mg, 6.04 mmol) in water (1 ml) and ethanol (20 ml) was stirred at rt for 4 h. The mixture was diluted with ethyl acetate and water. The organic phase was washed with brine, dried and concentrated. The crude product was purified by flash column chromatography on silica gel after pre-absorption onto silica gel. The product was eluted with 2:1 petrol:ethyl acetate to afford an off-white foamy solid (195 mg, 63%). $^1$H NMR (400 MHz, DMSO-d6) δ ppm 1.32-1.57 (m, 4 H), 1.57-1.73 (m, 2 H), 1.73-1.83 (m, 2 H), 1.89-2.00 (m, 2 H), 4.30 (s, 2 H), 5.22-5.30 (m, 1 H), 7.03-7.07 (d, J=6.4 Hz 1 H), 7.84 (d, J=6.4 Hz, 1 H).

Intermediate 44

2-[4-(Cyclohexyloxy)-1H-pyrazolo[4,3-c]pyridin-3-yl]ethanamine

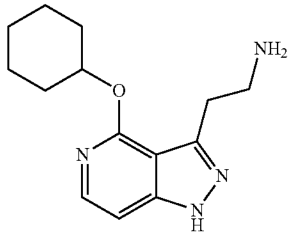 [SMILES: NCCc1n[nH]c2ccnc(OC3CCCCC3)c12]

Lithium aluminium hydride, 1 M in diethyl ether (4.9 ml, 4.9 mmol) was added to an ice-cooled solution of Intermediate 43 (598 mg, 2.33 mmol) in diethyl ether (35 ml). The mixture was allowed to warm to rt and stirred overnight. The mixture was cooled to −10° C. and water (186 μl) was added very carefully. This was followed by the addition of 15% aqueous sodium hydroxide solution (186 μl) and additional water (559 μl). The mixture was stirred rapidly for 1 hour, filtered through Celite and the filtrate was concentrated. The residue was purified by flash column chromatography on silica gel eluting with 10:1 DCM:2 M ammonia in methanol to give a colourless oil (75 mg, 12%). $^1$H NMR (400 MHz, DMSO-d6) δ ppm 1.35-1.79 (m, 8 H), 1.84-1.98 (m, 2 H), 2.86-2.97 (m, 2 H), 2.97-3.10 (m, 2 H), 3.34 (br. s., 2 H), 5.23-5.30 (m, 1 H), 6.97 (d, J=6.0 Hz, 1 H), 7.76 (d, J=6.0 Hz, 1 H).

Intermediate 45

4-(Cyclohexyloxy)-3-ethenyl-1-trityl-1H-pyrazolo[4,3-c]pyridine

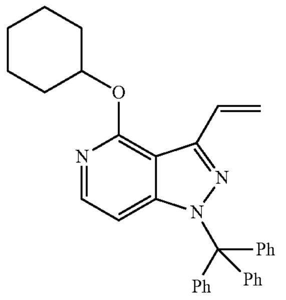 [SMILES: C=Cc1nn(C(c2ccccc2)(c2ccccc2)c2ccccc2)c2ccnc(OC3CCCCC3)c12]

A round bottomed flask was charged with Intermediate 11 (1 g, 1.71 mmol), potassium vinyltrifluoroborate (690 mg, 5.12 mmol), [1,1'-bis(diphenylphosphino)ferrocene]dichloropalladium(II) (140 mg, 0.17 mmol) and triethylamine (710 μl, 5.12 mmol), IPA (40 ml) and THF (10 ml). The solution was degassed for 15 minutes, prior to heating the reaction mixture to 90° C. overnight. The mixture was allowed to cool to rt, concentrated, and the residue was diluted with DCM and $H_2O$. The organic layer was separated, dried and concentrated. Purification by column chromatography using an Isolera 4 (petroleum ether/EtOAc gradient) gave the product as a white solid (646 mg, 78% yield). $^1$H NMR (400 MHz, CDCl3) δ ppm 1.24-1.88 (m, 10 H), 5.23-5.38 (m, 2 H), 5.66-5.74 (m, 1 H), 6.13-6.22 (m, 1 H), 7.10-7.38 (m, 16 H), 7.38-7.59 (m, 1 H); m/z (ES+APCI)$^+$: 486 [M+H]$^+$.

Intermediate 46

Methyl 1-isopropyl-4-(4,4,5,5-tetramethyl-1,3,2-dioxaborolan-2-yl)-1H pyrrole-2-carboxylate

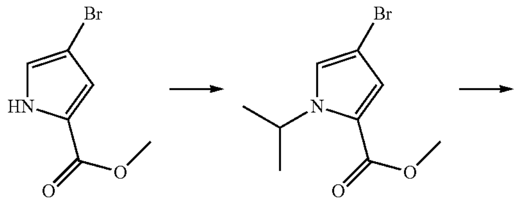

-continued

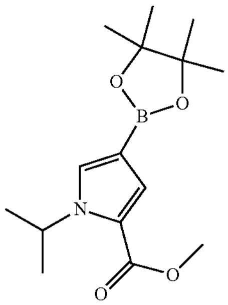

Step 1—Methyl 4-bromo-1-isopropyl-1H-pyrrole-2-carboxylate

To a mixture of methyl 4-bromo-1H-pyrrole-2-carboxylate (4.5 g, 0.022 mol) in DMF (20 mL) was added NaH (60% dispersion, 2.6 g, 0.066 mol) at 0° C. The reaction was stirred at 0° C. for 30 minutes. 2-Bromopropane (8.1 g, 0.066 mol) was added to the reaction mixture and stirred overnight at 90° C. After cooling to room temperature, the reaction was quenched with 100 mL of water and extracted with ethyl acetate (3×50 mL). The organic layer was washed with water and brine, dried over anhydrous $Na_2SO_4$, filtered and concentrated. The residue was purified by column chromatography (50% ethyl acetate in pet. ether). The desired compound was obtained as a yellowish oil (4.55 g, 84%). LCMS (Method A): m/z=246 $[M+H]^+$; 2.19 min.

Step 2—Methyl 1-isopropyl-4-(4,4,5,5-tetramethyl-1,3,2-dioxaborolan-2-yl)-1H pyrrole-2-carboxylate A mixture of methyl 4-bromo-isopropyl-1H-pyrrole-2-carboxylate (1.0 g, 0.004 mol), 4,4,4',4',5,5,5',5'-octamethyl-2,2'-bi(1,3,2-dioxaborolane) (1.56 g, 0.006 mol), anhydrous KOAc (1.2 g, 0.012 mol), and $PdCl_2$(dppf) dichloromethane adduct (0.6 g, 0.0008 mol) in DMF (15 mL) was stirred overnight under nitrogen at 80° C. Ethyl acetate (100 mL) and water (100 mL) were added. The organic layer was washed with water (50 mL) and brine, dried over anhydrous $Na_2SO_4$, filtered and concentrated in vacuo. The residue was purified by column chromatography (pet. ether-ethyl acetate, 20:1). The desired compound was obtained as a yellowish oil (0.6 g, 51%). LC-MS (Method A): m/z=294 $[M+H]^+$; 2.24 min. $^1$H-NMR (500 MHz, $CDCl_3$): δ 7.86 (s, 1H), 7.71 (s, 1H), 7.49 (d, J=6.0, 1H), 7.33 (d, J=5.5, 1H), 7.20-7.28 (m, 15H), 5.47-5.52 (m, 1H), 5.59-5.63 (m, 1H), 5.77 (d, J=6.5, 1H), 1.52 (d, J=6.5, 6H), 1.49 (d, J=7.0, 6H).

Intermediate 47

3-(2-Chloropyridin-4-yl)-4-(tetrahydro-2H-pyran-4-yloxy)-1-trityl-1H-pyrazolo[4,3-c]pyridine

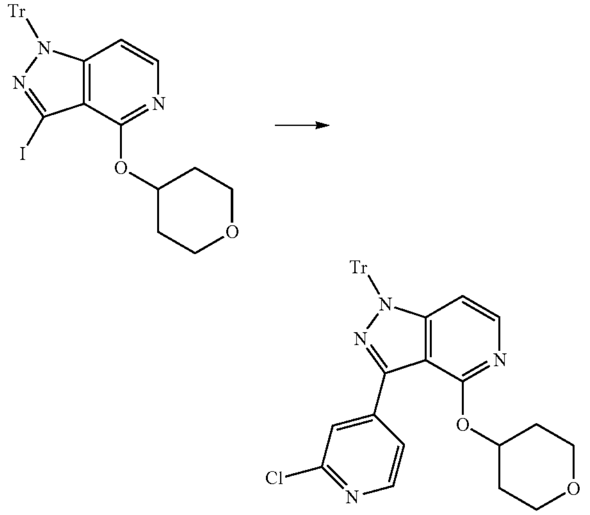

To a microwave vial was charged 3-iodo-4-(tetrahydro-2H-pyran-4-yloxy)-1-trityl-1H-pyrazolo[4,3-c]pyridine (1.00 g, 1.70 mmol), 2-chloropyridin-4-ylboronic acid (0.281 g, 1.79 mmol) and bis(diphenylphosphino)ferrocenepalladium chloride (139 mg, 0.170 mmol). Acetonitrile (11 mL, 210 mmol) and 1.0 M of potassium acetate in water (4.1 mL) were then added and the reaction mixture was degassed with nitrogen for 10 minutes and then heated to 100° C. under microwave irradiation for 30 minutes. Upon reaction completion, the reaction mixture was diluted with dichloromethane, filtered through Celite® and concentrated in vacuo. The crude residue was purified by column chromatography eluting with 0-100% EtOAc in heptane to give the title compound (0.648 g, 66%). LC-MS (Method H): m/z=573.4 $[M+H]^+$; 1.56 min. $^1$H-NMR (400 MHz, $CDCl_3$): δ 8.37 (d, J=5.2, 1H), 8.13 (s, 1H), 7.80 (d, J=5.2, 1H), 7.54 (d, J=6.2, 1H), 7.35-7.27 (m, 9H), 7.22-7.14 (m, 6H), 5.90 (d, J=6.2, 1H), 5.55-5.46 (m, 1H), 4.01-3.92 (m, 2H), 3.69-3.60 (m, 2H), 2.23-2.13 (m, 2H), 1.99-1.87 (m, 2H).

Intermediate 48

3-(2-Chloropyridin-4-yl)-4-methoxy-1-trityl-1H-pyrazolo[4,3-c]pyridine

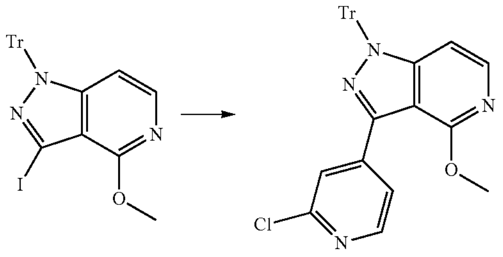

To a microwave vial was charged 3-iodo-4-methoxy-1-trityl-1H-pyrazolo[4,3-c]pyridine (1.14 g, 2.21 mmol), 2-chloropyridin-4-ylboronic acid (0.366 g, 2.32 mmol) and bis(diphenylphosphino)ferrocenepalladium chloride (181 mg, 0.221 mmol). Acetonitrile (14 mL, 270 mmol) and 1.0 M of potassium acetate in water (5.3 mL) were then added and the reaction mixture was degassed with nitrogen for 10 minutes and then heated to 100° C. under microwave irradiation for 40 minutes. Upon reaction completion, the reaction mixture was diluted with dichloromethane, filtered through Celite® and concentrated in vacuo. The crude residue was purified by column chromatography eluting with 0-2% EtOAc in DCM to give the title compound (0.887 g, 80%). LC-MS (Method H): m/z=503.3 $[M+H]^+$, 1.55 min. $^1$H-NMR (400 MHz, $CDCl_3$): δ 8.38 (d, J=4.6, 1H), 8.06 (s, 1H), 7.86 (d, J=4.8, 1H), 7.58 (d, J=6.0, 1H), 7.35-7.28 (m, 9H), 7.23-7.14 (m, 6H), 5.91 (d, J=6.2, 1H), 4.11 (s, 3H.

Example 1

1-[(3R)-3-Phenylpiperidin-1-yl]-3-[4-(tetrahydro-2H-pyran-4-ylamino)-1H-pyrazolo[4,3-c]pyridin-3-yl]propan-1-one

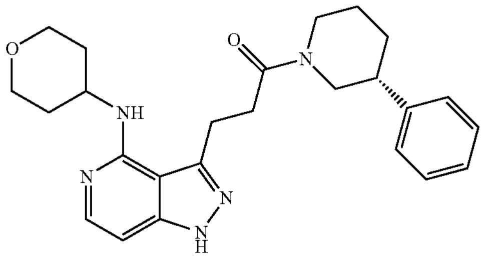 [SMILES: O=C(CCc1n[nH]c2ccnc(NC3CCOCC3)c12)N1CCC[C@H](c2ccccc2)C1]

To a solution of Intermediate 9 (45 mg, 0.16 mmol) in DMF (1 ml) at room temperature was added HATU (62 mg, 0.16 mmol) and N,N-diisopropylethylamine (162 μl, 0.93 mmol). (R)-3-Phenylpiperidine (25 mg, 0.16 mmol) was then added, and the resulting solution was left to stir at room temperature overnight. The volatiles were removed under reduced pressure and the crude product was re-dissolved in DCM and eluted though an (solute-$NH_2$ cartridge. The solvents were removed and the crude product purified by mass triggered preparative LCMS (high pH buffer) to give a white solid (6 mg, 9%) $^1$H NMR (400 MHz, DMSO-$d_6$) δ ppm 1.18-1.38 (m, 1 H), 1.49-1.77 (m, 4 H), 1.77-1.88 (m, 1 H), 1.88-2.00 (m, 2 H), 2.38-2.49 (m, 1 H), 2.53-2.70 (m, 1 H), 2.72-2.95 (m, 2 H), 2.95-3.10 (m, 1 H), 3.16-3.27 (m, 2 H), 3.36-3.49 (m, 2 H), 3.81-3.97 (m, 3 H), 4.18-4.28 (m, 1 H), 4.41-4.52 (m, 1 H), 6.50-6.67 (m, 2 H), 7.15-7.35 (m, 5 H), 7.66-7.71 (m, 1 H); m/z $(ES+APCI)^+$: 434 $[M+H]^+$.

Examples 2-4

Examples 2-4 in the following table were prepared analogously to Example 1 from Intermediate 9 and the corresponding amine.

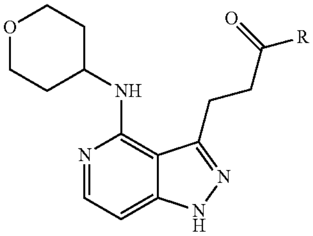

| Example | R group | Name | m/z (ES + APCI)+ | HPLC retention time (min)* |
|---|---|---|---|---|
| 2 | 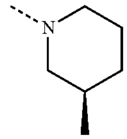 | 1-[(3R)-3-methylpiperidin-1-yl]-3-[4-(tetrahydro-2H-pyran-4-ylamino)-1H-pyrazolo-[4,3-c]pyridin-3-yl]propan-1-one | 372 | 1.39 |
| 3 | 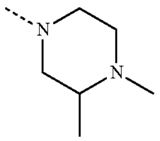 | 1-(3,4-dimethylpiperazin-1-yl)-3-[4-(tetrahydro-2H-pyran-4-ylamino)-1H-pyrazolo[4,3-c]pyridin-3-yl]-propan-1-one | 387 | 1.07 |
| 4 | 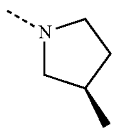 | 1-[(3R)-3-methylpyrrolidin-1-yl]-3-[4-(tetrahydro-2H-pyran-4-ylamino)-1H-pyrazolo[4,3-c]pyridin-3-yl]-propan-1-one | 358 | 1.27 |

*HPLC column: 4.6 x 50 mm (5 μm) C-18 Xbridge; flow rate: 3 ml/min; Run time: 3.2 min: Solvent A: 0.1% Ammonium Hydroxide in water Solvent B: Acetonitrile; Gradient - 10-100% B; Gradient time: 2.35 min.

Example 5

Methyl (2E)-3-[4-(tetrahydro-2H-pyran-4-ylamino)-1H-pyrazolo[4,3-c]pyridin-3-yl]prop-2-enoate

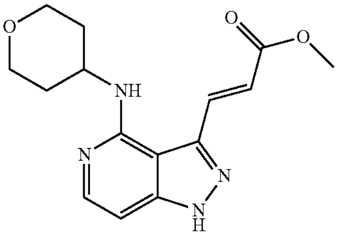 [SMILES: COC(=O)/C=C/c1n[nH]c2ccnc(NC3CCOCC3)c12]

A solution of Intermediate 5 (1.25 g, 2.96 mmol) in TFA (10 ml) was stirred at 70° C. overnight. The reaction mixture was cooled to room temperature and then evaporated. The crude residue was re-dissolved in 100% EtOAc and eluted through an SCX cartridge, eluting first with 100% EtOAc, followed by 2M/$NH_3$ in methanol to yield a brown gum (0.8 g, 89%). $^1$H NMR (400 MHz, DMSO-$d_6$) δ ppm 1.43-1.75 (m, 2 H), 1.76-2.00 (m, 2 H), 3.36-3.50 (m, 2 H), 3.74 (s, 3 H), 3.82-4.00 (m, 2 H), 4.11-4.33 (m, 1 H), 6.38 (d, J=7.3 Hz, 1 H), 6.59-6.86 (m, 2 H), 7.76 (d, J=6.0 Hz, 1 H), 8.10 (d, J=15.6 Hz, 1 H); m/z (ES+APCI)$^+$: 303 [M+H]$^+$.

Example 6

3-[4-(Cyclohexyloxy)-1H-pyrazolo[4,3-c]pyridin-3-yl]-1-[(3R)-3-phenylpiperidin-1-yl]propan-1-one

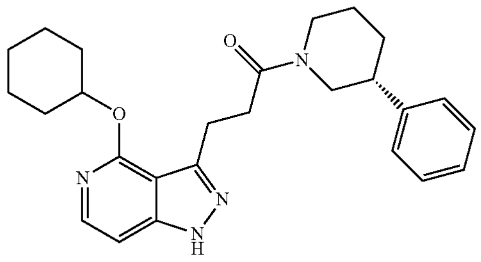 [SMILES: O=C(CCc1n[nH]c2ccnc(OC3CCCCC3)c12)N1CCC[C@H](c2ccccc2)C1]

To a solution of Intermediate 15 (27 mg, 0.09 mmol) in DMF (1 ml) at room temperature was added HATU (37 mg, 0.10 mmol) and N,N-diisopropylethylamine (97 μl, 0.56 mmol). (R)-3-Phenylpiperidine (25 mg, 0.16 mmol) was then added, and the resulting solution was left to stir at room temperature overnight. The volatiles were removed under reduced pressure and the crude product was re-dissolved in DCM and eluted though an (solute-$NH_2$ cartridge. The solvents were removed and the crude product purified by mass triggered preparative LCMS (high pH buffer) to give a white solid (18 mg, 45%). $^1$H NMR (400 MHz, DMSO-$d_6$) δ ppm 1.25-2.03 (m, 14 H), 2.50-2.67 (m, 2 H), 2.69-2.90 (m, 2 H), 2.93-3.25 (m, 3 H), 3.62-4.14 (m, 1 H), 4.28-4.67 (m, 1 H), 4.93-5.52 (m, 1 H), 6.83-7.08 (m, 1 H), 7.11-7.44 (m, 5 H), 7.56-8.32 (m, 1 H); m/z (ES+APCI)$^+$: 433 [M+H]$^+$.

Example 7

(4-{2-[4-(Cyclohexylamino)-1H-pyrazolo[4,3-c]pyridin-3-yl]ethyl}phenyl)(4-methylpiperazin-1-yl)methanone

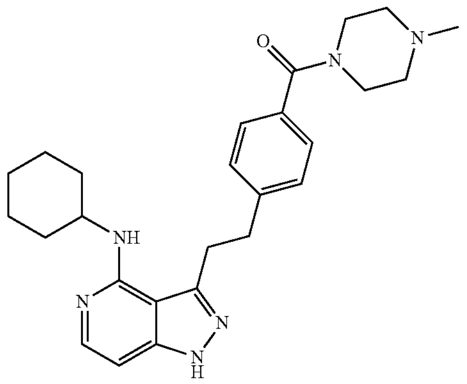 [SMILES: CN1CCN(C(=O)c2ccc(CCc3n[nH]c4ccnc(NC5CCCCC5)c34)cc2)CC1]

Prepared analogously to Example 6 from Intermediate 20 and 1-methyl piperazine to give the desired product as a white solid (23 mg, 62%) $^1$H NMR (400 MHz, DMSO-$d_6$) δ ppm 1.12-1.48 (m, 5 H), 1.53-1.82 (m, 3 H), 1.87-2.04 (m, 2 H), 2.20 (s, 3 H), 2.21-2.43 (m, 4 H), 2.95-3.13 (m, 2 H), 3.18-3.76 (m, 6 H), 3.92-4.19 (m, 1 H), 5.54 (d, J=7.8 Hz, 1 H), 6.59 (d, J=6.4 Hz, 1 H), 7.22-7.43 (m, 4 H), 7.68 (d, J=6.0 Hz, 1 H); m/z (ES+APCI)$^+$: 447 [M+H]$^+$.

Example 8

(4-{2-[4-(Cyclohexylamino)-1H-pyrazolo[4,3-c]pyridin-3-yl]ethyl}phenyl)(4-cyclopropylpiperazin-1-yl)methanone

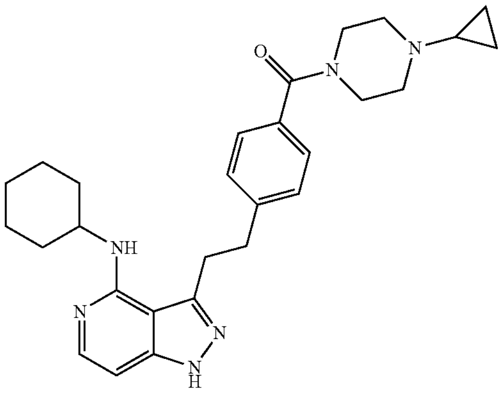 [SMILES: O=C(c1ccc(CCc2n[nH]c3ccnc(NC4CCCCC4)c23)cc1)N1CCN(C2CC2)CC1]

Prepared analogously to Example 6 from Intermediate 20 and 1-cyclopropyl piperazine to give the desired product as a white solid (25 mg, 64%). $^1$H NMR (400 MHz, DMSO-$d_6$) δ ppm 0.29-0.36 (m, 2 H), 0.39-0.51 (m, 2 H), 0.95-1.49 (m, 5 H), 1.54-1.81 (m, 4 H), 1.86-2.15 (m, 2 H), 2.37-2.63 (m, 4 H), 3.03 (d, J=7.8 Hz, 2 H), 3.18-3.74 (m, 6 H), 3.78-4.43 (m, 1 H), 5.54 (d, J=7.8 Hz, 1 H), 6.59 (d, J=6.0 Hz, 1 H), 7.13-7.42 (m, 4H), 7.68 (d, J=6.0 Hz, 1 H); m/z (ES+APCI)$^+$: 473 [M+H]$^+$.

Example 9

3-[2-(Morpholin-4-yl)pyridin-4-yl]-N-(tetrahydro-2H-pyran-4-yl)-1H-pyrazolo[4,3-c]pyridin-4-amine

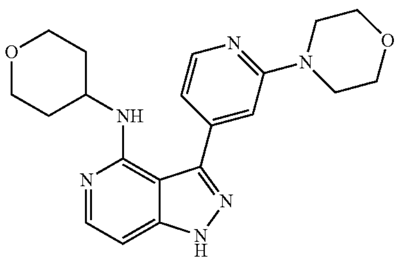 [SMILES: c1cc(-c2n[nH]c3ccnc(NC4CCOCC4)c23)cc(N2CCOCC2)n1]

A solution of Intermediate 22 (0.11 g, 0.22 mmol) in TFA (1.5 ml) was stirred at 70° C. overnight. The reaction mixture was cooled to room temperature and then evaporated. The crude residue was re-dissolved in DCM and eluted through an SCX cartridge, eluting first with DCM, followed by 2M/$NH_3$ in methanol. The solvents were removed and the crude product purified by mass triggered preparative LCMS (high pH buffer) to give a white solid (28 mg, 34%). $^1$H NMR (400 MHz, DMSO-$d_6$) δ ppm 1.33-1.47 (m, 2 H), 1.87-2.00 (m, 2

H), 3.39-3.49 (m, 2 H), 3.49-3.63 (m, 4 H), 3.63-3.92 (m, 6 H), 4.17-4.29 (m, 1 H), 5.33 (d, J=7.33 Hz, 1 H), 6.77 (d, J=6.0 Hz, 1 H), 6.98 (dd, J=5.0, 0.9 Hz, 1 H), 7.07 (s, 1 H), 7.81 (d, J=6.0 Hz, 1 H), 8.29 (d, J=5.5 Hz, 1 H); m/z (ES+APCI)$^+$: 381 [M+H]$^+$.

Example 10

3-[2-(Morpholin-4-yl)pyridin-4-yl]-4-(tetrahydro-2H-pyran-4-yloxy)-1H-pyrazolo[4,3-c]pyridine

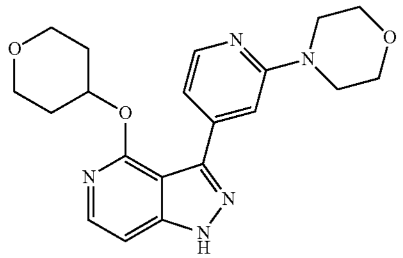 [SMILES: c1cc(-c2n[nH]c3ccnc(OC4CCOCC4)c23)cc(N2CCOCC2)n1]

A solution of Intermediate 25 (92 mg, 0.15 mmol) in 10% TFA/DCM (0.2/1.8 ml) was stirred at room temperature overnight. The reaction mixture was evaporated and the crude residue was re-dissolved in 100% EtOAc and eluted through an SCX cartridge, eluting first with 100% EtOAc, followed by 2M/$NH_3$ in methanol. The solvents were removed and the crude product purified by mass triggered preparative LCMS (high pH buffer) to give a white solid (20 mg, 36%) $^1$H NMR (400 MHz, DMSO-$d_6$) δ ppm 1.61-1.75 (m, 2 H), 2.00-2.14 (m, 2 H), 3.46-3.59 (m, 6 H), 3.66-3.95 (m, 6 H), 5.38-5.59 (m, 1 H), 7.17 (d, J=5.95 Hz, 1 H), 7.23-7.28 (m, 1 H), 7.30 (s, 1 H), 7.90 (d, J=6.0 Hz, 1 H), 8.22 (d, J=4.6 Hz, 1 H); m/z (ES+APCI)$^+$: 382 [M+H]$^+$.

Example 11

3-[3-(Morpholin-4-yl)phenyl]-N-(tetrahydro-2H-pyran-4-yl)-1H-pyrazolo[4,3-c]pyridin-4-amine

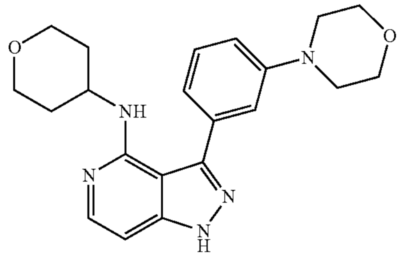 [SMILES: c1cc(-c2n[nH]c3ccnc(NC4CCOCC4)c23)cc(N2CCOCC2)c1]

Prepared analogously to Example 9 from Intermediate 23 to give the desired product as a white solid (26 mg, 32%). $^1$H NMR (400 MHz, DMSO-$d_6$) δ ppm 1.20-1.34 (m, 2 H), 1.85-1.97 (m, 2 H), 2.94-3.24 (m, 4 H), 3.38-3.57 (m, 2 H), 3.57-3.86 (m, 6 H), 4.00-4.25 (m, 1 H), 5.12 (d, J=7.3 Hz, 1 H), 6.74 (d, J=6.0 Hz, 1 H), 6.97-7.21 (m, 3 H), 7.38-7.45 (m, 1 H), 7.77 (d, J=6.0 Hz, 1 H); m/z (ES+APCI)$^+$: 380 [M+H]$^+$.

Example 12

3-[3-(Morpholin-4-yl)phenyl]-4-(tetrahydro-2H-pyran-4-yloxy)-1H-pyrazolo[4,3-c]pyridine

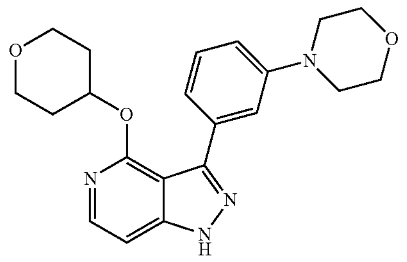 [SMILES: c1cc(-c2n[nH]c3ccnc(OC4CCOCC4)c23)cc(N2CCOCC2)c1]

Prepared analogously to Example 10 from Intermediate 26 to give the desired product as a pink solid (13 mg, 20%) $^1$H NMR (400 MHz, DMSO-$d_6$) δ ppm 1.60-1.72 (m, 2 H), 1.97-2.08 (m, 2 H), 3.09-3.26 (m, 4 H), 3.50 (s, 2 H), 3.66-3.86 (m, 6 H), 5.31-5.87 (m, 1 H), 7.01 (s, 1 H), 7.13 (d, J=6.4 Hz, 1 H), 7.33 (t, J=8.0 Hz, 1 H), 7.38-7.43 (m, 1 H), 7.44-7.51 (m, 1 H), 7.88 (d, J=6.0 Hz, 1 H); m/z (ES+APCI)$^+$: 381 [M+H]$^+$.

Example 13

3-[2-(4-Methylpiperazin-1-yl)pyridin-4-yl]-N-(tetrahydro-2H-pyran-4-yl)-1H-pyrazolo[4,3-c]pyridin-4-amine

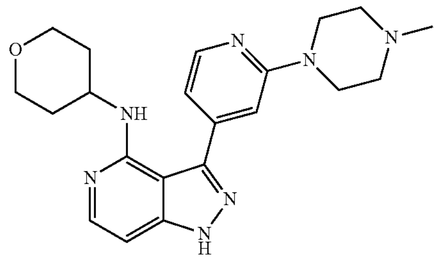 [SMILES: CN1CCN(c2cc(-c3n[nH]c4ccnc(NC5CCOCC5)c34)ccn2)CC1]

Prepared analogously to Example 9 from Intermediate 24 to give the desired product (29 mg, 35%). $^1$H NMR (400 MHz, DMSO-$d_6$) δ ppm 1.33-1.45 (m, 2 H), 1.85-1.97 (m, 2 H), 2.23 (s, 3 H), 2.41 (t, J=4.8 Hz, 4 H), 3.36-3.50 (m, 2 H), 3.50-3.64 (m, 4 H), 3.72-3.83 (m, 2 H), 4.18-4.28 (m, 1 H), 5.33 (d, J=7.3 Hz, 1 H), 6.77 (d, J=6.0 Hz, 1 H), 6.91-6.95 (m, 1 H), 7.05 (s, 1 H), 7.81 (d, J=6.0 Hz, 1 H), 8.26 (d, J=5.0 Hz, 1 H); m/z (ES+APCI)$^+$: 394 [M+H]$^+$.

Example 14

3-[2-(4-Methylpiperazin-1-yl)pyridin-4-yl]-4-(tetrahydro-2H-pyran-4-yloxy)-1H-pyrazolo[4,3-c]pyridine

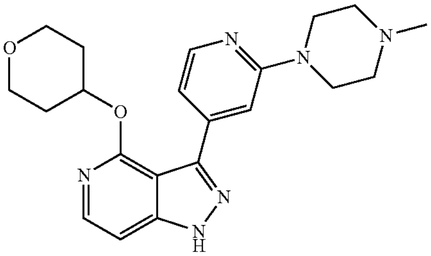 [SMILES: CN1CCN(c2cc(-c3n[nH]c4ccnc(OC5CCOCC5)c34)ccn2)CC1]

Prepared analogously to Example 10 from Intermediate 27 to give the desired product (35 mg, 52%) $^1$H NMR (400 MHz, DMSO-$d_6$) δ ppm 1.61-1.72 (m, 2 H), 2.00-2.09 (m, 2 H), 2.24 (s, 3 H), 2.32-2.49 (m, 4 H), 3.45-3.61 (m, 6 H), 3.70-3.81 (m, 2 H), 5.46-5.53 (m, 1 H), 7.15-7.22 (m, 2 H), 7.31 (s, 1 H), 7.91 (d, J=6.4 Hz, 1 H), 8.18-8.22 (m, 1 H); m/z (ES+APCI)$^+$: 395 [M+H]$^+$.

Example 15

[(3R)-3-Phenylpiperidin-1-yl]{2-[4-(tetrahydro-2H-pyran-4-yloxy)-1H-pyrazolo[4,3-c]pyridin-3-yl]cyclopropyl}methanone

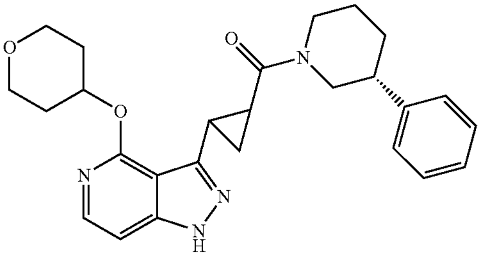 [SMILES: O=C(C1CC1c1n[nH]c2ccnc(OC3CCOCC3)c12)N1CCC[C@H](c2ccccc2)C1]

Step 1—To a solution of Intermediate 30 (56 mg, 0.1 mmol) in DMF (1 ml) at room temperature was added HATU (41 mg, 0.1 mmol) and N,N-diisopropylethylamine (107 μl, 0.61 mmol). (R)-3-Phenylpiperidine (20 mg, 0.12 mmol) was then added, and the resulting solution was left to stir at room temperature overnight, then evaporated to dryness. The crude residue was purified by flash chromatography, eluting with 25 to 60% ethyl acetate/petroleum ether gradient to give a white solid (52 mg) which was used in the next step without further purification Step 2—A solution of the crude product of step 1 (52 mg) in 10% TFA/DCM (0.2/1.8 ml) was stirred at room temperature overnight. The reaction mixture was evaporated and the crude residue was re-dissolved in 100% EtOAc and eluted through an SCX cartridge, eluting first with 100% EtOAc, followed by 2M/$NH_3$ in methanol. The solvents were removed and the crude product purified by mass triggered preparative LCMS (high pH buffer) to the desired product $^1$H NMR (400 MHz, DMSO-$d_6$) δ ppm 1.45-1.59 (m, 3 H), 1.67-1.82 (m, 4 H), 1.90-1.98 (m, 1 H), 2.03 (br. s., 2 H), 2.43 (d, J=4.6 Hz, 3 H), 2.59-2.77 (m, 1 H), 2.77-2.99 (m, 1 H), 3.51-3.62 (m, 2 H), 3.86 (d, J=4.1 Hz, 2 H), 4.20-4.45 (m, 2 H), 5.45-5.52 (m, 1 H), 6.87-7.07 (m, 1 H), 7.09-7.46 (m, 5 H), 7.80 (dd, J=8.7, 5.9 Hz, 1 H); m/z (ES+APCI)$^+$: 447 [M+H]$^+$.

Examples 16-18

Examples 16-18 were prepared analogously to Example 15, (the general structure is shown below followed by the tabulated examples).

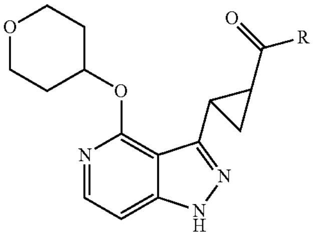

| Example | R group | Name | m/z (ES + APCI)$^+$ | HPLC retention time (min)* |
|---|---|---|---|---|
| 16 | 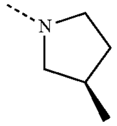 | [(3R)-3-methylpyrrolidin-1-yl]{2-[4-(tetrahydro-2H-pyran-4-yloxy)-1H-pyrazolo[4,3-c]pyridin-3-yl]cyclopropyl}-methanone | 371 | 1.36 |
| 17 | 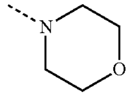 | Morpholin-4-yl{2-[4-(tetrahydro-2H-pyran-4-yloxy)-1H-pyrazolo-[4,3-c]pyridin-3-yl]-cyclopropyl}methanone | 373 | 1.17 |
| 18 | 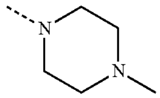 | (4-methylpiperazin-1-yl){2-[4-(tetrahydro-2H-pyran-4-yloxy)-1H-pyrazolo[4,3-c]pyridin-3-yl]cyclopropyl}-methanone | 386 | 1.13 |

*HPLC column: 4.6 x 50 mm (5 μm) C-18 Xbridge; flow rate: 3 ml/min; Run time: 3.2 min: Solvent A: 0.1% Ammonium Hydroxide in water Solvent B: Acetonitrile; Gradient - 10-100% B; Gradient time: 2.35 min.

Example 19

3-Cyclopropyl-N-(tetrahydro-2H-pyran-4-yl)-1H-pyrazolo[4,3-c]pyridin-4-amine

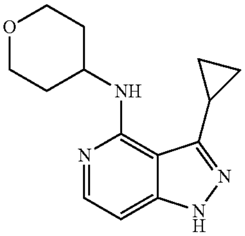 [SMILES: c1cc2[nH]nc(C3CC3)c2c(NC2CCOCC2)n1]

To a solution of Intermediate 35 (40 mg, 0.21 mmol) in 1-butanol (0.9 ml) at room temperature was added 4-aminotetrahydropyran (84 mg, 0.83 mmol). The resulting mixture was irradiated at 190° C. for 2 h in a Biotage I-60 microwave reactor. The reaction mixture was then evaporated to dryness and the crude residue was purified by preparative LCMS (high pH buffer) to give the product as a white solid (33 mg, 62%). $^{1}$H NMR (400 MHz, DMSO-$d_6$) δ ppm 0.81-0.86 (m, 2 H), 0.93-1.00 (m, 2 H), 1.56-1.68 (m, 2 H), 1.90-1.98 (m, 2 H), 2.31-2.38 (m, 1 H), 3.40-3.49 (m, 2 H), 3.84-3.93 (m, 2 H), 4.22-4.34 (m, 1 H), 5.79 (d, J=7.8 Hz, 1 H), 6.58 (d, J=6.0 Hz, 1 H), 7.66 (d, J=6.0 Hz, 1 H). m/z (ES+APCI)$^{+}$: 259 [M+H]$^{+}$.

Example 20

3-Cyclohexyl-N-(tetrahydro-2H-pyran-4-yl)-1H-pyrazolo[4,3-c]pyridin-4-amine

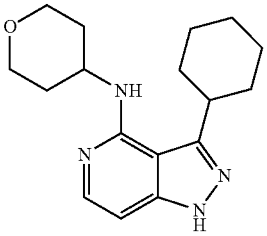 [SMILES: c1cc2[nH]nc(C3CCCCC3)c2c(NC2CCOCC2)n1]

Prepared analogously to Example 19 from Intermediate 34 and 4-aminotetrahydropyran to give the desired product as a white solid (21 mg, 34%). $^{1}$H (400 MHz, 60° C., DMSO-$d_6$) δ ppm 1.22-1.33 (m, 1 H), 1.47-1.69 (m, 6 H), 1.70-1.85 (m, 4 H), 1.94-2.09 (m, 4 H), 3.44-3.52 (m, 2 H), 3.84-3.92 (m, 2 H), 4.23-4.33 (m, 1 H), 5.28 (d, J=6.9 Hz, 1 H), 6.61 (d, J=6.0 Hz, 1 H), 7.68 (d, J=6.0 Hz, 1 H), 12.47 (br. s., 1 H). m/z (ES+APCI)$^{+}$: 301 [M+H]$^{+}$ Example 21

3-(Propan-2-yl)-N-(tetrahydro-2H-pyran-4-yl)-1H-pyrazolo[4,3-c]pyridin-4-amine

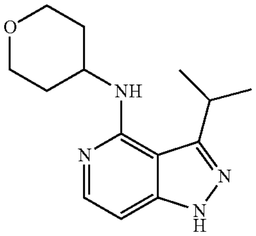 [SMILES: CC(C)c1n[nH]c2ccnc(NC3CCOCC3)c12]

Prepared analogously to Example 19 from Intermediate 33 and 4-aminotetrahydropyran to give the desired product as a white solid (20 mg, 37%). $^{1}$H NMR (400 MHz, DMSO-$d_6$) δ ppm 1.30 (d, J=6.9 Hz, 6 H), 1.59-1.71 (m, 2 H), 1.90 (s, 2 H), 3.38-3.47 (m, 2 H), 3.54-3.63 (m, 1 H), 3.84-3.92 (m, 2 H), 4.24-4.35 (m, 1 H), 5.53 (d, J=7.3 Hz, 1 H), 6.60 (d, J=6.0 Hz, 1 H), 7.67 (d, J=6.0 Hz, 1 H). m/z (ES+APCI)$^{+}$: 261 [M+H]$^{+}$.

Example 22

N,3-Dicyclohexyl-1H-pyrazolo[4,3-c]pyridin-4-amine

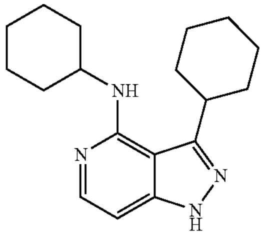 [SMILES: c1cc2[nH]nc(C3CCCCC3)c2c(NC2CCCCC2)n1]

Prepared analogously to Example 19 from Intermediate 34 and cyclohexylamine to give the desired product as a white solid (22 mg, 36%). $^{1}$H NMR (400 MHz, 60° C. DMSO-$d_6$) δ ppm 1.21-1.65 (m, 11 H), 1.66-1.78 (m, 3 H), 1.78-1.87 (m, 2 H), 1.93-2.08 (m, 4 H), 3.05-3.14 (m, 1 H), 4.04-4.13 (m, 1 H), 5.12 (br. s, 1 H), 6.58 (d, J=6.0 Hz, 1 H), 7.67 (d, J=6.0 Hz, 1 H), 12.45 (br. s., 1 H). m/z (ES+APCI)$^{+}$: 299 [M+H]$^{+}$ Example 23

N-Cyclohexyl-3-(propan-2-yl)-1H-pyrazolo[4,3-c]pyridin-4-amine

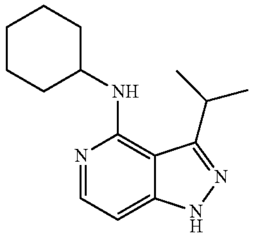 [SMILES: CC(C)c1n[nH]c2ccnc(NC3CCCCC3)c12]

Prepared analogously to Example 19 from Intermediate 33 and cyclohexylamine to give the desired product as a white solid (21 mg, 39%). $^{1}$H NMR (400 MHz, DMSO-$d_6$) δ ppm 1.14-1.25 (m, 1 H), 1.27-1.44 (m, 10 H), 1.56-1.64 (m, 1 H), 1.66-1.79 (m, 2 H), 1.87-2.00 (m, 2 H), 3.47-3.56 (m, 1 H), 4.01-4.14 (m, 1 H), 5.34 (d, J=7.79 Hz, 1 H), 6.56 (d, J=6.0 Hz, 1 H), 7.66 (d, J=6.0 Hz, 1 H). m/z (ES+APCI)$^{+}$: 259 [M+H]$^{+}$ Example 24

3-Cyclopropyl-4-(propan-2-yloxy)-1H-pyrazolo[4,3-c]pyridine

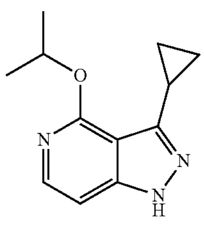 [SMILES: CC(C)Oc1nccc2[nH]nc(C3CC3)c12]

To a solution of propan-2-ol (95 µl, 1.24 mmol) in dioxane (2 ml) in a 2-5 ml microwave vial was added sodium hydride (60% in mineral oil, 44 mg, 1.09 mmol). The mixture was allowed to stir at room temperature for 2 h. A solution of Intermediate 35 (60 mg, 0.31 mmol) in dioxane (1 ml) was added, then the reaction mixture was irradiated at 190° C. for 2 h in a Biotage I-60 microwave reactor. The mixture was evaporated and water (10 ml) and ethyl acetate (10 ml) were added. The layers were separated and the aqueous extracted with further ethyl acetate. The organic layers were combined and washed with brine, dried ($MgSO_4$) and evaporated. The crude product was then purified by preparative LCMS (high pH buffer) to give the desired product as a white solid (11 mg, 16%). $^1H$ NMR (400 MHz, DMSO-$d_6$) δ ppm 0.90-1.01 (m, 4 H), 1.37 (d, J=6.0 Hz, 6 H), 2.40-2.48 (m, 1 H), 5.40-5.51 (m, 1 H), 6.95 (d, J=6.0 Hz, 1 H), 7.76 (d, J=6.4 Hz, 1 H). m/z (ES+APCI)$^+$: 218 [M+H]$^+$

Example 25

3-(Propan-2-yl)-4-(propan-2-yloxy)-1H-pyrazolo[4,3-c]pyridine

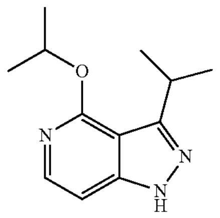 [SMILES: CC(C)Oc1nccc2[nH]nc(C(C)C)c12]

Prepared analogously to Example 24 from Intermediate 33 and propan-2-ol to give the desired product as a white solid (19 mg, 28%). $^1H$ NMR (400 MHz, DMSO-$d_6$) δ ppm 1.29-1.39 (m, 12 H), 3.37-3.47 (m, 1 H), 5.41-5.52 (m, 1 H), 6.97 (d, J=6.0 Hz, 1 H), 7.78 (d, J=6.0 Hz, 1 H). m/z (ES+APCI)$^+$: 220 [M+H]$^+$

Example 26

4-(Cyclohexyloxy)-3-cyclopropyl-1H-pyrazolo[4,3-c]pyridine

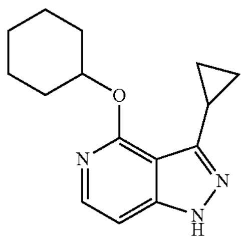 [SMILES: c1cc2[nH]nc(C3CC3)c2c(OC2CCCCC2)n1]

Prepared analogously to Example 24 from Intermediate 35 and cyclohexanol to give the desired product as a white solid (21 mg, 26%). $^1H$ NMR (400 MHz, DMSO-$d_6$) δ ppm 0.90-1.01 (m, 4 H), 1.33-1.56 (m, 4 H), 1.56-1.66 (m, 2 H), 1.69-1.79 (m, 2 H), 1.90-2.00 (m, 2 H), 2.41-2.48 (m, 1 H), 5.24-5.33 (m, 1 H), 6.95 (d, J=6.0 Hz, 1 H), 7.75 (d, J=6.0 Hz, 1 H). m/z (ES+APCI)$^+$: 258 [M+H]$^+$

Example 27

4-(Cyclohexyloxy)-3-(propan-2-yl)-1H-pyrazolo[4,3-c]pyridine

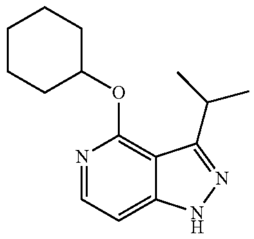 [SMILES: CC(C)c1n[nH]c2ccnc(OC3CCCCC3)c12]

Prepared analogously to Example 24 from Intermediate 33 and cyclohexanol to give the desired product as a white solid (28 mg, 35%). $^1H$ NMR (400 MHz, DMSO-$d_6$) δ ppm 1.34 (d, J=6.9 Hz, 6 H), 1.38-1.56 (m, 4 H), 1.57-1.67 (m, 2 H), 1.69-1.79 (m, 2 H), 1.89-1.99 (m, 2 H), 3.39-3.51 (m, 1 H), 5.25-5.33 (m, 1 H), 6.97 (d, J=6.0 Hz, 1 H), 7.77 (d, J=6.0 Hz, 1 H). m/z (ES+APCI)$^+$: 260 [M+H]$^+$

Example 28

3-Cyclopropyl-4-(tetrahydro-2H-pyran-4-yloxy)-1H-pyrazolo[4,3-c]pyridine

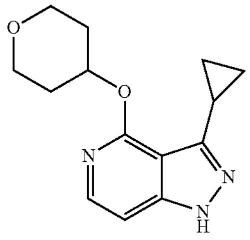 [SMILES: c1cc2[nH]nc(C3CC3)c2c(OC2CCOCC2)n1]

To a solution of tetrahydro-2H-pyran-4-ol (119 µl, 1.24 mmol) in dioxane (2 ml) in a 2-5 ml microwave vial was added sodium hydride (60% in mineral oil, 44 mg, 1.09 mmol). The mixture was allowed to stir at room temperature for 2 h. A solution of Intermediate 35 (60 mg, 0.31 mmol) in dioxane (1 ml) was added, then the reaction mixture was irradiated at 190° C. for 2 h in a Biotage I-60 microwave reactor. The mixture was evaporated, then water (10 ml) and ethyl acetate (10 ml) were added. The layers were separated and the aqueous extracted with further ethyl acetate. The organic layers were combined and washed with brine, dried ($MgSO_4$) and evaporated. The crude product was then purified by preparative LCMS (low pH buffer) then eluted through a 0.5 gram (solute-$NH_2$ cartridge with methanol to give the free base. $^1H$ NMR (400 MHz, DMSO-$d_6$) δ ppm 0.90-1.02 (m, 4 H), 1.68-1.79 (m, 2 H), 2.01-2.10 (m, 2 H), 2.42-2.48 (m, 1 H), 3.53-3.62 (m, 2 H), 3.82-3.91 (m, 2 H), 5.43-5.50 (m, 1 H), 6.98 (d, J=6.0 Hz, 1 H), 7.77 (d, J=6.4 Hz, 1 H). m/z (ES+APCI)$^+$: 260 [M+H]$^+$ Example 29

3-Cyclopropyl-4-[(2R)-butan-2-yloxy)-1H-pyrazolo [4,3-c]pyridine

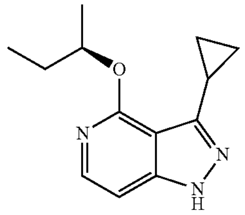 [SMILES: CC[C@@H](C)Oc1nccc2[nH]nc(C3CC3)c12]

Prepared analogously to Example 24 from Intermediate 35 and (2R)-butan-2-ol to give the desired product as a white solid (17 mg, 24%). $^1$H NMR (400 MHz, DMSO-$d_6$) δ ppm 0.87-1.05 (m, 7 H), 1.33 (d, J=6.41 Hz, 3 H), 1.62-1.82 (m, 2 H), 2.40-2.48 (m, 1 H), 5.25-5.36 (m, 1 H), 6.95 (d, J=6.4 Hz, 1 H), 7.76 (d, J=6.0 Hz, 1 H). m/z (ES+APCI)$^+$: 232 [M+H]$^+$ Example 30

4-[(2R)-Butan-2-yloxy]-3-(propan-2-yl)-1H-pyrazolo[4,3-c]pyridine

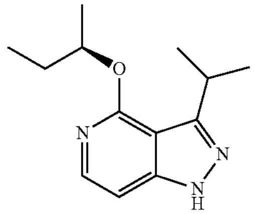 [SMILES: CC[C@@H](C)Oc1nccc2[nH]nc(C(C)C)c12]

Prepared analogously to Example 24 from Intermediate 33 and (2R)-butan-2-ol to give the desired product as a colourless oil (18 mg, 25%). $^1$H NMR (400 MHz, DMSO-$d_6$) δ ppm 0.96 (t, J=7.6 Hz, 3 H), 1.29-1.36 (m, 9 H), 1.65-1.81 (m, 2 H), 3.38-3.49 (m, 1 H), 5.31-5.40 (m, 1 H), 6.97 (d, J=6.0 Hz, 1 H), 7.77 (d, J=6.0 Hz, 1 H). m/z (ES+APCI)$^+$: 234 [M+H]$^+$.

Example 31

3-Cyclopropyl-4-[(3S)-tetrahydrofuran-3-yloxy]-1H-pyrazolo[4,3-c]pyridine

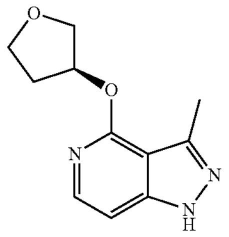 [SMILES: Cc1n[nH]c2ccnc(O[C@H]3CCOC3)c12]

Intermediate 32 (100 mg, 0.24 mmol), (3S)-tetrahydrofuran-3-ol (39 μl, 0.49 mmol), $Pd(OAc)_2$ (3.3 mg, 0.015 mmol), BINAP (12 mg, 0.02 mmol) and sodium tert-butoxide (70 mg, 0.73 mmol) were combined in toluene (3 ml). The mixture was degassed and placed under an atmosphere of nitrogen, then stirred at 100° C. for 18 h. The mixture was diluted with DCM, washed with water and the organic layer was recovered using a phase separation cartridge, dried ($MgSO_4$) and evaporated. The crude product was dissolved in trifluoroacetic acid (0.2 ml, 2.70 mmol) in DCM (2 ml) and stirred at rt for 18 h. The reaction mixture was evaporated and then purified by cation exchange chromatography using an (solute SCX cartridge. The crude product was then purified by preparative LCMS (high pH buffer) to give the product as an off-white solid (3.7 mg, 7%). $^1$H NMR (400 MHz, DMSO-$d_6$) δ ppm 2.06-2.13 (m, 1 H), 2.21-2.31 (m, 1 H), 2.53 (s, 3 H), 3.78-3.93 (m, 3 H), 3.95-4.01 (m, 1 H), 5.65-5.70 (m, 1 H), 7.01 (d, J=6.00 Hz, 1 H), 7.78 (d, J=5.95 Hz, 1H). m/z (ES+APCI)$^+$: 220 [M+H]$^+$ Example 32

3-Cyclobutyl-N-cyclohexyl-1H-pyrazolo[4,3-c]pyridin-4-amine

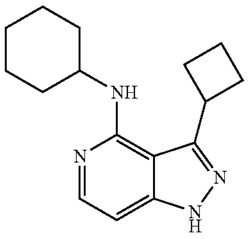 [SMILES: c1cc2[nH]nc(C3CCC3)c2c(NC2CCCCC2)n1]

To a solution of Intermediate 36 (40 mg, 0.19 mmol) in 1-butanol (1 ml) at room temperature was added cyclohexylamine (88 μl, 0.77 mmol). The resulting mixture was irradiated at 190° C. for 2 h in a Biotage I-60 microwave reactor. The reaction mixture was then evaporated to dryness and the crude residue was purified by preparative LCMS (high pH buffer) to give the product as an off-white solid (12 mg, 23%). $^1$H NMR (400 MHz, DMSO-$d_6$) δ ppm 1.15-1.27 (m, 1 H), 1.28-1.42 (m, 4 H), 1.56-1.65 (m, 1 H), 1.66-1.76 (m, 2 H), 1.81-1.99 (m, 3 H), 2.00-2.13 (m, 1 H), 2.27-2.42 (m, 4 H), 3.97-4.08 (m, 2 H), 5.13 (d, J=7.8 Hz, 1 H), 6.56 (d, J=6.4 Hz, 1 H), 7.65 (d, J=6.0 Hz, 1H). m/z (ES+APCI)$^+$: 271 [M+H]$^+$ Example 33

4-(Cyclohexyloxy)-3-(pyrimidin-5-yl)-1H-pyrazolo [4,3-c]pyridine

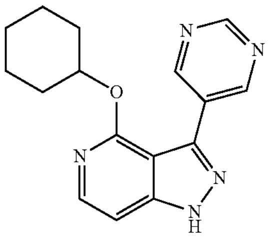 [SMILES: c1ncc(-c2n[nH]c3ccnc(OC4CCCCC4)c23)cn1]

Step 1—4-(Cyclohexyloxy)-3-(pyrimidin-5-yl)-1-trityl-1H-pyrazolo[4,3-c]pyridine

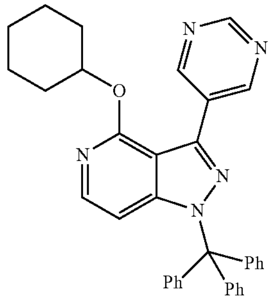 [SMILES: c1ccc(C(c2ccccc2)(c2ccccc2)n2nc(-c3cncnc3)c3c(OC4CCCCC4)nccc32)cc1]

Intermediate 11 (120 mg, 0.21 mmol), Pd(dppf)$Cl_2$ (16 mg, 0.02 mmol), 2M $Na_2CO_3$ (aq) (358 μl, 0.72 mmol) and pyrimidine-5-boronic acid (38 mg, 0.31 mmol) were combined in dioxane (1 ml) and the solution degassed with nitrogen. The vial was then flushed out with nitrogen and heated at 90° C. for 18 h. The solution was partitioned between DCM and water and filtered through a phase separator cartridge. The solvents were evaporated and the crude material purified by column chromatography gradient elution from 10-100% ethyl acetate/petroleum ether to give a white solid (73 mg, 66%). $^1$H NMR (400 MHz, DMSO-$d_6$) δ ppm 1.22-1.45 (m, 3 H), 1.45-1.59 (m, 3 H), 1.59-1.69 (m, 2 H), 1.93-2.02 (m, 2 H), 5.25 (m, 1 H), 5.90 (d, J=6.0 Hz, 1 H), 7.13-7.26 (m, 6 H), 7.26-7.42 (m, 10 H), 7.64 (d, J=6.4 Hz, 1 H), 9.21 (s, 2 H); Rf=0.67 (1:1, petroleum ether:ethyl acetate).

Step 2—4-(Cyclohexyloxy)-3-(pyrimidin-5-yl)-1H-pyrazolo[4,3-c]pyridine 4-(Cyclohexyloxy)-3-(pyrimidin-5-yl)-1-trityl-1H-pyrazolo[4,3-c]pyridine (70 mg, 0.13 mmol) was dissolved in 4:6 TFA:DCM mixture (1 ml) and stirred at room temperature for 2 h. The solvents were evaporated and the crude material purified by preparative LCMS (6 mg, 15%). $^1$H NMR (400 MHz, DMSO-$d_6$) δ ppm 1.24-1.47 (m, 3 H), 1.47-1.60 (m, 3 H), 1.60-1.70 (m, 2 H), 1.94-2.03 (m, 2 H), 5.20-5.40 (m, 1 H), 7.18 (d, J=6.0 Hz, 1 H), 7.93 (d, J=6.0 Hz, 1 H), 9.23 (s, 1 H), 9.32 (s, 2 H); m/z (ES+APCI)$^+$: 296 [M+H]$^+$.

Example 34

4-(Cyclohexyloxy)-3-(1-methyl-1H-pyrazol-5-yl)-1H-pyrazolo[4,3-c]pyridine

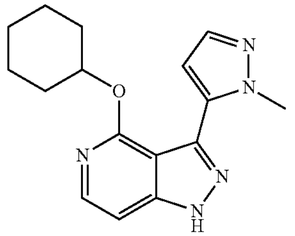 [SMILES: Cn1nccc1-c1n[nH]c2ccnc(OC3CCCCC3)c12]

Step 1—4-(Cyclohexyloxy)-3-(1-methyl-1H-pyrazol-5-yl)-1-trityl-1H-pyrazolo[4,3-c]pyridine

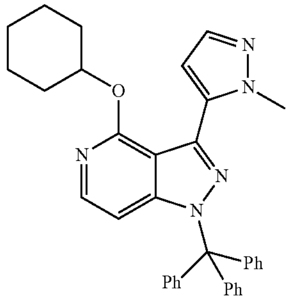 [SMILES: Cn1nccc1-c1nn(C(c2ccccc2)(c2ccccc2)c2ccccc2)c2ccnc(OC3CCCCC3)c12]

Intermediate 11 (120 mg, 0.21 mmol), Pd(dppf)$Cl_2$ (16 mg, 0.02 mmol), 2M $Na_2CO_3$ (aq) (358 μl, 0.72 mmol) and 1-methyl-1H-pyrazole-5-boronic acid pinacol ester (64 mg, 0.31 mmol) were combined in dioxane (1 ml) and the solution degassed with nitrogen. The vial was then flushed out with nitrogen and heated at 90° C. for 18 h. The solution was partitioned between DCM and water and filtered through a phase separation cartridge. The solvents were evaporated and the crude material purified by column chromatography eluting with 10% ethyl acetate/petroleum ether to 100% ethyl acetate to give a white solid (54 mg, 49%). $^1$H NMR (400 MHz, DMSO-$d_6$) δ ppm 1.23-1.42 (m, 2 H), 1.45-1.56 (m, 4 H), 1.63-1.72 (m, 2 H), 1.95-2.03 (m, 2 H), 3.76 (s, 3 H), 5.07-5.29 (m, 1 H), 5.88 (d, J=6.0 Hz, 1 H), 6.89 (d, J=1.8 Hz, 1 H), 7.09-7.26 (m, 6 H), 7.30-7.41 (m, 9 H), 7.50 (d, J=1.8 Hz, 1 H), 7.61 (d, J=6.4 Hz, 1H); Rf=0.72 (1:1, petroleum ether:ethyl acetate).

Step 2—4-(Cyclohexyloxy)-3-(1-methyl-1H-pyrazol-5-yl)-1H-pyrazolo[4,3-c]pyridine 4-(Cyclohexyloxy)-3-(1-methyl-1H-pyrazol-5-yl)-1-trityl-1H-pyrazolo[4,3-c]pyridine (50 mg, 0.09 mmol) was dissolved in 4:6 TFA:DCM mixture (1 ml) and stirred at room temperature for 2 h. The solvents were evaporated and the crude material purified by preparative LCMS (3.5 mg, 18%). $^1$H NMR (400 MHz, DMSO-$d_6$) δ ppm 1.23-1.43 (m, 3 H), 1.44-1.56 (m, 3 H), 1.58-1.69 (m, 2 H), 1.91-2.00 (m, 2 H), 3.96 (s, 3 H), 5.13-5.35 (m, 1 H), 6.77 (d, J=1.8 Hz, 1 H), 7.14 (d, J=6.0 Hz, 1 H), 7.53 (d, J=2.3 Hz, 1 H), 7.90 (d, J=6.0 Hz, 1H); m/z (ES+APCI)$^+$: 298 [M+H]$^+$.

Example 35

3-(Furan-3-yl)-4-(tetrahydro-2H-pyran-4-yloxy)-1H-pyrazolo[4,3-c]pyridine

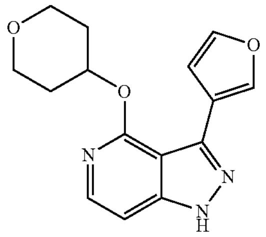 [SMILES: c1cc2[nH]nc(-c3ccoc3)c2c(OC2CCOCC2)n1]

A degassed solution of Intermediate 21 (120 mg, 0.20 mmol), Pd(dppf)$Cl_2$ (17 mg, 0.02 mmol), 2M $Na_2CO_3$ (aq)

(358 μl, 0.72 mmol) and furan-3-boronic acid (34 mg, 0.31 mmol) (1 ml) was heated at 90° C. for 18 h. The solution was cooled down, partitioned between water and DCM, filtered through a phase separation cartridge and solvents evaporated. The crude product was eluted through a short silica plug using 50% ethyl acetate/petroleum ether and solvents evaporated. The resulting solid was dissolved in 4:6 TFA/DCM (0.5 ml) and stirred at room temperature for 2 h. The solvents were evaporated and the crude product eluted through an Isolute-SCX cartridge, using EtOAc, followed by 1M $NH_3$ in methanol. The solvents were evaporated and the product purified by preparative LCMS to give a white solid (8 mg, 14%). $^1$H NMR (400 MHz, DMSO-$d_6$) δ ppm 1.73-1.83 (m, 2 H), 2.12-2.19 (m, 2 H), 3.50-3.57 (m, 2 H), 3.87-3.94 (m, 2 H), 5.42-5.54 (m, 1 H), 7.04 (dd, J=1.8, 0.92 Hz, 1 H), 7.11 (d, J=6.0 Hz, 1 H), 7.79 (t, J=1.6 Hz, 1 H), 7.87 (d, J=6.0 Hz, 1 H), 8.32-8.34 (m, 1 H); m/z (ES+APCI)$^+$: 286 [M+H]$^+$.

Example 36

3-[1-(Propan-2-yl)-1H-pyrazol-4-yl]-4-(tetrahydro-2H-pyran-4-yloxy)-1H-pyrazolo[4,3-c]pyridine

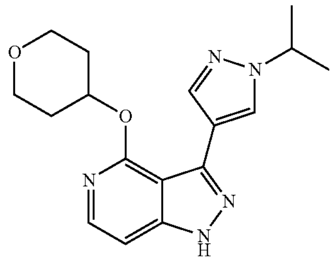 [SMILES: CC(C)n1cc(-c2n[nH]c3ccnc(OC4CCOCC4)c23)cn1]

Prepared analogously to Example 35 from Intermediate 21 and 1-isopropyl-1H-pyrazole-4-boronic acid, pinacol ester to give a white solid (1.2 mg, 2%). $^1$H NMR (400 MHz, METHANOL-$d_4$) δ ppm 1.57 (d, J=6.41 Hz, 6 H), 1.80-1.95 (m, 2 H), 2.19-2.27 (m, 2 H), 3.64 (m, 2 H), 3.95-4.02 (m, 2 H), 4.61 (m, 1 H), 5.47-5.55 (m, 1 H), 7.05 (d, J=6.0 Hz, 1 H), 7.84 (d, J=6.4 Hz, 1 H), 8.11 (s, 1 H), 8.27 (s, 1H); m/z (ES+APCI)$^+$: 328 [M+H]$^+$.

Example 37

3-(Furan-2-yl)-4-(tetrahydro-2H-pyran-4-yloxy)-1H-pyrazolo[4,3-c]pyridine

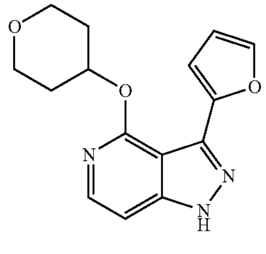 [SMILES: c1coc(-c2n[nH]c3ccnc(OC4CCOCC4)c23)c1]

Prepared analogously to Example 35 from Intermediate 21 and furan-2-boronic acid to give a white solid (1.0 mg, 2%). $^1$H NMR (400 MHz, DMSO-$d_6$) δ ppm 1.68-1.93 (m, 2 H), 2.12-2.25 (m, 2 H), 3.54 (t, J=9.39 Hz, 2 H), 3.89-4.02 (m, 2 H), 5.37-5.57 (m, 1 H), 6.67 (br. s., 1 H), 7.11 (d, J=6.0 Hz, 1 H), 7.25 (d, J=2.8 Hz, 1 H), 7.80 (br. s., 1 H), 7.88 (d, J=6.0 Hz, 1 H); m/z (ES+APCI)$^+$: 286 [M+H]$^+$.

Example 38

3-(1,3-Dimethyl-1H-pyrazol-4-yl)-4-(tetrahydro-2H-pyran-4-yloxy)-1H-pyrazolo[4,3-c]pyridine

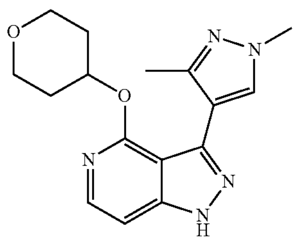 [SMILES: Cc1nn(C)cc1-c1n[nH]c2ccnc(OC3CCOCC3)c12]

Prepared analogously to Example 34 from Intermediate 21 and 1,3-dimethyl-1H-pyrazole-4-boronic acid, pinacol ester to give a white solid. $^1$H NMR (400 MHz, DMSO-$d_6$) δ ppm 1.70-1.80 (m, 2 H), 2.06-2.13 (m, 2 H), 2.36 (s, 3 H), 3.52 (ddd, J=11.7, 9.4, 2.8 Hz, 2 H), 3.78-3.87 (m, 5 H), 5.39-5.46 (m, 1 H), 7.07 (d, J=6.0 Hz, 1 H), 7.82 (d, J=6.0 Hz, 1 H), 8.11 (s, 1 H); m/z (ES+APCI)$^+$: 314 [M+H]$^+$.

Example 39

3-(1-Cyclopentyl-1H-pyrazol-4-yl)-4-(tetrahydro-2H-pyran-4-yloxy)-1H-pyrazolo[4,3-c]pyridine

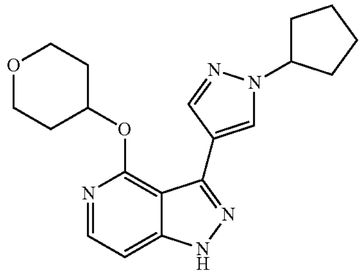 [SMILES: c1cc2[nH]nc(-c3cnn(C4CCCC4)c3)c2c(OC2CCOCC2)n1]

Prepared analogously to Example 34 from Intermediate 21 and 1-cyclopentyl-1H-pyrazole-4-boronic acid, pinacol ester to give a white solid (4.9 mg, 14%). $^1$H NMR (400 MHz, DMSO-$d_6$) δ ppm 1.62-1.88 (m, 6 H), 1.92-2.02 (m, 2 H), 2.09-2.19 (m, 4 H), 3.49-3.57 (m, 2 H), 3.86-3.93 (m, 2 H), 4.77 (m, 1 H), 5.39-5.53 (m, 1 H), 7.07 (d, J=6.0 Hz, 1 H), 7.83 (d, J=6.0 Hz, 1 H), 8.01 (s, 1 H), 8.27 (s, 1 H); m/z (ES+APCI)$^+$: 354 [M+H]$^+$.

Example 40

3-[1-(2-Methylpropyl)-1H-pyrazol-4-yl]-4-(tetrahydro-2H-pyran-4-yloxy)-1H-pyrazolo[4,3-c]pyridine

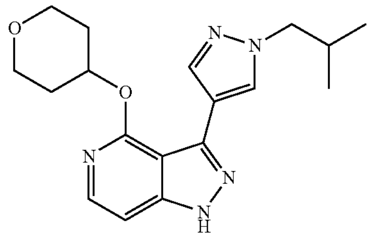 [SMILES: CC(C)Cn1cc(-c2n[nH]c3ccnc(OC4CCOCC4)c23)cn1]

Prepared analogously to Example 34 from Intermediate 21 and 1-isobutyl-1H-pyrazole-4-boronic acid, pinacol ester to give a white solid. $^1H$ NMR (400 MHz, DMSO-$d_6$) δ ppm 0.75-0.95 (m, 6 H), 1.72-1.83 (m, 2 H), 2.10-2.22 (m, 3 H), 3.48-3.56 (m, 2 H), 3.90 (m, 2 H), 3.99 (d, J=7.3 Hz, 2 H), 5.43-5.50 (m, 1 H), 7.07 (d, J=6.0 Hz, 1 H), 7.83 (d, J=6.0 Hz, 1 H), 8.01 (s, 1 H), 8.23 (s, 1 H); m/z (ES+APCI)$^+$: 342 [M+H]$^+$.

Example 41

3-[1-(Cyclobutylmethyl)-1H-pyrazol-4-yl]-4-(cyclohexyloxy)-1H-pyrazolo[4,3-c]pyridine

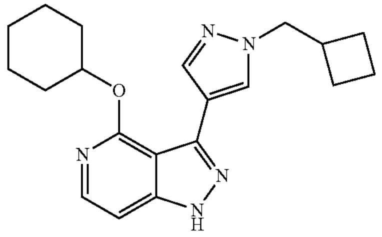 [SMILES: c1cc2[nH]nc(-c3cnn(CC4CCC4)c3)c2c(OC2CCCCC2)n1]

Step 1—3-[1-(Cyclobutylmethyl)-1H-pyrazol-4-yl]-4-(cyclohexyloxy)-1-trityl-1H-pyrazolo[4,3-c]pyridine

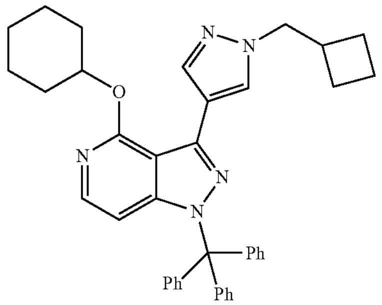 [SMILES: c1ccc(C(c2ccccc2)(c2ccccc2)n2nc(-c3cnn(CC4CCC4)c3)c3c(OC4CCCCC4)nccc32)cc1]

Intermediate 37 (100 mg, 0.19 mmol), caesium carbonate (232 mg, 0.38 mmol) and bromomethylcyclobutane (32 μl, 0.29 mmol) were combined in DMF (0.5 ml) and stirred at 90° C. for 18 h. The reaction mixture was cooled down, then partitioned between ethyl acetate and water, extracted twice with ethyl acetate and the combined organic extracts washed twice with brine, dried ($MgSO_4$) and solvents evaporated. Purification by column chromatography, eluting with 10% ethyl acetate/petroleum ether to 80% ethyl acetate/petroleum ether gave the products as a white solid (75 mg, 66%).

Step 2—3-[1-(Cyclobutylmethyl)-1H-pyrazol-4-yl]-4-(cyclohexyloxy)-1H-pyrazolo[4,3-c]pyridine (70 mg, 0.12 mmol) was dissolved in 4:6 TFA:DCM mixture (1 ml) and stirred at room temperature for 1.5 h. The solvents were evaporated and the crude material purified by preparative LCMS to give a white solid (5.7 mg, 14%). $^1H$ NMR (400 MHz, DMSO-$d_6$) δ ppm 1.34-1.48 (m, 2 H), 1.51-1.63 (m, 3 H), 1.72-1.90 (m, 7 H), 1.96-2.05 (m, 2 H), 2.07-2.15 (m, 2 H), 2.79 (m, 1 H), 4.18 (d, J=7.3 Hz, 2 H), 5.24-5.31 (m, 1 H), 7.03 (d, J=6.4 Hz, 1 H), 7.81 (d, J=6.4 Hz, 1 H), 8.01 (s, 1 H), 8.22 (s, 1 H); m/z (ES+APCI)$^+$: 352 [M+H]$^+$.

Example 42

3-[1-(2-Methoxyethyl)-1H-pyrazol-4-yl]-N-(tetrahydro-2H-pyran-4-yl)-1H-pyrazolo[4,3-c]pyridin-4-amine

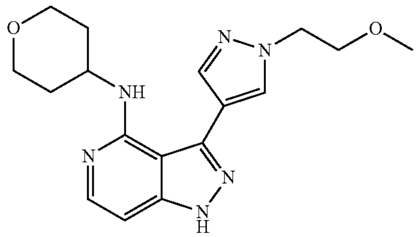 [SMILES: COCCn1cc(-c2n[nH]c3ccnc(NC4CCOCC4)c23)cn1]

Intermediate 38 (100 mg, 0.25 mmol), caesium carbonate (302 mg, 0.50 mmol) and 2-bromoethyl methyl ether (35 μl, 0.37 mmol) were combined in DMF (1 ml) and stirred at 90° C. for 18 h. The reaction mixture was cooled down, then partitioned between ethyl acetate and water, extracted twice with ethyl acetate and combined organic extracts dried ($MgSO_4$) and solvents evaporated. TFA (1 ml) was added to the crude reaction mixture and heated at 70° C. for 2 days. TFA was then evaporated and the product purified by preparative LCMS to give a clear oil (30 mg, 35%). $^1H$ NMR (400 MHz, DMSO-$d_6$) δ ppm 1.33-1.45 (m, 2 H), 1.90-1.98 (m, 2 H), 3.32 (s, 3 H), 3.42 (m, 2 H), 3.67-3.83 (m, 4 H), 4.11-4.21 (m, 1 H), 4.37 (t, J=5.0 Hz, 2 H), 5.24 (br. s., 1 H), 6.64-6.74 (m, 1 H), 7.69-7.78 (m, 2 H), 8.09 (s, 1 H); m/z (ES+APCI)$^+$: 343 [M+H]$^+$.

Examples 43-46

Examples 43-46 in the following table were prepared analogously to Example 42 from Intermediate 38 and the corresponding alkyl halide.

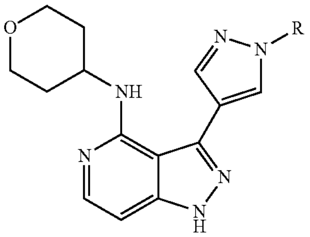

| Example | R group | Name | m/z (ES + APCI)$^+$ | HPLC retention time (min) |
|---|---|---|---|---|
| 43 | 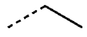 | 3-(1-ethyl-1H-pyrazol-4-yl)-N-(tetrahydro-2H-pyran-4-yl)-1H-pyrazolo[4,3-c]pyridin-4-amine | 313 | 1.12[a] |
| 44 | 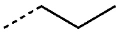 | 3-(1-propyl-1H-pyrazol-4-yl)-N-(tetrahydro-2H-pyran-4-yl)-1H-pyrazolo[4,3-c]pyridin-4-amine | 327 | 1.23[a] |
| 45 | 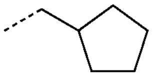 | 3-[1-(cyclopentylmethyl)-1H-pyrazol-4-yl]-N-(tetrahydro-2H-pyran-4-yl)-1H-pyrazolo[4,3-c]pyridin-4-amine | 367 | 1.51[a] |
| 46 | 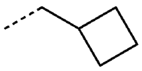 | 3-[1-(cyclobutylmethyl)-1H-pyrazol-4-yl]-N-(tetrahydro-2H-pyran-4-yl)-1H-pyrazolo[4,3-c]pyridin-4-amine | 353 | 1.69[b] |

[a]HPLC column: 4.6 x 50 mm (5 μm) C-18 Xbridge; flow rate: 3 ml/min; Run time: 3.2 min: Solvent A: 0.1% Ammonium Hydroxide in water Solvent B: Acetonitrile; Gradient - 10-100% B; Gradient time: 2.35 min.

[b]HPLC column: 4.6 x 30 mm (3.5 μm) C-18 Xbridge; flow rate: 2 ml/min; Run time: 3.2 min: Solvent A: 0.1% Formic acid in water, Solvent B: Methanol; Gradient - 10-100% B; Gradient time: 2.1 min.

Example 47

3-(1-Cyclopentyl-1H-pyrazol-4-yl)-N-(tetrahydro-2H-pyran-4-yl)-1H-pyrazolo[4,3-c]pyridin-4-amine

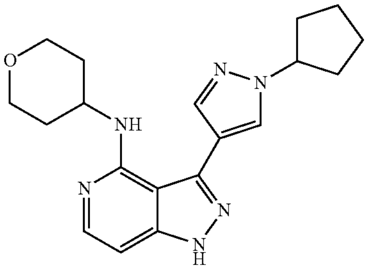 [SMILES: c1cc2[nH]nc(-c3cnn(C4CCCC4)c3)c2c(NC2CCOCC2)n1]

Intermediate 5 (80 mg, 0.17 mmol), Pd(dppf)$Cl_2$ (14 mg, 0.02 mmol), 2M $Na_2CO_3$ (aq) (302 μl, 0.60 mmol) and 1-cyclopentyl-1H-pyrazole-4-boronic acid, pinacol ester (68 mg, 0.26 mmol) were combined in dioxane (1 ml) and the mixture degassed with nitrogen for 1 min. The reaction mixture was then stirred to 90° C. for 18 h. The solution was cooled, partitioned between DCM and water, filtered through a phase separation cartridge and solvents evaporated. The crude material was heated to 60° C. in TFA (1 ml) for 2 days. The mixture was concentrated and purified by preparative LCMS to give a brown solid (39 mg, 64%). $^1$H NMR (400 MHz, DMSO-$d_6$) δ ppm 1.34-1.45 (m, 2 H), 1.63-1.74 (m, 2 H), 1.77-1.89 (m, 2 H), 1.93-2.05 (m, 4 H), 2.09-2.19 (m, 2 H), 3.38-3.48 (m, 2 H), 3.78 (m, 2 H), 4.12-4.22 (m, 1 H), 4.81 (quin, J=7.1 Hz, 1 H), 5.27 (br. s., 1 H), 6.71 (d, J=6.0 Hz, 1 H), 7.72-7.78 (m, 2 H), 8.16 (s, 1 H); m/z (ES+APCI)$^+$: 353 $[M+H]^+$.

Example 48

3-[1-(2-Methylpropyl)-1H-pyrazol-4-yl]-N-(tetrahydro-2H-pyran-4-yl)-1H-pyrazolo[4,3-c]pyridin-4-amine

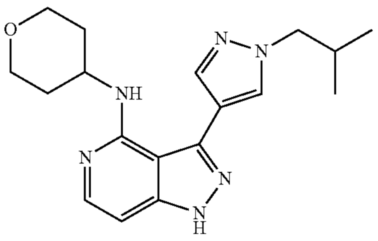 [SMILES: CC(C)Cn1cc(-c2n[nH]c3ccnc(NC4CCOCC4)c23)cn1]

Prepared analogously to Example 47 from Intermediate 5 and 1-isobutyl-1H-pyrazole-4-boronic acid, pinacol ester to give a brown solid. $^1$H NMR (400 MHz, DMSO-$d_6$) δ ppm 0.89 (d, J=6.4 Hz, 6 H), 1.30-1.42 (m, 2 H), 1.90-2.03 (m, 2 H), 2.14-2.25 (m, 1 H), 3.42 (m, 2 H), 3.79 (m, 2 H), 4.03 (d, J=7.3 Hz, 2 H), 4.12-4.22 (m, 1 H), 5.20 (br. s., 1 H), 6.71 (d, J=6.0 Hz, 1 H), 7.71-7.78 (m, 2 H), 8.10 (s, 1H); m/z (ES+APCI)$^+$: 341 $[M+H]^+$.

Example 49

3-[1-(1-Methylpiperidin-4-yl)-1H-pyrazol-4-yl]-N-(tetrahydro-2H-pyran-4-yl)-1H-pyrazolo[4,3-c]pyridin-4-amine

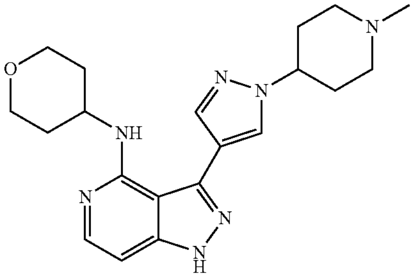 [SMILES: CN1CCC(n2cc(-c3n[nH]c4ccnc(NC5CCOCC5)c34)cn2)CC1]

Step 1—1-(4-Methoxybenzyl)-3-[1-(1-methylpiperidin-4-yl)-1H-pyrazol-4-yl]-N-(tetrahydro-2H-pyran-4-yl)-1H-pyrazolo[4,3-c]pyridin-4-amine

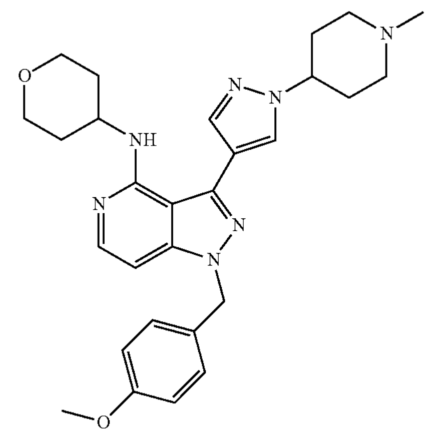 [SMILES: COc1ccc(Cn2nc(-c3cnn(C4CCN(C)CC4)c3)c3c(NC4CCOCC4)nccc32)cc1]

To a solution of Intermediate 39 (105 mg, 0.18 mmol) in dry THF (1 ml) at 0° C. was added 1M $LiAlH_4$ in diethyl ether (894 μl, 0.89 mmol), and the resulting mixture was warmed to rt over 15 min, then heated to 55° C. for 2.5 h. The solution was cooled to 0° C., water added, followed by aqueous NaOH (15% w/v). The aqueous phase was extracted with ethyl acetate, the combined organic extracts washed with brine, dried ($MgSO_4$) and solvents evaporated. Purification by column chromatography (gradient elution from 2%-10% MeOH in DCM) gave a white solid. $^1$H NMR (400 MHz, DMSO-$d_6$) δ ppm 1.29-1.47 (m, 2 H), 1.86-2.18 (m, 8 H), 2.24 (s, 3 H), 2.90 (d, J=10.1 Hz, 2 H), 3.42 (td, J=11.2, 2.3 Hz, 2 H), 3.69 (s, 3 H), 3.77 (dt, J=11.9, 3.7 Hz, 2 H), 4.10-4.27 (m, 2 H), 5.30 (d, J=7.3 Hz, 1 H), 5.45 (s, 2 H), 6.85-6.88 (m, 2 H), 6.91 (d, J=6.0 Hz, 1 H), 7.18-7.23 (m, 2 H), 7.75-7.78 (m, 2 H), 8.17-8.19 (m, 1 H); m/z (ES+APCI)$^+$: 502 [M+H]$^+$.

Step 2

The product of Step 1 (36 mg, 0.07 mmol) and heated at 60° C. for 18 h in TFA (1 ml). Concentration, followed by purification by preparative LCMS gave a white solid (11 mg, 41%). $^1$H NMR (400 MHz, DMSO-$d_6$) δ ppm 1.28-1.50 (m, 2 H), 1.92-2.18 (m, 8 H), 2.24 (s, 3 H), 2.87-2.95 (m, 2 H), 3.38-3.47 (m, 2 H), 3.78 (dt, J=11.4, 3.7 Hz, 2 H), 4.12-4.29 (m, 2 H), 5.24 (d, J=7.3 Hz, 1 H), 6.70 (d, J=6.0 Hz, 1 H), 7.72-7.79 (m, 2 H), 8.18 (s, 1 H); m/z (ES+APCI)$^+$: 382 [M+H]$^+$.

Example 50

N-{2-[4-(Cyclohexyloxy)-1H-pyrazolo[4,3-c]pyridin-3-yl]ethyl}-cyclohexanecarboxamide

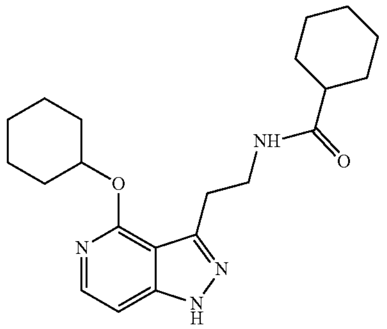 [SMILES: O=C(NCCc1n[nH]c2ccnc(OC3CCCCC3)c12)C1CCCCC1]

HATU (54 mg, 0.141 mmol) was added to a stirred solution of cyclohexanecarboxylic acid (17 mg, 0.135 mmol) and DIPEA (140 μl, 0.808 mmol) in DMF (1 ml). Intermediate 44 (35 mg, 0.135 mmol) in DMF (1 ml) was added and the mixture stirred at rt overnight. The reaction mixture was diluted with ethyl acetate and washed with water (×4) and brine (×1). The organic phase was dried and concentrated. The residue was purified by flash column chromatography on silica gel eluting with 20:1 DCM:methanol to provide a white foamy solid (25 mg, 50%). $^1$H NMR (400 MHz, DMSO-$d_6$) δ ppm 1.08-1.79 (m, 18 H), 1.88-2.10 (m, 3 H), 3.05 (t, J=7.3 Hz, 2 H), 3.35-3.53 (m, 2 H), 5.23-5.30 (m, 1 H), 6.97 (d, J=6.0 Hz, 1 H), 7.70 (t, J=5.7 Hz, 1 H), 7.77 (d, J=6.0 Hz, 1 H). m/z (ES+APCI)+: 371 [M+H]+.

Example 51

4-(Cyclohexyloxy)-3-ethyl-1H-pyrazolo[4,3-c]pyridine

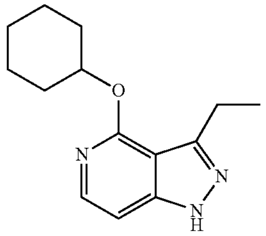 [SMILES: CCc1n[nH]c2ccnc(OC3CCCCC3)c12]

Step 1—4-(Cyclohexyloxy)-3-ethyl-1-(triphenylmethyl)-1H-pyrazolo[4,3-c]pyridine

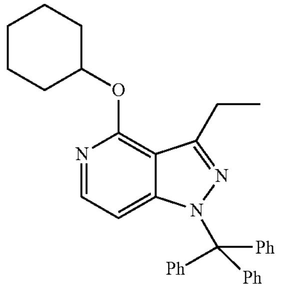 [SMILES: CCc1nn(C(c2ccccc2)(c2ccccc2)c2ccccc2)c2ccnc(OC3CCCCC3)c12]

To a round bottom flask was added Intermediate 45 (100 mg, 0.206 mmol) and 10% palladium on charcoal (10 mg) in ethanol (5 ml) and the mixture was stirred at rt under a hydrogen atmosphere for 18 h. The reaction mixture was filtered through Celite and the filtrate was concentrated to afford the product as a yellow solid (99 mg, 99% yield). $^1$H NMR (400 MHz, $CDCl_3$) δ ppm 1.14-2.15 (m, 13 H), 2.92-3.05 (m, 2 H), 5.23-5.37 (m, 1 H), 5.57-5.66 (m, 1 H), 7.11-7.49 (m, 16 H)); m/z (ES+APCI)$^+$: 488 [M+H]$^+$.

Step 2—4-(Cyclohexyloxy)-3-ethyl-1H-pyrazolo[4,3-c]pyridine

To a RB flask was added 4-(cyclohexyloxy)-3-ethyl-1-(triphenylmethyl)-1H-pyrazolo[4,3-c]pyridine (99 mg, 0.203 mmol) and TFA (200 μl) in DCM (2 ml). The mixture was allowed to stir at rt overnight under a nitrogen atmosphere. The mixture was diluted with DCM and $NaHCO_3$. The organic layer was separated, dried and concentrated. The residue was purified by mass triggered preparative HPLC (low pH buffer). The purified material was passed through an aminopropyl cartridge to afford the product as a white solid (16 mg, 32% yield). $^1$H NMR (400 MHz, CDCl3) δ ppm 1.35-1.64 (m, 7 H), 1.64-1.94 (m, 4 H), 1.94-2.11 (m, 2 H), 3.10 (q, J=7.33 Hz, 2 H), 5.30-5.40 (m, 1 H), 6.87 (d, J=5.95 Hz, 1 H), 7.87 (d, J=5.95 Hz, 1 H), 10.45 (br. s., 1 H); m/z (ES+APCI)$^+$: 246 [M+H]$^+$.

Example 52

4-(Cyclohexyloxy)-3-[(E)-2-(1-methyl-1H-pyrazol-4-yl)ethenyl]-1H-pyrazolo[4,3-c]pyridine

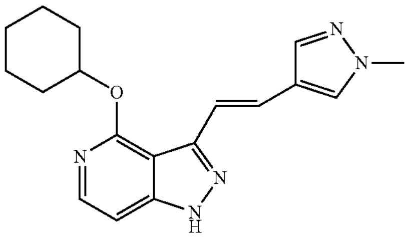 [SMILES: Cn1cc(/C=C/c2n[nH]c3ccnc(OC4CCCCC4)c23)cn1]

Step 1—4-(Cyclohexyloxy)-3-[(E)-2-(1-methyl-1H-pyrazol-4-yl)ethenyl]-1-trityl-1H-pyrazolo[4,3-c]pyridine

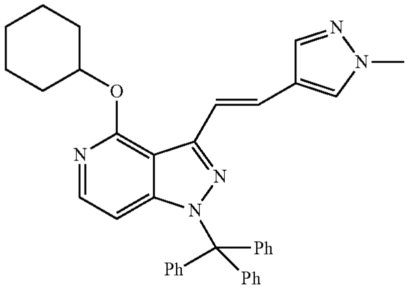 [SMILES: Cn1cc(/C=C/c2nn(C(c3ccccc3)(c3ccccc3)c3ccccc3)c3ccnc(OC4CCCCC4)c23)cn1]

To a stirred solution of 1-methyl-4-iodo-1H-pyrazole (750 mg, 3.60 mmol) and tetrabutylammonium iodide (380 mg, 1.03 mmol) in DMF/water/triethylamine (8 ml/170 μl/170 μl) was added Intermediate 45 (250 mg, 0.515 mmol) and [1,1'-bis(diphenylphosphino)ferrocene]-dichloropalladium(II) (84 mg, 0.103 mmol). The reaction mixture was heated at 70° C. overnight under a nitrogen atmosphere. The mixture was allowed to cool to rt, concentrated, and the residue was diluted with DCM and $H_2O$. The organic layer was separated, dried, concentrated and then purified by column chromatography using an Isolera 4 (DCM/MeOH gradient) followed by further purification by column chromatography (petroleum ether/EtOAc gradient) to afford the desired product as a yellow solid (96 mg, 33% yield). $^1$H NMR (400 MHz, CDCl3) δ ppm 1.38-1.67 (m, 4 H), 1.67-1.90 (m, 4 H), 1.96-2.21 (m, 2 H), 3.90 (s, 3 H), 5.24-5.37 (m, 1 H), 5.69 (d, J=6.41 Hz, 1 H), 7.16-7.38 (m, 18 H), 7.39-7.47 (m, 2H); m/z (ES+APCI)$^+$: 566 [M+H]$^+$.

Step 2—4-(Cyclohexyloxy)-3-[(E)-2-(1-methyl-1H-pyrazol-4-yl)ethenyl]-1H-pyrazolo[4,3-c]pyridine To a RB flask was added the product of Step 1 (96 mg, 0.170 mmol) and TFA (200 μl) in DCM (2 ml). The mixture was allowed to stir at rt overnight under a nitrogen atmosphere. The mixture was diluted with DCM and $NaHCO_3$, the organic layer was separated, dried, concentrated and the crude residue was purified by column chromatography using an Isolera 4 (petroleum ether/EtOAc gradient). Further purification by mass triggered preparative HPLC (high pH buffer) gave the desired product as a white solid (23 mg, 42% yield). $^1$H NMR (400 MHz, CDCl3) δ ppm 1.35-1.96 (m, 8 H), 2.00-2.16 (m, 2 H), 3.93 (s, 3 H), 5.35-5.44 (m, 1 H), 6.82-6.98 (m, 1 H), 7.38 (d, J=16.5 Hz, 1 H), 7.50 (s, 1 H), 7.58 (d, J=16.5 Hz, 1 H), 7.75 (s, 1 H), 7.85-7.92 (m, 1 H), 10.42 (br. s., 1 H); m/z (ES+APCI)$^+$: 324 [M+H]$^+$.

Example 53

4-(4-Isopropoxy-1H-pyrazolo[4,3-c]pyridine-3-yl)-1-isopropyl-N-methyl-1H-pyrrole-2-carboxamide

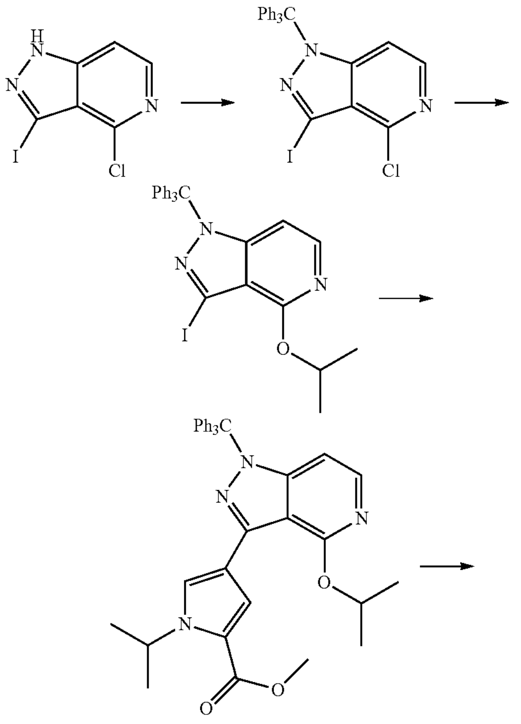

-continued

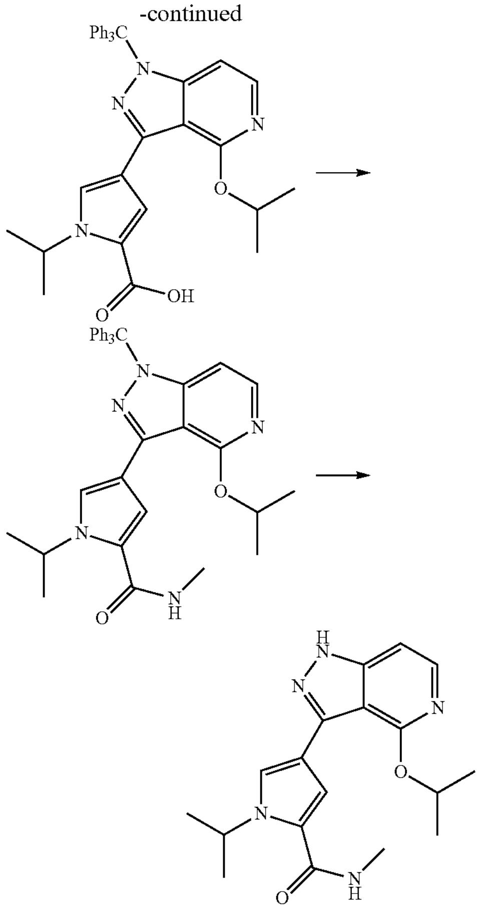

Step 1—4-Chloro-3-iodo-1-trityl-1H-pyrazolo[4,3-c]pyridine

A suspension of 4-chloro-3-iodo-1H-pyrozolo[4,3-c]pyridine (7.88 g, 0.028 mol) in DCM (100 mL) was chilled in an ice-bath and stirred for 5 minutes. TEA (5.62 g, 0.056 mol) was added and stirred for 10 minutes. Trityl chloride was introduced and stirred for 3 hours. 100 mL water was added to the reaction mixture and the organic phase was separated. The organic phase was then washed with brine, dried with anhydrous sodium sulfate and filtered. The filtrate was concentrated at reduced pressure to give the crude desired product as an off-white solid (13.2 g, 89%). LC-MS (Method A): m/z=544 $[M+Na]^+$; 1.19 min. $^1$H-NMR (500 MHz, $CDCl_3$): 7.75 (d, J=6.5, 1H), 7.27-7.33 (m, 9H), 7.12-7.14 (m, 6H), 6.18 (d, J=6.5, 1H)

Step 2—3-Iodo-4-isopropoxyl-1-trityl-1H-pyrazolo[4,3-c]pyridine

To a suspension of NaH (60% dispersion, 0.46 g, 0.019 mol) in THF (40 mL) at room temperature was added isopropanol (0.46 g, 0.0076 mol) and stirred for 30 minutes. 4-chloro-3-iodo-1-trityl-1H-pyrazolo[4,3-c]pyridine (2.00 g, 0.0038 mol) in THF (10 mL) was added to the sodium i-propanoxide suspension and refluxed for 4 hours. THF was removed at reduced pressure. Water was added to the residue and the suspension was filtered and solid was washed with water to give the crude desired product as white solid (1.92 g, 92%). LC-MS (Method A): m/z=546 $[M+H]^+$; 2.65 min. $^1$H-NMR (500 MHz, $CDCl_3$): 7.46 (d, J=6.5, 1H), 7.27-7.33 (m, 9H), 7.15-7.17 (m, 6H), 5.72 (d, J=6.5, 1H), 5.42-5.47 (m, 1H), 1.45 (d, J=6.0, 6H)

Step 3—4-(4-Isopropoxy-1-trityl-1H-pyrazolo[4,3-c]pyridine-3-yl)-1-isopropyl-1H-pyrrole-2-carboxylate A mixture of 3-iodo-4-isopropoxyl-1-trityl-1H-pyrazolo[4,3-c]pyridine (517 mg, 1 mmole), methyl 1-isopropyl-4-(4,4,5,5-tetramethyl-1,3,2-dioxaborolan-2-yl)-1H pyrrole-2-carboxylate (410 mg, 1.4 mmole), bis(di-tert-butyl(4-dimethylaminophenyl)phosphine)dichloropalladium (71 mg, 0.1 mmole), KOAc (294 mg, 3 mmole), acetonitrile (7.5 mL) and water was degassed with nitrogen and then heated to 145° C. under microwave irradiation for 40 min. The reaction mixture was concentrated in vacuo and purified with column chromatography (pet. ether-ethyl acetate, 10:1). The desired product was obtained as a yellowish solid (0.35 g, 63%). LC-MS (Method A): m/z=585 $[M+H]^+$; 1.70 min.

Step 4—4-(4-Isopropoxy-1-trityl-1H-pyrazolo[4,3-c]pyridine-3-yl)-1-isopropyl-1H-pyrrole-2-carboxylic acid Methyl 4-(4-isopropoxy-1-trityl-1H-pyrazolo[4,3-c]pyridine-3-yl)-1-isopropyl-1H-pyrrole-2-carboxylate (200 mg, 0.64 mmol) was dissolved in THF (8 mL). A 1 N LiOH solution (8 mL) was introduced and the resulting mixture was refluxed for 12 hours. After cooling to room temperature, the mixture was neutralized to pH 7 with 5 N HCl. THF was removed at reduced pressure. The residue was partitioned between ethyl acetate (30 mL) and water (30 mL). The organic phase was washed with brine and dried over anhydrous $Na_2SO_4$ and concentrated to give the crude desired product as a yellow solid (170 mg, 88%). LC-MS (Method A): m/z=571 $[M+H]^+$; 2.46 min. $^1$H-NMR (500 MHz, $CDCl_3$): δ 7.93 (d, J=6.0, 1H), 7.86 (s, 1H), 7.16 (s 1H), 6.95 (d, J=6.0, 1H), 6.0 (s 1H), 5.55-5.60 (m 1H), 4.16 (s 3H), 2.95 (d, J=4.5, 3H), 1.51 (d, J=7.0, 6H).

Step 5—4-(4-Isopropoxy-1-trityl-1H-pyrazolo[4,3-c]pyridine-3-yl)-1-isopropyl-N-methyl-1H-pyrrole-2-carboxamide A mixture of 4-(4-isopropoxy-1-trityl-1H-pyrazolo[4,3-c]pyridine-3-yl)-1-isopropyl-1H-pyrrole-2-carboxylic acid (150 mg, 0.26 mmol), methylamine hydrochloride (191 mg, 1.32 mmol), HATU (150 mg, 0.40 mole), DIPEA (0.2 mL) in DMF (10 mL) was stirred overnight at 25° C. Ethyl acetate (100 mL) and water (50 mL) were added. The organic layer was separated and washed by water (30 mL) and brine, dried over anhydrous $Na_2SO_4$, filtered and concentrated in vacuo to give the title compound as a yellowish oil (190 mg) without further purification. LCMS (Method A): m/z=584 $[M+H]^+$; 2.47 min.

Step 6—4-(4-Isopropoxy-1H-pyrazolo[4,3-c]pyridine-3-yl)-1-isopropyl-N-methyl-1H-pyrrole-2-carboxamide To a mixture of 4-(4-isopropoxy-1-trityl-1H-pyrazolo[4,3-c]pyridine-3-yl)-1-isopropyl-N-methyl-1H-pyrrole-2-carboxamide (190 mg, crude) in dichloromethane (5 mL) was added trifluoroacetic acid (1 mL) and triethylsilane (0.2 mL). The mixture was stirred under reflux for 1 hour. After cooling to room temperature, the reaction mixture was neutralized to pH=7 with saturated $NaHCO_3$ solution. It was then extracted with ethyl acetate (30 mL×3). The organic layer was combined and concentrated in vacuo. The residue was purified by reverse phase HPLC to give the title compound as a white solid (15 mg, 0.044 mmol). LC-MS (Method D): m/z=342 $[M+H]^+$; 4.71 min. $^1$H-NMR (500 MHz, $CDCl_3$): δ 8.09-8.14 (br, 1H), 7.86 (d, J=2.0, 1H), 7.82 (d, J=6.0, 1H), 7.28 (d, J=1.5, 1H), 6.70 (d, J=6.0, 1H), 5.52-5.61 (m, 2H), 2.72 (d, J=4.0, 3H), 1.45 (d, J=6.5, 6H), 1.42 (d, J=6.5, 6H).

Example 54

4-(4-isopropoxy-1H-pyrazolo[4,3-c]pyridine-3-yl)-1-isopropyl-N,N-dimethyl-1H-pyrrole-2-carboxamide

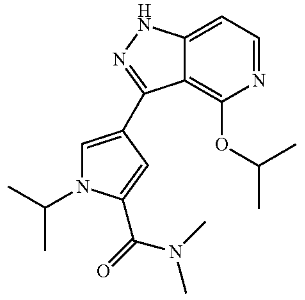 [SMILES: CC(C)Oc1nccc2[nH]nc(-c3cc(C(=O)N(C)C)n(C(C)C)c3)c12]

4-(4-isopropoxy-1H-pyrazolo[4,3-c]pyridine-3-yl)-1-isopropyl-N,N-dimethyl-1H-pyrrole-2-carboxamide was prepared by the procedure described in Example 53 by substituting methylamine hydrochloride with dimethylamine. LC-MS (Method D): m/z=356 $[M+H]^+$; 1.66 min. $^1$H-NMR (500 MHz, DMSO): δ 7.90 (d, J=2.5, 1H), 7.89 (d, J=1.5, 1H), 7.02 (d, J=1.5, 1H), 6.90 (d, J=6.0, 1H), 5.66-5.71 (m, 1H), 4.94-5.00 (m, 1H), 3.20 (s, 6H), 1.51 (d, J=5.5, 12H).

Example 55

Azetidin-1-yl(4-(4-isopropoxy-1H-pyrazolo[4,3-c]pyridin-3-yl)-1-isopropyl-1H-pyrrol-2-yl)methanone

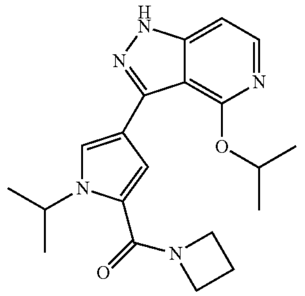 [SMILES: CC(C)Oc1nccc2[nH]nc(-c3cc(C(=O)N4CCC4)n(C(C)C)c3)c12]

The title compound was prepared by the procedure described in Example 53 by substituting methylamine hydrochloride with azetidine. LC-MS (Method F): m/z=368

$[M+H]^+$; 5.30 min. $^1$H-NMR (500 MHz, $CDCl_3$): δ 10.16 (br, 1H), 7.96 (d, J=1.5, 1H), 7.89 (d, J=6.0, 1H), 7.09 (d, J=1.0, 1H), 6.91 (d, J=6.0, 1H), 5.66-5.71 (m, 1H), 5.54-5.60 (m, 1H), 4.16-4.51 (m, 4H), 2.30-2.39 (m, 2H), 1.52 (d, J=2.5, 6H), 1.51 (d, J=2.0, 6H).

Example 56

(4-(4-Isopropoxy-1H-pyrazolo[4,3-c]pyridin-3-yl)-1-isopropyl-1H-pyrrol-2-yl)(piperidin-1-yl)methanone

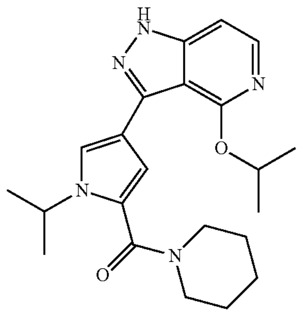 [SMILES: CC(C)Oc1nccc2[nH]nc(-c3cc(C(=O)N4CCCCC4)n(C(C)C)c3)c12]

The title compound was prepared by the procedure described in Example 53 by substituting methylamine hydrochloride with piperidine. LC-MS (Method D): m/z=396 $[M+H]^+$; 5.49 min. $^1$H-NMR (500 MHz, $CDCl_3$): δ 7.89 (d, J=6.0, 1H), 7.87 (d, J=2.0, 1H), 7.94 (d, J=1.5, 1H), 6.89 (d, J=6.0, 1H), 5.64-5.69 (m, 1H), 4.87-4.92 (m, 1H), 3.72-3.74 (m, 4H), 1.68-1.71 (m, 2H), 1.59-1.66 (m, 4H), 1.51 (d, J=2.5, 6H), 1.50 (d, J=1.5, 6H).

Example 57

(4-(4-Isopropoxy-1H-pyrazolo[4,3-c]pyridin-3-yl)-1-isopropyl-1H-pyrrol-2-yl)(morpholino)methanone

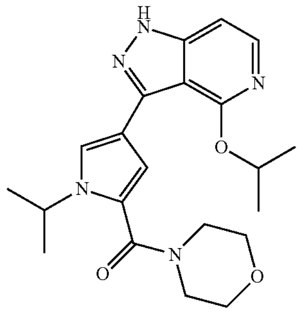 [SMILES: CC(C)Oc1nccc2[nH]nc(-c3cc(C(=O)N4CCOCC4)n(C(C)C)c3)c12]

The title compound was prepared by the procedure described in Example 53 by substituting methylamine hydrochloride with morpholine. LC-MS (Method D): m/z=398 $[M+H]^+$; 1.66 min. $^1$H-NMR (500 MHz, DMSO): δ 7.91 (d, J=2.0, 1H), 7.90 (d, J=6.0, 1H), 6.96 (d, J=1.5, 1H), 6.91 (d, J=6.0, 1H), 5.65-5.70 (m, 1H), 4.92-4.98 (m, 1H), 3.83 (t, 4H), 3.73 (t, 4H), 1.52 (d, J=7.0, 6H), 1.51 (d, J=7.0, 6H).

Example 58

N-Cyclopropyl-4-(4-isopropoxy-1H-pyrazolo[4,3-c]pyridin-3-yl)-1-isopropyl-1H-pyrrole-2-carboxamide

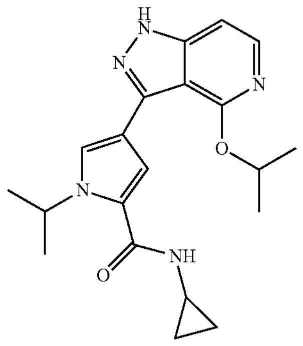 [SMILES: CC(C)Oc1nccc2[nH]nc(-c3cc(C(=O)NC4CC4)n(C(C)C)c3)c12]

The title compound was prepared by the procedure described in Example 53 by substituting methylamine hydrochloride with cyclopropanamine. LC-MS (Method D): m/z=368 $[M+H]^+$; 5.09 min. $^1$H-NMR (500 MHz, $CDCl_3$): δ 8.15 (d, J=4.0, 1H), 7.85 (d, J=2.0, 1H), 7.80 (d, J=6.0, 1H), 7.30 (d, J=1.5, 1H), 7.02 (d, J=5.5, 1H), 5.51-5.59 (m, 2H), 2.78-2.81 (m, 1H), 1.44 (d, J=6.5, 6H), 1.43 (d, J=7.0, 6H), 0.64-0.67 (m, 2H), 0.54-0.56 (m, 2H).

Example 59

4-(4-Isopropoxy-1H-pyrazolo[4,3-c]pyridin-3-yl)-1-isopropyl-N-(oxetan-3-yl)-1H-pyrrole-2-carboxamide

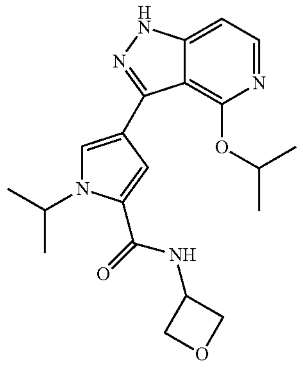 [SMILES: CC(C)Oc1nccc2[nH]nc(-c3cc(C(=O)NC4COC4)n(C(C)C)c3)c12]

The title compound was prepared by the procedure described in Example 53 by substituting methylamine hydrochloride with oxetan-3-amine. LC-MS (Method D): m/z=384 $[M+H]^+$; 3.68 min. $^1$H-NMR (500 MHz, $CDCl_3$): δ 7.88 (d, J=2.0, 1H), 7.81 (d, J=6.0, 1H), 7.27 (d, J=1.0, 1H), 7.03 (d, J=6.0, 1H), 5.64-5.69 (m, 1H), 5.53-5.59 (m, 1H), 4.79 (br, 1H), 4.28-4.32 (m, 2H), 4.15 (t, 1H), 3.59-3.61 (m, 1H), 3.43-3.46 (m, 1H), 0.54-0.56 (m, 2H), 1.42-1.45 (m, 12H).

Example 60

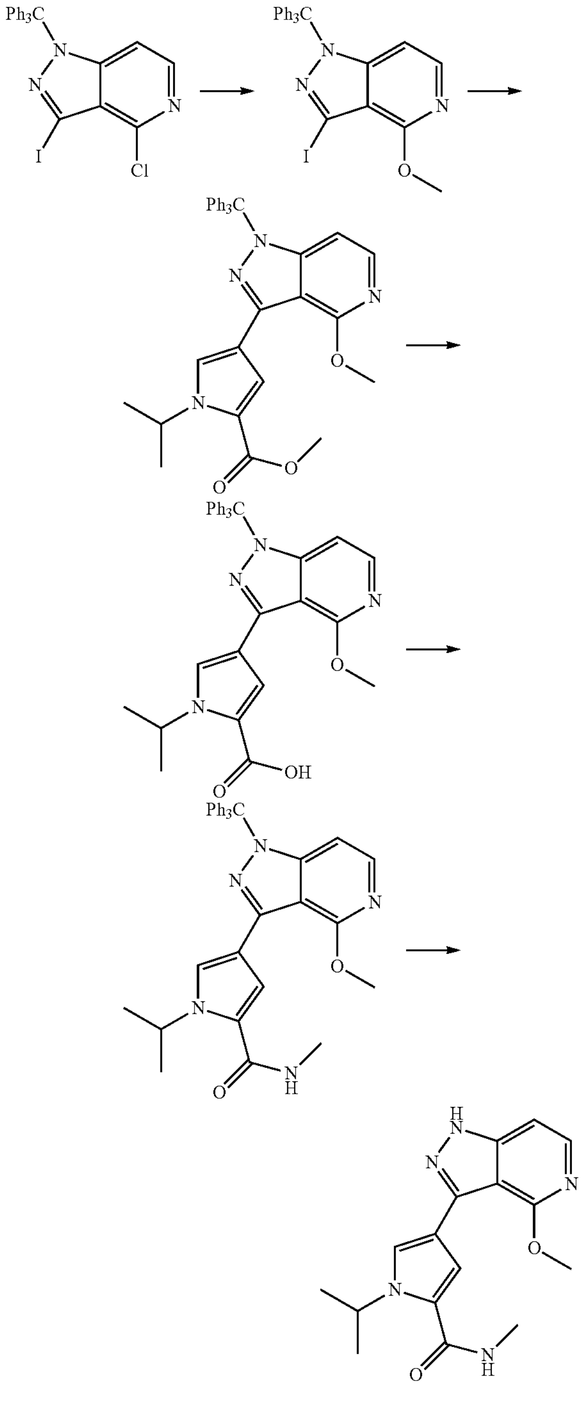

Step 1—3-iodo-4-Methoxy-1-trityl-1H-pyrazolo[4,3-c]pyridine

The title compound was prepared by the procedure described in step 2 of Example 53 by substituting sodium i-propoxide with sodium methoxide. LC-MS (Method A): m/z=518.7 $[M+H]^+$; 2.39 min. $^1$H-NMR (500 MHz, $CDCl_3$): δ 7.49 (d, J=6.0, 1H), 7.20-7.31 (m, 9H), 7.14-7.15 (m, 6 H), 5.78 (d, J=6.0, 1H), 4.07 (s, 3H).

Step 2—Methyl 1-isopropyl-4-(4-methoxy-1-trityl-1H-pyrazolo[4,3-c]pyridin-3-yl)-1H-pyrrole-2-carboxylate The title compound was prepared by the procedure described in step 3 of Example 53 by substituting 3-iodo-4-isopropoxyl-1-trityl-1H-pyrazolo[4,3-c]pyridine with 3-iodo-4-methoxy-1-trityl-1H-pyrazolo[4,3-c]pyridine. LCMS (Method A): m/z=557 $[M+H]^+$; 2.58 min.

Step 3—1-Isopropyl-4-(4-methoxy-1-trityl-1H-pyrazolo[4,3-c]pyridin-3-yl)-1H-pyrrole-2-carboxylic acid The title compound was prepared by the procedure described in Example 53 by using methyl 1-isopropyl-4-(4-methoxy-1-trityl-1H-pyrazolo[4,3-c]pyridin-3-yl)-1H-pyrrole-2-carboxylate. LCMS (Method A): m/z=543 $[M+H]^+$; 2.36 min.

Step 4—1-isopropyl-4-(4-methoxy-1-trityl-1H-pyrazolo[4,3-c]pyridin-3-yl)-N-methyl-1H-pyrrole-2-carboxamide The title compound was prepared by the procedure described in Example 53 by using 1-isopropyl-4-(4-methoxy-1-trityl-1H-pyrazolo[4,3-c]pyridin-3-yl)-1H-pyrrole-2-carboxylic acid. LC-MS (Method A): m/z=556 $[M+H]^+$; 2.37 min.

Step 5—1-Isopropyl-4-(4-methoxy-1H-pyrazolo[4,3-c]pyridin-3-yl)-N-methyl-1H-pyrrole-2-carboxamide The title compound was prepared by the procedure described in Example 53 by using 1-isopropyl-4-(4-methoxy-1-trityl-1H-pyrazolo[4,3-c]pyridin-3-yl)-N-methyl-1H-pyrrole-2-carboxamide. LC-MS (Method E): m/z=314 $[M+H]^+$; 4.31 min. $^1$H-NMR (500 MHz, $CDCl_3$): δ 7.93 (d, J=6.0, 1H), 7.86 (s, 1H), 7.16 (s, 1H), 6.95 (d, J=6.0, 1H), 6.0 (s, 1H), 5.55-5.60 (m, 1H), 4.16 (s, 3H), 2.95 (d, J=4.5, 3H), 1.51 (d, J=7.0, 6H).

Example 61

1-Isopropyl-4-(4-methoxy-1H-pyrazolo[4,3-c]pyridin-3-yl)-N,N-dimethyl-1H-pyrrole-2-carboxamide

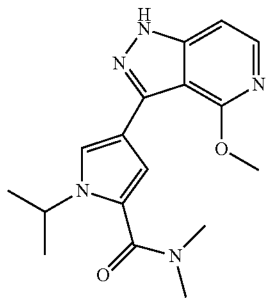 [SMILES: COc1nccc2[nH]nc(-c3cc(C(=O)N(C)C)n(C(C)C)c3)c12]

The title compound was prepared by the procedure described in Example 60 by substituting methylamine hydrochloride with dimethylamine hydrochloride. LCMS (Method E): m/z=328 $[M+H]^+$; 4.39 min. $^1$H-NMR (500 MHz, $CDCl_3$): δ 10.19 (s, 1H), 7.91 (d, J=6.0, 1H), 7.77 (d, J=1.5, 1H), 7.01 (d, J=1.5, 1H), 6.94 (d, J=6.0, 1H), 4.96 (m, 1H), 4.14 (s, 3H), 3.20 (s, 6H), 1.50 (d, J=7.0, 6H).

Example 62

1-Isopropyl-4-(4-methoxy-1H-pyrazolo[4,3-c]pyridin-3-yl)-1H-pyrrol-2-yl)(morpholino)methanone

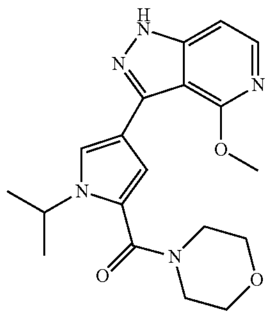 [SMILES: COc1nccc2[nH]nc(-c3cc(C(=O)N4CCOCC4)n(C(C)C)c3)c12]

The title compound was prepared by the procedure described in Example 60 by substituting methylamine hydrochloride with morpholine. LC-MS (Method E): m/z=370 $[M+H]^+$; 4.41 min. $^1$H-NMR (500 MHz, $CDCl_3$): δ 7.88 (d, J=6.0, 1H), 7.80 (s, 1H), 6.96 (s, 1H), 6.84 (d, J=6.0, 1H), 4.93-4.97 (m, 1H), 4.13 (s, 3H), 3.81 (t, J=5.0, 4H), 3.70 (t, J=5.0, 4H), 1.50 (d, J=7.0, 6H).

Example 63

N-Cyclopropyl-1-isopropyl-4-(4-methoxy-1H-pyrazolo[4,3-c]pyridin-3-yl)-1H-pyrrole-2-carboxamide

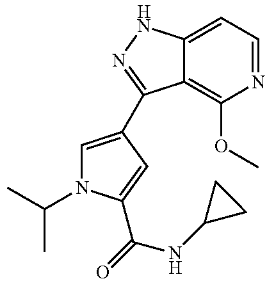 [SMILES: COc1nccc2[nH]nc(-c3cc(C(=O)NC4CC4)n(C(C)C)c3)c12]

The title compound was prepared by the procedure described in Example 60 by substituting methylamine hydrochloride with cyclopropanamine. LC-MS (Method E): m/z=340 $[M+H]^+$; 4.67 min. $^1$H-NMR (500 MHz, $CDCl_3$): δ 10.3 (s, 1H), 7.93 (d, J=6.0, 1H), 7.88 (d, J=1.5, 1H), 7.12 (d, J=1.5, 1H), 6.95 (d, J=6.0, 1H), 6.11 (s, 1H), 5.57-5.60 (m, 1H), 4.15 (s, 3H), 2.82-2.84 (m, 1H), 1.51 (d, J=7.0, 6H), 0.82-0.86 (m, 2H), 0.56-0.59 (m, 2H).

Example 64

1-isopropyl-4-(4-methoxy-1H-pyrazolo[4,3-c]pyridin-3-yl)-N-(oxetan-3-yl)-1H-pyrrole-2-carboxamide

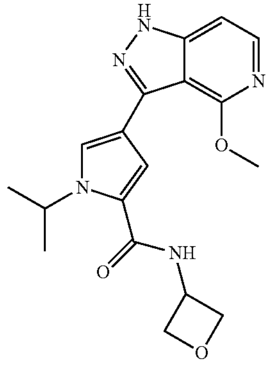 [SMILES: COc1nccc2[nH]nc(-c3cc(C(=O)NC4COC4)n(C(C)C)c3)c12]

The title compound was prepared by the procedure described in Example 60 by substituting methylamine hydrochloride with oxetan-3-amine. LC-MS (Method D): m/z=356 $[M+H]^+$; 3.08 min. $^{1}$H-NMR (500 MHz, $CDCl_3$): δ 7.84 (d, J=6.0, 1H), 7.83 (s, 1H), 7.48 (d, J=1.5, 1H), 6.89 (d, J=6.0, 1H), 5.51-5.57 (m, 1H), 4.43-4.50 (m, 1H), 4.36-4.40 (m, 1H), 4.19 (t, J=8.0, 1H), 4.12 (s, 3H), 3.89-3.92 (m, 1H), 3.67-3.70 (m, 1H), 1.46 (d, J=7.0, 6H).

Example 65

(1-isopropyl-4-(4-(tetrahydro-2H-pyran-4-yloxy)-1H-pyrazolo[4,3-c]pyridin-3-yl)-1H-pyrrol-2-yl)(morpholino)methanone

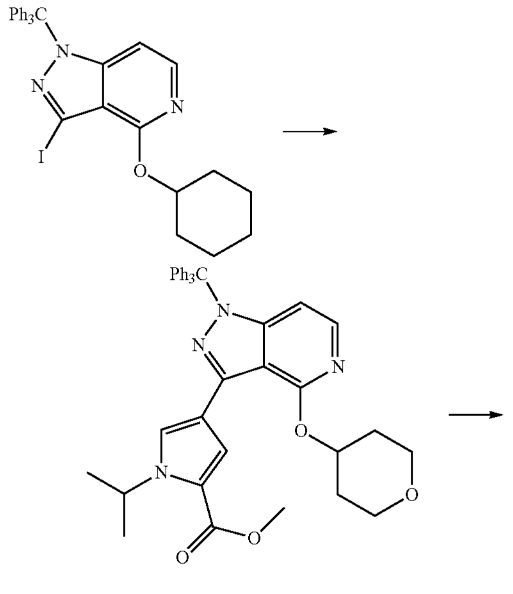

-continued

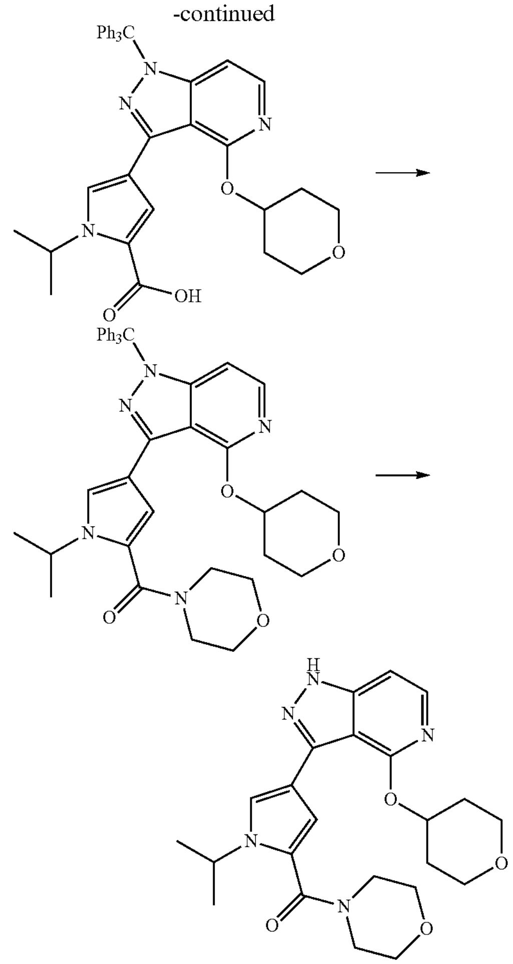

Step 1—Methyl 1-isopropyl-4-(4-(tetrahydro-2H-pyran-4-yloxy)-1-trityl-1H-pyrazolo[4,3-c]pyridin-3-yl)-1H-pyrrole-2-carboxylate A mixture of 3-iodo-4-(tetrahydro-2H-pyran-4-yloxy)-1-trityl-1H-pyrazolo[4,3-c]pyridine (587 mg, 1 mmol), methyl 1-isopropyl-4-(4,4,5,5-tetramethyl-1,3,2-dioxaborolan-2-yl)-1H pyrrole-2-carboxylate (410 mg, 1.4 mmol), bis(di-tert-butyl(4-dimethylaminophenyl)phosphine)dichloro-palladium (71 mg, 0.1 mmol), KOAc (294 mg, 3 mmol), acetonitrile (7.5 mL) and water was degassed with nitrogen and then heated to 145° C. under microwave irradiation for 40 minutes. The reaction mixture was concentrated in vacuo and purified with column chromatography (pet. ether-ethyl acetate, 10:1). The title compound was obtained as a yellowish solid (290 mg, 46%). LC-MS (Method C): m/z=627.4 $[M+H]^+$; 2.77 min.

Step 2—1-Isopropyl-4-(4-(tetrahydro-2H-pyran-4-yloxy)-1-trityl-1H-pyrazolo[4,3-c]pyridin-3-yl)-1H-pyrrole-2-carboxylic acid Methyl 1-isopropyl-4-(4-(tetrahydro-2H-pyran-4-yloxy)-1-trityl-1H-pyrazolo[4,3-c]pyridin-3-yl)-1 H-pyrrole-2-carboxylate (200 mg, 0.32 mmol) was dissolved in THF (8 mL). A 1 N LiOH solution (8 mL) was introduced and resulting mixture was refluxed for 12 hours. After cooling to room temperature, the mixture was neutralized to pH 7 with 5 N HCl. THF was removed at reduced pressure. The residue was partitioned between ethyl acetate (30 mL) and water (30 mL).

The organic phase was washed with brine and dried over anhydrous $Na_2SO_4$ and concentrated to give the crude desired product as a yellow solid (190 mg, 97%). LC-MS (Method F): m/z=613.4 $[M+H]^+$; 6.19 min. $^1$H-NMR (500 MHz, $CDCl_3$): δ 7.74 (s, 1H), 7.53 (d, J=6.0, 1H), 7.30-7.37 (m, 9H), 7.23 (s, 1H), 7.16 (d, J=7.5, 6H), 5.79 (d, J=6.0, 1H), 5.41-5.48 (m, 2H), 3.91 (d, J=11.5, 2H), 3.49 (t, J=11.0, 2H), 2.15 (d, J=12.0, 2H), 1.72-1.79 (m, 2H), 1.42 (d, J=7.0, 6H).

Step 3—(1-Isopropyl-4-(4-(tetrahydro-2H-pyran-4-yloxy)-1-trityl-1H-pyrazolo[4,3-c]pyridin-3-yl)-1H-pyrrol-2-yl)(morpholino)methanone A mixture of 1-isopropyl-4-(4-(tetrahydro-2H-pyran-4-yloxy)-1-trityl-1H-pyrazolo[4,3-c]pyridin-3-yl)-1H-pyrrole-2-carboxylic acid (150 mg, 0.24 mmol), morpholine (50 mg, 0.98 mmol), HATU (137 mg, 0.36 mmol), DIPEA (0.3 mL) in DMF (10 mL) was stirred overnight at 25° C. Ethyl acetate (100 mL) and water (50 mL) were added. The organic layer was separated and washed by water (30 mL) and brine, dried over anhydrous $Na_2SO_4$, filtered and concentrated in vacuo to give the desired product title compound as a yellowish oil (160 mg, 96%) without further purification. LC-MS (Method A): m/z=682.3 $[M+H]^+$; 2.44 min.

Step 4—(1-Isopropyl-4-(4-(tetrahydro-2H-pyran-4-yloxy)-1H-pyrazolo[4,3-c]pyridin-3-yl)-1H-pyrrol-2-yl)(morpholino)methanone To a mixture of (1-isopropyl-4-(4-(tetrahydro-2H-pyran-4-yloxy)-1-trityl-1H-pyrazolo[4,3-c]pyridin-3-yl)-1H-pyrrol-2-yl)(morpholino)methanone (160 mg, 0.23 mmol) in dichloromethane (5 mL) was added trifluoroacetic acid (1 mL) and triethylsilane (0.2 mL). The mixture was stirred at reflux for 1 hour. After cooling down, the reaction mixture was neutralized to pH 7 with saturated $NaHCO_3$ solution. It was then extracted with ethyl acetate (3×30 mL). The organic layer was combined and concentrated in vacuo The residue was purified by reverse phase HPLC to give compound the title compound as a white solid (38 mg, 37%). LC-MS (Method D): m/z=440.1 $[M+H]^+$; 4.40 min. $^1$H-NMR (500 MHz, $CDCl_3$): δ 7.89 (d, J=6.0, 1H), 7.81 (d, J=1.5, 1H), 6.95 (t, J=1.5, 1H), 6.93 (s, 1H), 5.56-5.61 (m, 1H), 4.92-4.97 (m, 1H), 4.05-4.09 (m 2H), 3.83 (t, J=4.5, 4H), 3.73 (t, J=4.5, 4H), 3.61-3.66 (m, 2H), 2.25-2.27 (m, 2H), 1.87-1.95 (m, 2H), 1.52 (d, J=7.0, 6H).

Example 66

1-isopropyl-N,N-dimethyl-4-(4-(tetrahydro-2H-pyran-4-yloxy)-1H-pyrazolo[4,3-c]pyridin-3-yl)-1H-pyrrole-2-carboxamide

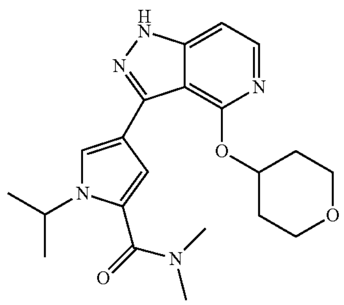 [SMILES: CC(C)n1cc(-c2n[nH]c3ccnc(OC4CCOCC4)c23)cc1C(=O)N(C)C]

The title compound was prepared by the procedure described in Example 65 by substituting morpholine with dimethylamine hydrochloride. LC-MS (Method D): m/z=398.1 $[M+H]^+$; 4.38 min. $^1$H-NMR (500 MHz, $CDCl_3$): δ 7.88 (d, J=6.0, 1H), 7.79 (d, J=1.5, 1H), 7.01 (d, J=2.0, 1H), 6.94 (d, J=6.0, 1H), 5.55-5.61 (m, 1H), 4.93-4.99 (m, 1H), 4.05-4.09 (m, 2H), 3.61-3.66 (m, 2H), 3.20 (s, 6H), 2.26 (d, J=5.0, 2H), 1.89-1.96 (m, 2H), 1.51 (d, J=7.0, 6H).

Example 67

N-Cyclobutyl-1-isopropyl-4-(4-(tetrahydro-2H-pyran-4-yloxy)-1H-pyrazolo[4,3-c]pyridin-3-yl)-1H-pyrrole-2-carboxamide

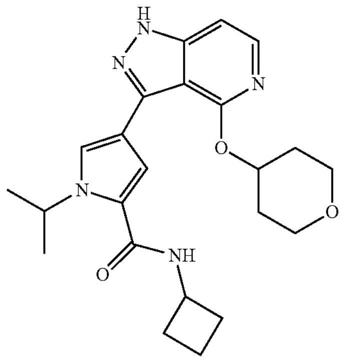 [SMILES: CC(C)n1cc(-c2n[nH]c3ccnc(OC4CCOCC4)c23)cc1C(=O)NC1CCC1]

The title compound was prepared by the procedure described in Example 65 by substituting morpholine with cyclobutanamine. LC-MS (Method D): m/z=424.2 $[M+H]^+$; 5.23 min. $^1$H-NMR (500 MHz, DMSO-$d_6$): δ 13.20 (s, 1H), 8.32 (s, 1H), 7.82 (d, J=6.0, 1H), 7.77 (d, J=2.0, 1H), 7.40 (s, 1H), 7.05 (d, J=6.0, 1H), 5.49 (d, J=5.5, 2H), 4.36-4.41 (m, 1H), 3.92 (d, J=6.8, 2H), 3.51 (d, J=11.0, 2H), 2.19 (d, J=9.5, 4H), 2.06 (d, J=9.5, 2H), 1.75-1.81 (m, 2H), 1.62-1.67 (m, 2H), 1.42 (d, J=7.0, 6H).

Example 68

(1-Isopropyl-4-(4-(tetrahydro-2H-pyran-4-yloxy)-1H-pyrazolo[4,3-c]pyridin-3-yl)-1H-pyrrol-2-yl)(pyrrolidin-1-yl)methanone

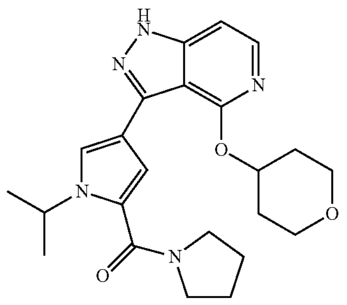 [SMILES: CC(C)n1cc(-c2n[nH]c3ccnc(OC4CCOCC4)c23)cc1C(=O)N1CCCC1]

The title compound was prepared by the procedure described in Example 65 by substituting morpholine with pyrrolidine. LC-MS (Method D): m/z=424.2 $[M+H]^+$; 4.75 min. $^1$H-NMR (500 MHz, DMSO-$d_6$): δ 13.16 (s, 1H), 7.82 (d, J=6.0, 1H), 7.75 (s, 1H), 7.06 (d, J=6.0, 1H), 7.00 (s, 1H), 5.49-5.54 (m, 1H), 4.99-5.04 (m, 1H), 3.92-3.95 (m, 2H), 3.49-3.61 (m, 6H), 2.18 (d, J=10.5, 2H), 1.87 (t, J=6.5, 4H), 1.70-1.78 (m, 2H), 1.42 (d, J=7.0, 6H).

Example 69

N-Cyclopropyl-1-isopropyl-4-(4-(tetrahydro-2H-pyran-4-yloxy)-1H-pyrazolo[4,3-c]pyridin-3-yl)-1 H-pyrrole-2-carboxamide

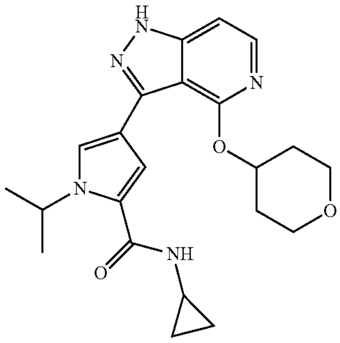 [SMILES: CC(C)n1cc(-c2n[nH]c3ccnc(OC4CCOCC4)c23)cc1C(=O)NC1CC1]

The title compound was prepared by the procedure described in Example 65 by substituting morpholine with cyclopropanamine. LC-MS (Method D): m/z=410.1 $[M+H]^+$; 4.69 min. $^1$H-NMR (500 MHz, $CDCl_3$): δ 7.89 (d, J=6.0, 1H), 7.82 (d, J=2.0, 1H), 7.17 (d, J=1.5, 1H), 6.94 (d, J=6.0, 1H), 6.13 (s, 1H), 5.55-5.62 (m, 2H), 4.05-4.08 (m, 2H), 3.62-3.69 (m, 2H), 2.81-2.86 (m, 1H), 2.26-2.28 (m, 2H), 1.87-1.95 (m, 2H), 1.52 (d, J=7.0, 6H), 0.83-0.86 (m, 2H), 0.56-0.59 (m, 2H).

Example 70

1-isopropyl-N-(oxetan-3-yl)-4-(4-(tetrahydro-2H-pyran-4-yloxy)-1H-pyrazolo[4,3-c]pyridin-3-yl)-1H-pyrrole-2-carboxamide

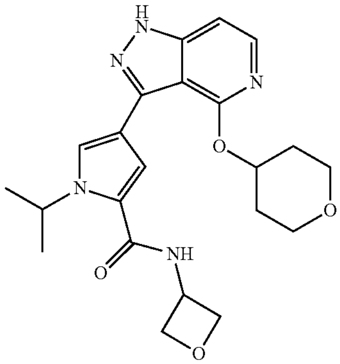 [SMILES: CC(C)n1cc(-c2n[nH]c3ccnc(OC4CCOCC4)c23)cc1C(=O)NC1COC1]

The title compound was prepared by the procedure described in Example 65 by substituting morpholine with oxetan-3-amine. LC-MS (Method F): m/z=426.3 $[M+H]^+$; 4.45 min $^1$H-NMR (500 MHz, DMSO-$d_6$): δ 13.21 (s, 1H), 7.82 (s, 2H), 7.28 (s, 1H), 7.06 (d, J=6.0, 1H), 5.64-5.70 (m, 1H), 5.48-5.51 (m, 1H), 4.80 (d, J=5.0, 1H), 4.31 (s, 2H), 4.15 (s, 1H), 3.91-3.94 (m, 2H), 3.44-3.59 (m, 4H), 2.16 (d, J=11.5, 2H), 1.74-1.80 (m, 2H), 1.44 (dd, J=11.0, J=6.2, 6H)

Example 71

Isopropyl 1-isopropyl-4-(4-methoxy-1H-pyrazolo[4,3-c]pyridin-3-yl)-1H-pyrrole-2-carboxylate

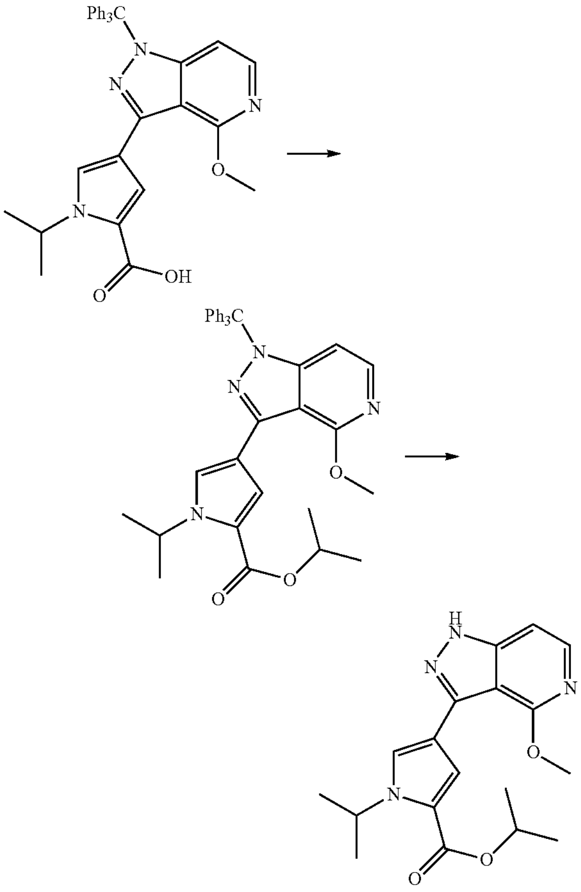

Step 1—Isopropyl 1-isopropyl-4-(4-methoxy-1-trityl-1H-pyrazolo[4,3-c]pyridin-3-yl)-1H-pyrrole-2-carboxylate A mixture of 1-isopropyl-4-(4-methoxy-1-trityl-1H-pyrazolo[4,3-c]pyridin-3-yl)-1H-pyrrole-2-carboxylic acid (200 mg, 0.37 mmol), 2-iodopropane (310 mg, 1.80 mmol), $Cs_2CO_3$ (360 mg, 1.1 mmol) in THF (50 mL) was stirred at reflux for 6 hours. After cooling down, ethyl acetate (100 mL) and water (50 mL) were added. The organic layer was separated and washed by water (30 mL) and brine, dried over anhydrous $Na_2SO_4$, filtered and concentrated in vacuo to give the title compound as a yellowish oil (100 mg).

LCMS (Method A): m/z=585 $[M+H]^+$; 2.63 min.

Step 2—Isopropyl 1-isopropyl-4-(4-methoxy-1H-pyrazolo[4,3-c]pyridin-3-yl)-1H-pyrrole-2-carboxylate The title compound was prepared by the procedure described in Example 65. LC-MS (Method E): m/z=343 $[M+H]^+$; 6.14 min. $^1$H-NMR (500 MHz, $CDCl_3$): δ 7.92 (d, J=6.0, 1H), 7.90 (s, 1H), 7.65 (d, J=1.5, 1H), 6.96 (d, J=6.0, 1H), 5.52 (q, J=6.5, 1H), 5.19 (q, J=6.5, 1H), 4.16 (s, 3H), 1.52 (d, J=6.5, 6H), 1.34 (d, J=6.0, 6H)

Example 72

N,N-Dimethyl-4-(4-(tetrahydro-2H-pyran-4-yloxy)-1H-pyrazolo[4,3-c]pyridin-3-yl)picolinamide

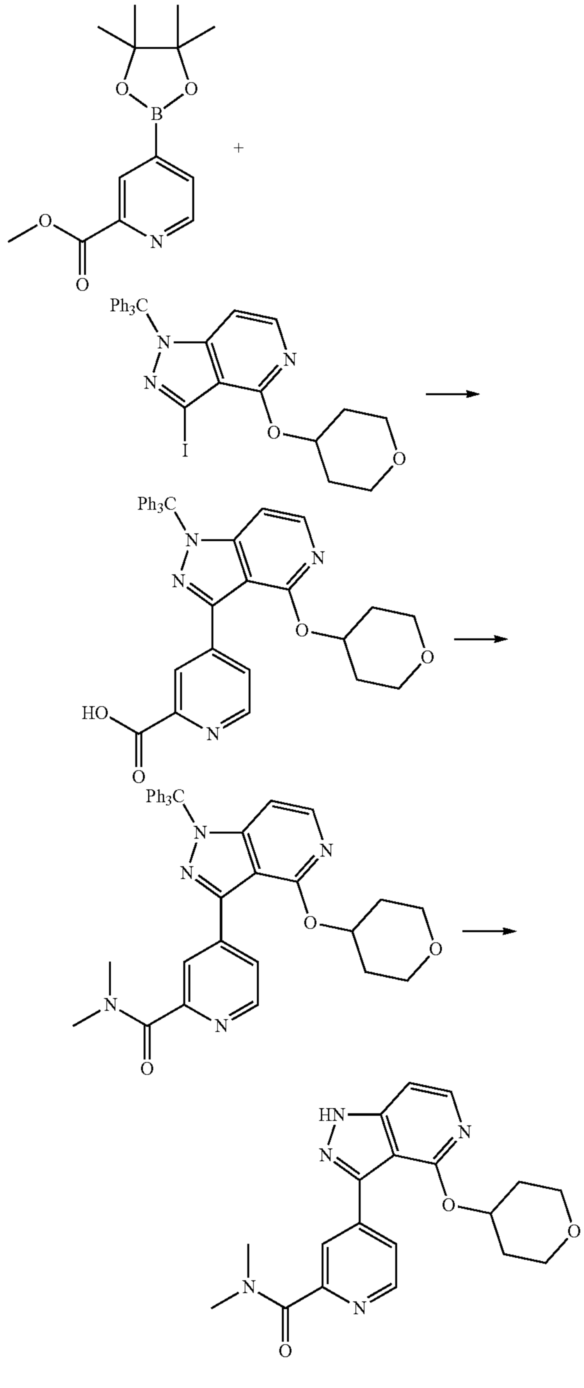

Step 1—4-(4-(Tetrahydro-2H-pyran-4-yloxy)-1-trityl-1H-pyrazolo[4,3-c]pyridin-3-yl)picolinic acid A mixture of 3-iodo-4-(tetrahydro-2H-pyran-4-yloxy)-1-trityl-1H-pyrazolo[4,3-c]pyridine (569 mg, 0.96 mmol), methyl 4-(4,4,5,5-tetramethyl-1,3,2-dioxaborolan-2-yl)picolinate (280 mg, 1.06 mmol), bis(di-tert-butyl(4-dimethylaminophenyl)phosphine)dichloropalladium (109 mg, 0.096 mmol), 1M sodium carbonate water solution (2 mL), N,N-dimethylformamide (10 mL) was degassed with nitrogen. It was then heated at 120° C. for 20 hours. The reaction mixture was extracted with ethyl acetate. The organic layers were combined, concentrated in vacuo and purified with reverse-phase HPLC. The title compound was obtained as a yellowish solid (0.20 g, 37%). LCMS (Method A): m/z=583 $[M+H]^+$; 2.20 min.

Step 2—N,N-Dimethyl-4-(4-(tetrahydro-2H-pyran-4-yloxy)-1-trityl-1H-pyrazolo[4,3-c]pyridin-3-yl)picolinamide A mixture of 4-(4-(tetrahydro-2H-pyran-4-yloxy)-1-trityl-1H-pyrazolo[4,3-c]pyridin-3-yl)picolinic acid (100 mg, 0.17 mmole), dimethylamine hydrochloride (30 mg, 0.34 mmole), HATU (100 mg, 0.26 mole), DIPEA (0.2 mL) in DMF (20 mL) was stirred overnight at 25° C. Ethyl acetate (100 mL) and water (50 mL) were added. The organic layer was separated and washed with water (30 mL) and brine, dried over anhydrous $Na_2SO_4$, filtered and concentrated in vacuo to give the crude desired product as a yellowish oil (70 mg, 68%). LCMS (Method A): m/z=610 $[M+H]^+$; 2.33 min.

Step 3—N,N-Dimethyl-4-(4-(tetrahydro-2H-pyran-4-yloxy)-1H-pyrazolo[4,3-c]pyridin-3-yl)picolinamide To a mixture of N,N-dimethyl-4-(4-(tetrahydro-2H-pyran-4-yloxy)-1-trityl-1H-pyrazolo[4,3-c]pyridin-3-yl)picolinamide (60 mg, 0.098 mmol) in dichloromethane (3 mL) was added trifluoroacetic acid (1 mL) and triethylsilane (0.2 mL). The mixture was stirred under reflux for 1 hour. After cooling to room temperature, the reaction mixture was neutralized to pH 7 with saturated $NaHCO_3$ solution. It was then extracted with ethyl acetate. The organic layers were combined and concentrated in vacuo. The residue was purified by reverse-phase HPLC to give the title compound as a yellowish oil (13 mg, 36%). LC-MS (Method E): m/z=368 $[M+H]^+$; 3.62 min. $^1$H-NMR (500 MHz, $CDCl_3$): δ 12.02 (s, 1H), 8.64 (d, J=5.0, 1H), 8.47 (s, 1H), 8.09 (m, 1H), 7.88 (d, J=6.0, 1H), 7.01 (d, J=6.0, 1H), 5.49-5.54 (m, 1H), 3.88-3.93 (m, 2H), 3.60-3.64 (m, 2H), 3.22 (s, 3H), 3.17 (s, 3H), 2.12-2.16 (m, 2H), 1.63-1.68 (m, 2H).

Example 73

Morpholino(4-(4-(tetrahydro-2H-pyran-4-yloxy)-1H-pyrazolo[4,3-c]pyridin-3-yl)pyridin-2-yl)methanone

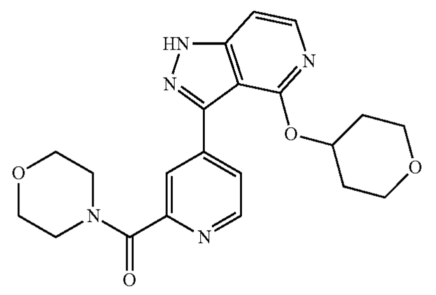 [SMILES: O=C(c1cc(-c2n[nH]c3ccnc(OC4CCOCC4)c23)ccn1)N1CCOCC1]

The title compound was prepared by the procedure described in Example 72 by substituting dimethylamine hydrochloride with morpholine. LC-MS (Method D):

m/z=410 [M+H]$^+$; 3.77 min. $^1$H-NMR (500 MHz, DMSO): δ 8.66 (d, J=6.0, 1H), 8.46 (d, J=1.0, 1H), 8.10 (d, J=2.0, 1H), 8.09 (d, J=1.5, 1H), 7.95 (d, J=6.0, 1H), 7.04 (d, J=6.0, 1H) 5.52-5.57 (m, 1H), 3.88-3.94 (m, 4H), 3.83-3.85 (m, 2H), 3.74 (s, 2H), 3.61-3.65 (m, 2H), 2.15-2.18 (m, 2H), 1.84-1.91 (m, 2H)

Example 74

4-(4-(4-(2,2,2-Trifluoroethoxy)-1H-pyrazolo[4,3-c]pyridin-3-yl)pyridin-2-yl)morpholine

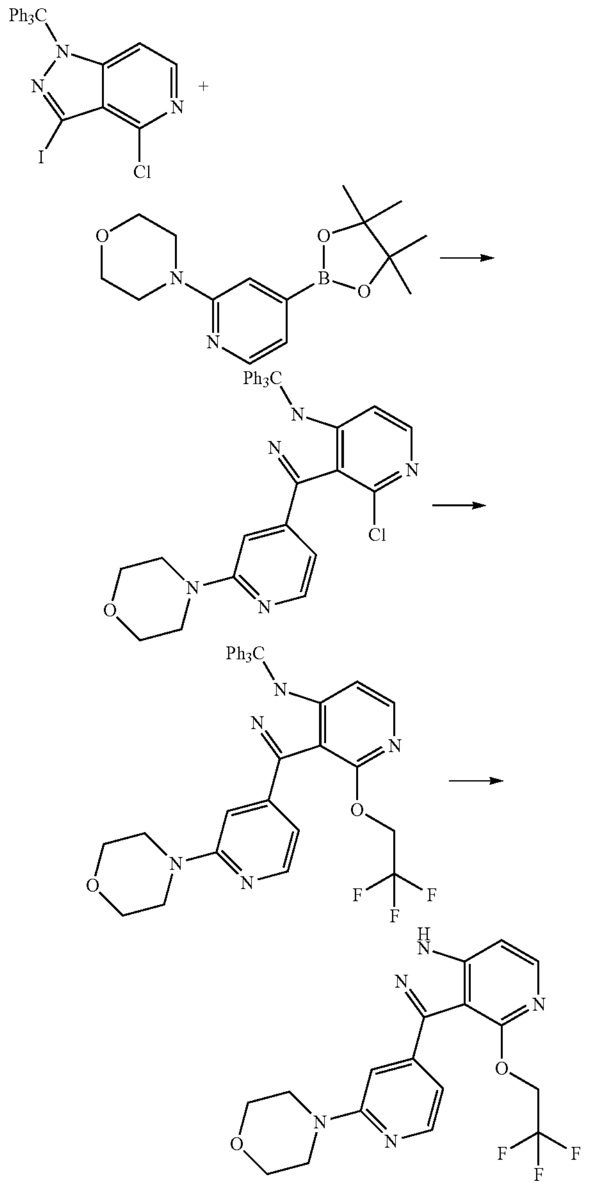

Step 1—4-(4-(4-Chloro-1-trityl-1H-pyrazolo[4,3-c]pyridin-3-yl)pyridine-2-yl)morpholine 4-Chloro-3-iodo-1-trityl-1H-pyrazolo[4,3-c]pyridine (45 mg, 0.086 mmol), 4-(4-(4,4,5,5-tetramethyl-1,3,2-dioxaborolan-2-yl)pyridin-2-yl)morpholine (30 mg, 0.103 mmol), potassium acetate (24 mg, 0.172 mmol), bis(di-tert-butyl(4-dimethylaminophenyl)phosphine)dichloropalladium (6 mg, 0.0086 mmol) were weighed into a microwave vial equipped with a stirring bar. Acetonitrile (2 mL) and degassed water (0.2 mL) were then added and the reaction mixture was degassed with $N_2$ and then heated at 120° C. under microwave irradiation for 45 min. The reaction mixture was filtered through a pad of Celite® with ethyl acetate. The filtrate was concentrated to dryness and purified by flash column chromatography (EtOAc-pet. ether, 1:5) to provide the title compound (22 mg, 46%). LCMS (Method A): m/z=558 [M+H]$^+$; 1.99 min.

Step 2—4-(4-(4-(2,2,2-Trifluoroethoxy)-1-trityl-1H-pyrazolo[4,3-c]pyridin-3-yl)pyridine-2-yl)morpholine To a solution of 2,2,2-trifluoroethanol (60 mg, 0.6 mmol) in THF was added sodium hydride (60% dispersion, 71 mg, 1.78 mmol). The suspension was stirred vigorously at room temperature for 1 hour. 4-(4-(4-chloro-1-trityl-1H-pyrazolo[4,3-c]pyridin-3-yl)pyridin-2-yl)morpholine (30 mg, 0.198 mmol) was added to the performed sodium trifluoroethanoxide solution and refluxed for 4 hours. THF was removed at reduced pressure. Water was added to the residue and the suspension was filtered and the solid was washed with water to give the crude desired product as yellow solid (40 mg, 33%). LCMS (Method A): m/z=622 [M+H]$^+$; 2.05 min.

Step 3—4-(4-(4-(2,2,2-Trifluoroethoxy)-1H-pyrazolo[4,3-c]pyridin-3-yl)pyridin-2-yl)morpholine To a mixture of 4-(4-(4-(2,2,2-trifluoroethoxy)-1-trityl-1H-pyrazolo[4,3-c]pyridin-3-yl)pyridin-2-yl)morpholine (40 mg, 0.064 mmol) in dichloromethane (5 mL) was added trifluoroacetic acid (2 mL) and triethylsilane (0.5 mL). The mixture was stirred at room temperature for 2 hours. The reaction mixture was neutralized to pH 7 with saturated $NaHCO_3$ solution. It was then extracted with ethyl acetate. The organic layers were combined and concentrated in vacuo. The residue was purified by reverse-phase HPLC to give the title compound as a pink solid (10 mg, 42%). LC-MS (Method F): m/z=380 [M+H]$^+$; 5.28 min. $^1$H-NMR (500 MHz, $CDCl_3$): δ 10.83 (s, 1H), 8.32 (d, J=5.0, 1H), 7.97 (d, J=5.0, 1H), 7.10-7.30 (m, 3H), 4.92-4.97 (m, 2H), 3.85 (t, J=5.0, 4H), 3.6 (t, J=5.0, 4H).

Example 75

4-(4-(4-Ethoxy-1H-pyrazolo[4,3-c]pyridin-3-yl)pyridin-2-yl)Morpholine

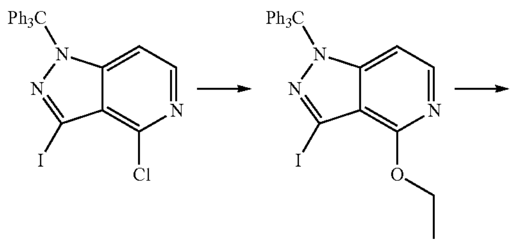

-continued

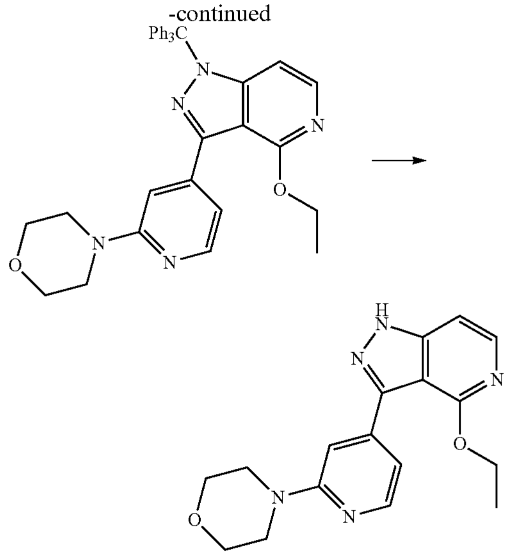

Step 1—4-Ethoxy-3-iodo-1-trityl-1H-pyrazolo[4,3-c]pyridine

To a solution of 4-chloro-3-iodo-1-trityl-1H-pyrazolo[4,3-c]pyridine (300 mg, 0.58 mmol) in THF (10 mL) at room temperature was added sodium ethoxide (195 mg, 2.879 mmol). The reaction mixture was refluxed for 4 hours. THF was removed at reduced pressure. Water was added to the residue and the suspension was filtered. The solid was washed with water to give the crude title compound as a yellow solid (270 mg, 90%) LC-MS (Method A): m/z=532.7 $[M+H]^+$; 2.44 min. $^1$H-NMR (500 MHz, $CDCl_3$): δ 7.46 (d, J=5.5, 1H), 7.14-7.31 (m, 15H), 5.75 (d, J=5.5, 1H), 4.50 (q, J=7.5, 2H), 1.49 (t, J=7.5, 3H).

Step 2—4-(4-(4-Ethoxy-1-trityl-1H-pyrazolo[4,3-c]pyridin-3-yl)pyridin-2-yl)morpholine To a solution of 4-ethoxy-3-iodo-1-trityl-1H-pyrazolo[4,3-c]pyridine (100 mg, 0.19 mmol) and 4-(4-(4,4,5,5-tetramethyl-1,3,2-dioxaborolan-2-yl)pyridin-2-yl)morpholine (76.5 mg, 0.264 mmol) in $CH_3CN$ (5.0 ml) was added a 1M solution of aqueous KOAc (0.38 mL, 0.38 mmol) and followed by the addition of bis(di-tert-butyl(4-dimethylaminophenyl)phosphine)dichloropalladium (13.3 mg, 0.019 mmol). The microwave vial was sealed and the reaction mixture was irradiated by microwave at 120° C. for 40 min. The reaction mixture was concentrated in vacuo and purified by prep-TLC (pet. ether-ethyl acetate, 1:1) to afford the title compound as a yellow solid (63 mg, 59%). LCMS (Method A): m/z=568.2 $[M+H]^+$; 1.96 min.

Step 3—4-(4-(4-Ethoxy-1H-pyrazolo[4,3-c]pyridin-3-yl)pyridin-2-yl)morpholine

To a solution of 4-(4-(4-ethoxy-1-trityl-1H-pyrazolo[4,3-c]pyridin-3-yl)pyridin-2-yl)morpholine (27) (63 mg, 0.11 mmole) in dichloromethane (3 mL) was added trifluoroacetic acid (0.5 mL) and triethylsilane (0.2 mL). The mixture was stirred at reflux for 1 hour. After cooling down to room temperature, the reaction mixture was neutralized to pH 7 with saturated $NaHCO_3$ solution. It was then extracted with ethyl acetate (3×30 mL). The organic layers were combined and concentrated in vacuo. The residue was purified by reverse-phase HPLC to give the title compound as a white solid (22 mg, 62%). LC-MS (Method D): m/z=340.7 $[M+H]^+$; 5.78 min. $^1$H-NMR (500 MHz, $CDCl_3$): δ 10.40 (br s, 1H), 8.30 (s, J=5.5, 1H), 7.97 (d, J=6.0, 1H), 7.36-7.38 (t, J=5.5, 2H), 7.01 (d, J=6.0, 1H), 4.57 (q, J=7.0, 2H), 3.87(t, J=4.5, 4H), 3.61 (t, J=4.5, 4H), 1.45 (t, J=7.0, 3H).

Example 76

3-(1-Isopropyl-1H-pyrazol-4-yl)-4-(2,2,2-trifluoroethoxy)-1H-pyrazolo[4,3-c]pyridine

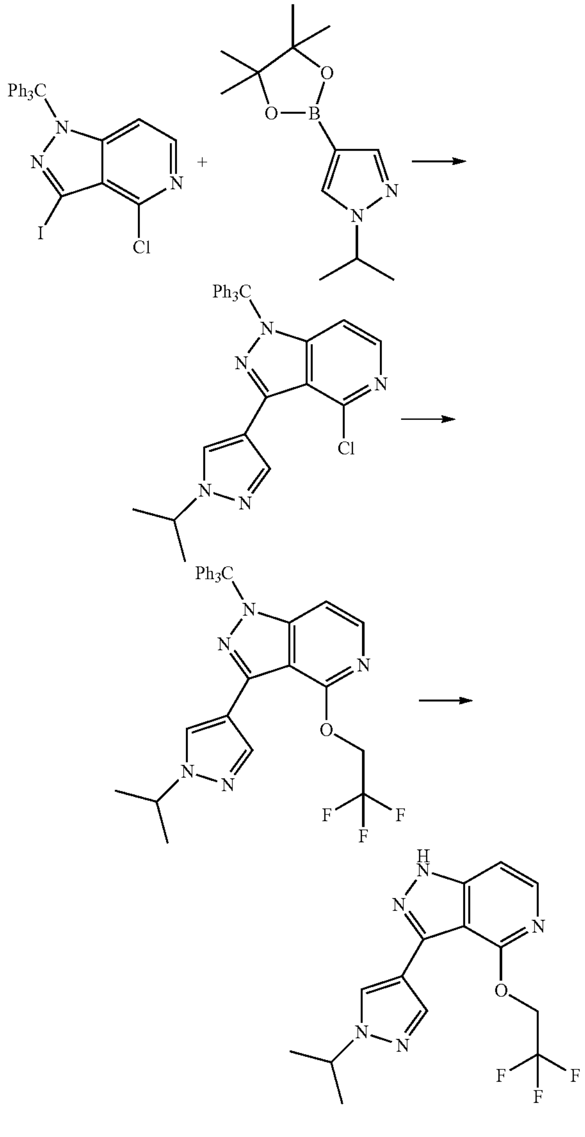

Step 1—4-Chloro-3-(1-isopropyl-1H-pyrazol-4-yl)-1-trityl-1H-pyrazolo-[4,3-c]pyridine 4-Chloro-3-iodo-1-trityl-1H-pyrazolo[4,3-c]pyridine (600 mg, 1.15 mmol), 1-isopropyl-4-(4,4,5,5-tetramethyl-1,3,2-dioxaborolan-2-yl)-1H-pyrazole (300 mg, 1.27 mmol), potassium acetate (278 mg, 2.0 mmol), bis(di-tert-butyl(4-dimethylaminophenyl)phosphine)dichloropalladium(II) (81 mg, 0.11 mmol) were weighed into a microwave vial equipped with a stirring bar. Acetonitrile (10 mL) and degassed water (2 mL) were added and the reaction mixture was degassed with $N_2$ and then heated at 120° C. under microwave irradiation for 45 min. The reaction mixture was filtered through a pad of Celite® with ethyl acetate. The filtrate was concentrated to dryness and purified by flash column chromatography (EtOAc-pet ether, 1:5) to give the title compound (300 mg, 52%). LCMS (Method A): m/z=504 $[M+H]^+$; 2.41 min.

Step 2—3-(1-Isopropyl-1H-pyrazol-4-yl)-4-(2,2,2-trifluoroethoxy)-1-trityl-1H-pyrazolo[4,3-c]pyridine To a solution of 2,2,2-trifluoroethanol (180 mg, 1.8 mmol) in THF was added sodium hydride (60% dispersion, 120 mg, 3 mmol). The resulting suspension was stirred vigorously at room temperature for 1 hour. 4-chloro-3-(1-isopropyl-1H-pyrazol-4-yl)-1-trityl-1H-pyrazolo[4,3-c]pyridine (200 mg, 0.39 mmol) was added to the performed sodium trifluoroethanoxide solution and reflux for 4 hours. THF was removed at reduced pressure. Water was added to the residue and the suspension was filtered. The solid was washed with water to give the title compound as a white solid (260 mg, 68%). LCMS (Method A): m/z=568 $[M+H]^+$; 2.46 min.

Step 3—3-(1-Isopropyl-1H-pyrazol-4-yl)-4-(2,2,2-trifluoroethoxy)-1H-pyrazolo[4,3-c]pyridine To a mixture of 3-(1-isopropyl-1H-pyrazol-4-yl)-4-(2,2,2-trifluoroethoxy)-1-trityl-1H-pyrazolo[4,3-c]pyridine (260 mg, 458 mmol) in dichloromethane (6 mL) was added trifluoroacetic acid (2 mL) and triethylsilane (0.5 mL). The mixture was stirred at reflux for 2 hours. After cooling down, the reaction mixture was neutralized to pH 7 by adding a saturated $NaHCO_3$ solution. The mixture was then extracted with ethyl acetate. The organic layers were combined and concentrated in vacuo. The residue was purified by reverse-phase HPLC to give the title compound as a white solid (105 mg, 71%). LCMS (Method D): m/z=326 $[M+H]^+$; 5.78 min. $^1$H-NMR (500 MHz, $CDCl_3$): δ 8.22 (s, 1H), 8.15 (s, 1H), 7.91 (d, J=6.0, 1H), 7.07 (d, J=6.0, 1H), 4.94-4.99 (m, 2H), 4.55-4.63 (m, 1H), 1.58 (d, J=6.5, 6H)

Example 77

3-(1-isopropyl-1H-pyrazol-4-yl)-4-(tetrahydro-2H-pyran-3-yloxy)-1H-pyrazolo[4,3-c]pyridine

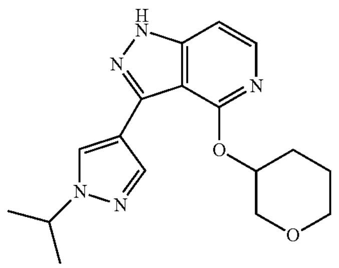 [SMILES: CC(C)n1cc(-c2n[nH]c3ccnc(OC4CCCOC4)c23)cn1]

The title compound was prepared by the procedure described in Example 76 by substituting 2,2,2-trifluoroethanol with tetrahydro-2H-pyran-3-ol. LC-MS (Method F): m/z=300 $[M+H]^+$; 5.46 min. $^1$H-NMR (500 MHz, $CDCl_3$): δ 8.64 (s, 1H), 8.17 (s, 1H), 7.83 (d, J=6.0, 1H), 7.04 (d, J=6.0, 1H), 5.4 (s, 1H), 4.59-4.63 (m, 1H), 3.89-4.0 (m, 3H), 3.66-3.71 (m, 1H), 1.92-2.16 (m, 3H), 1.55-1.59 (m, 7H).

Example 78

3-(1-Isopropyl-1H-pyrazol-4-yl)-4-(2,2,2-trifluoro-1-methyl-ethoxy)-1H-pyrazolo[4,3-c]pyridine

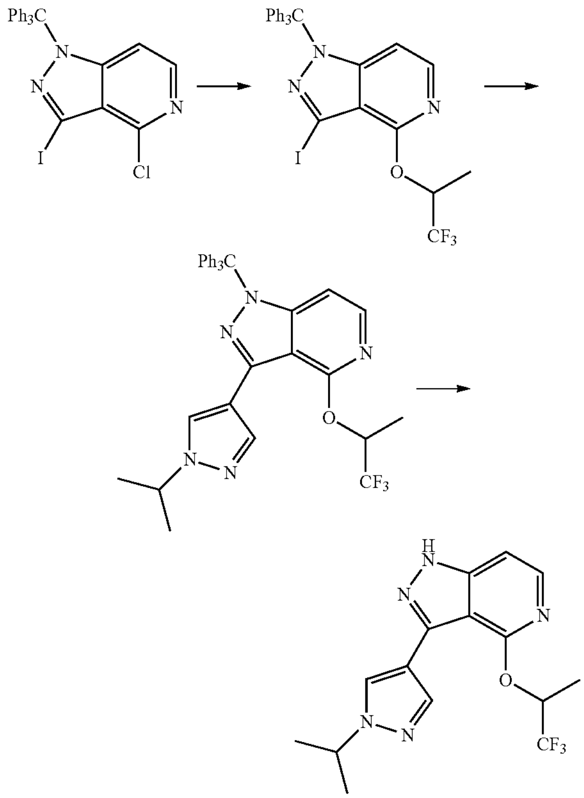

Step 1—3-Iodo-4-(2,2,2-trifluoro-1-methyl-ethoxy)-1-trityl-1H-pyrazolo[4,3-c]pyridine To a suspension of NaH (60% dispersion, 55.0 mg, 2.29 mmol) in THF (10 mL) at room temperature was added 1,1,1-trifluoropropan-2-ol (259.9 mg, 2.28 mmol) and stirred for 30 minutes. 4-chloro-3-iodo-1-trityl-1H-pyrazolo[4,3-c]pyridine (300 mg, 0.57 mmol) in THF (3 mL) was added to the preformed sodium 1,1,1-trifluoropropan-2-olate solution and refluxed for 4 hours. THF was removed at reduced pressure. Water was added to the residue and the suspension was filtered. The solid was washed with water to give the crude title compound as a yellow solid (310 mg, 89%). LCMS (Method A): m/z=600.7 $[M+H]^+$; 2.63 min.

Step 2—3-(1-Isopropyl-1H-pyrazol-4-yl)-4-(2,2,2-trifluoro-1-methyl-ethoxy)-1-trityl-1H-pyrazolo[4,3-c]pyridine To a solution of 3-iodo-4-(2,2,2-trifluoro-1-methyl-ethoxy)-1-trityl-1H-pyrazolo[4,3-c]pyridine (150 mg, 0.25 mmol) and 1-isopropyl-4-(4,4,5,5-tetramethyl-[1,3,2]dioxaborolan-2-yl)-1H-pyrazole (82 mg, 0.35 mmol) in $CH_3CN$ (5.0 ml) was added a 1M solution of aqueous KOAc (0.50 mL, 0.50 mmol) followed by the addition of bis(di-tert-butyl(4-dimethylaminophenyl)phosphine)dichloropalladium (18 mg, 0.025 mmol). The microwave vial was sealed and the reaction mixture was irradiated in the microwave reactor at 120° C. for 40 min. The reaction mixture was concentrated in vacuo and purified by prep-TLC (pet. ether-ethyl acetate, 1:1) to afford the title compound as a white solid (62 mg, 42%). LCMS (Method A): m/z=582.2 $[M+H]^+$; 2.64 min.

Step 3—3-(1-Isopropyl-1H-pyrazol-4-yl)-4-(2,2,2-trifluoro-1-methyl-ethoxy)-1H-pyrazolo[4,3-c]pyridine To a mixture of 3-(1-isopropyl-1H-pyrazol-4-yl)-4-(2,2,2-trifluoro-1-methyl-ethoxy)-1-trityl-1H-pyrazolo[4,3-c]pyridine (62 mg, 0.11 mmole) in dichloromethane (3 mL) was added trifluoroacetic acid (0.5 mL) and triethylsilane (0.2 mL). The mixture was stirred at reflux for 1 hour. After cooling to room temperature, the reaction mixture was neutralized to pH 7 with a saturated $NaHCO_3$ solution. The mixture was then extracted with ethyl acetate. The organic layers were combined and concentrated in vacuo. The residue was purified by reverse-phase HPLC to give compound the title compound as a white solid (18 mg, 50%).

LC-MS (Method F): m/z=340.7 $[M+H]^+$; 5.78 min. $^1$H-NMR (500 MHz, $CDCl_3$): δ 8.22 (s, 1H), 8.16 (s, 1H), 7.88 (d, J=6.0, 1H), 7.02 (d, J=6.0, 1H), 6.10 (d, J=6.5, 1H), 4.59 (m, 1H), 1.61 (d, J=6.5, 3H), 1.58 (d, J=7.0, 6H)

Example 79

4-Ethoxy-3-(1-isopropyl-1H-pyrazol-4-yl)-1H-pyrazolo[4,3-c]pyridine

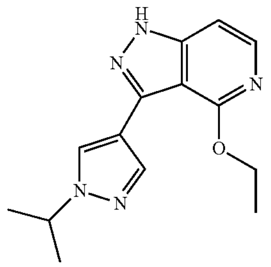 [SMILES: CCOc1nccc2[nH]nc(-c3cnn(C(C)C)c3)c12]

The title compound was prepared by the procedure described in Example 78 by substituting 1,1,1-trifluoropropan-2-ol with ethanol. LC-MS (Method D): m/z=272.7 $[M+H]^+$; 4.27 min. $^1$H-NMR (500 MHz, $CDCl_3$): δ 10.02 (br s, 1H), 8.25 (s, 1H), 8.23 (s, 1H), 7.91 (d, J=5.5, 1H), 6.94 (d, J=5.5, 1H), 4.56-4.62 (m, 3H), 1.59 (s, 3H), 1.58 (s, 6H)

Example 80

3-(1-Isopropyl-1H-pyrazol-4-yl)-4-(2-methoxy-ethoxy)-1H-pyrazolo[4,3-c]pyridine

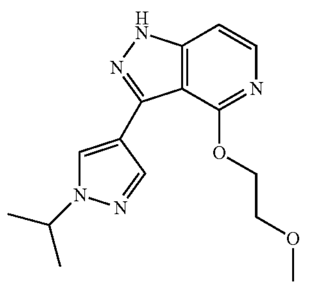 [SMILES: COCCOc1nccc2[nH]nc(-c3cnn(C(C)C)c3)c12]

The title compound was prepared by the procedure described in Example 78 by substituting 2,2,2-trifluoroethanol with 2-methoxyethanol. LC-MS (Method F): m/z=302 $[M+H]^+$; 4.29 min. $^1$H-NMR (500 MHz, $CDCl_3$): δ 8.39 (s, 1H), 8.24 (s, 1H), 7.86 (d, J=6.0, 1H), 6.89 (d, J=6.0, 1H), 4.69-4.71 (m, 2H), 4.57-4.60 (m, 1H), 3.86-3.88 (m, 1H), 3.48 (s, 1H), 1.59 (d, J=6.5, 6H)

Example 81

3-(1-isopropyl-1H-pyrazol-4-yl)-4-(2-methylcyclopentyloxy)-1H-pyrazolo[4,3-c]pyridine

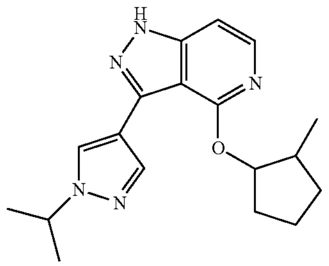 [SMILES: CC1CCCC1Oc1nccc2[nH]nc(-c3cnn(C(C)C)c3)c12]

The title compound was prepared by the procedure described in Example 78 by substituting 2,2,2-trifluoroethanol with 2-methylcyclopentanol. LC-MS (Method F): m/z=326 $[M+1]^+$; 6.1 min. $^1$H-NMR (500 MHz, $CDCl_3$): δ 8.23 (s, 2H), 7.90 (d, J=6.0, 1H), 6.89 (d, J=6.0, 1H), 5.24-5.26 (m, 1H), 4.57-4.60 (m, 1H), 2.32-2.35 (m, 2H), 2.25-2.28 (m, 1H), 1.59 (d, J=7.0, 6H), 1.13-1.34 (m, 7H).

Example 82

3-(1-Ethyl-1H-pyrazole-4-yl)-4-isopropoxyl-1H-pyrazolo[4,3-c]pyridine

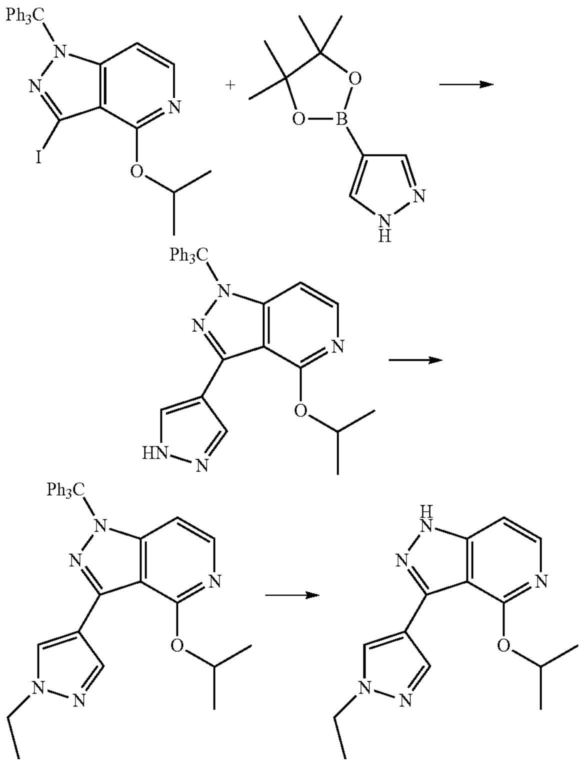

Step 1—4-Isopropoxy-3-(1H-pyrazole-4-yl)-1-trityl-1H-pyrazolo[4,3-c]pyridine

To a microwave vial equipped with a stirring bar was added 3-iodo-4-isopropoxy-1-trityl-1H-pyrazolo[4,3-c]pyridine (1.7 g, 3.1 mmol), 4-(4,4,5,5-tetramethyl-1,3,2-dioxaborolan-2-yl)-1H-pyrazole (847 mg, 4.3 mmol), potassium acetate (425 mg, 4.3 mmol), $Na_2CO_3$ (455 mg, 4.3 mmol), bis(di-tert-butyl (4-dimethylamino phenyl)phosphine) dichloropalladium (219 mg, 0.31 mmol), $CH_3CN$ (22 mL) and degassed water (5.6 mL). The reaction mixture was degassed with $N_2$ and then heated at 150° C. under microwave irradiation for 45 minutes. It was then filtered through a pad of Celite® with ethyl acetate. The filtrate was concentrated to dryness and purified with flash chromatography (pet. ether-ethyl acetate, 8:1) to provide the title compound (896 mg 59%). LC-MS (Method A): m/z=486.2 $[M+H]^+$; 2.22 min. $^1H$-NMR (500 MHz, $CDCl_3$): δ 8.24 (s, 2H), 7.63 (s, 1H), 7.48 (d, J=6.5, 1H), 7.18-7.29 (m, 15H), 5.76 (d, J=6.5, 1H), 5.52-5.60 (m, 1H), 1.49 (d, J=6.5, 6H).

Step 2—3-(1-Ethyl-1H-pyrazole-4-yl)-4-isopropoxyl-1-trityl-1H-pyrazolo[4,3-c]pyridine At 0° C., a solution of 4-ispropoxy-3-(1H-pyrazole-4-yl)-1-trityl-1H-pyrazolo[4,3-c]pyridine (100 mg, 0.2060 mmol) in DMF (2 mL) was added dropwise to a suspension of NaH (60% dispersion, 24.7 mg, 1.03 mmol) in DMF (5 mL). It was then stirred at room temperature for 1 hour and quenched with water. The reaction mixture was extracted with ethyl acetate, dried over anhydrous sodium sulfate and filtered. The filtrate was concentrated at reduced pressure to give the crude desired product as yellow solid (100 mg, 95%). LCMS (Method A): m/z=514 $[M+H]^+$; 2.39 min.

Step 3—3-(1-Ethyl-1H-pyrazole-4-yl)-4-isopropoxyl-1H-pyrazolo[4,3-c]pyridine

To a mixture of 3-(1-ethyl-1H-pyrazole-4-yl)-4-isopropoxyl-1-trityl-1H-pyrazolo[4,3-c]pyridine (100 mg, 0.19 mmol) in dichloromethane (5 mL) was added trifluoroacetic acid (1 mL) and triethylsilane (0.2 mL). The mixture was stirred under reflux for 1 hour. After cooling down, the reaction mixture was neutralized to pH 7 with a saturated $NaHCO_3$ solution. It was then extracted with ethyl acetate. The organic layers were combined and concentrated in vacuo. The residue was purified by reverse-phase HPLC to give the title compound as a yellow solid (25 mg, 48%). LC-MS (Method D): m/z=272 $[M+H]^+$; 4.31 min. $^1H$-NMR (500 MHz, $CDCl_3$): δ 11.12 (s, 1H), 8.25 (s, 1H), 8.22 (s 1H), 7.88 (d, J=6.0, 1H), 6.86 (d, J=6.0, 1H), 5.57-5.64 (m, 1H), 4.25 (q, J=7.0, 2H), 1.56 (t, J=7.0, 3H), 1.49 (d, J=6.0, 6H).

Example 83

3-(1-sec-butyl-1H-pyrazol-4-yl)-4-isopropoxyl-1H-pyrazolo[4,3-c]pyridine

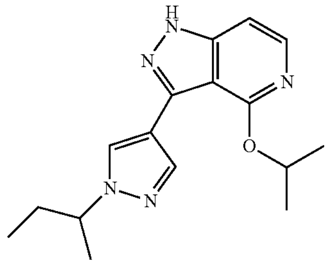 [SMILES: CCC(C)n1cc(-c2n[nH]c3ccnc(OC(C)C)c23)cn1]

The title compound was prepared by the procedure described in Example 82 by substituting bromoethane with 2-bromobutane. LCMS (Method D): m/z=300 $[M+H]^+$; 5.14 min. $^1H$-NMR (500 MHz, $CDCl_3$): δ 8.24 (s, 2H), 7.92 (d, J=6.0, 1H), 6.95 (d, J=6.0, 1H), 5.64-5.69 (m, 1H), 4.31 (m, 1H), 1.98 (m, 1H), 1.85 (m, 1H), 1.57 (d, J=6, 3H), 1.51 (d, J=5.5, 6H), 0.89 (t, J=7, 3H).

Example 84

4-(4-(4-(tetrahydro-2H-pyran-4-yloxy)-1H-pyrazolo[4,3-c]pyridin-3-yl)pyrimidin-2-yl)morpholine

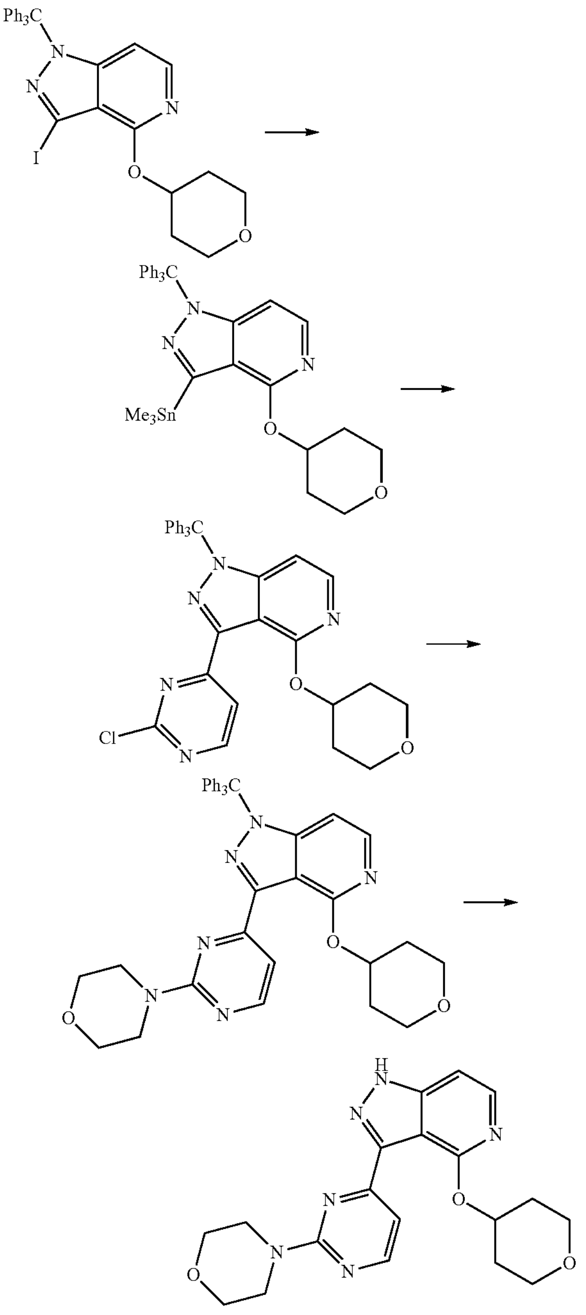

Step 1—4-(Tetrahydro-2H-pyran-4-yloxy)-3-(trimethylstannyl)-1-trityl-1H-pyrazolo[4,3-c]pyridine 3-Iodo-4-(tetrahydro-2H-pyran-4-yloxy)-1-trityl-1H-pyrazolo[4,3-c]pyridine (1.5 g, 2.55 mmol) was added to a microwave vial that was purged with nitrogen. Toluene (10 mL) and hexamethylditin (1.67 g, 5.11 mmol) were added, followed by the addition of bis(di-tert-butyl(4-dimethylaminophenyl)phosphine)dichloropalladium (177 mg, 0.25 mmol). The reaction mixture was stirred at 140° C. for 2 hours. The reaction was diluted with EtOAc, filter through Celite® and evaporated to dryness. The residue was purified by flash column chromatography (pet. ether-ethyl acetate, 10:1) to give the title compound as an off-white solid (1.12 g, 70%). LCMS (Method A): m/z=626 $[M+H]^+$; 1.70 min.

Step 2—3-(2-Chloropyrimidin-4-yl)-4-(tetrahydro-2H-pyran-4-yloxy)-1-trityl-1H-pyrazolo[4,3-c]pyridine To a microwave vial was added 4-(tetrahydro-2H-pyran-4-yloxy)-3-(trimethylstannyl)-1-trityl-1H-pyrazolo[4,3-c]pyridine (120 mg, 0.192 mmol), 2,4-dichloropyrimidine (57 mg, 0.384 mmol), copper(I) thiophene-2-carboxylate (73 mg, 0.384 mol) and 1,1'-bis(diphenylphosphino) ferrocenepalladium chloride (16 mg, 0.019 mol). The vial was flushed with nitrogen for 2 minutes before adding toluene (3.5 mL). The reaction was then heated in a microwave reactor at 140° C. for 15 minutes. The reaction mixture was diluted with EtOAc and washed with a saturated $NaHCO_3$ solution. The aqueous layer was extracted with EtOAc. The combined extracts were washed with sat. $NaHCO_3$ and brine, dried over $Na_2SO_4$, filtered and concentrated. The crude product was purified by prep-TLC (pet. ether-ethyl acetate, 8:1) to give a white solid (65 mg, 59%). LCMS (Method A): m/z=574 $[M+H]^+$; 2.46 min.

Step 3—4-(4-(4-(tetrahydro-2H-pyran-4-yloxy)-1-trityl-1H-pyrazolo[4,3-c]pyridin-3-yl)pyrimidin-2-yl)morpholine To a suspension of 3-(2-chloropyrimidin-4-yl)-4-(tetrahydro-2H-pyran-4-yloxy)-1-trityl-1H-pyrazolo[4,3-c]pyridine (38) (65.0 mg, 0.113 mmol) in ethanol (8 mL) was added sodium carbonate (36 mg, 0.34 mmol) and morpholine (29 uL, 0.34 mmol) and the reaction mixture was heated at 85° C. for 4 h. The solvent was evaporated, diluted with water, and extracted with DCM. The combined DCM extract was dried, filtered and concentrated to provide the title compound as a white solid (64 mg, 91%). LCMS (Method A): m/z=625 $[M+H]^+$; 2.32 min.

Step 4—4-(4-(4-(tetrahydro-2H-pyran-4-yloxy)-1H-pyrazolo[4,3-c]pyridin-3-yl)pyrimidin-2-yl)morpholine To a solution of 4-(4-(4-(tetrahydro-2H-pyran-4-yloxy)-1-trityl-1H-pyrazolo[4,3-c]pyridin-3-yl)pyrimidin-2-yl)morpholine (39) (64 mg, 0.102 mmole) in dichloromethane (3 mL) was added trifluoroacetic acid (0.5 mL) and triethylsilane (0.2 mL). The mixture was stirred at reflux for 1 hour. After cooling down, the reaction mixture was neutralized to pH 7 with saturated $NaHCO_3$ solution. The reaction was then extracted with ethyl acetate. The organic layers were combined and concentrated in vacuo. The residue was purified by reverse-phase HPLC to give the title compound as a white solid (18 mg, 45%). LCMS (Method D): m/z=383 $[M+H]^+$; 4.21 min. $^1$H-NMR (500 MHz, $CDCl_3$): δ 8.48 (s, 1H), 7.93 (d, J=6.0, 1H), 7.46 (s, 1H), 7.08 (d, J=6.0, 1H), 5.56-5.54 (m 1H), 3.96-3.90 (m, 6H), 3.81 (t, J=5.0, 4H), 3.67-3.62 (m, 2H), 2.16-2.14 (m, 2H), 1.88-1.84 (m, 2H).

Example 85

3-(6-Morpholin-4-yl-pyridin-2-yl)-4-(tetrahydro-pyran-4-yloxy)-1H-pyrazolo[4,3-c]pyridine

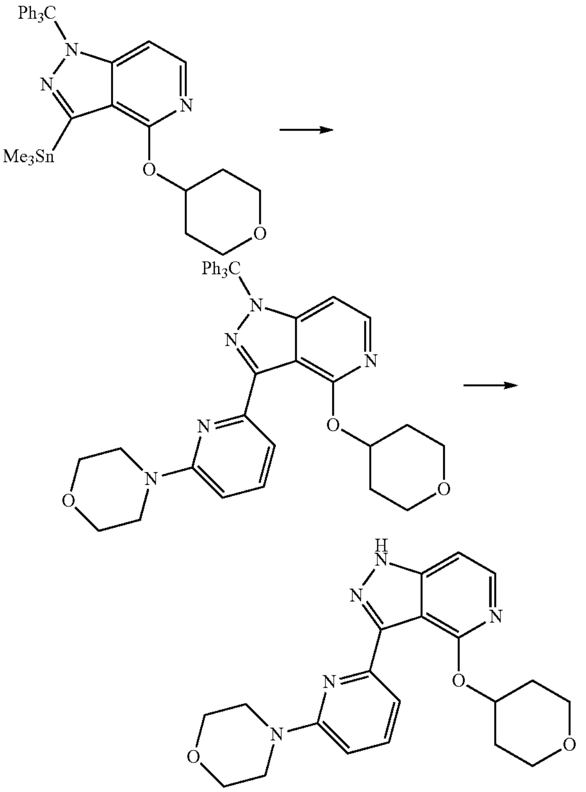

Step 1—4-(6-(4-(Tetrahydro-2H-pyran-4-yloxy)-1-trityl-1H-pyrazolo[4,3-c]pyridin-3-yl)pyridin-2-yl) morpholine To a microwave vial was added 4-(tetrahydro-2H-pyran-4-yloxy)-3-(trimethylstannyl)-1-trityl-1H-pyrazolo[4,3-c]pyridine (100 mg, 0.16 mmol), 4-(6-bromo-pyridin-2-yl)-morpholine (77 mg, 0.32 mmol), copper(I) thiophene-2-carboxylate (61 mg, 0.32 mol) and 1,1'-bis (diphenylphosphino) ferrocenepalladium chloride (13 mg, 0.016 mol). The vial was flushed with nitrogen for 2 minutes before adding toluene (3.0 mL). The reaction was heated in a microwave reactor at 140° C. for 15 min. The reaction was then diluted with EtOAc and washed with sat. $NaHCO_3$. The aqueous layer was further extracted with EtOAc. The combined EtOAc extract was washed with sat. $NaHCO_3$ then brine, dried over $Na_2SO_4$, filtered and concentrated. The crude product was purified by prep-TLC (pet. ether-ethyl acetate, 8:1) to give a white solid (54 mg, 55%). LCMS (Method A): m/z=624 $[M+H]^+$; 2.09 min.

Step 2—3-(6-Morpholin-4-yl-pyridin-2-yl)-4-(tetrahydro-pyran-4-yloxy)-1H-pyrazolo[4,3-c]pyridine To a solution of 4-(6-(4-(tetrahydro-2H-pyran-4-yloxy)-1-trityl-1H-pyrazolo[4,3-c]pyridin-3-yl)pyridin-2-yl)morpholine (54 mg, 0.087 mmole) in dichloromethane (3 mL) was added trifluoroacetic acid (0.5 mL) and triethylsilane (0.2 mL). The mixture was stirred at reflux for 1 hour. After cooling down, the reaction mixture was neutralized to pH 7 with a saturated $NaHCO_3$ solution. The reaction was extracted with ethyl acetate. The organic layers were combined and concentrated in vacuo. The residue was purified by reverse-phase HPLC to give the title compound as a white solid (15 mg, 45%). LCMS (Method C): m/z=382 $[M+H]^+$; 1.78 min. $^1$H-NMR (500 MHz, $CDCl_3$): δ 7.87 (d, J=6.0, 1H), 7.73 (s, 1H), 7.64 (t, J=8.5, 1H), 7.09 (d, J=6.0, 1H), 6.73 (d, J=8.0, 1H), 5.57-5.56 (m, 1H), 3.94-3.90 (m, 2H), 3.86 (t, J=5.0, 4H), 3.66-3.60 (m, 6H), 2.15 (t, J=4.5, 2H), 1.88-1.85 (m, 2H).

Example 86

4-Methoxy-3-1-(oxetan-3-yl)-1H-pyrazol-4-yl)-1H-pyrazolo[4,3-c]pyridine

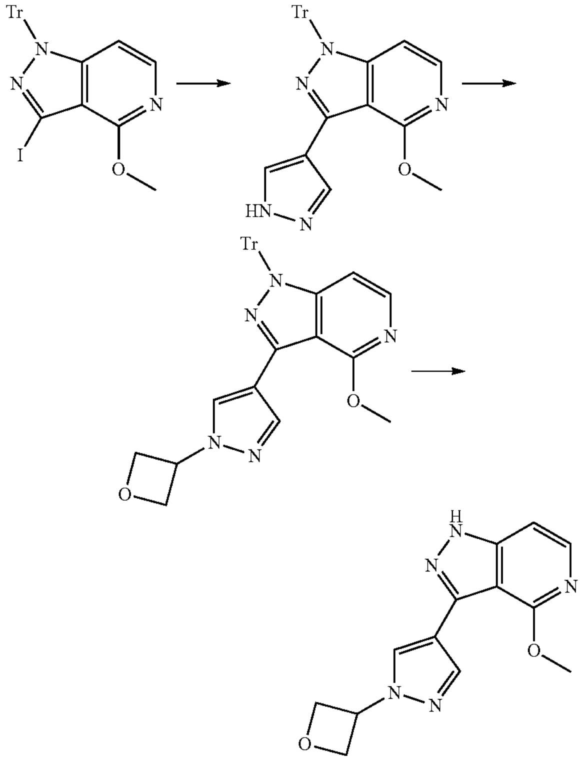

Step 1—4-Methoxy-3-(1H-pyrazol-4-yl)-1-trityl-1H-pyrazolo[4,3-c]pyridine

To a microwave vial was charged 3-iodo-4-methoxy-1-trityl-1H-pyrazolo[4,3-c]pyridine (0.750 g, 1.45 mmol), 4,4,5,5-tetramethyl-2-(1H-pyrazol-4-yl)-1,3,2-dioxaborolane (0.394 g, 2.03 mmol), potassium acetate (0.199 g, 2.03 mmol), sodium carbonate (0.215 g, 2.03 mmol) and bis(di-tert-butyl(4-dimethylaminophenyl)phosphine)dichloropalladium (0.103 g, 0.145 mmol). Acetonitrile (11 mL, 210 mmol) and degassed water (3 mL, 200 mmol) were then added and the reaction mixture was degassed with nitrogen for 10 minutes and then heated to 150° C. under microwave irradiation for 90 minutes. Upon reaction completion, the reaction mixture was filtered through Celite®, washing with EtOAc and concentrated in vacuo dryness. The crude product was purified by column chromatography eluting with 0-100% EtOAc in heptane to give the title compound (65%).

Step 2—4-Methoxy-3-(1-(oxetan-3-yl)-1H-pyrazol-4-yl)-1-trityl-1H-pyrazolo[4,3-c]pyridine To a 2 dram vial was added 4-methoxy-3-(1H-pyrazol-4-yl)-1-trityl-1H-pyrazolo[4,3-c]pyridine (0.100 g, 0.218 mmol), cesium carbonate (0.107 g, 0.328 mmol), followed by N,N-dimethylformamide (0.57 mL, 7.4 mmol). 3-iodooxetane (0.0804 g, 0.437 mmol) was added, the vial was capped, sealed with parafilm and heated to 90° C. for 16 hours. Upon reaction completion, the reaction mixture was diluted with water and EtOAc, the layers were separated and the aqueous layer was extracted with EtOAc. The combined organics were washed with brine, dried over sodium sulfate, filtered and concentrated in vacuo to give the title compound.

Step 3—4-Methoxy-3-1-(oxetan-3-yl)-1H-pyrazol-4-yl)-1H-pyrazolo[4,3-c]pyridine

To crude 4-methoxy-3-(1-(oxetan-3-yl)-1H-pyrazol-4-yl)-1-trityl-1H-pyrazolo[4,3-c]pyridine (0.112 g, 0.218 mmol) dissolved in methylene chloride (3 mL, 50 mmol) and triethylsilane (0.139 mL, 0.872 mmol) was added trifluoroacetic acid (3 mL, 40 mmol) at 0° C. The reaction mixture was stirred for 30 min and concentrated in vacuo. The crude residue was purified by reverse-phase HPLC to give the title compound (10.3 mg, 17% over two steps). LC-MS (Method G): m/z=272.0 $[M+H]^+$, 2.82 min. $^1$H-NMR (400 MHz, DMSO): δ 13.32 (s, 1H), 8.40 (s, 1H), 8.16 (s, 1H), 7.86 (d, J=5.9, 1H), 7.10 (d, J=6.0, 1H), 5.81-5.63 (m, 1H), 4.96 (d, J=7.0, 4H), 4.07 (s, 3H).

Example 87

3-(1-(Cyclobutylmethyl)-1H-pyrazol-4-yl)-4-methoxy-1H-pyrazolo[4,3-c]pyridine

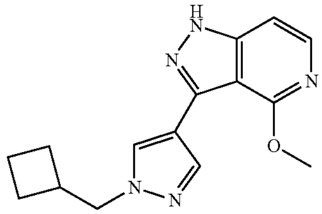 [SMILES: COc1nccc2[nH]nc(-c3cnn(CC4CCC4)c3)c12]

Prepared according to the general procedure described in Example 86 by reacting 4-methoxy-3-(1H-pyrazol-4-yl)-1-trityl-1H-pyrazolo[4,3-c]pyridine with (bromomethyl)cyclobutane to give the title compound (39.6 mg, 64% over two steps). LC-MS (Method G): m/z=284.1 $[M+H]^+$; 3.72 min. $^1$H-NMR (400 MHz, DMSO): δ 13.73 (s, 1H), 8.13 (s, J=1.4, 1H), 8.04 (dd, J=8.0, J=1.4, 1H), 7.94 (d, J=6.0, 1H), 7.50 (d, J=8.0, 1H), 7.19 (d, J=6.0, 1H), 4.02 (s, 3H), 3.68 (s, 5H), 3.61-3.54 (m, 3H), 3.26-3.20 (m, 3H).

Example 88

4-Methoxy-3-(1-(2,2,2-trifluoroethyl)-1H-pyrazol-4-yl)-1H-pyrazolo[4,3-u]pyridine

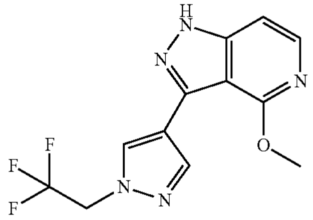 [SMILES: COc1nccc2[nH]nc(-c3cnn(CC(F)(F)F)c3)c12]

Prepared following the general procedure described in Example 86, by reacting 4-methoxy-3-(1H-pyrazol-4-yl)-1-trityl-1H-pyrazolo[4,3-c]pyridine with trifluoroethanol triflate to give the title compound (27.6 mg, 42% over two steps). LC-MS (Method G): m/z=298.0 $[M+H]^+$; 3.40 min. $^1$H-NMR (400 MHz, DMSO): δ 13.37 (s, 1H), 8.45 (s, 1H), 8.13 (s, 1H), 7.87 (d, J=6.0, 1H), 7.11 (d, J=6.0, 1H), 5.33-5.17 (m, 2H), 4.07 (s, 3H).

Example 89

4-Methoxy-3-(1-((3-methyloxetan-3-yl)methyl)-1H-pyrazol-4-yl)-1H-pyrazolo[4,3-c]pyridine

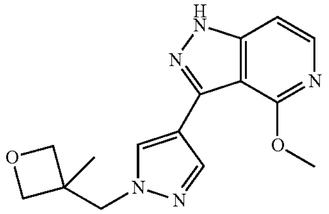 [SMILES: COc1nccc2[nH]nc(-c3cnn(CC4(C)COC4)c3)c12]

Prepared according to the general procedure described in Example 86, by reacting 4-methoxy-3-(1H-pyrazol-4-yl)-1-trityl-1H-pyrazolo[4,3-c]pyridine with 3-(bromomethyl)-3-methyloxetane to give the title compound (23.1 mg, 35% over two steps). LC-MS (Method G): m/z=300.0 $[M+H]^+$; 2.54 min. $^1$H-NMR (400 MHz, DMSO) δ 8.75 (s, 2H), 7.47 (d, J=5.8, 1H), 7.00 (d, J=6.0, 1H), 4.54 (d, J=11.7, 2H), 4.31 (d, J=11.8, 2H), 4.01 (s, 2H), 3.50 (s, 5H), 1.31 (s, 3H).

Example 90

3-(1-(Cyclopropylmethyl)-1H-pyrazol-4-yl)-4-methoxy-1H-pyrazolo[4,3-c]pyridine

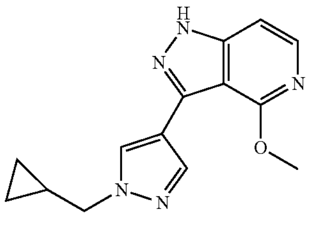 [SMILES: COc1nccc2[nH]nc(-c3cnn(CC4CC4)c3)c12]

Prepared according to the general procedure described in Example 86, by reacting 4-methoxy-3-(1H-pyrazol-4-yl)-1-trityl-1H-pyrazolo[4,3-c]pyridine with cyclopropylmethyl bromide to give the title compound (21.3 mg, 45% over two steps). LC-MS (Method G): m/z=270.0 $[M+H]^+$; 3.41 min. $^1$H-NMR (400 MHz, DMSO): δ 13.25 (s, 1H), 8.33 (s, 1H), 7.99 (s, 1H), 7.85 (d, J=5.7, 1H), 7.08 (d, J=5.9, 1H), 4.09-4.03 (m, 5H), 1.37-1.24 (m, 1H), 0.63-0.54 (m, 2H), 0.46-0.39 (m, 2H).

Example 91

3-(1-((2,2-Difluorocyclopropyl)methyl)-1H-pyrazol-4-yl)-4-methoxy-1H-pyrazolo[4,3-c]pyridine

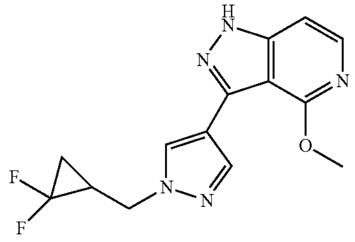 [SMILES: COc1nccc2[nH]nc(-c3cnn(CC4CC4(F)F)c3)c12]

Prepared according to the general procedure described in Example 86, by reacting 4-methoxy-3-(1H-pyrazol-4-yl)-1-trityl-1H-pyrazolo[4,3-c]pyridine with 1-bromomethyl-2,2-difluorocyclopropane to give the title compound (29.4 mg, 55% over two steps). LC-MS (Method G): m/z=306.0 $[M+H]^+$, 3.49 min. $^1$H-NMR (400 MHz, DMSO): δ 13.28 (s, 1H), 8.34 (s, 1H), 8.04 (s, 1H), 7.86 (d, J=5.8, 1H), 7.09 (d, J=5.9, 1H), 4.43-4.26 (m, 2H), 4.06 (s, 3H), 2.37-2.23 (m, 1H), 1.79-1.67 (m, 1H), 1.60-1.49 (m, 1H).

Example 92

3-(1-(Cyclopropylmethyl)-1H-pyrazol-4-yl)-4-(tetrahydro-2H-pyran-4-yloxy)-1H-pyrazolo[4,3-c]pyridine

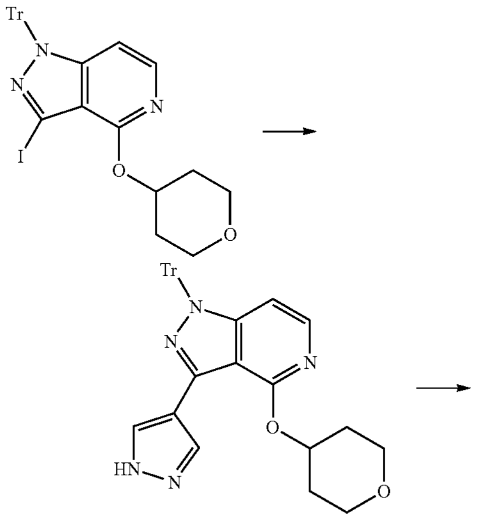

-continued

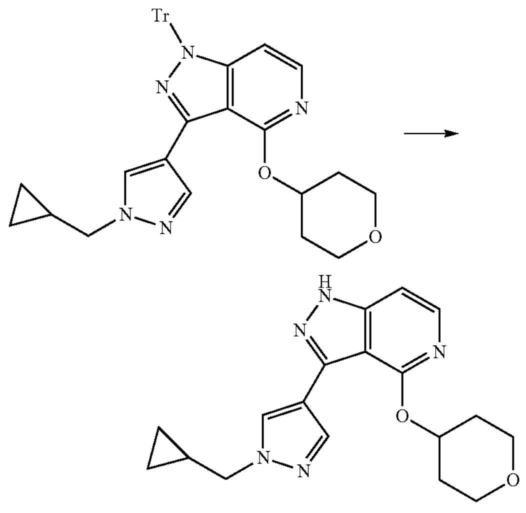

Prepared by a procedure analogous to Example 86 using 3-iodo-4-(tetrahydro-2H-pyran-4-yloxy)-1-trityl-1H-pyrazolo[4,3-c]pyridine as starting material and by reacting 3-(1H-pyrazol-4-yl)-4-(tetrahydro-2H-pyran-4-yloxy)-1-trityl-1H-pyrazolo[4,3-c]pyridine with (bromomethyl)cyclopropane to give the title compound (45.5 mg, 71% over two steps). LC-MS (Method G): m/z=340.1 $[M+H]^+$; 3.63 min. $^1$H-NMR (400 MHz, DMSO): δ 13.27 (s, 1H), 8.28 (s, 1H), 8.01 (s, 1H), 7.83 (d, J=5.9, 1H), 7.07 (d, J=6.0, 1H), 5.53-5.43 (m, 1H), 4.06 (d, J=7.0, 2H), 3.95-3.85 (m, 2H), 3.53 (t, J=10.3, 2H), 2.20-2.10 (m, 2H), 1.86-1.72 (m, 2H), 1.35-1.24 (m, 1H), 0.62-0.53 (m, 2H), 0.45-0.38 (m, 2H).

Example 93

3-(1-((Tetrahydro-2H-pyran-4-yl)methyl)-1H-pyrazol-4-yl)-4-(tetrahydro-2H-pyran-4-yloxy)-1H-pyrazolo[4,3-c]pyridine

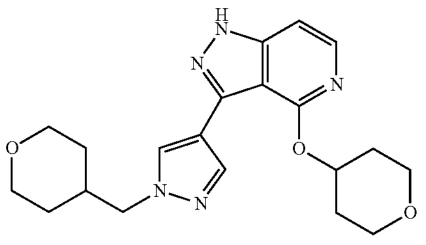 [SMILES: c1cc2[nH]nc(-c3cnn(CC4CCOCC4)c3)c2c(OC2CCOCC2)n1]

Prepared according to the general procedure described in Example 92, by reacting 4-methoxy-3-(1H-pyrazol-4-yl)-1-trityl-1H-pyrazolo[4,3-c]pyridine with tetrahydro-2H-pyran-4-yl trifluoromethanesulfonate to give the title compound (36 mg, 99%). LC-MS (Method G): m/z=384.1 $[M+H]^+$; 3.44 min. 1H-NMR (400 MHz, DMSO): δ 13.26 (s, 1H), 8.23 (s, 1H), 8.01 (s, 1H), 7.87-7.81 (m, 1H), 7.14-7.02 (m, 2H), 5.54-5.43 (m, 1H), 4.13-4.06 (m, 2H), 3.95-3.80 (m, 4H), 3.59-3.48 (m, 2H), 3.28-3.23 (m, 1H), 2.19-2.06 (m, 3H), 1.85-1.70 (m, 2H), 1.52-1.40 (m, 2H), 1.37-1.20 (m, 2H).

Example 94

3-(1-((3-Methyloxetan-3-yl)methyl)-1H-pyrazol-4-yl)-4-(tetrahydro-2H-pyran-4-yloxy)-1H-pyrazolo[4,3-c]pyridine

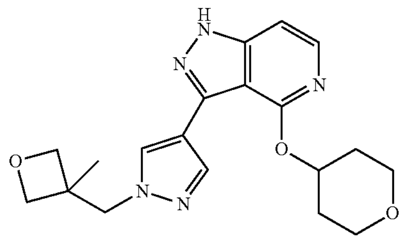 [SMILES: CC1(Cn2cc(-c3n[nH]c4ccnc(OC5CCOCC5)c34)cn2)COC1]

Prepared according to the general procedure described in Example 92, by reacting 4-methoxy-3-(1H-pyrazol-4-yl)-1-trityl-1H-pyrazolo[4,3-c]pyridine with 3-(bromomethyl)-3-methyloxetane to give the title compound (40.7 mg, 58% over two steps). LC-MS (Method B): m/z=370.1 $[M+H]^+$; 2.85 min. $^1$H-NMR (400 MHz, DMSO): δ 13.27 (s, 1H), 8.28 (s, 1H), 8.01 (s, 1H), 7.83 (d, J=5.9 Hz, 1H), 7.07 (d, J=6.0 Hz, 1H), 5.53-5.43 (m, 1H), 4.06 (d, J=7.0 Hz, 2H), 3.95-3.85 (m, 2H), 3.53 (t, J=10.3 Hz, 2H), 2.20-2.10 (m, 2H), 1.86-1.72 (m, 2H), 1.35-1.24 (m, 1H), 0.62-0.53 (m, 2H), 0.45-0.38 (m, 2H).

Example 95

3-(1-((2,2-Difluorocyclopropyl)methyl)-1H-pyrazol-4-yl)-4-(tetrahydro-2H-pyran-4-yloxy)-1H-pyrazolo[4,3-c]pyridine

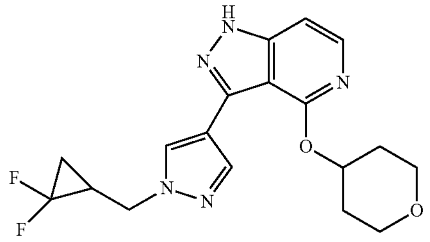 [SMILES: FC1(F)CC1Cn1cc(-c2n[nH]c3ccnc(OC4CCOCC4)c23)cn1]

Prepared according to the general procedure described in Example 92, by reacting 4-methoxy-3-(1H-pyrazol-4-yl)-1-trityl-1H-pyrazolo[4,3-c]pyridine with 1-bromomethyl-2,2-difluorocyclopropane to give the title compound (59.7 mg, 84% over two steps). LC-MS (Method G): m/z=376.1 $[M+H]^+$; 3.72 min. $^1$H-NMR (400 MHz, DMSO): δ 13.30 (s, 1H), 8.29 (5, 1H), 8.06 (s, 1H), 7.84 (d, J=6.0, 1H), 7.08 (d, J=6.0, 1H), 5.54-5.40 (m, 1H), 4.41-4.28 (m, 2H), 3.97-3.84 (m, 2H), 3.53 (t, J=10.3, 2H), 2.35-2.24 (m, 1H), 2.20-2.09 (m, 2H), 1.87-1.67 (m, 3H), 1.62-1.49 (m, 1H).

Example 96

4-(tetrahydro-2H-pyran-4-yloxy)-3-(1-(2,2,2-trifluoroethyl)-1H-pyrazol-4-yl)-1H-pyrazolo[4,3-c]pyridine

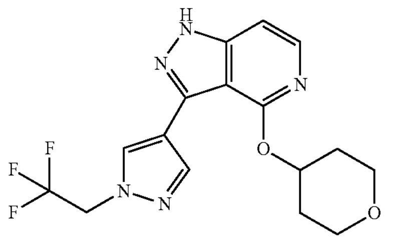 [SMILES: FC(F)(F)Cn1cc(-c2n[nH]c3ccnc(OC4CCOCC4)c23)cn1]

Prepared according to the general procedure described in Example 92, by reacting 4-methoxy-3-(1H-pyrazol-4-yl)-1-trityl-1H-pyrazolo[4,3-c]pyridine with trifluoroethanol triflate to give the title compound (49.5 mg, 71% over two steps). LC-MS (Method G): m/z=368.1 $[M+H]^+$, 3.69 min. $^1$H-NMR (400 MHz, DMSO): δ 13.37 (s, 1H), 8.39 (s, 1H), 8.13 (s, 1H), 7.85 (d, J=5.8, 1H), 7.09 (d, J=6.0, 1H), 5.57-5.40 (m, 1H), 5.27 (q, J=9.1, 2H), 3.98-3.85 (m, 2H), 3.52 (t, J=10.6, 2H), 2.22-2.03 (m, 2H), 1.91-1.73 (m, 2H).

Example 97

3-(1-(Tetrahydro-2H-pyran-4-yl)-1H-pyrazol-4-yl)-4-(tetrahydro-2H-pyran-4-yloxy)-1H-pyrazolo[4,3-c]pyridine

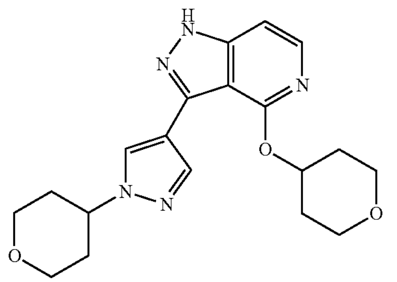 [SMILES: c1cc2[nH]nc(-c3cnn(C4CCOCC4)c3)c2c(OC2CCOCC2)n1]

Prepared according to the general procedure described in example 92, by reacting 4-methoxy-3-(1H-pyrazol-4-yl)-1-trityl-1H-pyrazolo[4,3-c]pyridine with tetrahydro-2H-pyran-4-yl methanesulfonate to give the title compound (26.5 mg, 41% over two steps). LC-MS (Method G): m/z=300.1 $[M+H]^+$; 3.09 min. $^1$H-NMR (400 MHz, DMSO): δ 13.26 (s, 1H), 8.31 (s, 1H), 8.03 (s, 1H), 7.85 (d, J=5.3, 1H), 7.08 (d, J=5.6, 1H), 4.51 (s, 1H), 4.06 (s, 3H), 4.04-3.93 (m, 2H), 3.58-3.44 (m, 2H), 2.13-1.92 (m, 4H).

Example 98

4-(Tetrahydro-2H-pyran-4-yloxy)-3-(1-(tetrahydrofuran-3-yl)-1H-pyrazol-4-yl)-1H-pyrazolo[4,3-c]pyridine

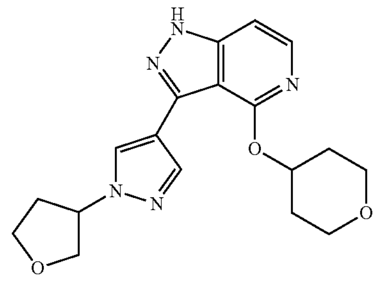 [SMILES: c1cc2[nH]nc(-c3cnn(C4CCOC4)c3)c2c(OC2CCOCC2)n1]

Prepared according to the general procedure described in Example 92, by reacting 4-methoxy-3-(1H-pyrazol-4-yl)-1-trityl-1H-pyrazolo[4,3-c]pyridine with tetrahydrofuran-3-yl methanesulfonate to give the title compound as a mixture of enantiomers. The enantiomers were separated via supercritical fluid chromatography to give the separated enantiomers. (7.9 mg, 7.7 mg, total yield 24% over two steps). LC-MS (Method G): m/z=286.1 $[M+H]^+$; 2.97 min. $^1$H-NMR (400 MHz, DMSO): δ 13.27 (s, 1H), 8.32 (s, 1H), 8.04 (s, 1H), 7.85 (d, J=6.0, 1H), 7.09 (d, J=6.0 1H), 5.17-5.09 (m, 1H), 4.06 (s, 3H), 4.05-3.98 (m, 2H), 3.95 (dd, J=9.4, J=3.7, 1H), 3.91-3.83 (m, 1H), 2.47-2.36 (m, 1H), 2.36-2.25 (m, 1H).

Example 99

3-(1H-Pyrazol-5-yl)-4-(tetrahydro-2H-pyran-4-yloxy)-1H-pyrazolo[4,3-c]pyridine

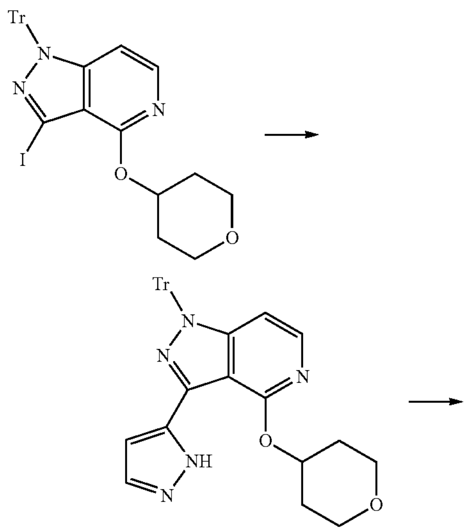

-continued

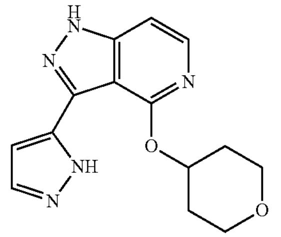

Step 1—3-(1H-Pyrazol-5-yl)-4-(tetrahydro-2H-pyran-4-yloxy)-1-trityl-1H-pyrazolo[4,3-c]pyridine To a microwave vial was charged 3-iodo-4-(tetrahydro-2H-pyran-4-yloxy)-1-trityl-1H-pyrazolo[4,3-c]pyridine (0.100 g, 0.170 mmol), 1H-pyrazol-5-ylboronic acid (0.0310 g, 0.238 mmol), potassium acetate (0.0234 g, 0.238 mmol), sodium carbonate (0.0252 g, 0.238 mmol) and bis(di-tert-butyl(4-dimethylaminophenyl)phosphine)dichloropalladium(II) (0.0120 g, 0.017 mmol). Acetonitrile (1.3 mL, 25 mmol) and degassed water (0.4 mL, 20 mmol) were then added and the reaction mixture was degassed with nitrogen for 10 minutes and then heated to 150° C. under microwave irradiation for 90 minutes. Upon reaction completion, the reaction mixture was filtered through Celite®, washing with EtOAc and concentrated in vacuo dryness to give the title compound.

Step 2—3-(1H-Pyrazol-5-yl)-4-(tetrahydro-2H-pyran-4-yloxy)-1H-pyrazolo[4,3-c]pyridine To crude 3-(1H-pyrazol-5-yl)-4-(tetrahydro-2H-pyran-4-yloxy)-1-trityl-1H-pyrazolo[4,3-c]pyridine (0.0898 g, 0.170 mmol) dissolved in methylene chloride (2 mL, 40 mmol) and triethylsilane (0.109 mL, 0.681 mmol) was added trifluoroacetic acid (2 mL, 30 mmol). The reaction mixture was stirred at room temperature for 30 minutes. Upon reaction completion, the reaction mixture was concentrated in vacuo. The crude residue was purified by reverse-phase HPLC to give the title compound (5.9 mg, 12% over two steps). LC-MS (Method G): m/z=286.0 $[M+H]^+$, 2.99 min. $^1$H-NMR (400 MHz, DMSO): δ 13.62 (s, 1H), 13.19 (s, 1H), 7.88 (s, 1H), 7.59 (s, 1H), 7.12 (s, 1H), 6.96 (s, 1H), 5.56-5.43 (m, 1H), 3.97-3.79 (m, 2H), 3.64-3.45 (m, 2H), 2.20-1.95 (m, 2H), 1.88-1.61 (m, 2H).

Example 100

3-(2,6-Dimethylpyridin-4-yl)-4-(tetrahydro-2H-pyran-4-yloxy)-1H-pyrazolo[4,3-c]pyridine

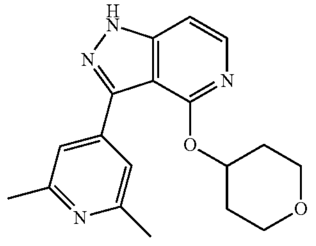 [SMILES: Cc1cc(-c2n[nH]c3ccnc(OC4CCOCC4)c23)cc(C)n1]

Prepared according to the general procedure described in Example 99, by reacting 3-iodo-4-(tetrahydro-2H-pyran-4-yloxy)-1-trityl-1H-indazole with 2,6-dimethylpyridin-4-ylboronic acid to give the title compound (43.3 mg, 79% over two steps). LC-MS (Method G): m/z=325.1 $[M+H]^+$; 3.13 min. $^1$H-NMR (400 MHz, DMSO): δ 14.11 (s, 1H), 8.06 (br s, 2H), 8.01-7.92 (m, 1H), 7.30-7.19 (m, 1H), 5.58-5.44 (m, 1H), 3.89-3.77 (m, 2H), 3.62-3.50 (m, 2H), 2.66 (s, 6H), 2.21-2.07 (m, 2H), 1.83-1.68 (m, 2H).

Example 101

3-(2-Methoxypyridin-4-yl)-4-(tetrahydro-2H-pyran-4-yloxy)-1H-pyrazolo[4,3-c]pyridine

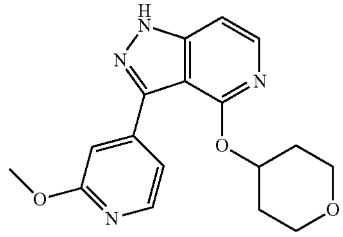 [SMILES: COc1cc(-c2n[nH]c3ccnc(OC4CCOCC4)c23)ccn1]

Prepared according to the general procedure described in Example 99, by reacting 3-iodo-4-(tetrahydro-2H-pyran-4-yloxy)-1-trityl-1H-indazole with 2-methoxypyridin-4-ylboronic acid to give the title compound (33.6 mg, 61% over two steps). LC-MS (Method G): m/z=327.1 $[M+H]^+$; 3.63 min. $^1$H-NMR (400 MHz, DMSO): δ 13.77 (br s, 1H), 8.25 (d, J=5.3, 1H), 7.92 (d, J=5.9, 1H), 7.59 (d, J=5.3, 1H), 7.49 (s, 1H), 7.18 (d, J=6.0, 1H), 5.58-5.46 (m, 1H), 3.92 (s, 3H), 3.86-3.74 (m, 2H), 3.61-3.48 (m, 2H), 2.12-2.01 (m, J=7.0, 2H), 1.80-1.65 (m, 2H).

Example 102

4-(4-(4-(Tetrahydro-2H-pyran-4-yloxy)-1H-pyrazolo[4,3-c]pyridin-3-yl)pyridin-2-yl)morpholine

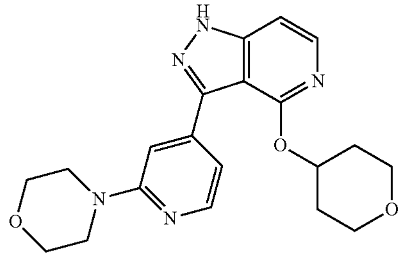

Prepared according to the general procedure described in Example 99, by reacting 3-iodo-4-(tetrahydro-2H-pyran-4-yloxy)-1-trityl-1H-indazole with 3-morpholinophenylboronic acid to give the title compound (98.4 mg, 63% over two steps). LC-MS (Method G): m/z=382.1 $[M+H]^+$; 3.15 min. $^1$H-NMR (400 MHz, DMSO): δ 13.69 (s, 1H), 8.22 (d, J=4.4, 1H), 7.91 (d, J=5.5, 1H), 7.30 (s, 1H), 7.26 (d, J=4.3, 1H), 7.16 (d, J=5.5, 1H), 5.54-5.44 (m, 1H), 3.81-3.69 (m, 6H), 3.56-3.46 (m, 6H), 2.10-1.99 (m, 2H), 1.74-1.60 (m, 2H).

Example 103

4-(3-Fluoro-4-(4-(tetrahydro-2H-pyran-4-yloxy)-1H-pyrazolo[4,3-c]pyridin-3-yl)pyridin-2-yl)morpholine

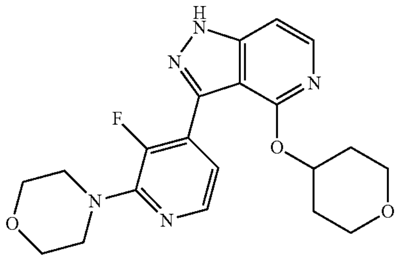 [SMILES: Fc1c(-c2n[nH]c3ccnc(OC4CCOCC4)c23)ccnc1N1CCOCC1]

Prepared according to the general procedure described in Example 99, by reacting 3-iodo-4-(tetrahydro-2H-pyran-4-yloxy)-1-trityl-1H-indazole with 4-(3-fluoro-4-(4,4,5,5-tetramethyl-1,3,2-dioxaborolan-2-yl)pyridin-2-yl)morpholine to give the title compound (43.6 mg, 64% over two steps). LC-MS (Method G): m/z=400.1 $[M+H]^+$; 3.66 min. $^1$H-NMR (400 MHz, DMSO): δ 13.74 (s, 1H), 8.10 (d, J=4.9, 1H), 7.89 (d, J=6.0, 1H), 7.16 (d, J=6.0, 1H), 7.11-7.06 (m, 1H), 5.45-5.36 (m, 1H), 3.79-3.70 (m, 4H), 3.61-3.52 (m, 2H), 3.51-3.40 (m, 6H), 1.99-1.88 (m, 2H), 1.61-1.48 (m, 2H).

Example 104

4-Methoxy-3-(pyridin-4-yl)-1H-pyrazolo[4,3-c]pyridine

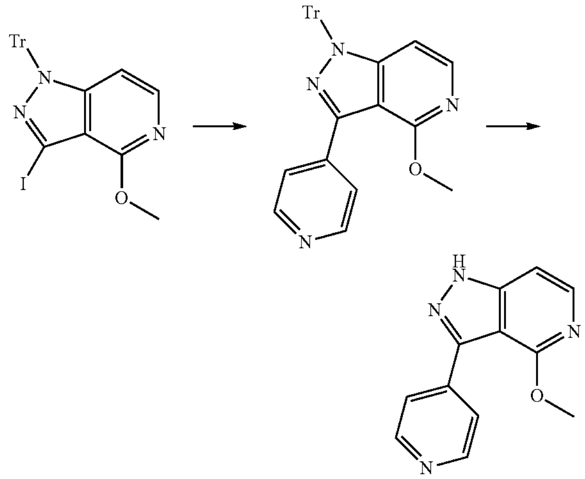

Step 1—4-Methoxy-3-(pyridin-4-yl)-1-trityl-1H-pyrazolo[4,3-c]pyridine

To a microwave vial was charged 3-iodo-4-methoxy-1-trityl-1H-pyrazolo[4,3-c]pyridine (0.100 g, 0.193 mmol), 4-pyridineboronic acid (0.0333 g, 0.271 mmol), potassium acetate (0.0266 g, 0.271 mmol), sodium carbonate (0.0287 g, 0.271 mmol) and bis(di-tert-butyl(4-dimethylaminophenyl) phosphine)dichloropalladium (0.0137 g, 0.0193 mmol). Acetonitrile (1.5 mL, 28 mmol) and degassed water (0.5 mL, 20 mmol) were then added and the reaction mixture was degassed with nitrogen for 10 minutes and then heated to 150° C. under microwave irradiation for 40 minutes. Upon reaction completion, the reaction mixture was filtered through Celite®, washing with EtOAc and concentrated in vacuo dryness to give the title compound.

Step 2—4-Methoxy-3-(pyridin-4-yl)-1H-pyrazolo[4,3-c]pyridine

To crude 4-methoxy-3-(pyridin-4-yl)-1-trityl-1H-pyrazolo[4,3-c]pyridine from Step 1 dissolved in methylene chloride (2.5 mL, 39 mmol) and triethylsilane (0.123 mL, 0.773 mmol) was added trifluoroacetic acid (5.0 mL, 65 mmol). The reaction mixture was stirred at room temperature for 60 minutes. Upon reaction completion, the reaction mixture was concentrated in vacuo. The crude residue was purified by reverse-phase HPLC to give the title compound (21.7 mg, 50% over two steps). LC-MS (Method G): m/z=227.1 $[M+H]^+$; 2.56 min. $^1$H-NMR (400 MHz, DMSO): δ 13.84 (s, 1H), 8.68 (d, J=5.7, 2H), 7.99 (d, J=5.8, 2H), 7.96 (d, J=6.0, 1H), 7.21 (d, J=6.0, 1H), 4.04 (s, 3H).

Example 105

4-(3-Fluoro-4-(4-methoxy-1H-pyrazolo[4,3-c]pyridin-3-yl)pyridin-2-yl)morpholine

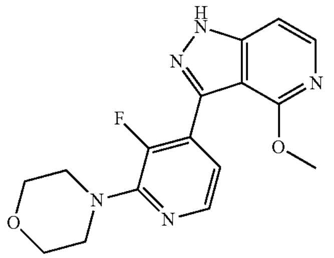 [SMILES: COc1nccc2[nH]nc(-c3ccnc(N4CCOCC4)c3F)c12]

Prepared according to the general procedure described in Example 104, by reacting 3-iodo-4-methoxy-1-trityl-1H-indazole with 4-(3-fluoro-4-(4,4,5,5-tetramethyl-1,3,2-dioxaborolan-2-yl)pyridin-2-yl)morpholine to give the title compound (16.9 mg, 27% over two steps). LC-MS (Method G): m/z=330.1 $[M+H]^+$; 3.66 min. $^1$H-NMR (400 MHz, DMSO) δ 13.78 (s, 1H), 8.09 (d, J=4.9, 1H), 7.93 (d, J=6.0, 1H), 7.19 (d, J=6.0, 1H), 7.12-7.06 (m, 1H), 3.90 (s, 3H), 3.81-3.72 (m, 4H), 3.47-3.40 (m, 4H).

Example 106

4-Methoxy-3-(2-methoxypyridin-4-yl)-1H-pyrazolo[4,3-c]pyridine

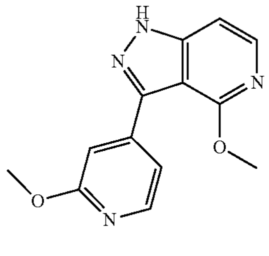

The title compound was prepared according to the general procedure described in Example 104, by reacting 3-iodo-4-methoxy-1-trityl-1H-indazole with 2-methoxypyridin-4-ylboronic acid to give the title compound (24.9 mg, 50% over two steps). LC-MS (Method G): m/z=257.0 $[M+H]^+$; 3.32 min. $^1$H-NMR (400 MHz, DMSO): δ 13.82 (s, 1H), 8.29-8.21 (m, 1H), 7.95 (d, J=5.9, 1H), 7.63-7.56 (m, 1H), 7.46 (s, 1H), 7.20 (d, J=5.9, 1H), 4.03 (s, 3H), 3.92 (s, 3H)

Example 107

4-(4-(4-Methoxy-1H-pyrazolo[4,3-c]pyridin-3-yl)pyridin-2-yl)morpholine

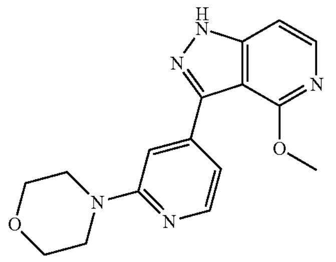 [SMILES: COc1nccc2[nH]nc(-c3ccnc(N4CCOCC4)c3)c12]

Prepared according to the general procedure described in Example 104, by reacting 3-iodo-4-methoxy-1-trityl-1H-indazole with 3-morpholinophenylboronic acid to give the title compound (36.8 mg, 61% over two steps). LC-MS (Method G): m/z=312.0 $[M+H]^+$; 2.99 min. $^1$H-NMR (400 MHz, DMSO): δ 13.73 (s, 1H), 8.21 (d, J=4.4, 1H), 7.94 (d, J=5.7, 1H), 7.50 (s, 1H), 7.27 (d, J=4.3, 1H), 7.19 (d, J=5.8, 1H), 4.02 (s, 3H), 3.79-3.72 (m, 4H), 3.57-3.47 (m, 4H).

Example 108

4-Methoxy-3-(2-(trifluoromethyl)pyridin-4-yl)-1H-pyrazolo[4,3-c]pyridine

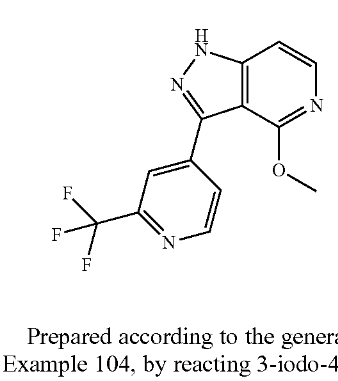

Prepared according to the general procedure described in Example 104, by reacting 3-iodo-4-methoxy-1-trityl-1H-indazole with 4-(4,4,5,5-tetramethyl-1,3,2-dioxaborolan-2-yl)-2-(trifluoromethyl)pyridine to give the title compound (24.3 mg, 43% over two steps). LC-MS (Method G): m/z=295.0 $[M+H]^+$; 4.20 min. $^1$H-NMR (400 MHz, DMSO): δ 14.00 (s, 1H), 8.87 (d, J=5.1, 1H), 8.54 (s, 1H), 8.35 (d, J=5.0, 1H), 7.98 (d, J=6.0, 1H), 7.25 (d, J=6.0, 1H), 4.06 (s, 3H).

Example 109

(2-Chloro-4-(4-methoxy-1H-pyrazolo[4,3-c]pyridin-3-yl)phenyl)(morpholino)methanone

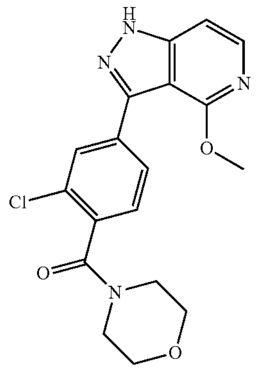 [SMILES: COc1nccc2[nH]nc(-c3ccc(C(=O)N4CCOCC4)c(Cl)c3)c12]

Prepared according to the general procedure described in Example 99, by reacting 3-iodo-4-methoxy-1-trityl-1H-indazole with 3-chloro-4-(morpholine-4-carbonyl)phenylboronic acid to give the title compound (50.3 mg, 70% over two steps). LC-MS (Method G): m/z=373.1 $[M+H]^+$; 3.54 min. $^1$H-NMR (400 MHz, DMSO): δ 13.73 (s, 1H), 8.13 (s, J=1.4, 1H), 8.04 (dd, J=8.0, 1.4, 1H), 7.94 (d, J=6.0, 1H), 7.50 (d, J=8.0, 1H), 7.19 (d, J=6.0, 1H), 4.02 (s, 3H), 3.68 (s, 5H), 3.61-3.54 (m, 3H), 3.26-3.20 (m, 3H).

Example 110

3-(2-(Pyrrolidin-1-yl)pyridin-4-yl)-4-(tetrahydro-2H-pyran-4-yloxy)-1H-pyrazolo[4,3-c]pyridine

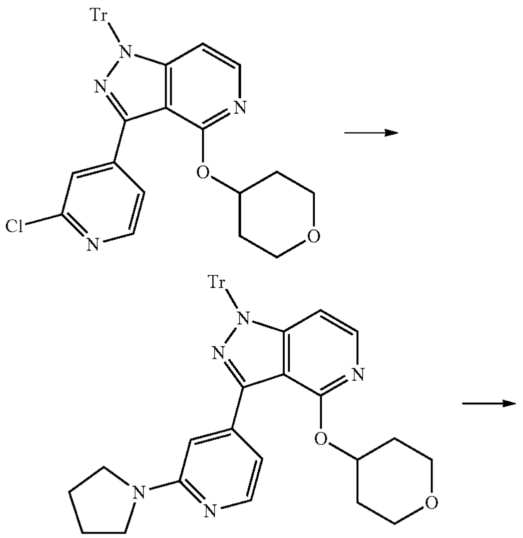

-continued

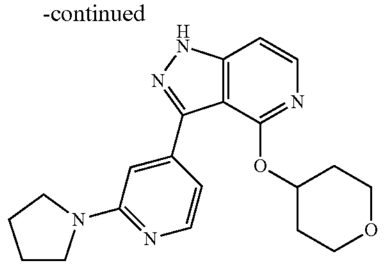

Step 1—3-(2-(Pyrrolidin-1-yl)pyridin-4-yl)-4-(tetrahydro-2H-pyran-4-yloxy)-1-trityl-1H-pyrazolo[4,3-c]pyridine To a microwave vial was added 3-(2-chloropyridin-4-yl)-4-(tetrahydro-2H-pyran-4-yloxy)-1-trityl-1H-pyrazolo[4,3-c]pyridine (0.050 g, 0.087 mmol) and pyrrolidine (0.20 mL, 2.00 mmol). The vial was capped and heated to 130° C. for 2 hours. Upon reaction completion, the reaction mixture was diluted with methylene chloride and washed with sat. aq. $NaHCO_3$, water, then brine. The combined organics were dried over sodium sulfate, filtered and concentrated in vacuo to give the title compound.

Step 2—3-(2-(Pyrrolidin-1-yl)pyridin-4-yl)-4-(tetrahydro-2H-pyran-4-yloxy)-1H-pyrazolo[4,3-c]pyridine To crude 3-(2-(pyrrolidin-1-yl)pyridin-4-yl)-4-(tetrahydro-2H-pyran-4-yloxy)-1-trityl-1H-pyrazolo[4,3-c]pyridine (0.053 g, 0.87 mmol) dissolved in methylene chloride (1 mL, 20 mmol) and triethylsilane (0.056 mL, 0.349 mmol) was added trifluoroacetic acid (2.6 mL, 33 mmol) at room temperature. The reaction mixture was stirred for 2 hours and concentrated in vacuo. The crude residue was purified by reverse-phase HPLC to give the title compound (16.7 mg, 53% over two steps). LC-MS (Method G): m/z=366.1 $[M+H]^+$, 3.36 min. $^1H$-NMR (400 MHz, DMSO): δ 13.66 (br s, 1H), 8.19-8.11 (m, 1H), 7.90 (d, J=4.9, 1H), 7.16 (d, J=5.0, 1H), 7.14-7.10 (m, 1H), 6.91 (s, 1H), 5.50 (s, 1H), 3.86-3.70 (m, 2H), 3.58-3.42 (m, 6H), 2.11-2.01 (m, 2H), 2.01-1.90 (m, 4H), 1.76-1.59 (m, J=8.3, 2H).

Example 111

3-(2-(3-Methylpiperidin-1-yl)pyridin-4-yl)-4-(tetrahydro-2H-pyran-4-yloxy)-1H-pyrazolo[4,3-c]pyridine

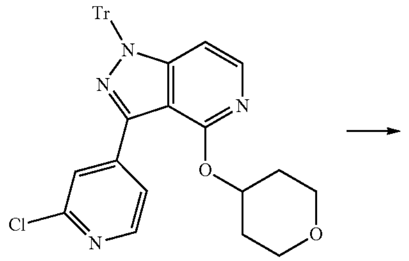

-continued

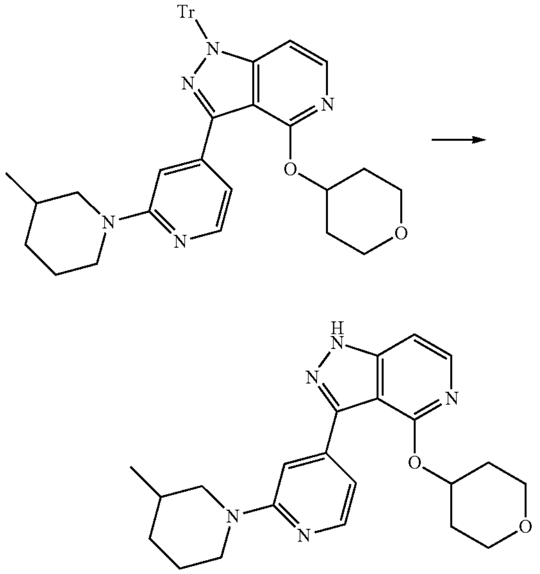

Step 1—3-(2-(3-Methylpiperidin-1-yl)pyridin-4-yl)-4-(tetrahydro-2H-pyran-4-yloxy)-1-trityl-1H-pyrazolo[4,3-c]pyridine To a microwave vial was added 3-(2-chloropyridin-4-yl)-4-(tetrahydro-2H-pyran-4-yloxy)-1-trityl-1H-pyrazolo[4,3-c]pyridine (0.050 g, 0.087 mmol) and 3-methylpiperidine (0.3 mL, 2.00 mmol). The vial was capped and heated to 130° C. for 4 hours. The reaction mixture was diluted with methylene chloride and washed with sat. aq. $NaHCO_3$, water, then brine. The combined organics were dried over sodium sulfate, filtered and concentrated in vacuo to give the title compound.

Step 2—3-(2-(3-Methylpiperidin-1-yl)pyridin-4-yl)-4-(tetrahydro-2H-pyran-4-yloxy)-1H-pyrazolo[4,3-c]pyridine To crude 3-(2-(3-methylpiperidin-1-yl)pyridin-4-yl)-4-(tetrahydro-2H-pyran-4-yloxy)-1-trityl-1H-pyrazolo[4,3-c]pyridine (0.055 g, 0.87 mmol) dissolved in methylene chloride (1 mL, 20 mmol) and triethylsilane (0.056 mL, 0.349 mmol) was added trifluoroacetic acid (2.6 mL, 33 mmol) at room temperature. The reaction mixture was stirred overnight and concentrated in vacuo. The crude residue was purified by reverse-phase HPLC to give the title compound (12.6 mg, 37% over two steps). LC-MS (Method G): m/z=394.2 $[M+H]^+$, 3.70 min. $^1H$-NMR (400 MHz, DMSO): δ 13.66 (br s, 1H), 8.20-8.13 (m, 1H), 7.94-7.87 (m, 1H), 7.30 (s, 1H), 7.19-7.12 (m, 2H), 5.56-5.45 (m, 1H), 4.26 (t, J=13.7, 2H), 3.83-3.73 (m, 2H), 3.56-3.45 (m, 2H), 2.79 (t, J=12.5, 1H), 2.10-2.00 (m, 2H), 1.86-1.75 (m, 1H), 1.75-1.56 (m, 4H), 1.56-1.40 (m, 1H), 1.20-1.06 (m, 1H), 0.97-0.88 (m, 3H).

Example 112

(1S,4S)-5-(4-(4-(Tetrahydro-2H-pyran-4-yloxy)-1H-pyrazolo[4,3-c]pyridin-3-yl)pyridin-2-yl)-2-oxa-5-azabicyclo[2.2.1]heptane

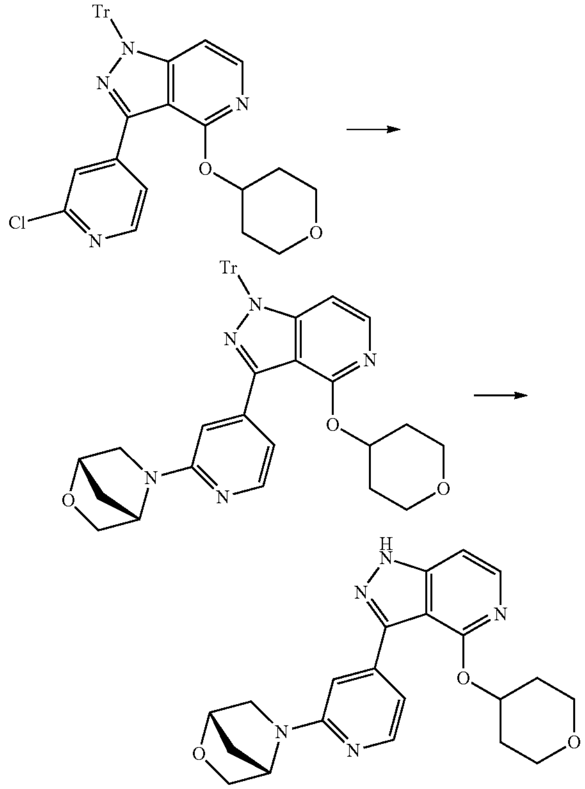

Step 1—(1S,4S)-5-(4-(4-(Tetrahydro-2H-pyran-4-yloxy)-1-trityl-1H-pyrazolo[4,3-c]pyridin-3-yl)pyridin-2-yl)-2-oxa-5-azabicyclo[2.2.1]heptane To a microwave vial was added 3-(2-chloropyridin-4-yl)-4-(tetrahydro-2H-pyran-4-yloxy)-1-trityl-1H-pyrazolo[4,3-c]pyridine (0.0823 g, 0.144 mmol), (1S,4S)-2-oxa-5-azoniabicyclo[2.2.1]heptane chloride (0.0234 g, 0.172 mmol), RuPhos palladium phenethylamine chloride (0.0073 g, 0.010 mmol), RuPhos (0.0047 g, 0.010 mmol) and sodium tert-butoxide (0.0331 g, 0.344 mmol). 1,4-dioxane (1.6 mL, 20 mmol) was added and the reaction mixture was degassed for 5 minutes. The vial was capped and heated to 130° C. for 30 minutes under microwave irradiation. Upon reaction completion, the reaction mixture was diluted with methylene chloride and filtered through celite, eluting with methylene chloride and concentrated in vacuo to give the title compound.

Step 2—(1S,4S)-5-(4-(4-(Tetrahydro-2H-pyran-4-yloxy)-1H-pyrazolo[4,3-c]pyridin-3-yl)pyridin-2-yl)-2-oxa-5-azabicyclo[2.2.1]heptane Crude (1S,4S)-5-(4-(4-(tetrahydro-2H-pyran-4-yloxy)-1-trityl-1H-pyrazolo[4,3-c]pyridin-3-yl)pyridin-2-yl)-2-oxa-5-azabicyclo[2.2.1]heptane was dissolved in methylene chloride (2 mL, 30 mmol) and triethylsilane (0.092 mL, 0.574 mmol) was added trifluoroacetic acid (4 mL, 50 mmol) at 0° C. The reaction mixture was stirred for 1 hour and concentrated in vacuo. The crude residue was purified by reverse-phase HPLC to give the title compound (28.6 mg, 51% over two steps). LC-MS (Method G): m/z=394.1 $[M+H]^+$; 3.11 min. $^1$H-NMR (400 MHz, DMSO): δ 13.67 (s, 1H), 8.19-8.13 (m, 1H), 7.94-7.87 (m, 1H), 7.20-7.13 (m, 2H), 7.00-6.95 (m, 1H), 5.56-5.45 (m, J=3.6, 1H), 4.92 (s, 1H), 4.68 (s, 1H), 3.85-3.67 (m, 4H), 3.57-3.45 (m, 4H), 2.11-1.99 (m, 2H), 1.97-1.83 (m, 2H), 1.74-1.60 (m, 2H).

Example 113

N-(Oxetan-3-yl)-4-(4-(tetrahydro-2H-pyran-4-yloxy)-1H-pyrazolo[4,3-c]pyridin-3-yl)pyridin-2-amine

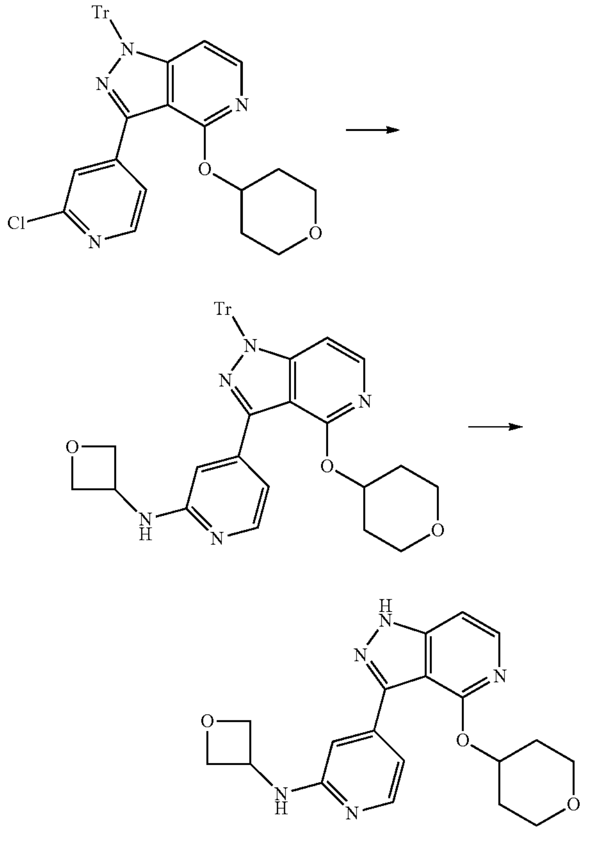

Prepared according to the procedure described in Example 111, by reacting 3-(2-chloropyridin-4-yl)-4-(tetrahydro-2H-pyran-4-yloxy)-1-trityl-1H-pyrazolo[4,3-c]pyridine with 3-aminooxetane hydrochloride for 70 minutes in Step 1 to give the title compound (13.3 mg, 19% over two steps). LC-MS (Method G): m/z=368.1 $[M+H]^+$; 2.93 min. $^1$H-NMR (400 MHz, DMSO): δ 13.68 (s, 1H), 8.24 (d, J=7.1, 1H), 7.96-7.91 (m, 1H), 7.63 (s, 1H), 7.54 (d, J=7.1, 1H), 7.24 (d, J=5.4, 1H), 5.55-5.40 (m, 2H), 3.91-3.81 (m, 2H), 3.68-3.46 (m, 5H), 2.18-1.99 (m, 2H), 1.91-1.78 (m, 2H).

Example 114

3-(2-(Azetidin-1-yl)pyridin-4-yl)-4-(tetrahydro-2H-pyran-4-yloxy)-1H-pyrazolo[4,3-c]pyridine

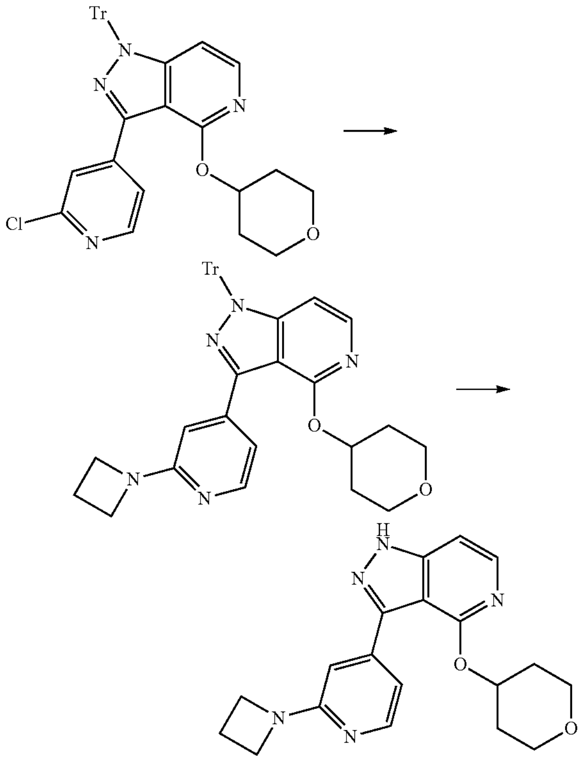

Prepared according to the procedure described in Example 111, by reacting 3-(2-chloropyridin-4-yl)-4-(tetrahydro-2H-pyran-4-yloxy)-1-trityl-1H-pyrazolo[4,3-c]pyridine with azetidine hydrochloride to give the title compound (11.3 mg, 22% over two steps). LC-MS (Method G): m/z=352.1 $[M+H]^+$; 3.24 min. $^1$H-NMR (400 MHz, DMSO): δ 13.72 (s, 1H), 8.17-8.11 (m, 1H), 7.91 (d, J=5.6, 1H), 7.29-7.22 (m, 1H), 7.17 (d, J=5.6, 1H), 6.93 (s, 1H), 5.56-5.46 (m, 1H), 4.09-3.95 (m, 4H), 3.85-3.75 (m, 2H), 3.58-3.48 (m, 2H), 2.41-2.31 (m, 2H), 2.11-2.01 (m, 2H), 1.77-1.63 (m, 2H).

Example 115

8-(4-(4-(Tetrahydro-2H-pyran-4-yloxy)-1H-pyrazolo[4,3-c]pyridin-3-yl)pyridin-2-yl)-3-oxa-8-azabicyclo[3.2.1]octane

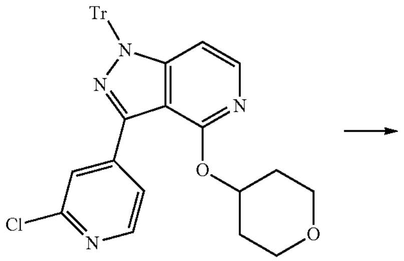

-continued

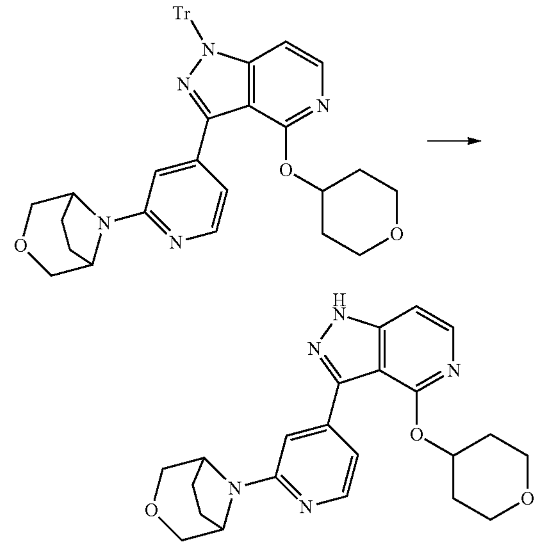

Prepared according to the procedure described in Example 111, by reacting 3-(2-chloropyridin-4-yl)-4-(tetrahydro-2H-pyran-4-yloxy)-1-trityl-1H-pyrazolo[4,3-c]pyridine with 3-oxa-8-azabicyclo[3.2.1]octane hydrochloride for 100 minutes in Step 1 to give the title compound (14.2 mg, 24% over two steps). LC-MS (Method G): m/z=408.1 $[M+H]^+$; 3.32 min. $^1$H-NMR (400 MHz, DMSO): δ 13.40 (s, 1H), 8.19 (d, J=4.3, 1H), 7.90 (d, J=5.7, 1H), 7.28 (s, 1H), 7.24-7.13 (m, 2H), 5.54-5.45 (m, 1H), 4.51 (s, 2H), 3.86-3.73 (m, 2H), 3.70 (d, J=10.6, 2H), 3.59-3.46 (m, 4H), 2.13-2.01 (m, 2H), 2.01-1.93 (m, J=6.9, 2H), 1.93-1.84 (m, 2H), 1.76-1.60 (m, 2H).

Example 116

3-(2-(1-Methyl-1H-pyrazol-4-yl)pyridin-4-yl)-4-(tetrahydro-2H-pyran-4-yloxy)-1H-pyrazolo[4,3-c]pyridine

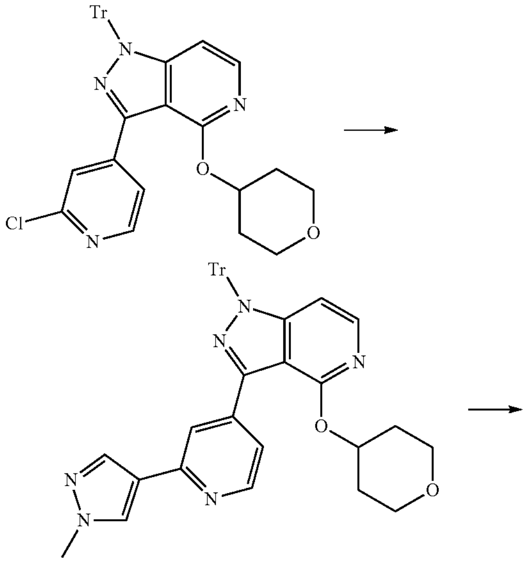

-continued

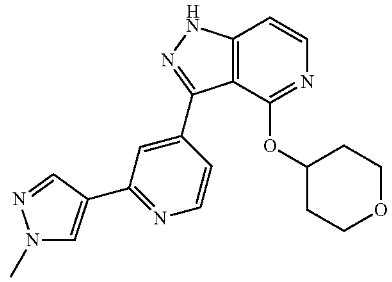

Step 1—3-(2-(1-Methyl-1H-pyrazol-4-yl)pyridin-4-yl)-4-(tetrahydro-2H-pyran-4-yloxy)-1-trityl-1H-pyrazolo[4,3-c]pyridine 3-(2-chloropyridin-4-yl)-4-(tetrahydro-2H-pyran-4-yloxy)-1-trityl-1H-pyrazolo[4,3-c]pyridine (0.100 g, 0.174 mmol), 1-methyl-4-(4,4,5,5-tetramethyl-1,3,2-dioxaborolan-2-yl)-1H-pyrazole (0.0508 g, 0.244 mmol), potassium acetate (0.0240 g, 0.244 mmol), sodium carbonate (0.0259 g, 0.244 mmol) and bis(di-tert-butyl(4-dimethylaminophenyl)phosphine)dichloropalladium(II) (0.0124 g, 0.0174 mmol) were weighed into a microwave vial equipped with a stir bar. Acetonitrile (1.3 mL, 25 mmol) and degassed Water (0.4 mL, 20 mmol) were then added and the reaction mixture was degassed with nitrogen for 10 mins and then heated to 150° C. under microwave irradiation for 90 min. Upon reaction completion, the reaction mixture was diluted with dichloromethane, filtered through Celite®, eluting with dichloromethane and concentrated in vacuo to give the title compound.

Step 2—3-(2-(1-Methyl-1H-pyrazol-4-yl)pyridin-4-yl)-4-(tetrahydro-2H-pyran-4-yloxy)-1H-pyrazolo[4,3-c]pyridine To crude 3-(2-(1-methyl-1H-pyrazol-4-yl)pyridin-4-yl)-4-(tetrahydro-2H-pyran-4-yloxy)-1-trityl-1 H-pyrazolo[4,3-c]pyridine (0.108 g, 0.174 mmol) dissolved in methylene chloride (2.5 mL, 39 mmol) and triethylsilane (0.111 mL, 0.698 mmol) was added trifluoroacetic acid (5.0 mL, 65 mmol) at room temperature. The reaction mixture was stirred for 1 hour and concentrated in vacuo. The crude residue was purified by reverse-phase HPLC to give the title compound (41.5 mg, 63% over two steps). LC-MS (Method G): m/z=377.1 $(M+H)^+$; 3.25 min. $^1H$-NMR (400 MHz, DMSO): δ 13.80 (s, 1H), 8.60 (d, J=4.5, 1H), 8.33 (s, 1H), 8.11 (s, 1H), 8.03 (s, 1H), 7.93 (d, J=5.7, 1H), 7.72 (d, J=4.5, 1H), 7.19 (d, J=5.8, 1H), 5.55-5.42 (m, 1H), 3.90 (s, 3H), 3.77-3.66 (m, 2H), 3.52-3.41 (m, 3H), 2.10-2.00 (m, J=12.7, 2H), 1.73-1.61 (m, 2H).

Example 117

8-(4-(4-Methoxy-1H-pyrazolo[4,3-c]pyridin-3-yl)pyridin-2-yl)-3-oxa-8-azabicyclo[3.2.1]octane

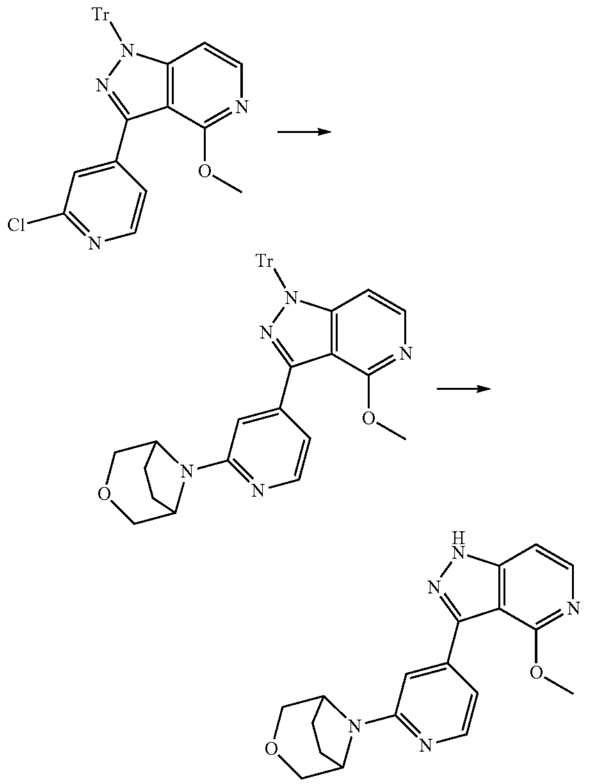

Step 1—8-(4-(4-Methoxy-1-trityl-1H-pyrazolo[4,3-c]pyridin-3-yl)pyridin-2-yl)-3-oxa-8-azabicyclo[3.2.1]octane 3-(2-chloropyridin-4-yl)-4-methoxy-1-trityl-1H-pyrazolo[4,3-c]pyridine (0.100 g, 0.199 mmol), 3-oxa-8-azabicyclo[3.2.1]octane hydrochloride (0.0537 g, 0.238 mmol), RuPhos Palladium phenethylamine chloride (0.0145 g, 0.0199 mmol), RuPhos (0.00928 g, 0.0199 mmol) and sodium tert-butoxide (0.0458 g, 0.477 mmol) were weighed into a microwave vial. 1,4-Dioxane (2.0 mL, 26 mmol) added via syringe and nitrogen was bubbled through the reaction mixture for 5 minutes. The vial was capped and heated to 150° C. for 80 min under microwave irradiation. Upon reaction completion, the reaction mixture was diluted with EtOAc and filtered through Celite®, eluting with EtOAc and concentrated in vacuo to give the title compound.

Step 2—8-(4-(4-Methoxy-1H-pyrazolo[4,3-c]pyridin-3-yl)pyridin-2-yl)-3-oxa-8-azabicyclo[3.2.1]octane To crude 8-(4-(4-methoxy-1-trityl-1H-pyrazolo[4,3-c]pyridin-3-yl)pyridin-2-yl)-3-oxa-8-azabicyclo[3.2.1]octane (0.199 mmol) dissolved in methylene chloride (2.8 mL, 44 mmol) and triethylsilane (0.127 mL, 0.795 mmol) was added trifluoroacetic acid (5.5 mL, 72 mmol) at room temperature. The reaction mixture was stirred for 2 hours and concentrated in vacuo. The crude residue was purified by reverse-phase HPLC to give the title compound (14.3 mg, 21% over two steps). LC-MS (Method G): m/z=338.1 $(M+H)^+$, 3.19 min. $^1$H-NMR (400 MHz, DMSO): δ 13.72 (s, 1H), 8.18 (d, J=4.7, 1H), 7.94 (d, J=5.8, 1H), 7.42 (s, 1H), 7.24-7.17 (m, 2H), 4.51 (s, 2H), 4.01 (s, 3H), 3.73 (d, J=10.7, 2H), 3.57 (d, J=10.6, 2H), 2.07-1.87 (m, 4H).

Example 118

(1S,4S)-5-(4-(4-Methoxy-1H-pyrazolo[4,3-c]pyridin-3-yl)pyridin-2-yl)-2-oxa-5-azabicyclo[2.2.1]heptanes

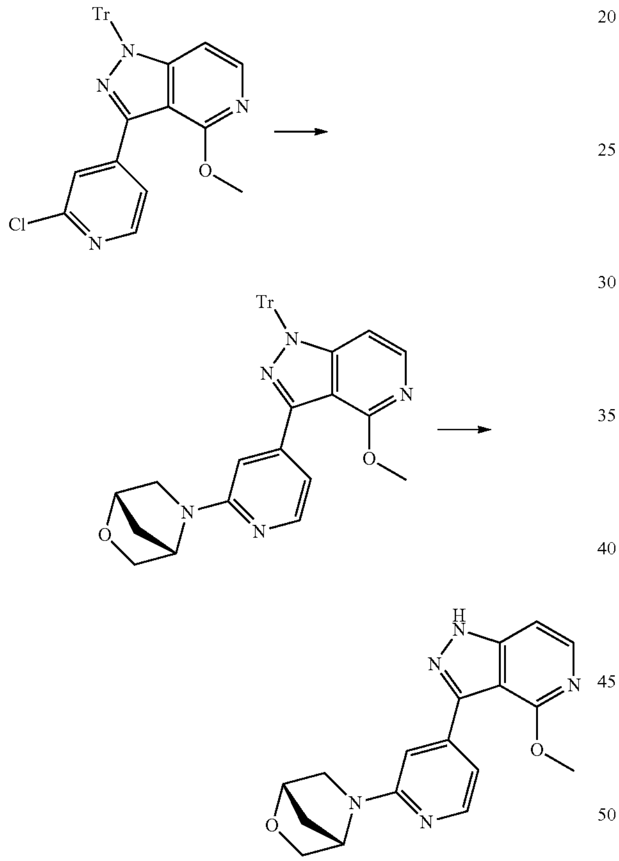

Prepared according to the procedure described in Example 117, by reacting 3-(2-chloropyridin-4-yl)-4-methoxy-1-trityl-1H-pyrazolo[4,3-c]pyridine with (1S,4S)-2-oxa-5-azoniabicyclo[2.2.1]heptane chloride for 40 minutes in Step 1 to give the title compound (22.5 mg, 35% over two steps). LC-MS (Method G): m/z=324.1 $[M+H]^+$, 2.94 min. $^1$H-NMR (400 MHz, DMSO): δ 13.70 (s, 1H), 8.13 (d, J=4.5, 1H), 7.93 (d, J=5.7, 1H), 7.22 (s, 1H), 7.21-7.16 (m, 2H), 4.89 (s, 1H), 4.69 (s, 1H), 4.02 (s, 3H), 3.83 (d, J=7.0, 1H), 3.73 (d, J=7.1, 1H), 3.55 (d, J=9.7, 1H), 1.96 (d, J=9.6, 1H), 1.88 (d, J=9.7, 1H).

Example 119

4-Methoxy-3-(2-(pyrrolidin-1-yl)pyridin-4-yl)-1H-pyrazolo[4,3-c]pyridine

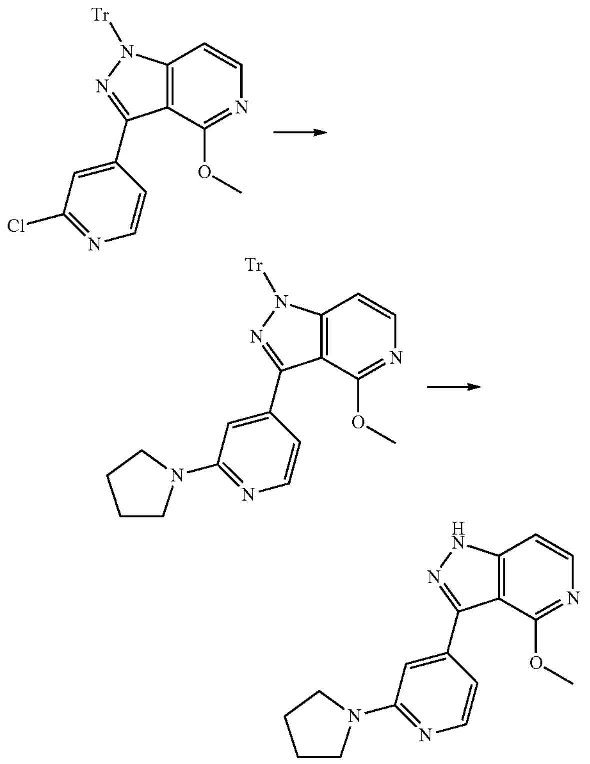

Step 1—4-Methoxy-3-(2-(pyrrolidin-1-yl)pyridin-4-yl)-1-trityl-1H-pyrazolo[4,3-c]pyridine 3-(2-chloropyridin-4-yl)-4-methoxy-1-trityl-1H-pyrazolo[4,3-c]pyridine (0.100 g, 0.199 mmol), 3-oxa-8-azabicyclo[3.2.1]octane hydrochloride (0.0199 mL, 0.238 mmol), RuPhos palladium(II) phenethylamine chloride (0.0145 g, 0.0199 mmol), RuPhos (0.00928 g, 0.0199 mmol) and sodium tert-butoxide (0.0458 g, 0.477 mmol) were weighed into a vial. 1,4-Dioxane (2.0 mL, 26 mmol) added via syringe and nitrogen was bubbled through the reaction mixture for 5 minutes. The vial was capped and heated to 110° C. for 20 hours in an oil bath. Upon reaction completion, the reaction mixture was diluted with EtOAc and filtered through Celite®, eluting with EtOAc and concentrated in vacuo. The crude residue was flashed with 0-10% MeOH in DCM to give the title compound.

Step 2—4-Methoxy-3-(2-(pyrrolidin-1-yl)pyridin-4-yl)-1H-pyrazolo[4,3-c]pyridine

To crude 4-methoxy-3-(2-(pyrrolidin-1-yl)pyridin-4-yl)-1-trityl-1H-pyrazolo[4,3-c]pyridine (0.199 mmol) dissolved in methylene chloride (2.8 mL, 44 mmol) and triethylsilane (0.127 mL, 0.795 mmol) was added trifluoroacetic acid (5.5 mL, 72 mmol) at room temperature. The reaction mixture was stirred for 2 hours and concentrated in vacuo. The crude residue was purified by reverse-phase HPLC to give the title compound (38.0 mg, 65% over two steps). LC-MS (Method G): m/z=296.1 $[M+H]^+$; 3.25 min. $^1$H-NMR (400 MHz, DMSO): δ 13.69 (s, 1H), 8.12 (d, J=5.4, 1H), 7.93 (d, J=6.0, 1H), 7.20-7.16 (m, 2H), 7.12 (d, J=5.3, 1H), 4.03 (s, 3H), 3.50-3.43 (m, 4H), 2.02-1.96 (m, 4H).

Example 120

3-(2-(3,5-Dimethylpiperidin-1-yl)pyridin-4-yl)-4-methoxy-1H-pyrazolo[4,3-c]pyridine

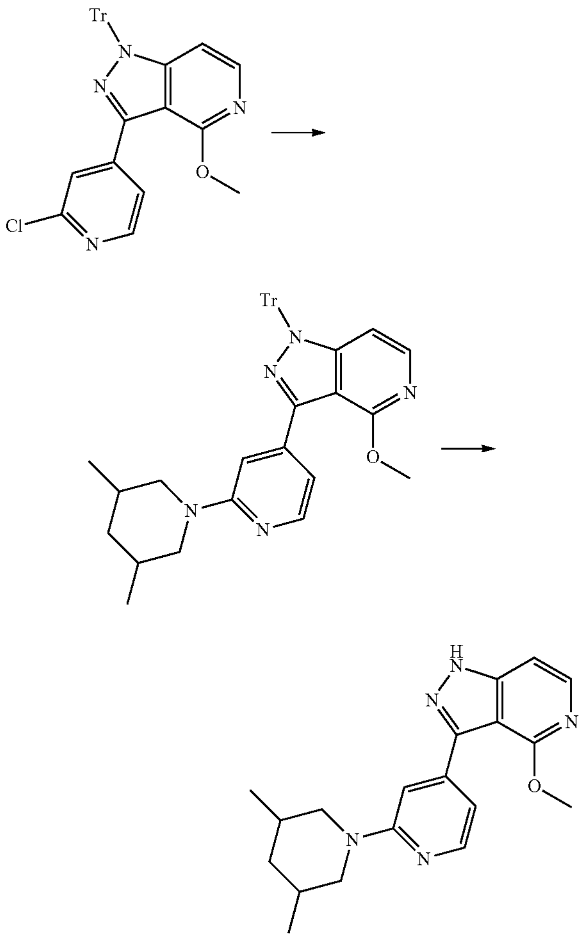

Prepared according to the procedure described in Example 117, by reacting 3-(2-chloropyridin-4-yl)-4-methoxy-1-trityl-1H-pyrazolo[4,3-c]pyridine with 2,6-dimethylmorpholine to give the title compound (21.9 mg, 32% over two steps). LC-MS (Method G): m/z=340.1 $[M+H]^+$; 3.38 min. $^1$H-NMR (500 MHz, DMSO): δ 13.81 (s, 1H), 8.19 (d, J=4.9, 1H), 7.94 (d, J=5.8, 1H), 7.52 (s, 1H), 7.25 (d, J=5.1, 1H), 7.20 (d, J=5.8, 1H), 4.23-4.14 (m, 2H), 4.02 (s, 3H), 3.72-3.61 (m, 2H), 2.48-2.41 (m, 2H), 1.19 (d, J=5.9, 6H).

Example 121

4-Methoxy-3-(2-(1-methyl-1H-pyrazol-4-yl)pyridin-4-yl)-1H-pyrazolo[4,3-c]pyridine

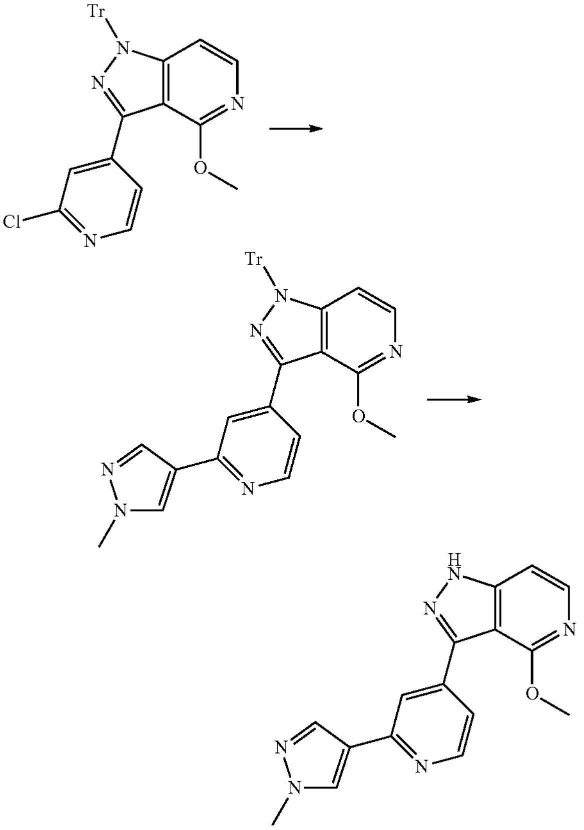

Prepared according to the procedure described in Example 116, by reacting 3-(2-chloropyridin-4-yl)-4-methoxy-1-trityl-1H-pyrazolo[4,3-c]pyridine with 1-methyl-4-(4,4,5,5-tetramethyl-1,3,2-dioxaborolan-2-yl)-1H-pyrazole to give the title compound (30.5 mg, 57% over two steps). LC-MS (Method G): m/z=307.0 $(M+H)^+$; 3.06 min. $^1$H-NMR (400 MHz, DMSO): δ 13.89 (br s, 1H), 8.60 (d, J=5.2, 1H), 8.34 (s, 1H), 8.22 (s, 1H), 8.03 (s, 1H), 7.97 (d, J=6.0, 1H), 7.75 (dd, J=5.2, 1.5 Hz, 1H), 7.23 (d, J=6.0, 1H), 4.05 (s, 3H), 3.91 (s, 3H).

Examples 122 and 123

3-(1-Isopropyl-1H-benzo[d]imidazol-6-yl)-4-(tetrahydro-2H-pyran-4-yloxy)-1H-pyrazolo[4,3-c]pyridine and 3-(1-isopropyl-1H-benzo[d]imidazol-5-yl)-4-(tetrahydro-2H-pyran-4-yloxy)-1H-pyrazolo[4,3-c]pyridine

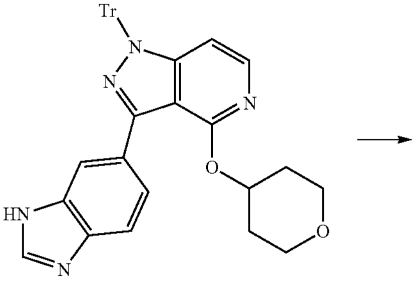

-continued

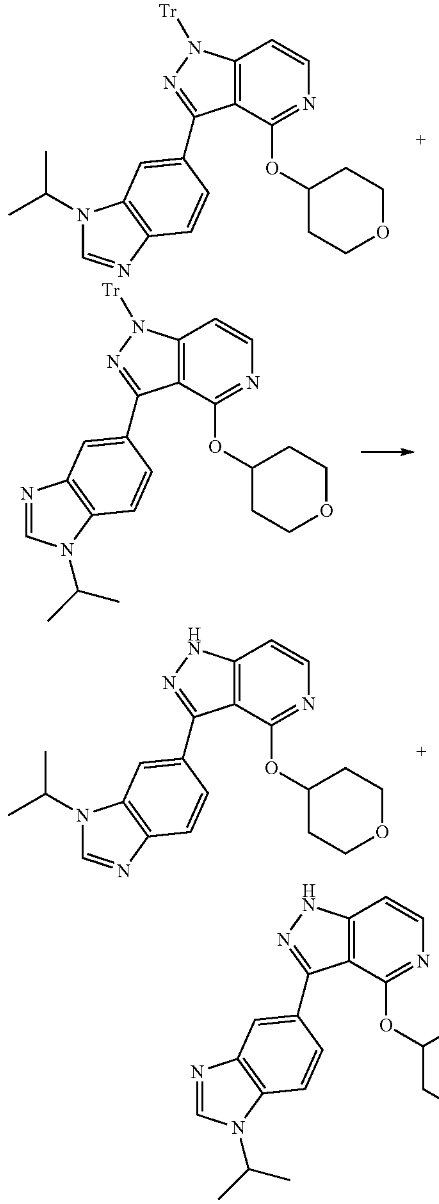

Step 1—3-(1-Isopropyl-1H-benzo[d]imidazol-6-yl)-4-(tetrahydro-2H-pyran-4-yloxy)-1-trityl-1H-pyrazolo[4,3-c]pyridine and 3-(1-isopropyl-1H-benzo[d]imidazol-5-yl)-4-(tetrahydro-2H-pyran-4-yloxy)-1-trityl-1H-pyrazolo[4,3-c]pyridine To a suspension of sodium hydride (60% dispersion, 10.2 mg, 0.254 mmol) in N,N-dimethylformamide (1.0 mL, 13 mmol) 0° C. was added 3-(1H-benzo[d]imidazol-6-yl)-4-(tetrahydro-2H-pyran-4-yloxy)-1-trityl-1H-pyrazolo[4,3-c]pyridine (98 mg, 0.17 mmol) in N,N-dimethylformamide (0.5 mL, 6 mmol) via cannula and stirred for 1 h at room temperature. Isopropyl iodide (25.4 uL, 0.254 mmol) was then added dropwise and the reaction mixture was stirred for 1 hour, then heated to 70° C. for 4 h. Upon reaction completion, the reaction mixture was quenched with water, extracted with dichloromethane, dried, filtered and concentrated in vacuo. To give the title compounds as a mixture of regioisomers.

Step 2—3-(1-Isopropyl-1H-benzo[d]imidazol-6-yl)-4-(tetrahydro-2H-pyran-4-yloxy)-1H-pyrazolo[4,3-c]pyridine and 3-(1-isopropyl-1H-benzo[d]imidazol-5-yl)-4-(tetrahydro-2H-pyran-4-yloxy)-1H-pyrazolo[4,3-c]pyridine A mixture of crude 3-(1-isopropyl-1H-benzo[d]imidazol-6-yl)-4-(tetrahydro-2H-pyran-4-yloxy)-1-trityl-1H-pyrazolo[4,3-c]pyridine and 3-(1-isopropyl-1H-benzo[d]imidazol-5-yl)-4-(tetrahydro-2H-pyran-4-yloxy)-1-trityl-1H-pyrazolo[4,3-c]pyridine (0.17 mmol) were dissolved in methylene chloride (2.5 mL, 39 mmol). triethylsilane (0.0789 g, 0.678 mmol) and trifluoroacetic Acid (2.5 mL, 32 mmol) were added and the mixture stirred for 15 mins then concentrated in vacuo. The crude residue was purified by reverse-phase HPLC to give the title compounds:

Isomer 1 (15.0 mg, 23% over two steps): LC-MS (Method G): m/z=378.1 $[M+H]^+$; 3.15 min. $^1$H-NMR (400 MHz, DMSO): δ 13.47 (s, 1H), 8.43 (s, 1H), 8.07 (s, 1H), 7.89 (d, J=6.0, 1H), 7.81 (d, J=8.5, 1H), 7.71 (d, J=8.4, 1H), 7.14 (d, J=6.0, 1H), 5.55-5.43 (m, 1H), 4.81 (d, J=6.8, 1H), 3.77-3.66 (m, 2H), 3.53-3.42 (m, 2H), 2.11-1.99 (m, 2H), 1.71-1.61 (m, 2H), 1.58 (d, J=6.7, 6H).

Isomer 2 (11.0 mg, 17% over two steps): LC-MS (Method G): m/z=378.1 $[M+H]^+$; 3.21 min. $^1$H-NMR (400 MHz, DMSO): δ 13.44 (s, 1H), 8.36 (s, 1H), 8.31 (s, 1H), 7.90-7.85 (m, 2H), 7.70 (d, J=8.5, 1H), 7.13 (d, J=6.0, 1H), 5.55-5.47 (m, 1H), 4.86-4.76 (m, 1H), 3.82-3.72 (m, 2H), 3.54-3.45 (m, 2H), 2.09-2.00 (m, 2H), 1.77-1.65 (m, 2H), 1.58 (d, J=6.7, 6H).

Examples 124 and 125

3-(1-(Oxetan-3-yl)-1H-benzo[d]imidazol-6-yl)-4-(tetrahydro-2H-pyran-4-yloxy)-1H-pyrazolo[4,3-c]pyridine and 3-(1-(oxetan-3-yl)-1H-benzo[d]imidazol-5-yl)-4-(tetrahydro-2H-pyran-4-yloxy)-1H-pyrazolo[4,3-c]pyridine

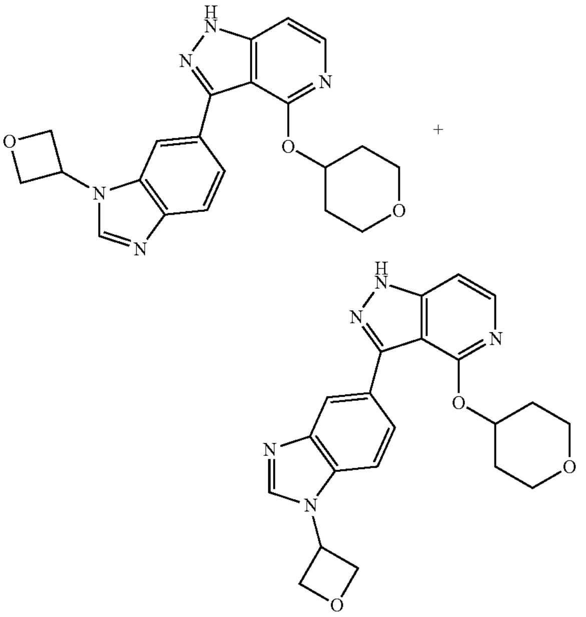

The title compounds were prepared according to the procedure described in Examples 172 and 173 by reacting 3-(1H-benzo[d]imidazol-6-yl)-4-(tetrahydro-2H-pyran-4-yloxy)-

1-trityl-1H-pyrazolo[4,3-c]pyridine with 3-iodooxetane and heating to 70° C. for 72 h to give the title compounds.

Isomer 1 (8.8 mg, 13% over two steps): LC-MS (Method G): m/z=392.1 $[M+H]^+$, 2.95 min. $^1H$ NMR (400 MHz, DMSO): δ 13.50 (br s, 1H), 8.62 (s, 1H), 8.16 (s, 1H), 7.89 (d, J=6.0, 1H), 7.86 (d, J=8.5, 1H), 7.76 (d, J=8.4, 1H), 7.15 (d, J=6.0, 1H), 5.88-5.77 (m, 1H), 5.53-5.43 (m, 1H), 5.11 (t, J=7.3, 2H), 5.05 (t, J=6.6, 2H), 3.76-3.67 (m, 2H), 3.52-3.42 (m, 2H), 2.09-1.98 (m, 2H), 1.69-1.57 (m, 2H).

Isomer 2 (8.1 mg, 12% over two steps): LC-MS (Method G): m/z=392.1 $[M+H]^+$, 3.00 min. $^1H$ NMR (400 MHz, DMSO) δ 13.47 (s, 1H), 8.52 (s, 1H), 8.36 (s, 1H), 7.94 (d, J=8.5, 1H), 7.88 (d, J=6.0, 1H), 7.82 (d, J=8.5, 1H), 7.14 (d, J=6.0, 1H), 5.87-5.75 (m, 1H), 5.51 (dt, J=8.0, J=4.0, 1H), 5.12 (t, J=7.4, 2H), 5.05 (t, J=6.6, 2H), 3.82-3.73 (m, 2H), 3.54-3.45 (m, 2H), 2.09-1.99 (m, 2H), 1.76-1.65 (m, 2H).

Examples 126 and 127

3-(1-((2,2-Difluorocyclopropyl)methyl)-1H-benzo[d]imidazol-6-yl)-4-(tetrahydro-2H-pyran-4-yloxy)-1H-pyrazolo[4,3-c]pyridine and 3-(1-((2,2-difluorocyclopropyl)methyl)-1H-benzo[d]imidazol-5-yl)-4-(tetrahydro-2H-pyran-4-yloxy)-1H-pyrazolo[4,3-c]pyridine

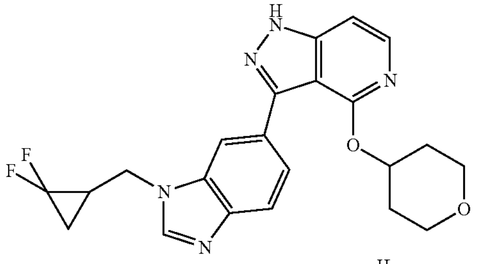

+

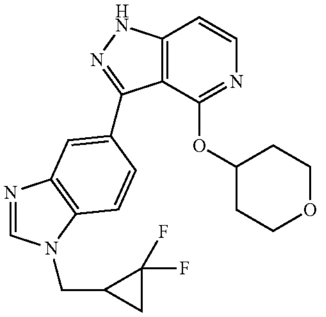

Prepared according to the procedure described in Examples 122 and 123 by reacting 3-(1H-benzo[d]imidazol-6-yl)-4-(tetrahydro-2H-pyran-4-yloxy)-1-trityl-1H-pyrazolo[4,3-c]pyridine with 1-bromomethyl-2,2-difluorocyclopropane and stirring for 1 hour at room temperature to give the title compounds.

Isomer 1 (23.8 mg, 33% over two steps): LC-MS (Method G): m/z=426.1 $[M+H]^+$, 3.34 min. $^1H$ NMR (400 MHz, DMSO) δ 13.49 (s, 1H), 8.33 (s, 1H), 8.15 (s, 1H), 7.89 (d, J=6.0, 1H), 7.86 (d, J=8.6, 1H), 7.74 (d, J=8.4, 1H), 7.14 (d, J=6.0, 1H), 5.54-5.44 (m, 1H), 4.54-4.36 (m, 2H), 3.77-3.67 (m, 2H), 3.54-3.43 (m, 2H), 2.46-2.35 (m, 1H), 2.10-1.98 (m, 2H), 1.77-1.54 (m, 4H).

Isomer 2 (18.3 mg, 25% over two steps): LC-MS (Method G): m/z=426.1 $[M+H]^+$; 3.42 min. $^1H$-NMR (400 MHz, DMSO): δ 13.44 (br s, 1H), 8.32 (s, 1H), 8.31 (s, 1H), 7.92 (d, J=8.5, 1H), 7.88 (d, J=6.0, 1H), 7.75 (d, J=8.5, 1H), 7.13 (d, J=6.0, 1H), 5.56-5.46 (m, 1H), 4.54-4.45 (m, 1H), 4.45-4.36 (m, 1H), 3.81-3.72 (m, 2H), 3.54-3.45 (m, 2H), 2.45-2.34 (m, 1H), 2.10-1.99 (m, 2H), 1.78-1.66 (m, 3H), 1.66-1.55 (m, 1H).

Examples 128 and 129

4-(Tetrahydro-2H-pyran-4-yloxy)-3-(1-(tetrahydrofuran-3-yl)-1H-benzo[d]imidazol-6-yl)-1H-pyrazolo[4,3-c]pyridine and 4-(tetrahydro-2H-pyran-4-yloxy)-3-(1-(tetrahydrofuran-3-yl)-1H-benzo[d]imidazol-5-yl)-1H-pyrazolo[4,3-c]pyridine

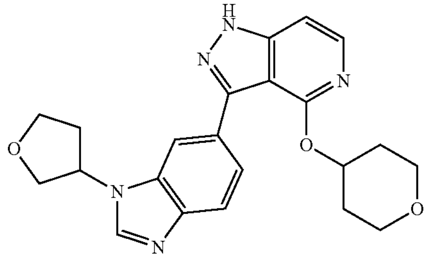

+

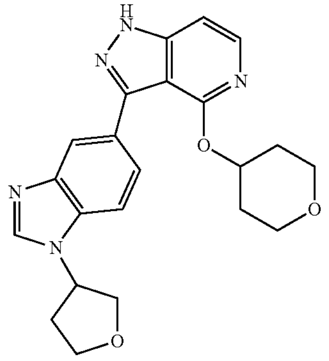

Prepared according to the procedure described in Examples 122 and 123 by reacting 3-(1H-benzo[d]imidazol-6-yl)-4-(tetrahydro-2H-pyran-4-yloxy)-1-trityl-1H-pyrazolo[4,3-c]pyridine with tetrahydrofuran-3-yl methanesulfonate and heating to 70° C. for 72 h to give the title compounds.

Isomer 1 (14.8 mg, 22% over two steps): LC-MS (Method G): m/z=406.1 $[M+H]^+$; 3.05 min. $^1H$ NMR (400 MHz, DMSO): δ 13.49 (br s, 1H), 8.31 (s, 1H), 8.11 (s, 1H), 7.89 (d, J=6.0, 1H), 7.83 (d, J=8.5, 1H), 7.73 (d, J=8.4, 1H), 7.14 (d, J=6.0, 1H), 5.54-5.44 (m, 1H), 5.35-5.27 (m, 1H), 4.20-4.11 (m, 1H), 4.07-3.96 (m, 2H), 3.90-3.80 (m, 1H), 3.76-3.66 (m, 2H), 3.52-3.42 (m, 2H), 2.63-2.53 (m, 1H), 2.31-2.21 (m, 1H), 2.04-1.99 (m, 1H), 1.72-1.58 (M, 2H).

Isomer 2 (18.9 mg, 27% over two steps): LC-MS (Method G): m/z=406.1 $[M+H]^+$, 3.10 min. $^1H$-NMR (400 MHz, DMSO): δ 13.44 (s, 1H), 8.33 (s, 1H), 8.29 (s, 1H), 7.92-7.86 (m, 2H), 7.73 (d, J=8.5, 1H), 7.13 (d, J=6.0, 1H), 5.51 (s, 1H), 5.32 (s, 1H), 4.20-4.11 (m, 1H), 4.09-3.98 (m, 2H), 3.90-3.82 (m, 1H), 3.81-3.72 (m, 2H), 3.53-3.45 (m, 2H), 2.63-2.53 (m, 1H), 2.31-2.22 (m, 1H), 2.10-1.99 (m, 2H), 1.76-1.64 (m, 2H).

Example 130

3-(3-Isopropyl-1H-1,2,4-triazol-5-yl)-4-(tetrahydro-2H-pyran-4-yloxy)-1H-pyrazolo[4,3-c]pyridine

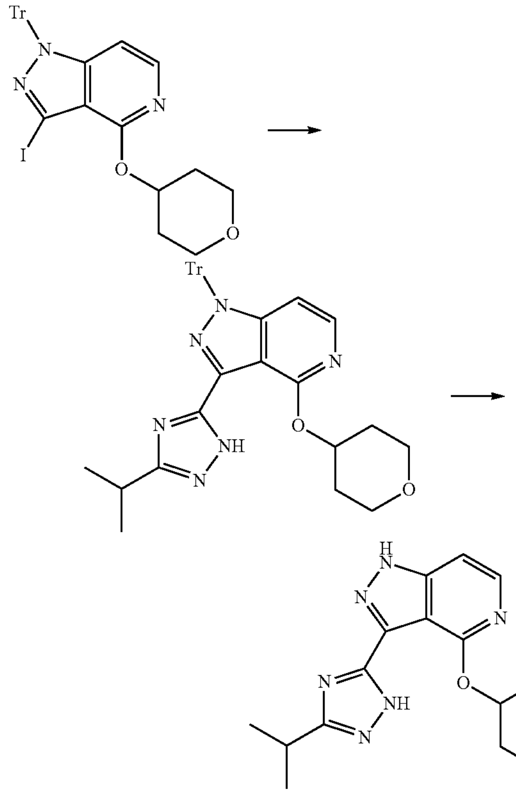

Step 1—3-(3-isopropyl-1H-1,2,4-triazol-5-yl)-4-(tetrahydro-2H-pyran-4-yloxy)-1-trityl-1H-pyrazolo[4,3-c]pyridine A round-bottomed flask was charged 3-iodo-4-(tetrahydro-2H-pyran-4-yloxy)-1-trityl-1H-pyrazolo[4,3-c]pyridine (0.300 g, 0.511 mmol), isopropylcarbamidine hydrochloride (0.0939 g, 0.766 mmol), palladium acetate (0.00573 g, 0.0255 mmol) and 4,5-bis(diphenylphosphino)-9,9-dimethylxanthene (0.0148 g, 0.0255 mmol). N,N-dimethylformamide (4.0 mL, 52 mmol) and triethylamine (0.48 mL, 3.4 mmol) were added via syringe and nitrogen was bubbled through the mixture for 5 mins. A carbon monoxide balloon was added and carbon monoxide was bubbled through the mixture for 2 mins. The reaction was heated to 80° C. for 2.5 hours. The carbon monoxide balloon was removed and replaced with a nitrogen balloon and the reaction mixture was cooled to room temperature, then 0° C. Acetic acid (2 mL, 40 mmol) and hydrazine hydrate (0.08 mL, 2 mmol) were added. The reaction was stirred at 0° C. for 5 minutes then warmed to room temperature for 1 hour. Upon reaction completion, the reaction mixture was diluted with 40 mL of EtOAc, washed with 1 N NaOH (aq) and brine. The extracts were dried over sodium sulfate, filtered and concentrated in vacuo to give the crude product.

Step 2—3-(3-Isopropyl-1H-1,2,4-triazol-5-yl)-4-(tetrahydro-2H-pyran-4-yloxy)-1H-pyrazolo[4,3-c]pyridine To crude 3-(3-isopropyl-1H-1,2,4-triazol-5-yl)-4-(tetrahydro-2H-pyran-4-yloxy)-1-trityl-1H-pyrazolo[4,3-c]pyridine from Step 1 dissolved in methylene chloride (7 mL, 100 mmol) and triethylsilane (0.326 mL, 2.04 mmol) was added trifluoroacetic acid (14 mL, 180 mmol). The reaction mixture was stirred at room temperature for 2 hours. Upon reaction completion, the reaction mixture was concentrated in vacuo. The crude residue was purified by reverse-phase HPLC to give the title compound (114.7 mg, 69% over two steps). LC-MS (Method G): m/z=329.1 $[M+H]^+$; 2.93 min. $^1$H-NMR (400 MHz, DMSO): δ 14.06-13.31 (m, 2H), 7.89 (s, 1H), 7.21 (s, 1H), 7.14 (s, 1H), 7.08 (s, 1H), 6.96 (s, 1H), 5.46 (s, 1H), 3.87-3.66 (m, 2H), 3.61-3.41 (m, 3H), 3.19-2.95 (m, 1H), 2.09-1.83 (m, 2H), 1.71-1.54 (m, 2H), 1.33 (d, J=6.6, 6H).

Example 131

3-(1-(Cyclobutylmethyl)-1H-pyrazol-4-yl)-4-(tetrahydro-2H-pyran-4-yloxy)-1H-pyrazolo[4,3-c]pyridine

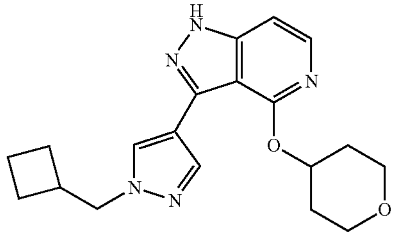 [SMILES: c1cc2[nH]nc(-c3cnn(CC4CCC4)c3)c2c(OC2CCOCC2)n1]

The title compound was prepared by the procedure described in Example 92 using (bromomethyl)cyclobutane. LC-MS (Method G): m/z=354 $[M+H]^+$; 8.96 min. $^1$H-NMR (400 MHz, DMSO): δ 13.26 (s, 1H), 8.21 (s, 1H), 8.00 (s, 1H), 7.83 (d, J=5.9, 1H), 7.07 (d, J=6.0, 1H), 5.52-5.42 (m, 1H), 4.20 (d, J=7.2, 2H), 3.90 (d, J=11.7, 2H), 3.53 (t, J=10.8, 2H), 2.80 (dt, J=14.2, J=7.2, 1H), 2.14 (d, J=10.9, 2H), 2.06-1.96 (m, 2H), 1.91-1.72 (m, 6H).

Example 132

3-((2-Chlorophenyl)ethynyl)-4-(tetrahydro-2H-pyran-4-yloxy)-1H-pyrazolo[4,3-c]pyridine

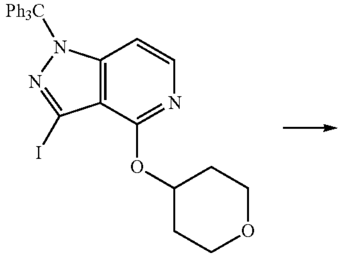

-continued

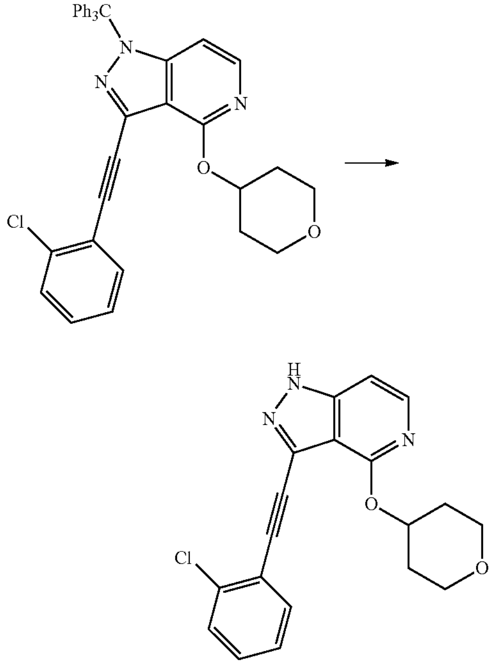

Step 1—3-((2-Chlorophenyl)ethynyl)-4-(tetrahydro-2H-pyran-4-yloxy)-1-trityl-1H-pyrazolo[4,3-c]pyridine To a solution of 3-iodo-4-(tetrahydro-2H-pyran-4-yloxy)-1-trityl-1H-pyrazolo[4,3-c]pyridine (75 mg, 0.128 mmol) in DMF (1.0 mL) was added 1-chloro-2-ethynylbenzene (23 μL, 0.192 mmol), $Pd(OAc)_2$ (2.87 mg, 0.013 mmol), and tetrabutylammonium acetate (57 mg, 0.192 mmol) and the reaction mixture stirred under nitrogen for 48 h. The crude mixture was concentrated, washed with water, extracted with EtOAc, dried ($Na_2SO_4$), filtered and concentrated to give the title compound.

Step 2—3-((2-Chlorophenyl)ethynyl)-4-(tetrahydro-2H-pyran-4-yloxy)-1H-pyrazolo[4,3-c]pyridine To 3-((2-chlorophenyl)ethynyl)-4-(tetrahydro-2H-pyran-4-yloxy)-1-trityl-1H-pyrazolo[4,3-c]pyridine (27 mg, 0.045 mmol) dissolved in $CH_2Cl_2$ (0.8 mL) was added triethylsilane (0.03 mL, 0.181 mmol) and trifluoroacetic acid (0.7 mL, 9 mmol) and the reaction mixture stirred at room temperature for 15 min. Toluene was then added and the mixture was concentrated. The crude residue was purified by reverse-phase HPLC to give the title compound (8.9 mg, 20% over two steps). LC-MS (Method G): m/z=354 $[M+H]^+$; 4.72 min. $^1$H-NMR (400 MHz, DMSO): δ 7.89 (d, J=5.7, 1H), 7.73-7.67 (m, 1H), 7.63 (d, J=7.5, 1H), 7.53-7.41 (m, 2H), 7.15 (d, J=5.7, 1H), 5.50-5.45 (m, 1H), 3.93-3.83 (m, 2H), 3.55-3.47 (m, 2H), 2.07-2.00 (m, 2H), 1.78-1.70 (m, 2H).

Example 133

Morpholino(4-(4-(tetrahydro-2H-pyran-4-yloxy)-1H-pyrazolo[4,3-c]pyridin-3-yl)phenyl)methanone

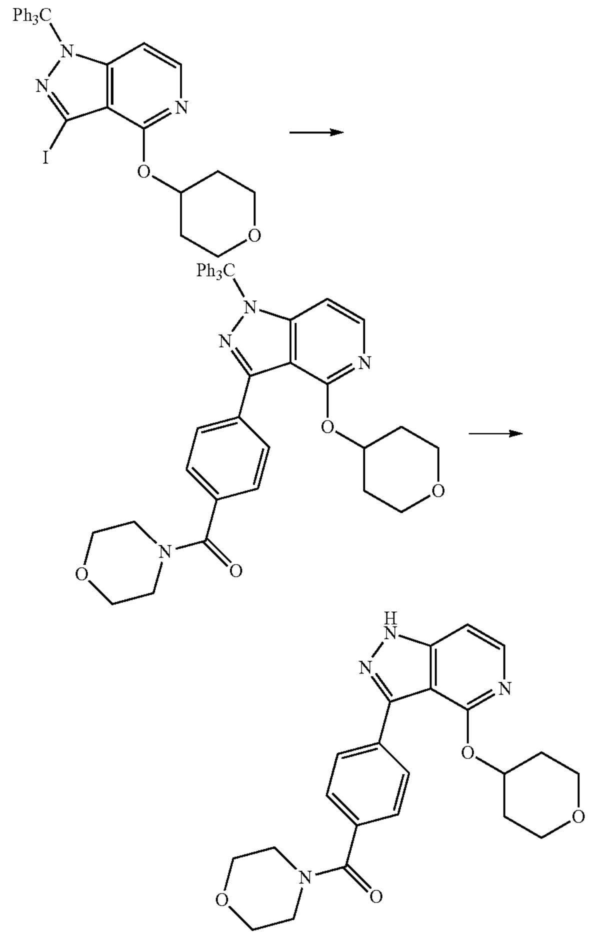

Step 1—Morpholino(4-(4-(tetrahydro-2H-pyran-4-yloxy)-1-trityl-1H-pyrazolo[4,3-c]pyridin-3-yl)phenyl)methanone 3-iodo-4-(tetrahydro-2H-pyran-4-yloxy)-1-trityl-1H-pyrazolo[4,3-c]pyridine (100 mg, 0.170 mmol), 4-(morpholine-4-carbonyl)phenylboronic acid (48 mg, 0.204 mmol), and 1,1'-bis(diphenylphosphino)ferrocenepalladium chloride (13.9 mg, 0.017 mmol) were charged in a microwave vial equipped with a stir bar. Acetonitrile (1.0 mL) and 1.0 M potassium acetate in water (0.41 mL) were then added, the reaction mixture was degassed with nitrogen for 5 min and then heated to 150° C. under microwave irradiation for 40 min. The crude mixture was filtered through Celite®, and concentrated to give the title compound.

Step 2—Morpholino(4-(4-(tetrahydro-2H-pyran-4-yloxy)-1H-pyrazolo[4,3-c]pyridin-3-yl)phenyl)methanone The title compound was prepared by the procedure described in step 2 of Example 132. LC-MS (Method G):

m/z=409 $[M+H]^+$; 3.42 min. $^1$H-NMR (400 MHz, DMSO): δ 13.59 (br s, 1H), 8.04 (d, J=7.8, 2H), 7.90 (d, J=5.9, 1H), 7.52 (d, J=7.8, 2H), 7.15 (d, J=6.0, 1H), 5.50-5.48 (m, 1H), 3.79-3.70 (m, 2H), 3.69-3.34 (m, 9H), 2.05 (br d, J=12.4, 2H), 1.73-1.67 (m, 2H).

Example 134

Morpholino(3-(4-(tetrahydro-2H-pyran-4-yloxy)-1H-pyrazolo[4,3-c]pyridin-3-yl)phenyl)methanone

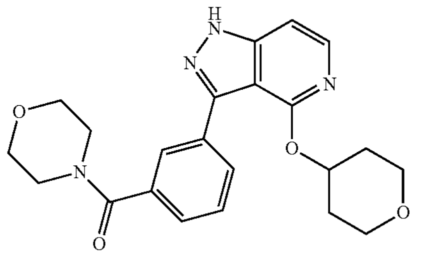 [SMILES: O=C(c1cccc(-c2n[nH]c3ccnc(OC4CCOCC4)c23)c1)N1CCOCC1]

The title compound was prepared by the procedures described in Example 133, by substituting 4-(morpholine-4-carbonyl)phenylboronic acid with 3-(morpholine-4-carbonyl)phenylboronic acid in step 1. LC-MS (Method G): m/z=409 $[M+H]^+$; 3.44 min. $^1$H-NMR (400 MHz, DMSO): δ 13.60 (br s, 1H), 8.09-8.07 (m, 2H), 7.89 (d, J=6.0, 1H), 7.56 (t, J=7.7, 1H), 7.46 (d, J=7.6, 1H), 7.15 (d, J=6.0, 1H), 5.54-5.43 (m, 1H), 3.81-3.73 (m, 2H), 3.72-3.35 (m, 9H), 2.09-2.03 (m, 2H), 1.76-1.62 (m, 2H).

Example 135

2-Fluoro-N,N-dimethyl-4-(4-(tetrahydro-2H-pyran-4-yloxy)-1H-pyrazolo[4,3-c]pyridin-3-yl)benzamide

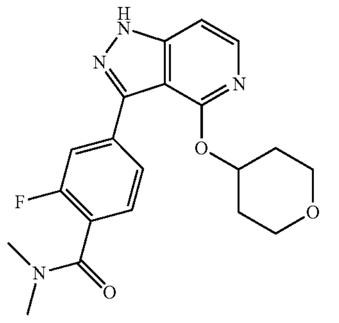 [SMILES: CN(C)C(=O)c1ccc(-c2n[nH]c3ccnc(OC4CCOCC4)c23)cc1F]

The title compound was prepared by the procedures described in Example 133, by substituting 4-(morpholine-4-carbonyl)phenylboronic acid with 4-(dimethylcarbamoyl)-3-fluorophenylboronic acid in step 1. LC-MS (Method G): m/z=385 $[M+H]^+$; 3.65 min. $^1$H-NMR (400 MHz, DMSO): δ 13.69 (s, 1H), 7.91 (d, J=7.1, 3H), 7.49 (t, J=7.5 Hz, 1H), 7.17 (d, J=6.0, 1H), 5.50 (br s, 1H), 3.82-3.71 (m, 2H), 3.53 (t, J=9.3, 2H), 3.04 (s, 3H), 2.91 (s, 3H), 2.08 (br d, J=10.4, 2H), 1.74-1.68 (m, 2H).

Example 136

3-(1-Methyl-1H-indazol-6-yl)-4-(tetrahydro-2H-pyran-4-yloxy)-1H-pyrazolo[4,3-c]pyridine

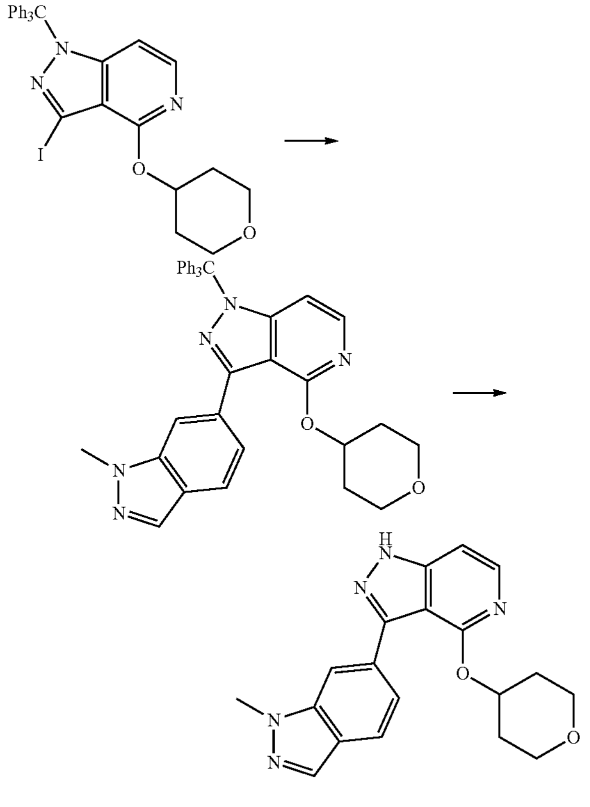

Step 1—3-(1-Methyl-1H-indazol-6-yl)-4-(tetrahydro-2H-pyran-4-yloxy)-1-trityl-1H-pyrazolo[4,3-c]pyridine 3-iodo-4-(tetrahydro-2H-pyran-4-yloxy)-1-trityl-1H-pyrazolo[4,3-c]pyridine (100 mg, 0.170 mmol), 1-methyl-1H-indazol-6-ylboronic acid (42 mg, 0.238 mmol), bis(di-tert-butyl(4-dimethylaminophenyl)phosphine) dichloropalladium (12 mg, 0.017 mmol), potassium acetate (23.4 mg, 0.238 mmol) and sodium carbonate (25.2 mg, 0.238 mmol) were charged into a microwave vial equipped with a stir bar. Acetonitrile (1.6 mL) and degassed water (0.6 mL) were then added and the reaction mixture was degassed with nitrogen for 5 min and then heated to 150° C. under microwave irradiation for 40 min. The crude mixture was filtered through Celite®, and concentrated to give the title compound.

Step 2—3-(1-Methyl-1H-indazol-6-yl)-4-(tetrahydro-2H-pyran-4-yloxy)-1H-pyrazolo[4,3-c]pyridine The title compound was prepared by the procedure described in step 2 of Example 132. LC-MS (Method G): m/z=350 $[M+H]^+$; 3.68 min. $^1$H-NMR (400 MHz, DMSO): δ 13.59 (s, 1H), 8.15 (s, 1H), 8.10 (s, 1H), 7.91 (d, J=6.0, 1H), 7.83 (d, J=8.4, 1H), 7.73 (d, J=8.4, 1H), 7.16 (d, J=5.9, 1H), 5.56-5.45 (m, 1H), 4.11 (s, 3H), 3.76-3.67 (m, 2H), 3.48 (t, J=9.0, 2H), 2.06 (d, J=9.2, 2H), 1.72-1.61 (m, 2H).

Example 137

3-(1H-Indazol-5-yl)-4-(tetrahydro-2H-pyran-4-yloxy)-1H-pyrazolo[4,3-c]pyridine

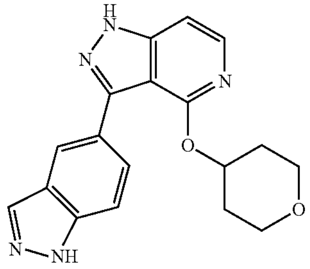 [SMILES: c1cc2[nH]nc(-c3ccc4[nH]ncc4c3)c2c(OC2CCOCC2)n1]

The title compound was prepared by the procedures described in Example 136, by substituting 1-methyl-1H-indazol-6-ylboronic acid with 1H-indazol-5-ylboronic acid. LC-MS (Method G): m/z=336 $[M+H]^+$; 3.25 min. $^1$H-NMR (400 MHz, DMSO): δ 13.45 (s, 1H), 13.15 (s, 1H), 8.40 (s, 1H), 8.14 (s, 1H), 7.95 (d, J=8.7, 1H), 7.88 (d, J=5.9 Hz, 1H), 7.61 (d, J=8.7, 1H), 7.13 (d, J=5.9, 1H), 5.50 (br s, 1H), 3.79-3.68 (m, 2H), 3.55-3.46 (m, 2H), 2.05 (d, J=9.5, 2H), 1.69 (d, J=8.8, 2H).

Example 138

3-(1H-Indazol-6-yl)-4-(tetrahydro-2H-pyran-4-yloxy)-1H-pyrazolo[4,3-c]pyridine

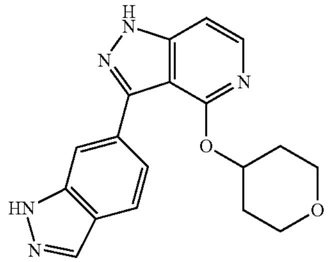 [SMILES: c1cc2[nH]nc(-c3ccc4cn[nH]c4c3)c2c(OC2CCOCC2)n1]

The title compound was prepared by the procedures described in Example 136, by substituting 1-methyl-1H-indazol-6-ylboronic acid with 1H-indazol-6-ylboronic acid in step 1. LC-MS (Method G): m/z=336 $[M+H]^+$; 3.44 min. $^1$H-NMR (400 MHz, DMSO): δ 13.54 (s, 1H), 13.22 (s, 1H), 8.14 (d, J=20.0, 2H), 7.90 (d, J=5.1, 1H), 7.82 (d, J=8.4, 1H), 7.73 (d, J=8.2, 1H), 7.15 (d, J=5.3, 1H), 5.56-5.42 (m, 1H), 3.74-3.70 (m, 2H), 3.49 (t, J=10.0, 2H), 2.12-2.02 (m, 2H), 1.77-1.70 (dd, J=8.7, J=3.2, 2H).

Example 139

3-(1H-Benzo[d]imidazol-6-yl)-4-(tetrahydro-2H-pyran-4-yloxy)-1H-pyrazolo[4,3-c]pyridine

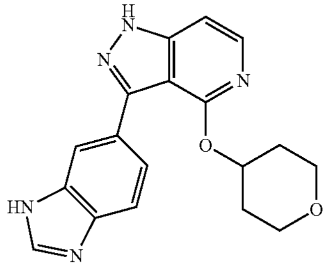 [SMILES: c1cc2[nH]nc(-c3ccc4nc[nH]c4c3)c2c(OC2CCOCC2)n1]

The title compound was prepared by the procedures described in Example 136, by substituting 1-methyl-1H-indazol-6-ylboronic acid with 6-(4,4,5,5-tetramethyl-1,3,2-dioxaborolan-2-yl)-1H-benzo[d]imidazole in step 1. LC-MS (Method G): m/z=336 $[M+H]^+$; 2.90 min. $^1$H-NMR (400 MHz, DMSO): δ 13.44 (d, J=11.6, 1H), 12.62 (s, 0.5H), 12.50 (s, 0.5H), 8.30-8.13 (m, 2H), 7.88-7.79 (m, 2H), 7.73-7.56 (m, 1H), 7.13 (d, J=6.0, 1H), 5.49 (br s, 1H), 3.74 (br s, 2H), 3.49 (t, J=9.3, 2H), 2.13-1.98 (m, 2H), 1.79-1.64 (m, 2H).

Examples 140 and 141

3-(1-Methyl-1H-indazol-5-yl)-4-(tetrahydro-2H-pyran-4-yloxy)-1H-pyrazolo[4,3-c]pyridine and 3-(2-methyl-2H-indazol-5-yl)-4-(tetrahydro-2H-pyran-4-yloxy)-1H-pyrazolo[4,3-c]pyridine

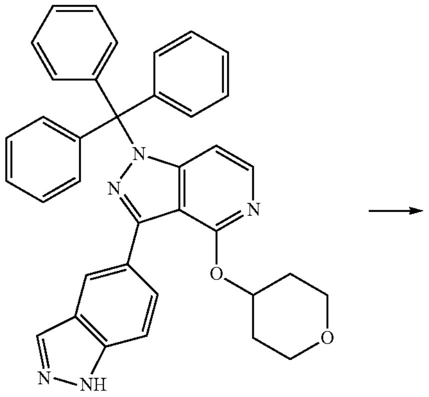

-continued

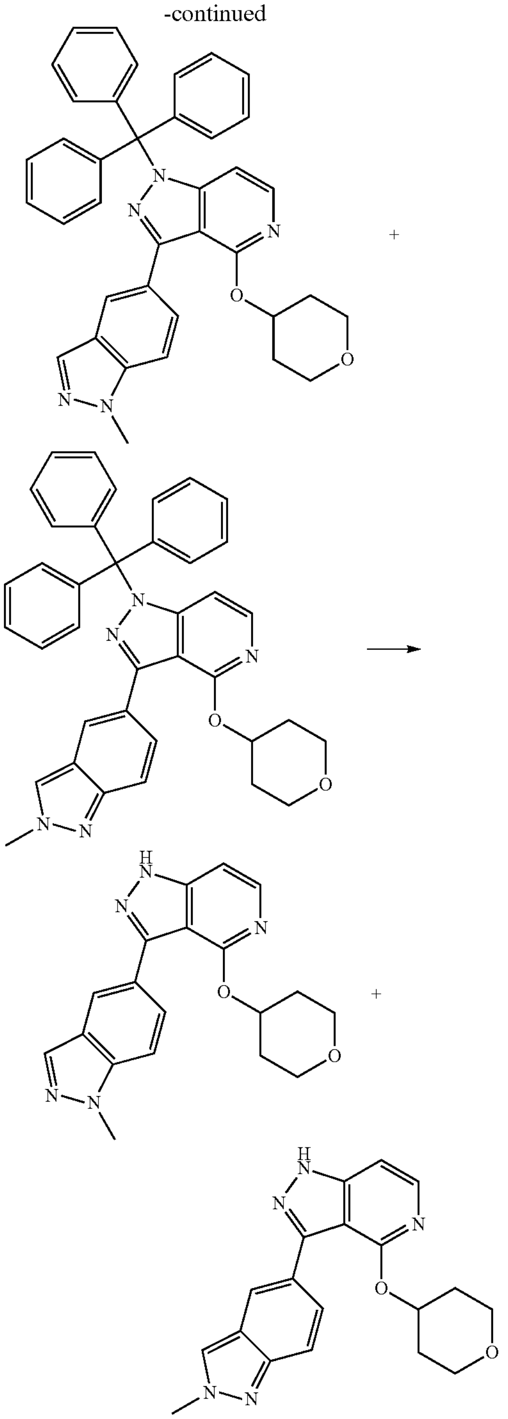

Step 1—3-(1-Methyl-1H-indazol-5-yl)-4-(tetrahydro-2H-pyran-4-yloxy)-1-trityl-1H-pyrazolo[4,3-c]pyridine and 3-(2-methyl-2H-indazol-5-yl)-4-(tetrahydro-2H-pyran-4-yloxy)-1-trityl-1H-pyrazolo[4,3-c]pyridine To 3-(1H-indazol-5-yl)-4-(tetrahydro-2H-pyran-4-yloxy)-1-trityl-1H-pyrazolo[4,3-c]pyridine (62.5 mg, 0.108 mmol, prepared as described in Example 136), dissolved in THF (1.0 mL) at 0° C. was added NaH (6.5 mg, 0.162 mmol, 60% dispersion in mineral oil) and after 10 min, dimethyl sulfate (5.63 µL, 0.06 mmol) was added. After stirring for 1 h, the reaction mixture was quenched with water, extracted with EtOAc, dried ($Na_2SO_4$), filtered and concentrated to provide a mixture of isomers 176 and 177.

Step 2—3-(1-Methyl-1H-indazol-5-yl)-4-(tetrahydro-2H-pyran-4-yloxy)-1H-pyrazolo[4,3-c]pyridine and 3-(2-methyl-2H-indazol-5-yl)-4-(tetrahydro-2H-pyran-4-yloxy)-1H-pyrazolo[4,3-c]pyridine The title compounds were prepared by the procedure described in step 2 of Example 132.

Major, slower eluting isomer 3-(1-methyl-1H-indazol-5-yl)-4-(tetrahydro-2H-pyran-4-yloxy)-1-trityl-1H-pyrazolo[4,3-c]pyridine: LC-MS of (Method G): m/z=350 $[M+H]^+$; 3.57 min. $^1$H-NMR (400 MHz, DMSO) δ 13.48 (s, 1H), 8.39 (s, 1H), 8.12 (s, 1H), 8.00 (d, J=8.8, 1H), 7.88 (d, J=5.9, 1H), 7.72 (d, J=8.8, 1H), 7.13 (d, J=6.0, 1H), 5.56-5.44 (m, 1H), 4.10 (s, 3H), 3.73 (dd, J=10.7, J=5.6, 2H), 3.50 (t, J=8.6, 2H), 2.12-2.01 (m, 2H), 1.73-1.66 (m, 2H).

Minor, faster eluting isomer 3-(2-methyl-2H-indazol-5-yl)-4-(tetrahydro-2H-pyran-4-yloxy)-1H-pyrazolo[4,3-c]pyridine: LC-MS of (Method G): m/z=350 $[M+H]^+$; 3.32 min. $^1$H-NMR (400 MHz, DMSO): δ 13.44 (s, 1H), 8.43 (s, 1H), 8.38 (s, 1H), 7.88 (d, J=6.0, 1H), 7.84 (d, J=9.0, 1H), 7.64 (d, J=8.9, 1H), 7.13 (d, J=6.0, 1H), 5.55-5.45 (m, 1H), 4.20 (s, 3H), 3.77-3.74 (m, 2H), 3.54-3.49 (m, 2H), 2.07-2.03 (m, 2H), 1.73-1.69 (m, 2H).

Examples 142 and 143

3-(1-isopropyl-1H-indazol-6-yl)-4-(tetrahydro-2H-pyran-4-yloxy)-1H-pyrazolo[4,3-c]pyridine and 3-(2-isopropyl-2H-indazol-6-yl)-4-(tetrahydro-2H-pyran-4-yloxy)-1H-pyrazolo[4,3-c]pyridine

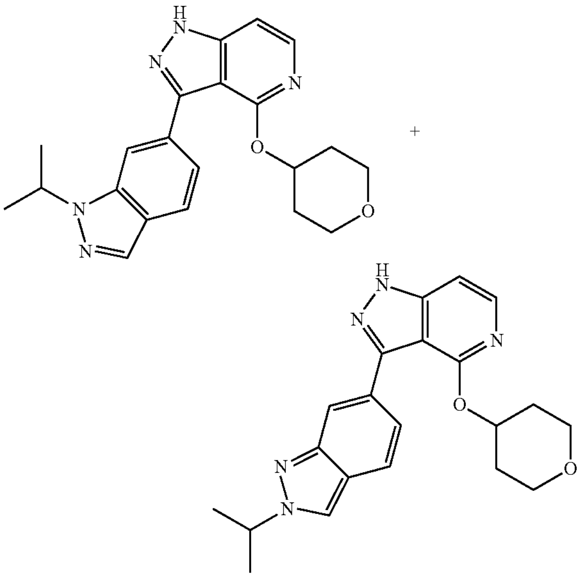

The title compounds were prepared by the procedures described in Examples 141 and 142 by using 1H-indazol-6-ylboronic acid in step 1 and 2-iodopropane in step 2.

Major, slower eluting isomer 3-(1-isopropyl-1H-indazol-6-yl)-4-(tetrahydro-2H-pyran-4-yloxy)-1H-pyrazolo[4,3-c]pyridine: LC-MS (Method G): m/z=378 $[M+H]^+$; 4.11 min.

$^1$H-NMR (400 MHz, DMSO): δ 13.56 (s, 1H), 8.13 (d, J=11.3, 2H), 7.90 (d, J=5.6 1H), 7.82 (d, J=8.4, 1H), 7.71 (d, J=8.4, 1H), 7.16 (d, J=6.0, 1H), 5.52-5.47 (m, 1H), 5.10-4.99 (m, 1H), 3.72 (d, J=11.2, 2H), 3.50-3.45 (m, 2H), 2.12-2.02 (m, 2H), 1.72-1.57 (m, 2H), 1.51 (d, J=6.4, 6H).

Minor, faster eluting isomer 3-(2-isopropyl-2H-indazol-6-yl)-4-(tetrahydro-2H-pyran-4-yloxy)-1H-pyrazolo[4,3-c]pyridine: LC-MS of (Method G): m/z=378 [M+H]$^+$; 3.82 min. $^1$H-NMR (400 MHz, DMSO): δ 13.49 (s, 1H), 8.42 (s, 1H), 8.27 (s, 1H), 7.88 (d, J=5.8, 1H), 7.74 (d, J=8.6, 1H), 7.64 (d, J=8.5, 1H), 7.14 (d, J=5.8, 1H), 5.52 (d, J=3.2, 1H), 4.92-4.80 (m, 1H), 3.80-3.70 (m, 2H), 3.54-3.44 (m, 2H), 2.09-2.00 (m, 2H), 1.80-1.68 (m, 2H), 1.59 (d, J=6.5, 6H).

Examples 144 and 145

3-(1-Methyl-1H-benzo[d]imidazol-6-yl)-4-(tetrahydro-2H-pyran-4-yloxy)-1H-pyrazolo[4,3-c]pyridine and 3-(1-methyl-1H-benzo[d]imidazol-5-yl)-4-(tetrahydro-2H-pyran-4-yloxy)-1H-pyrazolo[4,3-c]pyridine

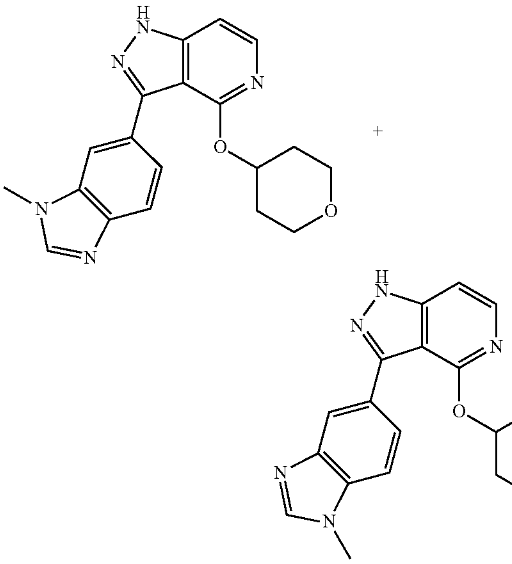

The title compounds were prepared by the procedures described in Examples 140 and 141, using 6-(4,4,5,5-tetramethyl-1,3,2-dioxaborolan-2-yl)-1H-benzo[d]imidazole in step 1.

Major, faster eluting isomer 3-(1-methyl-1H-benzo[d]imidazol-6-yl)-4-(tetrahydro-2H-pyran-4-yloxy)-1H-pyrazolo[4,3-c]pyridine: LC-MS (Method G): m/z=350 [M+H]$^+$; 2.96 min. $^1$H-NMR (400 MHz, DMSO): δ 13.48 (s, 1H), 8.23 (s, 1H), 8.09 (s, 1H), 7.89 (d, J=5.6, 1H), 7.83 (d, J=8.4, 1H), 7.70 (d, J=8.4, 1H), 7.14 (d, J=5.9, 1H), 5.56-5.46 (m, 1H), 3.90 (s, 3H), 3.77-3.68 (m, 2H), 3.53-3.44 (m, 2H), 2.05 (d, J=10.4, 2H), 1.71-1.63 (m, 2H).

Minor, slower eluting isomer 3-(1-methyl-1H-benzo[d]imidazol-5-yl)-4-(tetrahydro-2H-pyran-4-yloxy)-1H-pyrazolo[4,3-c]pyridine: LC-MS (Method G): m/z=350 [M+H]$^+$; 2.97 min. $^1$H-NMR (400 MHz, DMSO): δ 13.42 (s, 1H), 8.30 (s, 1H), 8.21 (s, 1H), 7.89 (t, J=8.3, 2H), 7.63 (d, J=8.4, 1H), 7.12 (d, J=5.6, 1H), 5.56-5.45 (m, 1H), 3.89 (s, 3H), 3.80-3.72 (m, 2H), 3.54-3.44 (m, 2H), 2.08-1.98 (m, 2H), 1.73-1.66 (m, 2H).

Examples 146 and 147

(R)-4-(Tetrahydro-2H-pyran-4-yloxy)-3-(1-(tetrahydrofuran-3-yl)-1H-pyrazol-4-yl)-1H-pyrazolo[4,3-c]pyridine and (S)-4-(tetrahydro-2H-pyran-4-yloxy)-3-(1-(tetrahydrofuran-3-yl)-1H-pyrazol-4-yl)-1H-pyrazolo[4,3-c]pyridine

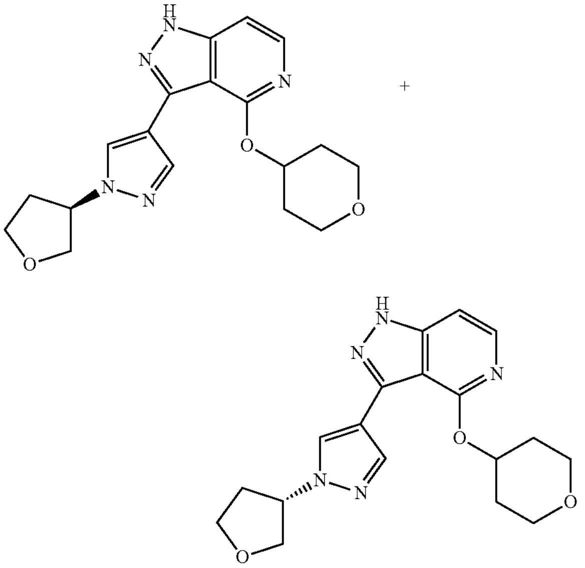

The title compounds were prepared by the procedures described in Examples 140 and 141 by using 4-(4,4,5,5-tetramethyl-1,3,2-dioxaborolan-2-yl)-1H-pyrazole in step 1 and tetrahydrofuran-3-yl methanesulfonate in step 2.

Major, faster eluting enantiomer (R)-4-(tetrahydro-2H-pyran-4-yloxy)-3-(1-(tetrahydrofuran-3-yl)-1H-pyrazol-4-yl)-1H-pyrazolo[4,3-c]pyridine: LC-MS (Method G): m/z=356 [M+H]$^+$;1.72 min. $^1$H-NMR (400 MHz, DMSO): δ 13.31 (s, 1H), 8.30 (s, 1H), 8.04 (s, 1H), 7.83 (d, J=5.9, 1H), 7.07 (d, J=5.9, 1H), 5.53-5.43 (m, 1H), 5.13-5.09 (m, 1H), 4.07-3.95 (m, 3H), 3.95-3.82 (m, 3H), 3.53 (t, J=11.0, 2H), 2.47-2.40 (m, 1H), 2.33-2.28 (m, 1H), 2.15 (d, J=12.9, 2H), 1.87-1.72 (m, 2H).

Minor, slower eluting enantiomer (S)-4-(tetrahydro-2H-pyran-4-yloxy)-3-(1-(tetrahydrofuran-3-yl)-1H-pyrazol-4-yl)-1H-pyrazolo[4,3-c]pyridine: LC-MS of (Method G): m/z=356 [M+H]$^+$; 1.86 min. $^1$H NMR (400 MHz, DMSO): δ 13.29 (s, 1H), 8.30 (s, 1H), 8.04 (s, 1H), 7.83 (d, J=5.9, 1H), 7.07 (d, J=5.9, 1H), 5.52-5.41 (m, 1H), 5.16-5.06 (m, 1H), 4.07-3.94 (m, 3H), 3.95-3.81 (m, 3H), 3.52 (t, J=10.9, 2H), 2.50-2.41 (m, 1H), 2.32-2.30 (m, 1H), 2.20-2.10 (m, 2H), 1.83-1.75 (m, 2H).

Example 148

4-(Cyclohexyloxy)-6-cyclopropyl-3-methyl-1H-pyrazolo[4,3-c]pyridine

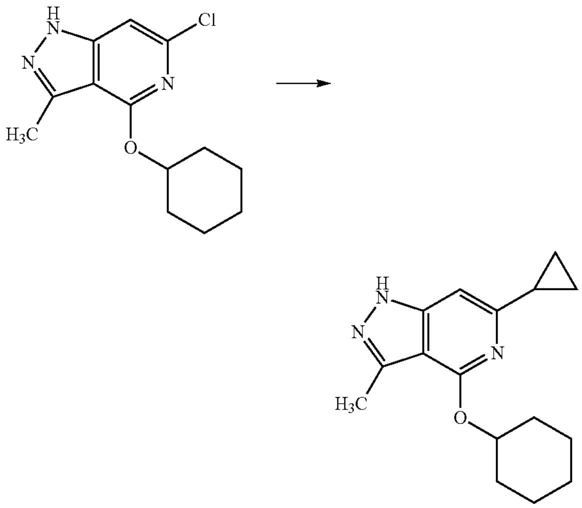

To a microwave tube was added 6-chloro-4-(cyclohexyloxy)-3-methyl-1H-pyrazolo[4,3-c]pyridine (49 mg, 0.18 mmol), cyclopropylboronic acid (80 mg, 0.9 mmol), Pd(dppf)$Cl_2$ (15 mg, 0.018 mmol). The tube was flushed with nitrogen for 2 minutes before adding a 2 M solution of sodium carbonate in water (0.28 mL) and 1,4-dioxane (2 mL). The tube was sealed and irradiated in a microwave at 160° C. for 25 minutes. The reaction mixture was then filtered and concentrated. The crude product was purified by reverse-phase HPLC to give the title compound (8.7 mg, 17%). LC-MS (Method G): m/z=272.1 $[M+H]^+$; 5.44 min. $^1$H-NMR (400 MHz, DMSO): δ 12.57 (s, 1H), 6.83 (s, 1H), 5.15 (m, 1H), 2.02 (m, 1H), 1.87 (m, 2H), 1.71 (m, 2H), 1.62 (m, 2H), 1.46 (m, 4H), 0.87 (m, 4H).

Example 149

5-(4-(Tetrahydro-2H-pyran-4-yloxy)-1H-pyrazolo[4,3-c]pyridin-3-yl)quinoline

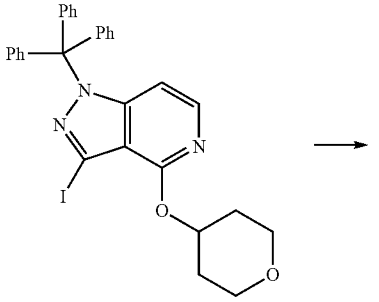

-continued

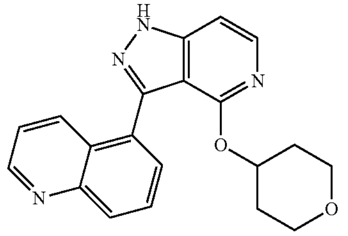

To a microwave tube was added 3-iodo-4-(tetrahydro-2H-pyran-4-yloxy)-1-trityl-1H-pyrazolo[4,3-c]pyridine (120 mg, 0.20 mmol), quinolin-5-ylboronic acid (43 mg, 0.25 mmol), bis(di-tert-butyl(4-dimethylaminophenyl)phosphine)dichloropalladium (14 mg, 0.02 mmol), a 2 M aqueous solution of sodium carbonate (0.20 mL) and acetonitrile (1.5 mL, 0.029 mmol). The tube was then sealed and the reaction was irradiated in a microwave reactor at 140° C. for 30 minutes. The reaction mixture was filtered through Celite® and concentrated. The crude residue was then dissolved in DCM (3 mL) and cooled to 0° C. To the cooled reaction mixture was added triethylsilane (0.13 mL, 0.80 mmol) and trifluoroacetic acid (3.0 mL, 0.039 mmol). The mixture was stirred at room temperature for 30 minutes before concentrated under vacuum. The resulting residue was re-suspended in methanol and filtered to remove insoluble solids. The filtrate was concentrated and purified by reverse-phase HPLC to give the title compound (30 mg, 43%). LC-MS (Method G): m/z=347.1 $[M+H]^+$; 2.98 min. $^1$H-NMR (400 MHz, DMSO): δ 13.69 (s, 1H), 8.94 (s, 1H), 8.23 (d, J=8.4, 1H), 8.14 (d, J=8.3, 1H), 7.89 (m, 2H), 7.78 (d, J=6.8, 1H), 7.49 (m, 1H), 7.22 (m, 1H), 5.28 (m, 1H), 3.24 (m, 2H), 3.06 (m, 2H), 1.69 (m, 2H), 1.17 (m, 3H).

Example 150

3-(4-(Tetrahydro-2H-pyran-4-yloxy)-1H-pyrazolo[4,3-c]pyridin-3-yl)quinoline

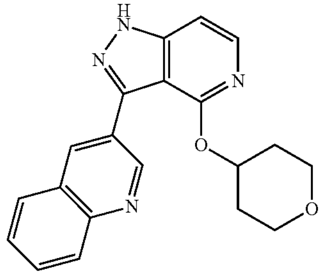 [SMILES: c1ccc2ncc(-c3n[nH]c4ccnc(OC5CCOCC5)c34)cc2c1]

The title compound was prepared by the procedure described in Example 149, by substituting quinolin-5-ylboronic acid with quinolin-3-ylboronic acid. LC-MS (Method G): m/z=347.1 $[M+H]^+$; 3.47 min. $^1$H-NMR (400 MHz, DMSO): δ 13.79 (s, 1H), 9.46 (s, 1H), 8.94 (s, 1H), 8.10 (m, 2H), 7.95 (m, 1H), 7.82 (m, 1H), 7.71 (m, 1H), 7.22 (m, 1H), 5.53 (m, 1H), 3.74 (m, 2H), 3.49 (m, 2H), 2.10 (m, 2H), 1.70 (m, 2H).

Example 151

2-(3-(4-(Tetrahydro-2H-pyran-4-yloxy)-1H-pyrazolo[4,3-c]pyridin-3-yl)phenyl)acetonitrile

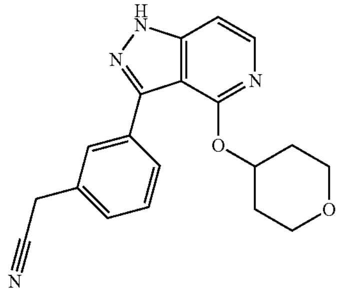 [SMILES: N#CCc1cccc(-c2n[nH]c3ccnc(OC4CCOCC4)c23)c1]

The title compound was prepared by the procedure described in Example 149, by substituting quinolin-5-ylboronic acid with 3-(cyanomethyl)phenylboronic acid. LC-MS (Method G): m/z=335.1 $[M+H]^+$, 3.74 min. $^1$H-NMR (400 MHz, DMSO): δ 13.57 (s, 1H), 7.92 (m, 3H), 7.52 (m, 1H), 7.42 (m, 1H), 7.14 (m, 1H), 5.45 (m, 1H), 4.13 (s, 2H), 3.75 (m, 2H), 3.54 (m, 2H), 2.07 (m, 2H), 1.70 (m, 2H).

Example 152

N-(2-(Dimethylamino)ethyl)-3-(4-(tetrahydro-2H-pyran-4-yloxy)-1H-pyrazolo[4,3-c]pyridin-3-yl)benzamide

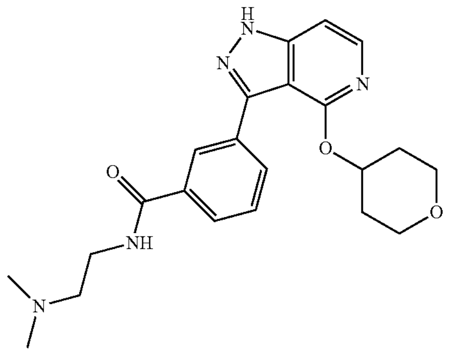 [SMILES: CN(C)CCNC(=O)c1cccc(-c2n[nH]c3ccnc(OC4CCOCC4)c23)c1]

The title compound was prepared by the procedure described in Example 149, by substituting quinolin-5-ylboronic acid with 3-(2-(dimethylamino)ethylcarbamoyl)phenylboronic acid. LC-MS (Method G): m/z=410.2 $[M+H]^+$; 3.03 min. $^1$H-NMR (400 MHz, DMSO): δ 13.60 (s, 1H), 8.43 (s, 2H), 8.07 (d, J=7.7, 1H), 7.88 (s, 2H), 7.56 (s, 1H), 7.15 (d, J=5.6, 1H), 5.47 (m, 1H), 3.48 (m, 2H), 3.37 (m, 2H), 2.43 (m, 2H), 2.02 (m, 2H), 1.68 (m, 2H).

Example 153

N,N-Dimethyl-3-(4-(tetrahydro-2H-pyran-4-yloxy)-1H-pyrazolo[4,3-c]pyridin-3-yl)aniline

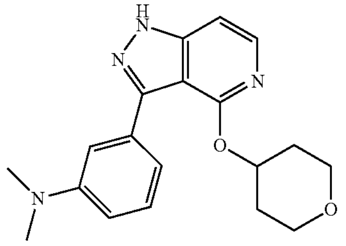 [SMILES: CN(C)c1cccc(-c2n[nH]c3ccnc(OC4CCOCC4)c23)c1]

The title compound was prepared by the procedure described in Example 149, by substituting quinolin-5-ylboronic acid with 3-(dimethylamino)phenylboronic acid. LC-MS (Method G): m/z=339.1 $[M+H]^+$; 3.13 min. $^1$H-NMR (400 MHz, DMSO): δ 13.40 (s, 1H), 7.86 (m, 1H), 7.24 (m, 3H), 7.11 (m, 1H), 6.80 (m, 1H), 5.47 (m, 1H), 3.74 (m, 2H), 3.49 (m, 2H), 2.95 (m, 6H), 1.64 (m, 2H).

Example 154

N-Isopropyl-3-(4-(tetrahydro-2H-pyran-4-yloxy)-1H-pyrazolo[4,3-c]pyridin-3-yl)benzamide

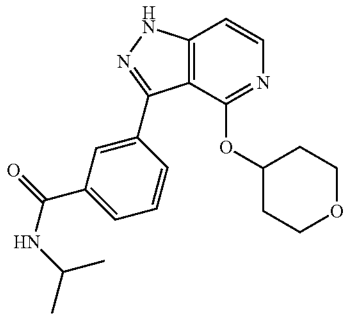 [SMILES: CC(C)NC(=O)c1cccc(-c2n[nH]c3ccnc(OC4CCOCC4)c23)c1]

The title compound was prepared by the procedure described in Example 149, by substituting quinolin-5-ylboronic acid with 3-(isopropylcarbamoyl)phenylboronic acid. LC-MS (Method G): m/z=381.1 $[M+H]^+$; 3.66 min. $^1$H-NMR (400 MHz, DMSO): δ 13.57 (s, 1H), 8.43 (m, 1H), 8.28 (m, 1H), 8.03 (m, 1H), 7.89 (m, 2H), 7.53 (m, 1H), 7.16 (m, 1H), 5.45 (m, 1H), 4.12 (m, 1H), 3.67 (m, 2H), 3.47 (m, 2H), 2.03 (m, 2H), 1.68 (m, 2H), 1.18 (d, J=5.9, 6H).

Example 155

N-Cyclopropyl-3-(4-(tetrahydro-2H-pyran-4-yloxy)-1H-pyrazolo[4,3-c]pyridin-3-yl)benzamide

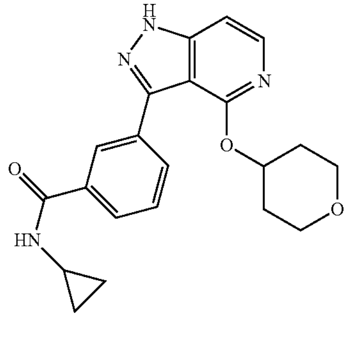 [SMILES: O=C(NC1CC1)c1cccc(-c2n[nH]c3ccnc(OC4CCOCC4)c23)c1]

The title compound was prepared by the procedure described in Example 149, by substituting quinolin-5-ylboronic acid with N-cyclopropyl-3-(4,4,5,5-tetramethyl-1,3,2-dioxaborolan-2-yl)benzamide. LC-MS (Method G): m/z=379.1 $[M+H]^+$; 3.49 min. $^1$H-NMR (400 MHz, DMSO): δ 13.58 (s, 1H), 8.49 (s, 1H), 8.41 (s, 1H), 8.05 (d, J=7.3, 1H), 7.87 (m, 2H), 7.54 (t, J=7.6, 1H), 7.15 (d, J=5.3, 1H), 5.46 (m, 1H), 3.67 (m, 2H), 3.50 (m, 2H), 2.86 (m, 1H), 2.00 (m, 2H), 1.69 (m, 2H), 0.70 (m, 2H), 0.59 (m, 2H).

Example 156

3-(4-(Tetrahydro-2H-pyran-4-yloxy)-1H-pyrazolo[4,3-c]pyridin-3-yl)benzonitrile

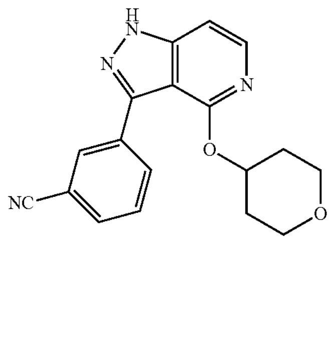 [SMILES: N#Cc1cccc(-c2n[nH]c3ccnc(OC4CCOCC4)c23)c1]

The title compound was prepared by the procedure described in Example 149, by substituting quinolin-5-ylboronic acid with 3-(4,4,5,5-tetramethyl-1,3,2-dioxaborolan-2-yl)benzonitrile. LC-MS (Method G): m/z=322.1 $[M+H]^+$; 3.69 min. $^1$H-NMR (400 MHz, DMSO): δ 9.39 (s, 1H), 9.08 (s, 1H), 8.83 (s, 1H), 7.94 (d, J=5.6, 1H), 7.22 (d, J=3.5, 1H), 6.52 (s, 1H), 5.49 (m, 1H), 3.76 (m, 2H), 3.54 (m, 3H), 2.10 (m, 2H), 1.71 (m, 2H).

Example 157

3-(1-Methylindolin-4-yl)-4-(tetrahydro-2H-pyran-4-yloxy)-1H-pyrazolo[4,3-c]pyridine

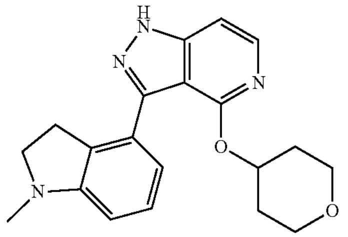 [SMILES: CN1CCc2c(-c3n[nH]c4ccnc(OC5CCOCC5)c34)cccc21]

The title compound was prepared by the procedure described in Example 149, by substituting quinolin-5-ylboronic acid with 1-methyl-1H-indol-4-ylboronic acid. LC-MS (Method G): m/z=351.1 $[M+H]^+$; 3.22 min. $^1$H-NMR (400 MHz, DMSO): δ 13.42 (s, 1H), 7.86 (d, J=4.9, 1H), 7.11 (s, 2H), 6.99 (d, J=7.5, 1H), 6.57 (d, J=7.7, 1H), 5.44 (m, 1H), 3.61 (m, 2H), 3.46 (m, 2H), 3.24 (m, 2H), 2.94 (m, 2H), 1.94 (m, 2H), 1.56 (m, 2H).

Example 158

3-(1H-Indol-4-yl)-4-(tetrahydro-2H-pyran-4-yloxy)-1H-pyrazolo[4,3-c]pyridine

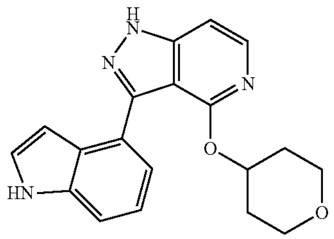 [SMILES: c1cc(-c2n[nH]c3ccnc(OC4CCOCC4)c23)c2cc[nH]c2c1]

The title compound was prepared by the procedure described in Example 149, by substituting quinolin-5-ylboronic acid with indole-4-boronic acid. LC-MS (Method G): m/z=355.1 $[M+H]^+$; 3.39 min. $^1$H-NMR (400 MHz, DMSO): δ 13.48 (s, 1H), 11.14 (s, 1H), 7.87 (d, J=5.3, 1H), 7.53 (d, J=7.1, 1H), 7.46 (d, J=7.9, 1H), 7.36 (s, 1H), 7.16 (m, 2H), 6.64 (s, 1H), 5.44 (m, 1H), 3.55 (m, 2H), 3.43 (m, 2H), 1.93 (m, 2H), 1.54 (m, 2H).

Example 159

3-(1H-Pyrrolo[2,3-b]pyridin-5-yl)-4-(tetrahydro-2H-pyran-4-yloxy)-1H-pyrazolo[4,3-c]pyridine

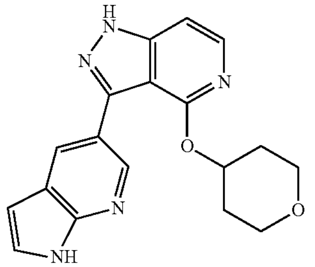 [SMILES: c1cc2[nH]nc(-c3cnc4[nH]ccc4c3)c2c(OC2CCOCC2)n1]

The title compound was prepared by the procedure described in example 149, by substituting quinolin-5-ylboronic acid with 1H-pyrrolo[2,3-b]pyridin-5-ylboronic acid. LC-MS (Method G): m/z=366.1 [M+H]$^+$; 3.26 min. $^1$H-NMR (400 MHz, DMSO): δ 13.49 (s, 1H), 11.73 (s, 1H), 8.77 (s, 1H), 8.50 (s, 1H), 7.89 (d, J=5.4, 1H), 7.52 (s, 1H), 7.14 (d, J=5.8, 1H), 6.52 (s, 1H), 5.52 (m, 1H), 3.72 (m, 2H), 3.51 (m, 2H), 2.04 (m, 2H), 1.68 (m, 2H).

Example 160

N-Methyl-3-(4-(tetrahydro-2H-pyran-4-yloxy)-1H-pyrazolo[4,3-c]pyridin-3-yl)benzamide

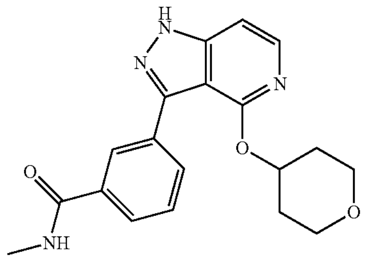 [SMILES: CNC(=O)c1cccc(-c2n[nH]c3ccnc(OC4CCOCC4)c23)c1]

The title compound was prepared by the procedure described in Example 149, by substituting quinolin-5-ylboronic acid with 3-(methylcarbamoyl)phenylboronic acid. LC-MS (Method G): m/z=353.1 [M+H]$^+$; 3.25 min. $^1$H-NMR (400 MHz, DMSO): δ 13.60 (s, 1H), 8.46 (d, J=13, 2H), 8.08 (d, J=7.5, 1H), 7.87 (m, 2H), 7.56 (t, J=7.7, 1H), 7.15 (d, J=5.9, 1H), 5.48 (m, 1H), 3.67 (m, 2H), 3.48 (m, 2H), 2.81 (m, 3H), 2.01 (m, 2H), 1.70 (m, 2H).

Example 161

4-(3-(4-(Tetrahydro-2H-pyran-4-yloxy)-1H-pyrazolo[4,3-c]pyridin-3-yl)benzyl)morpholine

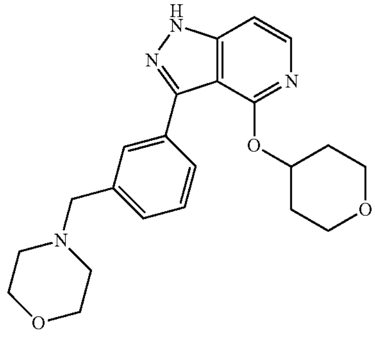 [SMILES: c1cc(CN2CCOCC2)cc(-c2n[nH]c3ccnc(OC4CCOCC4)c23)c1]

The title compound was prepared by the procedure described in Example 149, by substituting quinolin-5-ylboronic acid with 3-(morpholinomethyl)phenylboronic acid. LC-MS (Method G): m/z=395.1 [M+H]$^+$; 3.10 min. $^1$H-NMR (400 MHz, DMSO): δ 13.51 (s, 1H), 7.96 (m, 1H), 7.87 (m, 2H), 7.42 (m, 1H), 7.36 (m, 1H), 7.13 (m, 1H), 5.49 (m, 1H), 3.77 (m, 2H), 3.59 (m, 5H), 3.53 (m, 5H), 2.40 (m, 4H), 2.05 (m, 2H), 1.71 (m, 2H).

Example 162

N-(2-methoxypyridin-4-yl)-4-(tetrahydro-2H-pyran-4-yloxy)-1H-pyrazolo[4,3-c]pyridin-3-amine

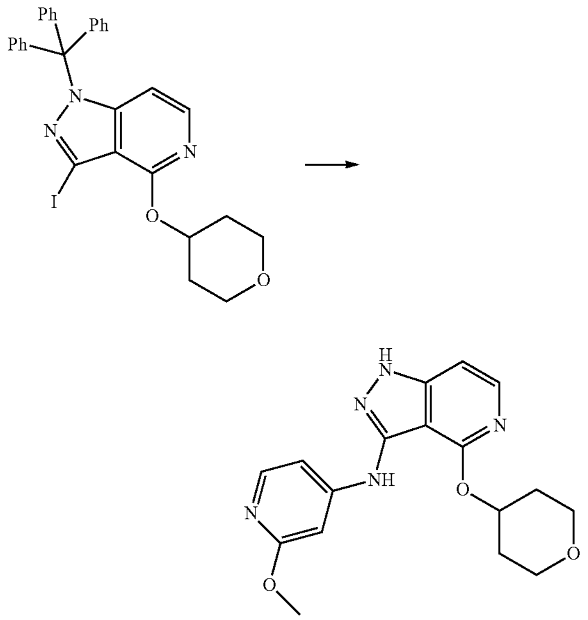 [SMILES: Ic1nn(C(c2ccccc2)(c2ccccc2)c2ccccc2)c2ccnc(OC3CCOCC3)c12 ; COc1cc(Nc2n[nH]c3ccnc(OC4CCOCC4)c23)ccn1]

To a microwave tube was added 3-iodo-4-(tetrahydro-2H-pyran-4-yloxy)-1-trityl-1H-pyrazolo[4,3-c]pyridine (260 mg, 0.44 mmol), 4-amino-2-methoxy-pyridine (66 mg, 0.53 mmol), cesium carbonate (0.29 g, 0.88 mmol), XPhos (21 mg, 0.044 mmol), and tris(dibenzylideneacetone)dipalladium (20 mg, 0.022 mmol). The tube was then flushed with nitrogen for 1 minute before the addition of 1,4-dioxane (2.5 mL). The tube was sealed and irradiated in the microwave at 140° C. for 35 minutes. The reaction mixture was filtered through Celite® and concentrated. The crude material was filtered through a silica gel column (EtOAc) and concentrated. To the residue was added DCM (3 mL), triethylsilane (0.1 mL, 0.63 mmol) and trifluoroacetic acid (0.50 mL, 6.5 mmol). The mixture was stirred at room temperature for 15 minutes before concentrated under vacuum. The crude material was purified by reverse phase HPLC to give the title compound (11 mg, 7.3% over 2 steps). LC-MS (Method G): m/z=342.1 [M+H]$^+$, 2.94 min. $^1$H-NMR (400 MHz, DMSO): δ 12.78 (s, 1H), 8.26 (s, 1H), 7.90 (d, J=5.6, 1H), 7.81 (d, J=6.0, 1H), 6.99 (d, J=6.0, 1H), 6.90 (d, J=5.4, 1H), 6.86 (s, 1H), 5.39 (m, 1H), 3.80 (m, 5H), 3.50 (m, 2H), 1.99 (m, 2H), 1.76 (m, 2H).

Example 163

N-(Pyridin-4-yl)-4-(tetrahydro-2H-pyran-4-yloxy)-1H-pyrazolo[4,3-c]pyridin-3-amine

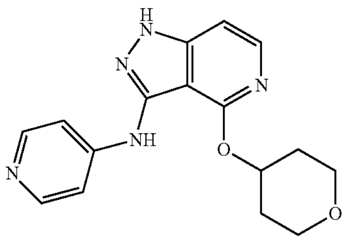 [SMILES: c1cc(Nc2n[nH]c3ccnc(OC4CCOCC4)c23)ccn1]

The title compound was prepared by the procedure described in Example 162, by substituting 4-amino-2-methoxy-pyridine with 4-aminopyridine. LC-MS (Method G): m/z=312.1 $[M+H]^+$, 2.68 min. $^1$H-NMR (400 MHz, DMSO): δ 12.79 (s, 1H), 8.23-8.34 (m, 3H), 7.82 (d, J=6.1, 1H), 7.31 (d, J=6.2, 2H), 7.00 (d, J=6.1, 1H), 5.39 (m, 1H), 3.78 (m, 2H), 3.49 (m, 2H), 1.75 (m, 2H).

Example 164

N-(1-Isopropyl-1H-pyrazol-4-yl)-4-(tetrahydro-2H-pyran-4-yloxy)-1H-pyrazolo[4,3-c]pyridin-3-amine

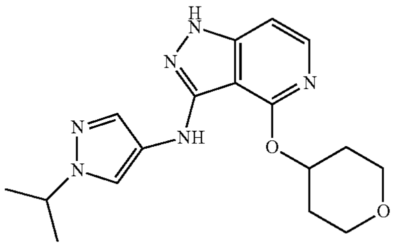 [SMILES: CC(C)n1cc(Nc2n[nH]c3ccnc(OC4CCOCC4)c23)cn1]

The title compound was prepared by the procedure described in Example 162, by substituting 4-amino-2-methoxy-pyridine with 1-isopropyl-4-aminopyrazole. LC-MS (Method G): m/z=343.1 $[M+H]^+$, 3.30 min. $^1$H-NMR (400 MHz, DMSO): δ 12.13 (s, 1H), 7.92 (s, 1H), 7.74 (d, J=6.1, 1H), 7.59 (s, 1H), 7.26 (s, 1H), 6.86 (d, J=6.1, 1H), 5.42 (m, 1H), 4.45 (m, 1H), 3.93 (m, 2H), 3.52 (m, 2H), 2.04 (m, 2H), 1.91 (m, 2H), 4.41 (d, J=6.7, 6H).

Example 165

3-(3-(Methylsulfonyl)phenyl)-4-(tetrahydro-2H-pyran-4-yloxy)-1H-pyrazolo[4,3-c]pyridine

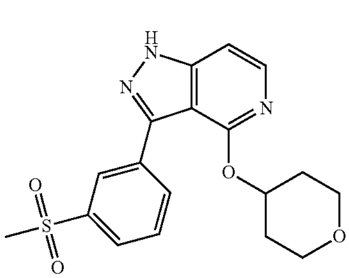 [SMILES: CS(=O)(=O)c1cccc(-c2n[nH]c3ccnc(OC4CCOCC4)c23)c1]

Prepared according to the general procedure described in Example 149, by reacting 3-iodo-4-(tetrahydro-2H-pyran-4-yloxy)-1-trityl-1H-indazole with 3-(methylsulfonyl)phenylboronic acid to give the title compound (31.8 mg, 44% over two steps). LC-MS (Method G): m/z=374.1 $[M+H]^+$, 3.53 min. $^1$H-NMR (400 MHz, DMSO): δ 13.70 (s, 1H), 8.49 (s, 1H), 8.34 (d, J=7.9, 1H), 7.99 (d, J=8.0, 1H), 7.92 (d, J=6.0, 1H), 7.81-7.75 (m, 1H), 7.18 (d, J=6.0, 1H), 5.54-5.44 (m, 1H), 3.80-3.70 (m, 2H), 3.53-3.44 (m, 3H), 3.27 (s, 3H), 2.08-1.99 (m, 2H), 1.83-1.70 (m, 2H).

Example 166

3-(4-(Methylsulfonyl)phenyl)-4-(tetrahydro-2H-pyran-4-yloxy)-1H-pyrazolo[4,3-c]pyridine

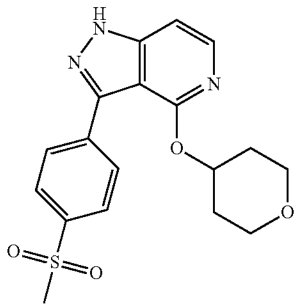 [SMILES: CS(=O)(=O)c1ccc(-c2n[nH]c3ccnc(OC4CCOCC4)c23)cc1]

Prepared according to the general procedure described in Example 149, by reacting 3-iodo-4-3-iodo-4-(tetrahydro-2H-pyran-4-yloxy)-1-trityl-1H-indazole with 4-(methylsulfonyl)phenylboronic acid to give the title compound (32.3 mg, 45% over two steps). LC-MS (Method G): m/z=374.1 $[M+H]^+$, 3.54 min. $^1$H-NMR (400 MHz, DMSO): δ 13.78 (s, 1H), 8.27 (d, J=8.4, 2H), 8.07-8.00 (m, 2H), 7.92 (d, J=6.0, 1H), 7.18 (d, J=6.0, 1H), 5.54-5.44 (m, 1H), 3.83-3.72 (m, 2H), 3.57-3.48 (m, 2H), 3.28 (s, 3H), 2.13-2.03 (m, 2H), 1.82-1.67 (m, 2H).

Example 167

4-Methoxy-3-(3-(methylsulfonyl)phenyl)-1H-pyrazolo[4,3-c]pyridine

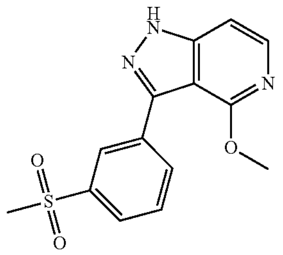

Prepared according to the general procedure described in Example 149, by reacting 3-iodo-4-methoxy-1-trityl-1H-indazole with 3-(methylsulfonyl)phenylboronic acid to give the title compound (35.7 mg, 61% over two steps). LC-MS (Method G): m/z=304.0 $[M+H]^+$, 3.32 min. $^1$H-NMR (400 MHz, DMSO): δ 13.75 (s, 1H), 8.60 (s, 1H), 8.32 (d, J=7.9, 1H), 7.99-7.92 (m, 2H), 7.77 (t, J=7.8, 1H), 7.20 (d, J=6.0, 1H), 4.02 (s, 3H), 3.28 (s, 3H).

Example 168

3-(5-Isopropyl-4H-1,2,4-triazol-3-yl)-N-(tetrahydro-2H-pyran-4-yl)-1H-pyrazolo[4,3-c]pyridin-4-amine

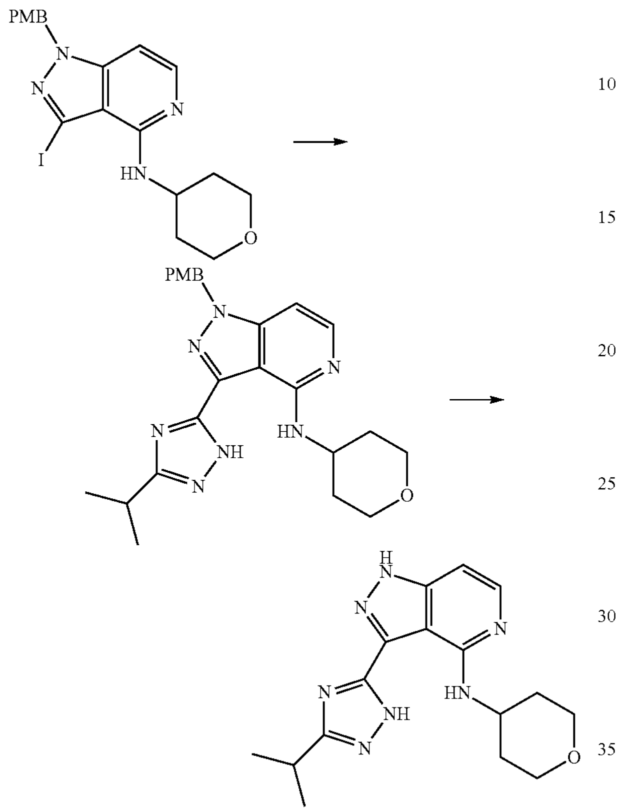

Step 1—3-(3-Isopropyl-1H-1,2,4-triazol-5-yl)-1-(4-methoxybenzyl)-N-(tetrahydro-2H-pyran-4-yl)-1H-pyrazolo[4,3-c]pyridin-4-amine To a round-bottomed flask was charged 3-iodo-4-(tetrahydro-2H-pyran-4-yloxy)-1-trityl-1H-pyrazolo[4,3-c]pyridine (0.200 g, 0.431 mmol), isopropylcarbamidine hydrochloride (0.0792 g, 0.646 mmol), palladium acetate (0.0048 g, 0.0215 mmol) and 4,5-bis(diphenylphosphino)-9,9-dimethylxanthene (0.0125 g, 0.0215 mmol). N,N-dimethylformamide (3.4 mL, 44 mmol) and triethylamine (0.40 mL, 2.9 mmol) were added via syringe and nitrogen was bubbled through the mixture for 5 mins. A carbon monoxide balloon was added and carbon monoxide was bubbled through the mixture for 2 mins. The reaction was heated to 80° C. for 2.5 hours. The carbon monoxide balloon was removed and replaced with a nitrogen balloon and the reaction mixture was cooled to room temperature, then 0° C. Acetic acid (2 mL, 30 mmol) and hydrazine hydrate (0.07 mL, 1 mmol) and the reaction was stirred at 0° C. for 5 minutes then warmed to room temperature for 1 hour. Upon reaction completion, the reaction mixture was diluted with 40 mL EtOAc, washed with 1 N NaOH (aq) and brine. Dried over sodium sulfate, filtered and concentrated in vacuo to give the crude product.

Step 2—3-(5-Isopropyl-4H-1,2,4-triazol-3-yl)-N-(tetrahydro-2H-pyran-4-yl)-1H-pyrazolo[4,3-c]pyridin-4-amine Crude 3-(3-isopropyl-1H-1,2,4-triazol-5-yl)-1-(4-methoxybenzyl)-N-(tetrahydro-2H-pyran-4-yl)-1H-pyrazolo[4,3-c]pyridin-4-amine from Step 1 was dissolved in trifluoroacetic acid (2.5 mL, 180 mmol) and the reaction mixture was heated to 75° C. for 16 hours, then heated to 95° C. for hours. At this point, trifluoromethanesulfonic acid (1 mL) was added and the reaction mixture was heated to 95° C. for 10 minutes. Upon reaction completion, the reaction mixture was diluted with dichloromethane and quenched by slow addition of sat. aq. solution of sodium bicarbonate until basic. The organic layer was separated and the aqueous layer was extracted with dichloromethane. The combined organics were dried over sodium sulfate, filtered and concentrated in vacuo. The crude residue was purified by reverse-phase HPLC to give the title compound (46.6 mg, 33% over two steps). LC-MS (Method G): m/z=328.1 $[M+H]^+$, 3.03 min. $^1$H-NMR (400 MHz, DMSO): δ 14.27 (s, 1H), 13.46 (s, 1H), 9.62 (s, 1H), 7.76 (d, J=6.0, 1H), 6.64 (d, J=6.0, 1H), 4.40-4.24 (m, 1H), 3.98-3.87 (m, 2H), 3.49 (t, J=10.5, 2H), 3.20-3.06 (m, 1H), 2.09-1.97 (m, 2H), 1.64-1.46 (m, 2H), 1.36 (d, J=6.9, 2H).

Example 169

N-(1-Methyl-1H-pyrazol-4-yl)-4-(tetrahydro-2H-pyran-4-yloxy)-1H-pyrazolo[4,3-c]pyridin-3-amine

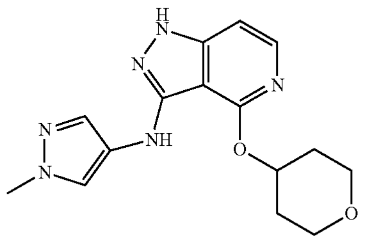 [SMILES: Cn1cc(Nc2n[nH]c3ccnc(OC4CCOCC4)c23)cn1]

The title compound was prepared according to the general procedure described in Example 162, using 1-methyl-4-aminopyrazole. LC-MS (Method G): m/z=315.1 $[M+H]^+$, 2.88 min. $^1$H-NMR (400 MHz, DMSO): δ 12.14 (s, 1H), 7.90 (s, 1H), 7.74 (d, J=6.1, 1H), 7.54 (s, 1H), 7.29 (s, 1H), 6.86 (d, J=6.1, 1H), 5.37-5.50 (m, 1H), 3.91 (m, 2H), 3.80 (m, 3H), 3.51 (m, 4H), 2.05 (m, 2H), 1.88 (m, 2H).

Example 170

3-Phenoxy-N-(tetrahydro-2H-pyran-4-yl)-1H-pyrazolo[4,3-c]pyridin-4-amine

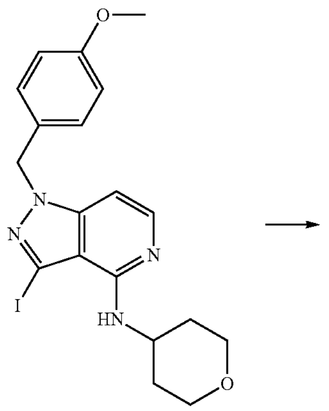

-continued

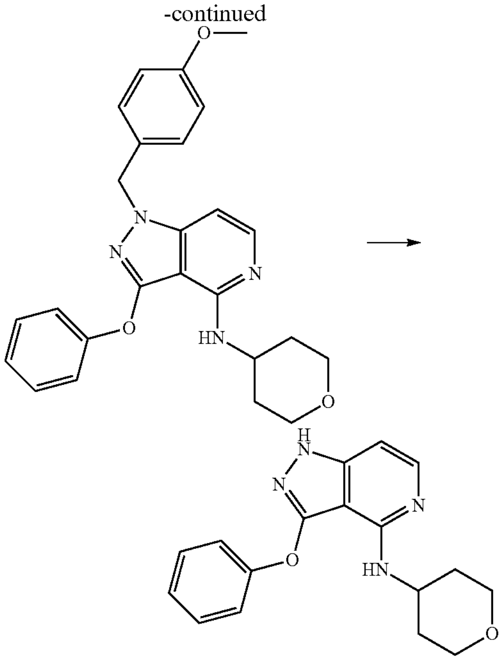

Step 1—1-(4-Methoxybenzyl)-3-phenoxy-N-(tetrahydro-2H-pyran-4-yl)-1H-pyrazolo[4,3-c]pyridin-4-amine To a pressure tube was added 3-iodo-1-(4-methoxybenzyl)-N-(tetrahydro-2H-pyran-4-yl)-1H-pyrazolo[4,3-c]pyridin-4-amine (0.60 g, 1.3 mmol), phenol (0.36 g, 3.9 mmol), Cu(I) iodide (25 mg, 0.13 mmol), caesium carbonate (1.3 g, 0.39 mol), N,N-dimethylglycine (33 mg, 0.32 mmol) and 1,4-dioxane (3.0 mL). The tube was flushed with nitrogen, sealed, and stirred at 120° C. for 24 hours. The reaction mixture was cooled, filtered and concentrated under reduced pressure. The residue was re-dissolved in ethyl acetate, filtered through a pad of silica gel, and concentrated to give crude 1-(4-methoxybenzyl)-3-phenoxy-N-(tetrahydro-2H-pyran-4-yl)-1H-pyrazolo[4,3-c]pyridin-4-amine which was used directly in the following step.

Step 2—3-Phenoxy-N-(tetrahydro-2H-pyran-4-yl)-1H-pyrazolo[4,3-c]pyridin-4-amine

The crude 1-(4-methoxybenzyl)-3-phenoxy-N-(tetrahydro-2H-pyran-4-yl)-1H-pyrazolo[4,3-c]pyridin-4-amine from step 1 was added to methylene chloride (5 mL) and trifluoromethanesulfonic acid (0.5 mL), and the resulting mixture was stirred at room temperature for two hours. The mixture was concentrated under reduced pressure and the residue was purified by reverse phase HPLC to give 3-phenoxy-N-(tetrahydro-2H-pyran-4-yl)-1H-pyrazolo[4,3-c]pyridin-4-amine: LC-MS (Method G): m/z=311.1; $^1$H NMR (400 MHz, DMSO): δ 12.43 (s, 1H), 7.73 (d, J=6.1, 1H), 7.42 (t, J=7.9, 2H), 7.26 (d, J=8.0, 2H), 7.19 (t, J=7.3, 1H), 6.60 (d, J=6.1, 1H), 5.43 (d, J=7.7, 1H), 4.19 (m, 1H), 3.79 (d, J=11.6, 2H, 1.83 (d, J=12.4, 2H), 1.43 (m, 2H).

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

References

1 Paisan-Ruiz, C., Jain, S., Evans, E. W., Gilks, W. P., Simon, J., van der Brug, M., Lopez de Munain, A., Aparicio, S., Gil, A. M., Khan, N., Johnson, J., Martinez, J. R., Nicholl, D., Carrera, I. M., Pena, A. S., de Silva, R., Lees, A., Marti-Masso, J. F., Perez-Tur, J., Wood, N. W. and Singleton, A. B. (2004) Cloning of the gene containing mutations that cause PARKS-linked Parkinson's disease. Neuron. 44, 595-600

2 Mata, I. F., Wedemeyer, W. J., Farrer, M. J., Taylor, J. P. and Gallo, K. A. (2006) LRRK2 in Parkinson's disease: protein domains and functional insights. Trends Neurosci. 29, 286-293

3 Taylor, J. P., Mata, I. F. and Farrer, M. J. (2006) LRRK2: a common pathway for parkinsonism, pathogenesis and prevention? Trends Mol. Med. 12, 76-82

4 Farrer, M., Stone, J., Mata, I. F., Lincoln, S., Kachergus, J., Hulihan, M., Strain, K. J. and Maraganore, D. M. (2005) LRRK2 mutations in Parkinson disease. Neurology. 65, 738-740

5 Zabetian, C. P., Samii, A., Mosley, A. D., Roberts, J. W., Leis, B. C., Yearout, D., Raskind, W. H. and Griffith, A. (2005) A clinic-based study of the LRRK2 gene in Parkinson disease yields new mutations. Neurology. 65, 741-744

6 Bosgraaf, L. and Van Haastert, P. J. (2003) Roc, a Ras/GTPase domain in complex proteins. Biochim Biophys Acta. 1643, 5-10

7 Marin, I. (2006) The Parkinson disease gene LRRK2: evolutionary and structural insights. Mol Biol Evol. 23, 2423-2433

8 Manning, G., Whyte, D. B., Martinez, R., Hunter, T. and Sudarsanam, S. (2002) The protein kinase complement of the human genome. Science. 298, 1912-1934

9 West, A. B., Moore, D. J., Biskup, S., Bugayenko, A., Smith, W. W., Ross, C. A., Dawson, V. L. and Dawson, T. M. (2005) Parkinson's disease-associated mutations in leucine-rich repeat kinase 2 augment kinase activity. Proc Natl Acad Sci USA. 102, 16842-16847

10 Greggio, E., Jain, S., Kingsbury, A., Bandopadhyay, R., Lewis, P., Kaganovich, A., van der Brug, M. P., Beilina, A., Blackinton, J., Thomas, K. J., Ahmad, R., Miller, D. W., Kesavapany, S., Singleton, A., Lees, A., Harvey, R. J., Harvey, K. and Cookson, M. R. (2006) Kinase activity is required for the toxic effects of mutant LRRK2/dardarin. Neurobiol Dis. 23, 329-341

11 Jaleel, M., Nichols, R. J., Deak, M., Campbell, D. G., Gillardon, F., Knebel, A. and Alessi, D. R. (2007) LRRK2 phosphorylates moesin at threonine-558: characterization of how Parkinson's disease mutants affect kinase activity. Biochem J. 405, 307-317

12 Goldberg, J. M., Bosgraaf, L., Van Haastert, P. J. and Smith, J. L. (2002) Identification of four candidate cGMP targets in Dictyostelium. Proc Natl Acad Sci USA. 99, 6749-6754

13 Bosgraaf, L., Russcher, H., Smith, J. L., Wessels, D., Soll, D. R. and Van Haastert, P. J. (2002) A novel cGMP signalling pathway mediating myosin phosphorylation and chemotaxis in Dictyostelium. Embo J. 21, 4560-4570

14 Cohen, P. and Knebel, A. (2006) KESTREL: a powerful method for identifying the physiological substrates of protein kinases. Biochem J. 393, 1-6

15 Bretscher, A., Edwards, K. and Fehon, R. G. (2002) ERM proteins and merlin: integrators at the cell cortex. Nat Rev Mol Cell Biol. 3, 586-599

16 Polesello, C. and Payre, F. (2004) Small is beautiful: what flies tell us about ERM protein function in development. Trends Cell Biol. 14, 294-302

17 Nichols, R. J., Dzamko, N., Hutti, J. E., Cantley, L. C., Deak, M., Moran, J., Bamborough, P., Reith, A. D. and Alessi, D. R. (2009) Substrate specificity and inhibitors of LRRK2, a protein kinase mutated in Parkinson's disease. Biochem J. 424, 47-60

The invention claimed is:

1. A compound selected from the following:

| No. | Structure |
|---|---|
| 1 | 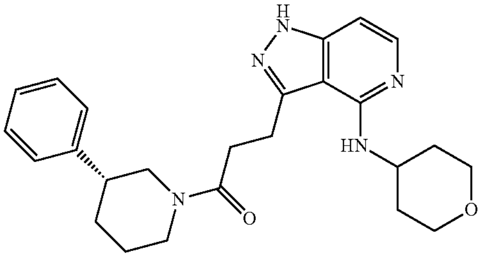 [SMILES: O=C(CCc1n[nH]c2ccnc(NC3CCOCC3)c12)N1CCC[C@H](c2ccccc2)C1] |
| 2 | 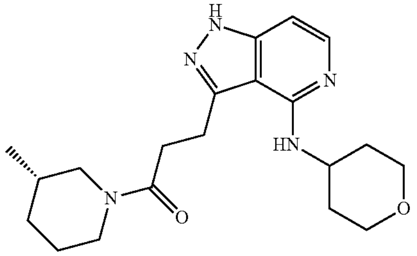 [SMILES: C[C@H]1CCCN(C(=O)CCc2n[nH]c3ccnc(NC4CCOCC4)c23)C1] |
| 3 | 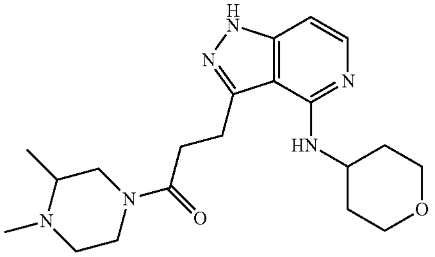 [SMILES: CC1CN(C(=O)CCc2n[nH]c3ccnc(NC4CCOCC4)c23)CCN1C] |
| 4 | 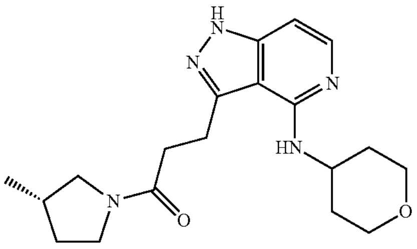 [SMILES: C[C@H]1CCN(C(=O)CCc2n[nH]c3ccnc(NC4CCOCC4)c23)C1] |

-continued

| No. | Structure |
|---|---|
| 5 | 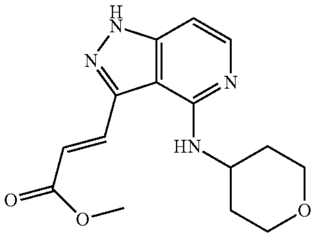 [SMILES: COC(=O)/C=C/c1n[nH]c2ccnc(NC3CCOCC3)c12] |
| 6 | 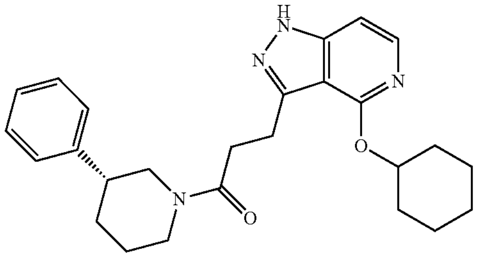 [SMILES: O=C(CCc1n[nH]c2ccnc(OC3CCCCC3)c12)N1CCC[C@H](c2ccccc2)C1] |
| 7 | 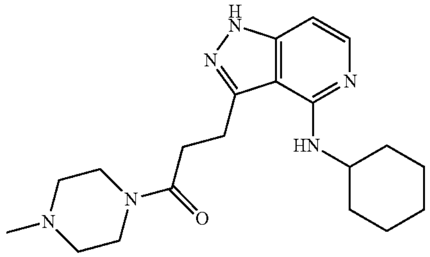 [SMILES: CN1CCN(C(=O)CCc2n[nH]c3ccnc(NC4CCCCC4)c23)CC1] |
| 8 | 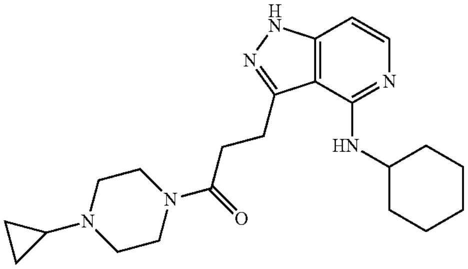 [SMILES: O=C(CCc1n[nH]c2ccnc(NC3CCCCC3)c12)N1CCN(C2CC2)CC1] |
| 9 | 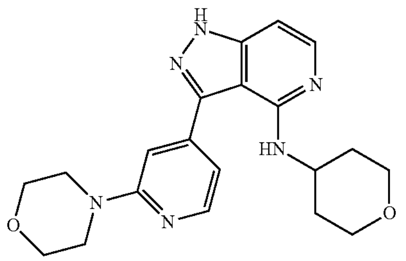 [SMILES: c1cc(-c2n[nH]c3ccnc(NC4CCOCC4)c23)cc(N2CCOCC2)n1] |
| 10 | 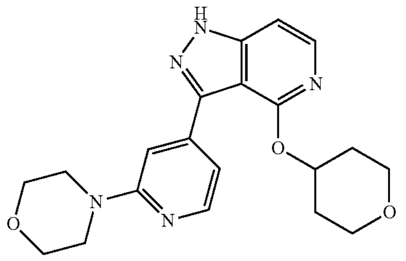 |

-continued
| No. | Structure |
|---|---|
| 11 | 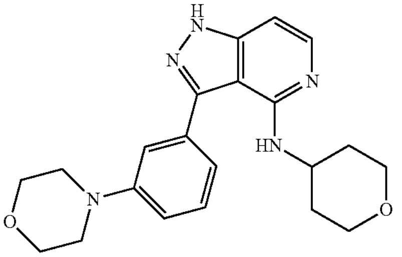 [SMILES: c1cc(-c2n[nH]c3ccnc(NC4CCOCC4)c23)cc(N2CCOCC2)c1] |
| 12 | 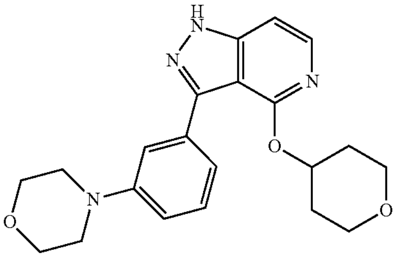 [SMILES: c1cc(-c2n[nH]c3ccnc(OC4CCOCC4)c23)cc(N2CCOCC2)c1] |
| 13 | 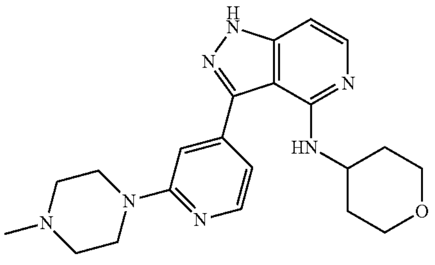 [SMILES: CN1CCN(c2cc(-c3n[nH]c4ccnc(NC5CCOCC5)c34)ccn2)CC1] |
| 14 | 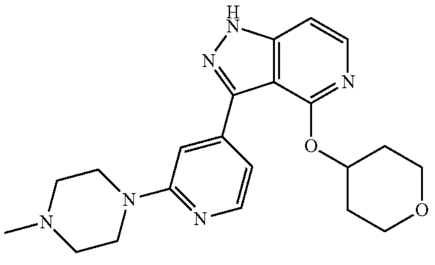 [SMILES: CN1CCN(c2cc(-c3n[nH]c4ccnc(OC5CCOCC5)c34)ccn2)CC1] |
| 15 | 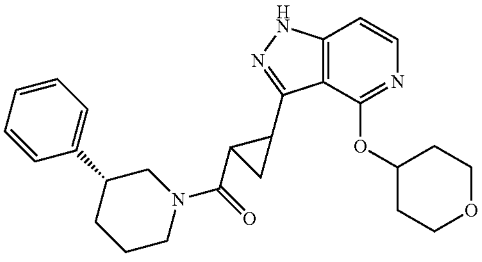 [SMILES: O=C(C1CC1c1n[nH]c2ccnc(OC3CCOCC3)c12)N1CCC[C@H](c2ccccc2)C1] |
| 16 | 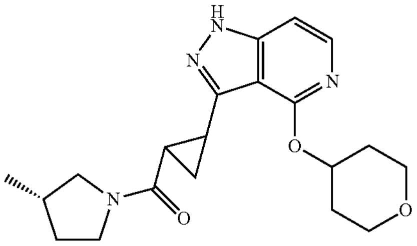 [SMILES: C[C@H]1CCN(C(=O)C2CC2c2n[nH]c3ccnc(OC4CCOCC4)c23)C1] |
-continued
| No. | Structure |
|---|---|
| 17 | 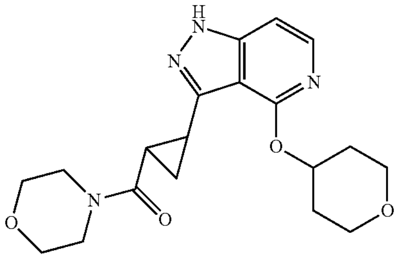 [SMILES: O=C(C1CC1c1n[nH]c2ccnc(OC3CCOCC3)c12)N1CCOCC1] |
| 18 | 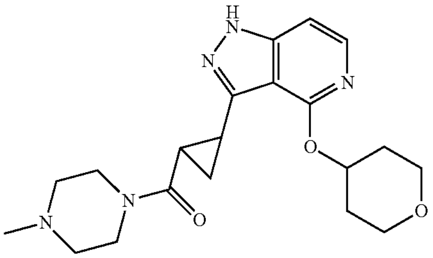 [SMILES: CN1CCN(C(=O)C2CC2c2n[nH]c3ccnc(OC4CCOCC4)c23)CC1] |
| 19 | 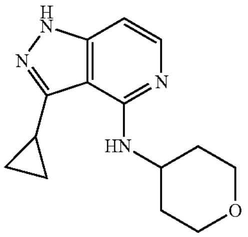 [SMILES: c1cc2[nH]nc(C3CC3)c2c(NC2CCOCC2)n1] |
| 20 | 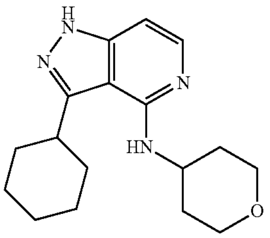 [SMILES: c1cc2[nH]nc(C3CCCCC3)c2c(NC2CCOCC2)n1] |
| 21 | 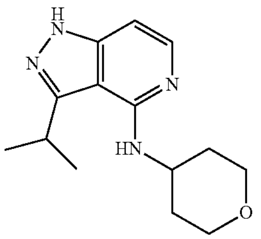 [SMILES: CC(C)c1n[nH]c2ccnc(NC3CCOCC3)c12] |
| 22 | 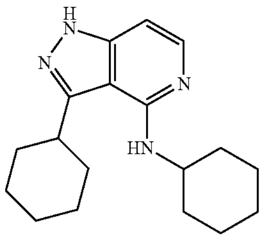 [SMILES: c1cc2[nH]nc(C3CCCCC3)c2c(NC2CCCCC2)n1] |

-continued
| No. | Structure |
|---|---|
| 23 | 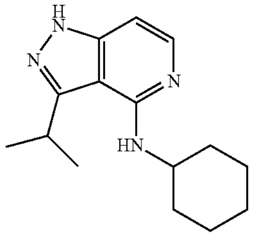 [SMILES: CC(C)c1n[nH]c2ccnc(NC3CCCCC3)c12] |
| 24 | 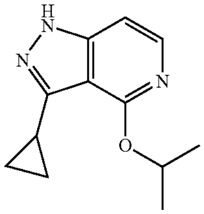 [SMILES: CC(C)Oc1nccc2[nH]nc(C3CC3)c12] |
| 25 | 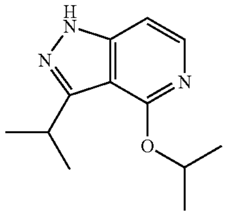 [SMILES: CC(C)Oc1nccc2[nH]nc(C(C)C)c12] |
| 26 | 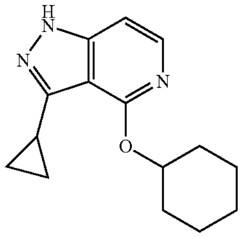 [SMILES: c1cc2[nH]nc(C3CC3)c2c(OC2CCCCC2)n1] |
| 27 | 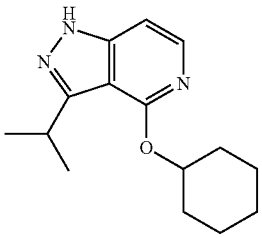 [SMILES: CC(C)c1n[nH]c2ccnc(OC3CCCCC3)c12] |
| 28 | 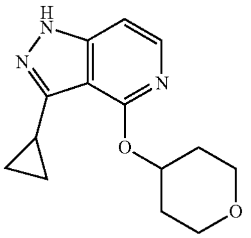 [SMILES: c1cc2[nH]nc(C3CC3)c2c(OC2CCOCC2)n1] |
-continued
| No. | Structure |
|---|---|
| 29 | 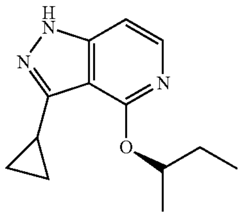 |
| 30 | 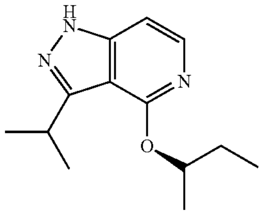 |
| 31 | 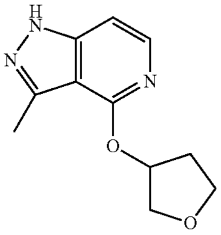 [SMILES: Cc1n[nH]c2ccnc(OC3CCOC3)c12] |
| 32 | 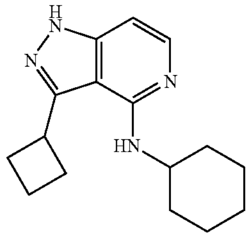 [SMILES: c1cc2[nH]nc(C3CCC3)c2c(NC2CCCCC2)n1] |
| 33 | 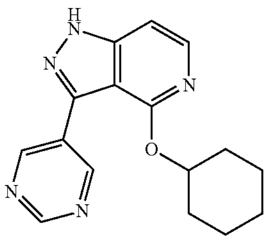 [SMILES: c1ncc(-c2n[nH]c3ccnc(OC4CCCCC4)c23)cn1] |
| 34 | 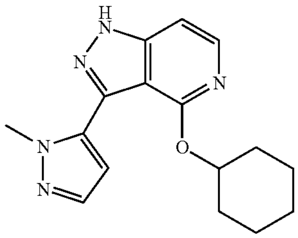 [SMILES: Cn1nccc1-c1n[nH]c2ccnc(OC3CCCCC3)c12] |

-continued
| No. | Structure |
|---|---|
| 35 | 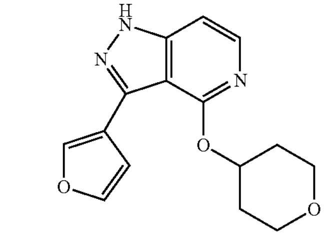 [SMILES: c1cc2[nH]nc(-c3ccoc3)c2c(OC2CCOCC2)n1] |
| 36 | 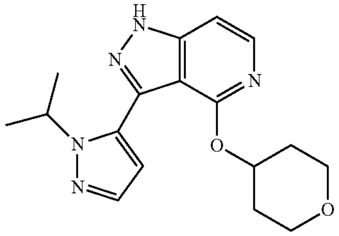 [SMILES: CC(C)n1nccc1-c1n[nH]c2ccnc(OC3CCOCC3)c12] |
| 37 | 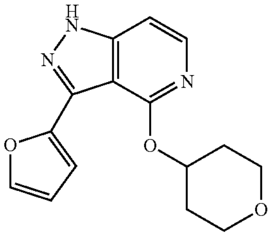 [SMILES: c1coc(-c2n[nH]c3ccnc(OC4CCOCC4)c23)c1] |
| 38 | 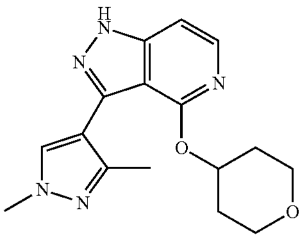 [SMILES: Cc1nn(C)cc1-c1n[nH]c2ccnc(OC3CCOCC3)c12] |
| 39 | 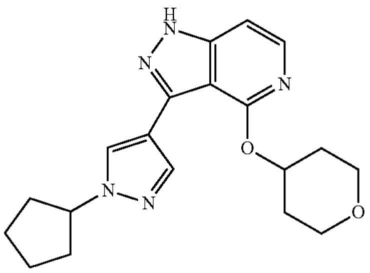 [SMILES: c1cc2[nH]nc(-c3cnn(C4CCCC4)c3)c2c(OC2CCOCC2)n1] |
| 40 | 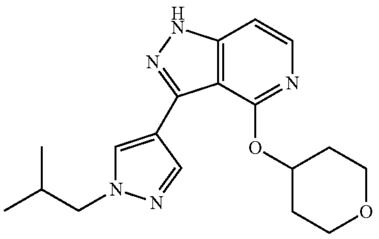 [SMILES: CC(C)Cn1cc(-c2n[nH]c3ccnc(OC4CCOCC4)c23)cn1] |
-continued
| No. | Structure |
|---|---|
| 41 | 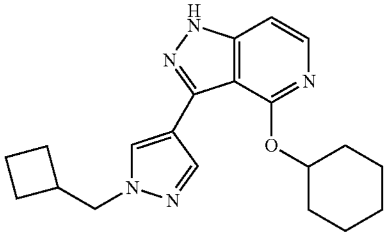 [SMILES: c1cc2[nH]nc(-c3cnn(CC4CCC4)c3)c2c(OC2CCCCC2)n1] |
| 42 | 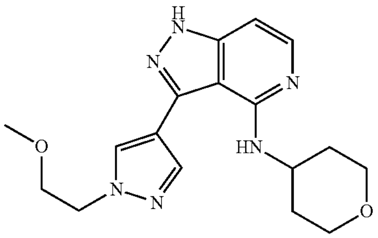 [SMILES: COCCn1cc(-c2n[nH]c3ccnc(NC4CCOCC4)c23)cn1] |
| 43 | 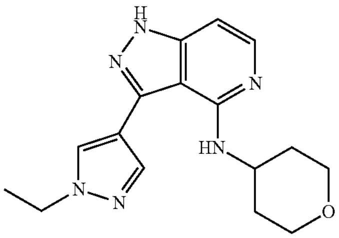 [SMILES: CCn1cc(-c2n[nH]c3ccnc(NC4CCOCC4)c23)cn1] |
| 44 | 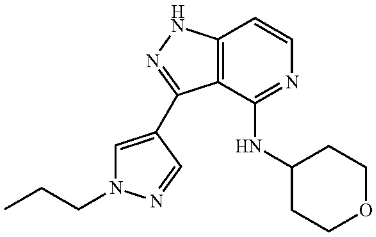 [SMILES: CCCn1cc(-c2n[nH]c3ccnc(NC4CCOCC4)c23)cn1] |
| 45 | 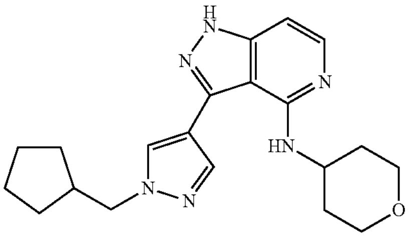 [SMILES: c1cc2[nH]nc(-c3cnn(CC4CCCC4)c3)c2c(NC2CCOCC2)n1] |
| 46 | 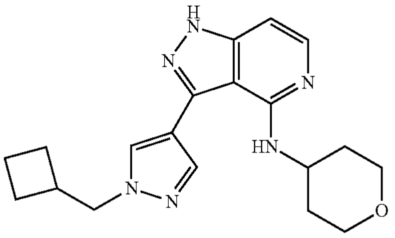 [SMILES: c1cc2[nH]nc(-c3cnn(CC4CCC4)c3)c2c(NC2CCOCC2)n1] |

-continued
| No. | Structure |
|---|---|
| 47 | 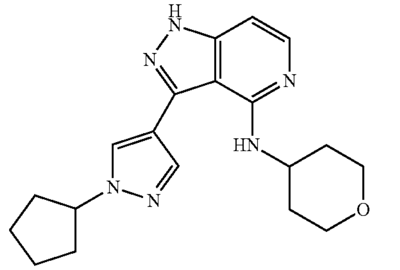 [SMILES: c1cc2[nH]nc(-c3cnn(C4CCCC4)c3)c2c(NC2CCOCC2)n1] |
| 48 | 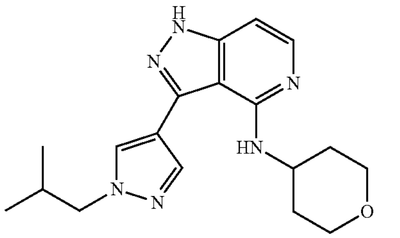 [SMILES: CC(C)Cn1cc(-c2n[nH]c3ccnc(NC4CCOCC4)c23)cn1] |
| 49 | 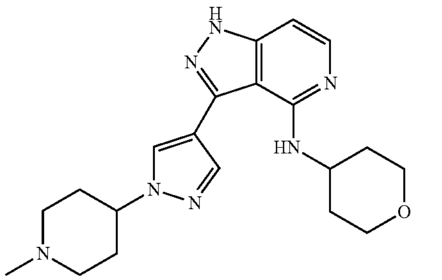 [SMILES: CN1CCC(n2cc(-c3n[nH]c4ccnc(NC5CCOCC5)c34)cn2)CC1] |
| 50 | 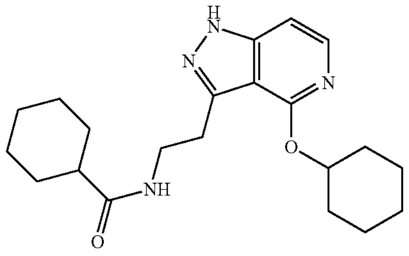 [SMILES: O=C(NCCc1n[nH]c2ccnc(OC3CCCCC3)c12)C1CCCCC1] |
| 51 | 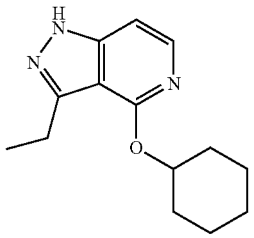 [SMILES: CCc1n[nH]c2ccnc(OC3CCCCC3)c12] |
| 52 | 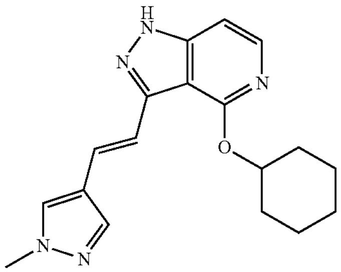 [SMILES: Cn1cc(/C=C/c2n[nH]c3ccnc(OC4CCCCC4)c23)cn1] |
-continued
| No. | Structure |
|---|---|
| 53 | 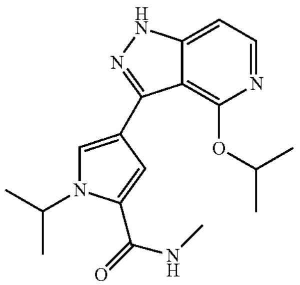 [SMILES: CNC(=O)c1cc(-c2n[nH]c3ccnc(OC(C)C)c23)cn1C(C)C] |
| 54 | 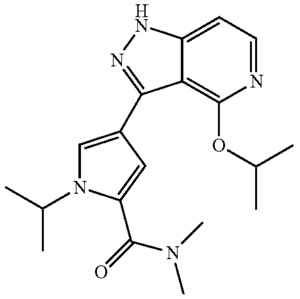 [SMILES: CC(C)Oc1nccc2[nH]nc(-c3cc(C(=O)N(C)C)n(C(C)C)c3)c12] |
| 55 | 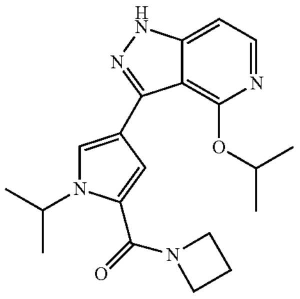 [SMILES: CC(C)Oc1nccc2[nH]nc(-c3cc(C(=O)N4CCC4)n(C(C)C)c3)c12] |
| 56 | 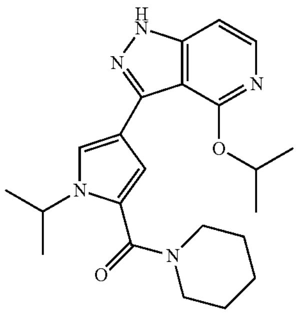 [SMILES: CC(C)Oc1nccc2[nH]nc(-c3cc(C(=O)N4CCCCC4)n(C(C)C)c3)c12] |
| 57 | 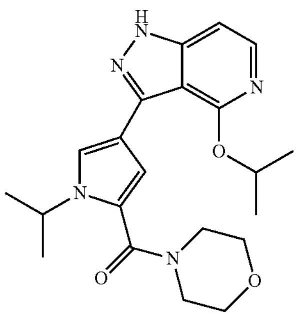 |

-continued
| No. | Structure |
| --- | --- |
| 58 | 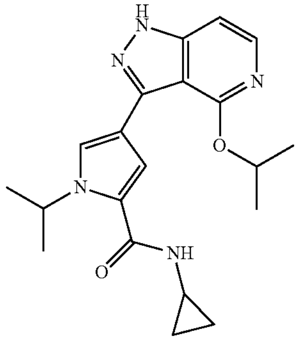 [SMILES: CC(C)Oc1nccc2[nH]nc(-c3cc(C(=O)NC4CC4)n(C(C)C)c3)c12] |
| 59 | 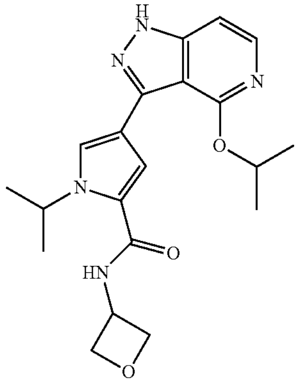 [SMILES: CC(C)Oc1nccc2[nH]nc(-c3cc(C(=O)NC4COC4)n(C(C)C)c3)c12] |
| 60 | 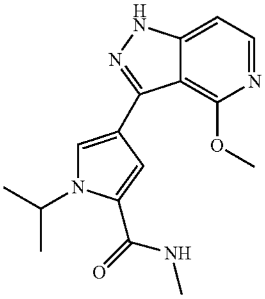 [SMILES: CNC(=O)c1cc(-c2n[nH]c3ccnc(OC)c23)cn1C(C)C] |
| 61 | 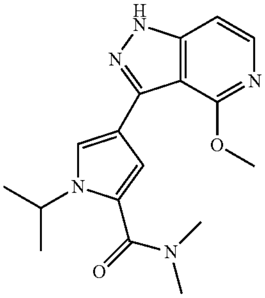 [SMILES: COc1nccc2[nH]nc(-c3cc(C(=O)N(C)C)n(C(C)C)c3)c12] |
| 62 | 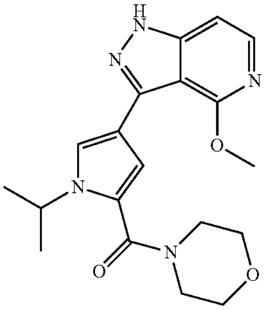 [SMILES: COc1nccc2[nH]nc(-c3cc(C(=O)N4CCOCC4)n(C(C)C)c3)c12] |
-continued
| No. | Structure |
| --- | --- |
| 63 | 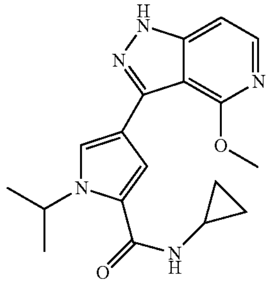 [SMILES: COc1nccc2[nH]nc(-c3cc(C(=O)NC4CC4)n(C(C)C)c3)c12] |
| 64 | 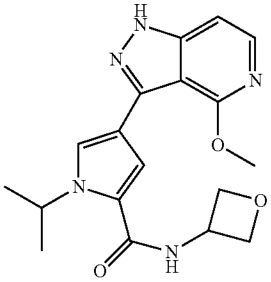 [SMILES: COc1nccc2[nH]nc(-c3cc(C(=O)NC4COC4)n(C(C)C)c3)c12] |
| 65 | 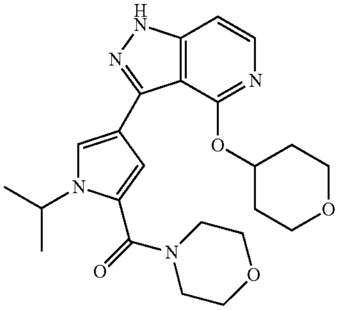 [SMILES: CC(C)n1cc(-c2n[nH]c3ccnc(OC4CCOCC4)c23)cc1C(=O)N1CCOCC1] |
| 66 | 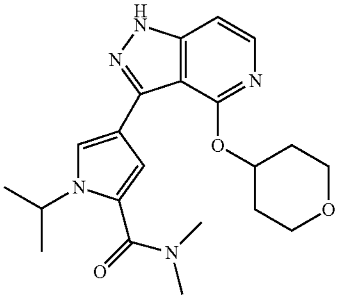 [SMILES: CC(C)n1cc(-c2n[nH]c3ccnc(OC4CCOCC4)c23)cc1C(=O)N(C)C] |
| 67 | 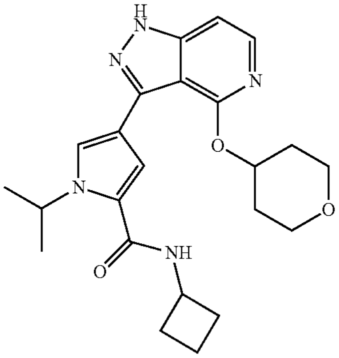 [SMILES: CC(C)n1cc(-c2n[nH]c3ccnc(OC4CCOCC4)c23)cc1C(=O)NC1CCC1] |

-continued
| No. | Structure |
|---|---|
| 68 | 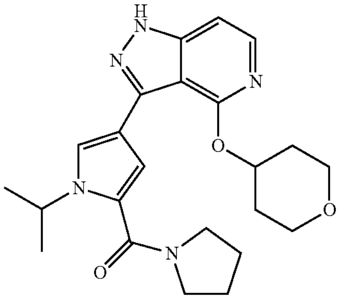 [SMILES: CC(C)n1cc(-c2n[nH]c3ccnc(OC4CCOCC4)c23)cc1C(=O)N1CCCC1] |
| 69 | 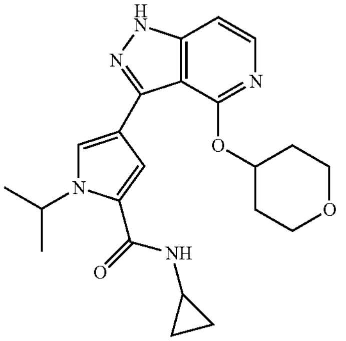 [SMILES: CC(C)n1cc(-c2n[nH]c3ccnc(OC4CCOCC4)c23)cc1C(=O)NC1CC1] |
| 70 | 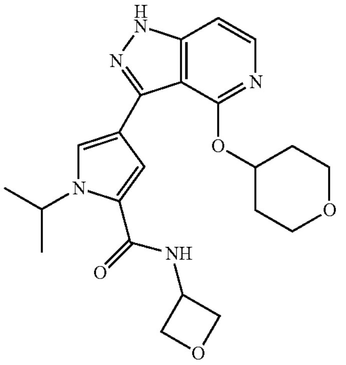 [SMILES: CC(C)n1cc(-c2n[nH]c3ccnc(OC4CCOCC4)c23)cc1C(=O)NC1COC1] |
| 71 | 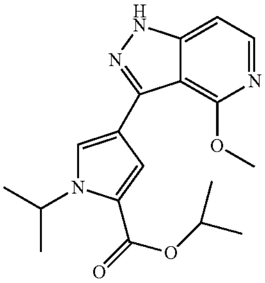 [SMILES: COc1nccc2[nH]nc(-c3cc(C(=O)OC(C)C)n(C(C)C)c3)c12] |
| 72 | 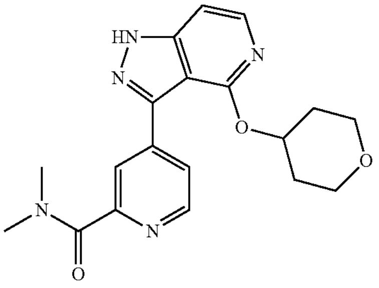 [SMILES: CN(C)C(=O)c1cc(-c2n[nH]c3ccnc(OC4CCOCC4)c23)ccn1] |
-continued
| No. | Structure |
|---|---|
| 73 | 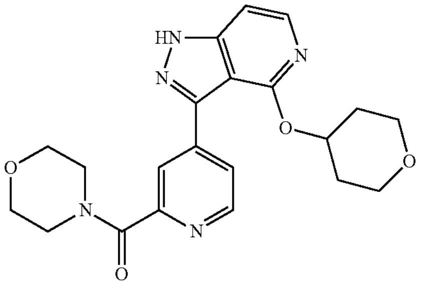 [SMILES: O=C(c1cc(-c2n[nH]c3ccnc(OC4CCOCC4)c23)ccn1)N1CCOCC1] |
| 74 | 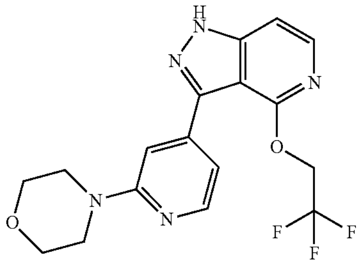 [SMILES: FC(F)(F)COc1nccc2[nH]nc(-c3ccnc(N4CCOCC4)c3)c12] |
| 75 | 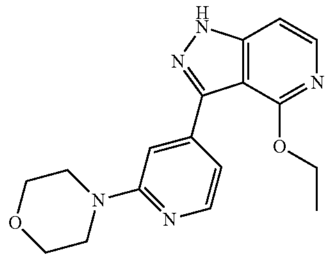 [SMILES: CCOc1nccc2[nH]nc(-c3ccnc(N4CCOCC4)c3)c12] |
| 76 | 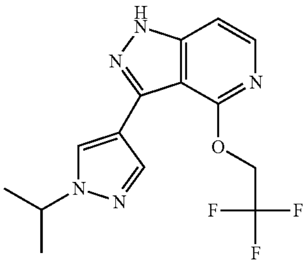 [SMILES: CC(C)n1cc(-c2n[nH]c3ccnc(OCC(F)(F)F)c23)cn1] |
| 77 | 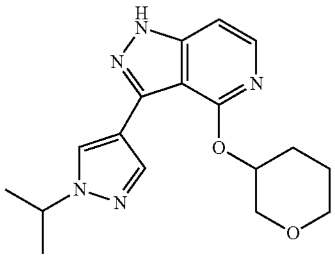 [SMILES: CC(C)n1cc(-c2n[nH]c3ccnc(OC4CCCOC4)c23)cn1] |

-continued
| No. | Structure |
| --- | --- |
| 78 | 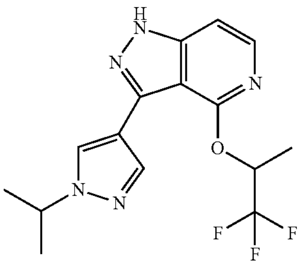 [SMILES: CC(C)n1cc(-c2n[nH]c3ccnc(OC(C)C(F)(F)F)c23)cn1] |
| 79 | 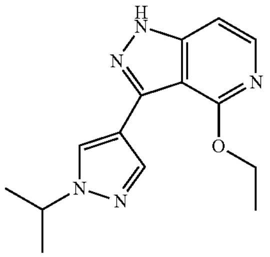 [SMILES: CCOc1nccc2[nH]nc(-c3cnn(C(C)C)c3)c12] |
| 80 | 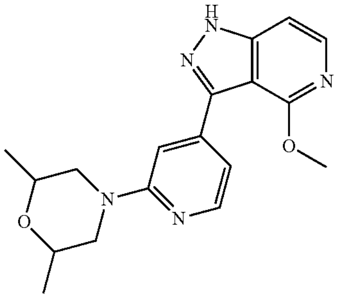 |
| 81 | 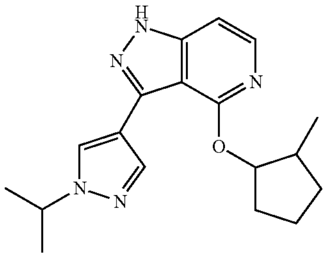 [SMILES: CC1CCCC1Oc1nccc2[nH]nc(-c3cnn(C(C)C)c3)c12] |
| 82 | 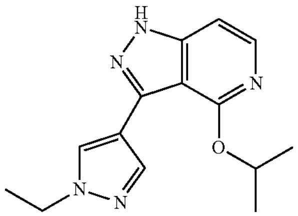 [SMILES: CCn1cc(-c2n[nH]c3ccnc(OC(C)C)c23)cn1] |
| 83 | 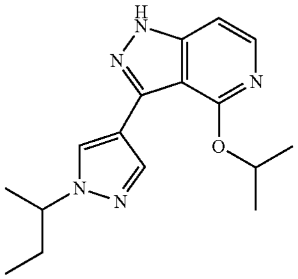 [SMILES: CCC(C)n1cc(-c2n[nH]c3ccnc(OC(C)C)c23)cn1] |
-continued
| No. | Structure |
| --- | --- |
| 84 | 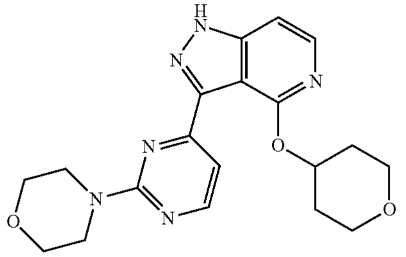 [SMILES: c1cc(-c2n[nH]c3ccnc(OC4CCOCC4)c23)nc(N2CCOCC2)n1] |
| 85 | 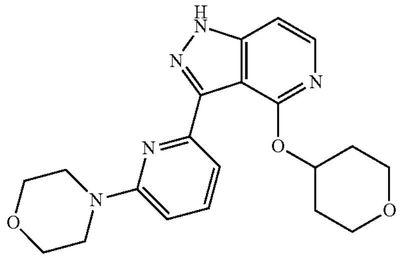 [SMILES: c1cc(-c2n[nH]c3ccnc(OC4CCOCC4)c23)nc(N2CCOCC2)c1] |
| 86 | 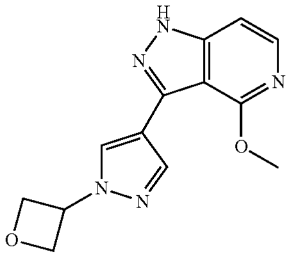 [SMILES: COc1nccc2[nH]nc(-c3cnn(C4COC4)c3)c12] |
| 87 | 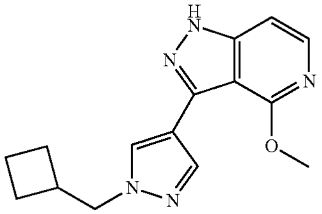 [SMILES: COc1nccc2[nH]nc(-c3cnn(CC4CCC4)c3)c12] |
| 88 | 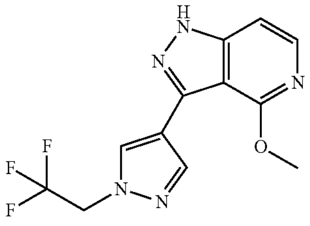 [SMILES: COc1nccc2[nH]nc(-c3cnn(CC(F)(F)F)c3)c12] |
| 89 | 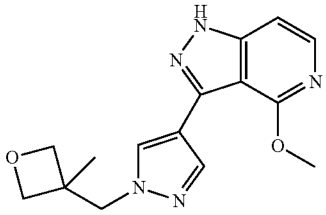 [SMILES: COc1nccc2[nH]nc(-c3cnn(CC4(C)COC4)c3)c12] |

-continued
| No. | Structure |
|---|---|
| 90 | 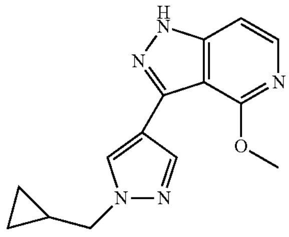 [SMILES: COc1nccc2[nH]nc(-c3cnn(CC4CC4)c3)c12] |
| 91 | 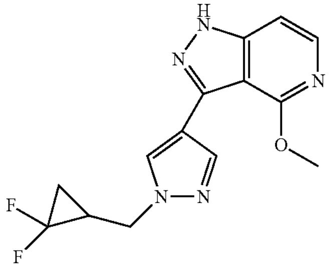 [SMILES: COc1nccc2[nH]nc(-c3cnn(CC4CC4(F)F)c3)c12] |
| 92 | 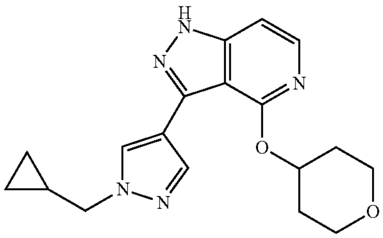 [SMILES: c1cc2[nH]nc(-c3cnn(CC4CC4)c3)c2c(OC2CCOCC2)n1] |
| 93 | 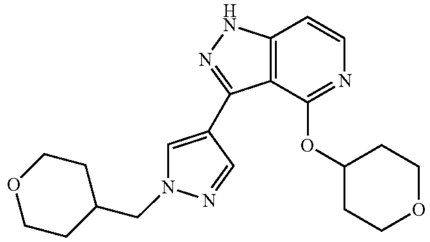 [SMILES: c1cc2[nH]nc(-c3cnn(CC4CCOCC4)c3)c2c(OC2CCOCC2)n1] |
| 94 | 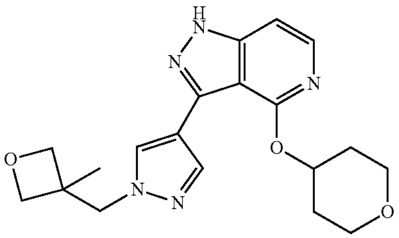 [SMILES: CC1(Cn2cc(-c3n[nH]c4ccnc(OC5CCOCC5)c34)cn2)COC1] |
| 95 | 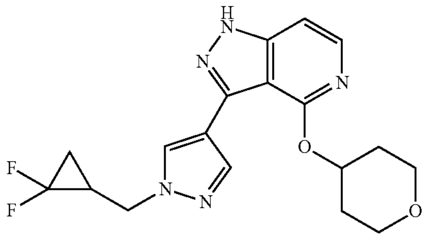 [SMILES: FC1(F)CC1Cn1cc(-c2n[nH]c3ccnc(OC4CCOCC4)c23)cn1] |
-continued
| No. | Structure |
|---|---|
| 96 | 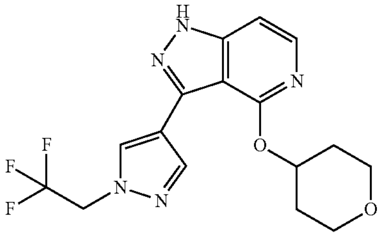 [SMILES: FC(F)(F)Cn1cc(-c2n[nH]c3ccnc(OC4CCOCC4)c23)cn1] |
| 97 | 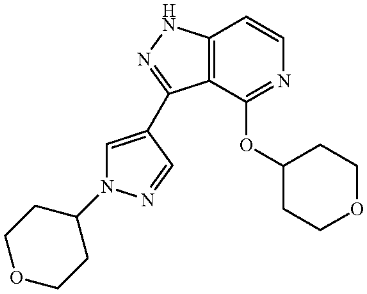 [SMILES: c1cc2[nH]nc(-c3cnn(C4CCOCC4)c3)c2c(OC2CCOCC2)n1] |
| 98 | 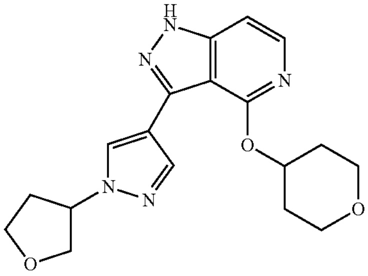 [SMILES: c1cc2[nH]nc(-c3cnn(C4CCOC4)c3)c2c(OC2CCOCC2)n1] |
| 99 | 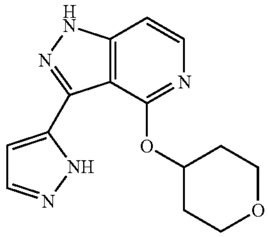 [SMILES: c1cc(-c2n[nH]c3ccnc(OC4CCOCC4)c23)[nH]n1] |
| 100 | 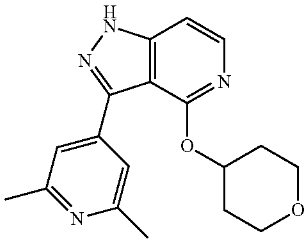 [SMILES: Cc1cc(-c2n[nH]c3ccnc(OC4CCOCC4)c23)cc(C)n1] |
| 101 | 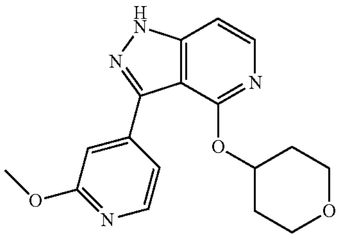 [SMILES: COc1cc(-c2n[nH]c3ccnc(OC4CCOCC4)c23)ccn1] |

-continued
| No. | Structure |
|---|---|
| 102 | 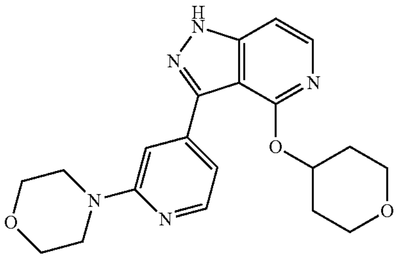 [SMILES: c1cc(-c2n[nH]c3ccnc(OC4CCOCC4)c23)cc(N2CCOCC2)n1] |
| 103 | 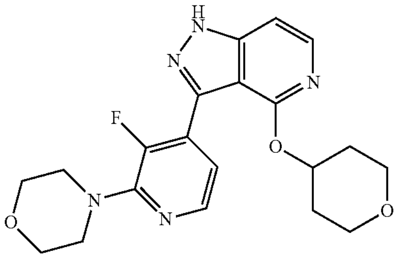 [SMILES: Fc1c(-c2n[nH]c3ccnc(OC4CCOCC4)c23)ccnc1N1CCOCC1] |
| 104 | 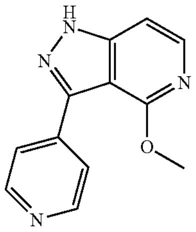 [SMILES: COc1nccc2[nH]nc(-c3ccncc3)c12] |
| 105 | 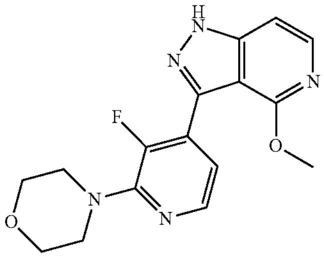 [SMILES: COc1nccc2[nH]nc(-c3ccnc(N4CCOCC4)c3F)c12] |
| 106 | 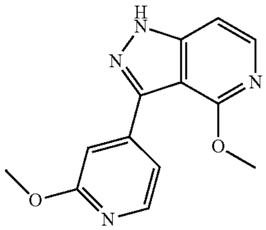 |
| 107 | 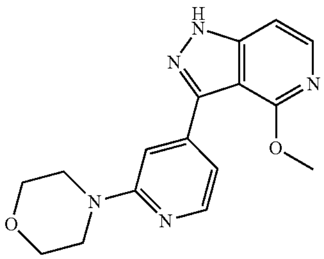 [SMILES: COc1nccc2[nH]nc(-c3ccnc(N4CCOCC4)c3)c12] |
-continued
| No. | Structure |
|---|---|
| 108 | 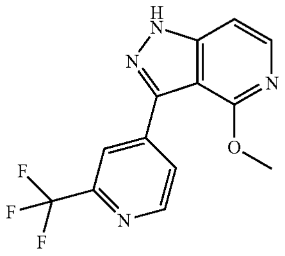 [SMILES: COc1nccc2[nH]nc(-c3ccnc(C(F)(F)F)c3)c12] |
| 109 | 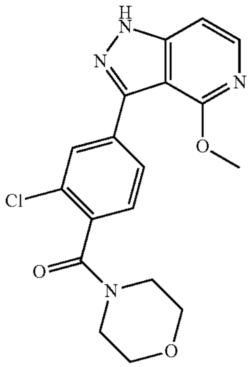 [SMILES: COc1nccc2[nH]nc(-c3ccc(C(=O)N4CCOCC4)c(Cl)c3)c12] |
| 110 | 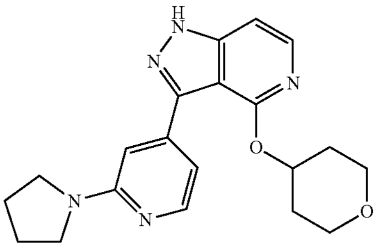 [SMILES: c1cc(-c2n[nH]c3ccnc(OC4CCOCC4)c23)cc(N2CCCC2)n1] |
| 111 | 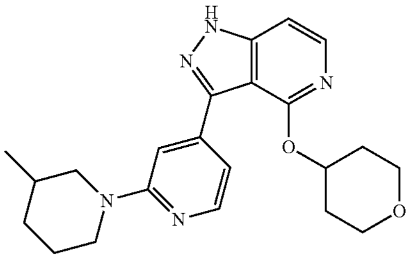 [SMILES: CC1CCCN(c2cc(-c3n[nH]c4ccnc(OC5CCOCC5)c34)ccn2)C1] |
| 112 | 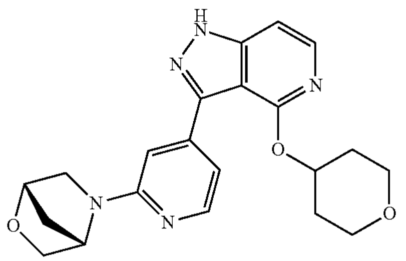 [SMILES: c1cc(-c2n[nH]c3ccnc(OC4CCOCC4)c23)cc(N2C[C@@H]3C[C@H]2CO3)n1] |

-continued
| No. | Structure |
|---|---|
| 113 | 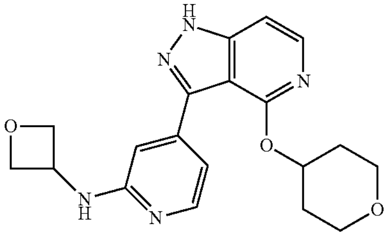 [SMILES: c1cc(-c2n[nH]c3ccnc(OC4CCOCC4)c23)cc(NC2COC2)n1] |
| 114 | 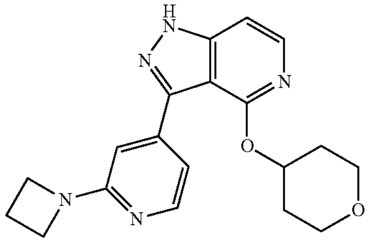 [SMILES: c1cc(-c2n[nH]c3ccnc(OC4CCOCC4)c23)cc(N2CCC2)n1] |
| 115 | 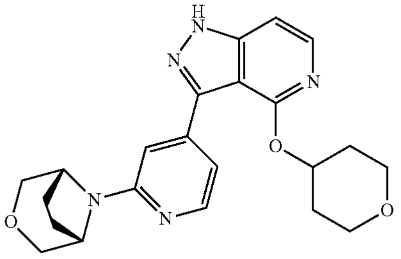 [SMILES: c1cc(-c2n[nH]c3ccnc(OC4CCOCC4)c23)cc(N2[C@@H]3CC[C@H]2COC3)n1] |
| 116 | 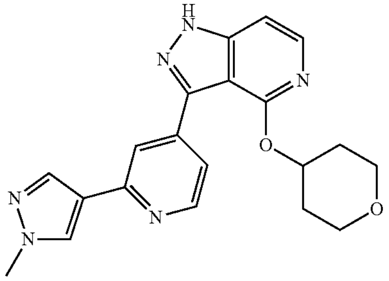 [SMILES: Cn1cc(-c2cc(-c3n[nH]c4ccnc(OC5CCOCC5)c34)ccn2)cn1] |
| 117 | 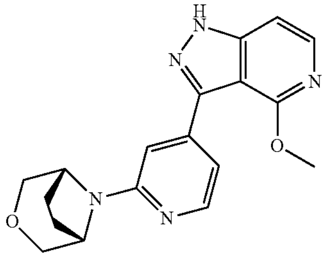 [SMILES: COc1nccc2[nH]nc(-c3ccnc(N4[C@@H]5CC[C@H]4COC5)c3)c12] |
| 118 | 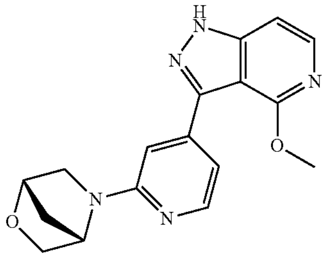 [SMILES: COc1nccc2[nH]nc(-c3ccnc(N4C[C@@H]5C[C@H]4CO5)c3)c12] |
-continued
| No. | Structure |
|---|---|
| 119 | 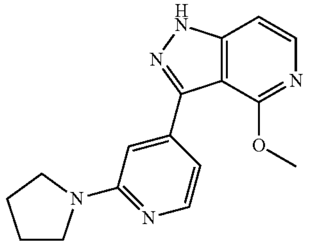 [SMILES: COc1nccc2[nH]nc(-c3ccnc(N4CCCC4)c3)c12] |
| 120 | 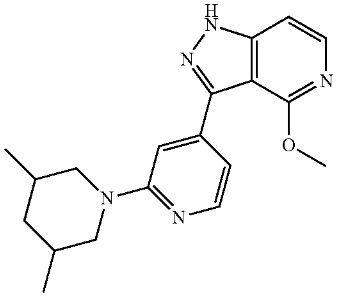 |
| 121 | 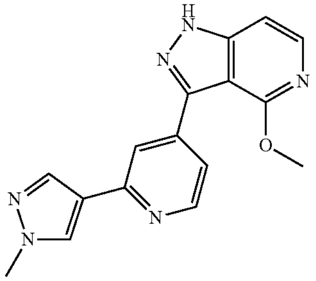 |
| 122 | 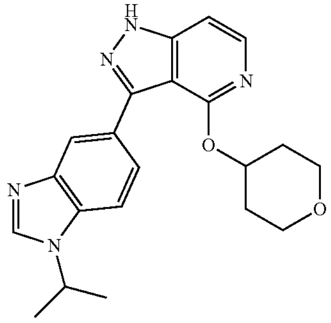 [SMILES: CC(C)n1cnc2cc(-c3n[nH]c4ccnc(OC5CCOCC5)c34)ccc21] |
| 123 | 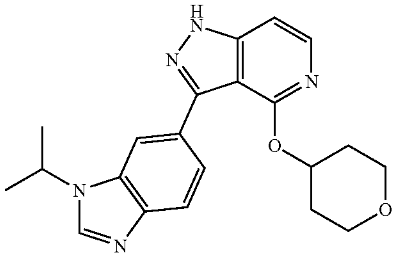 [SMILES: CC(C)n1cnc2ccc(-c3n[nH]c4ccnc(OC5CCOCC5)c34)cc21] |

-continued
| No. | Structure |
|---|---|
| 124 | 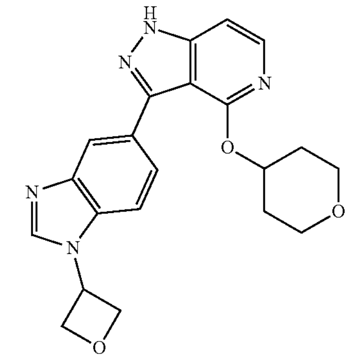 [SMILES: c1cc2[nH]nc(-c3ccc4c(c3)ncn4C3COC3)c2c(OC2CCOCC2)n1] |
| 125 | 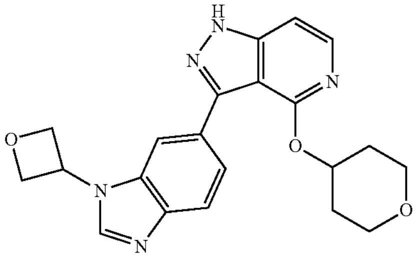 [SMILES: c1cc2[nH]nc(-c3ccc4ncn(C5COC5)c4c3)c2c(OC2CCOCC2)n1] |
| 126 | 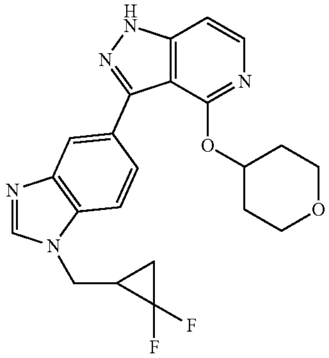 [SMILES: FC1(F)CC1Cn1cnc2cc(-c3n[nH]c4ccnc(OC5CCOCC5)c34)ccc21] |
| 127 | 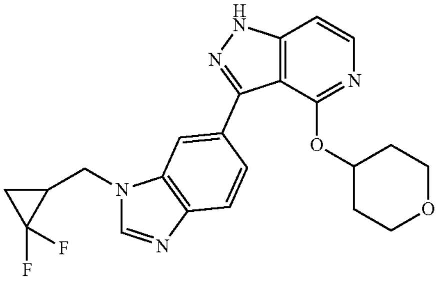 [SMILES: FC1(F)CC1Cn1cnc2ccc(-c3n[nH]c4ccnc(OC5CCOCC5)c34)cc21] |
| 128 | 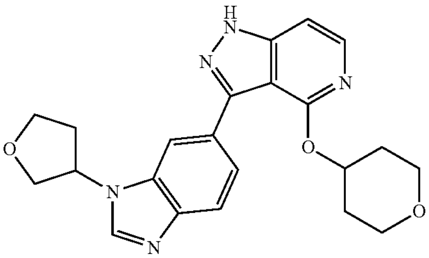 [SMILES: c1cc2[nH]nc(-c3ccc4ncn(C5CCOC5)c4c3)c2c(OC2CCOCC2)n1] |
-continued
| No. | Structure |
|---|---|
| 129 | 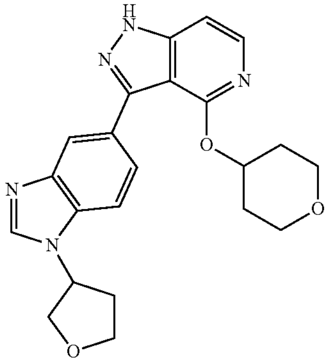 [SMILES: c1cc2[nH]nc(-c3ccc4c(c3)ncn4C3CCOC3)c2c(OC2CCOCC2)n1] |
| 130 | 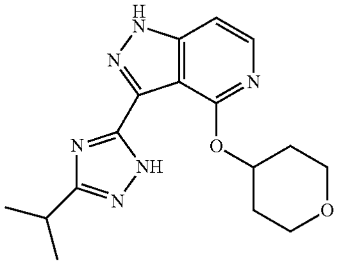 [SMILES: CC(C)c1n[nH]c(-c2n[nH]c3ccnc(OC4CCOCC4)c23)n1] |
| 131 | 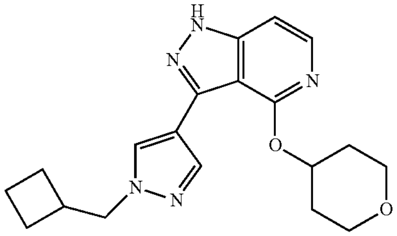 [SMILES: c1cc2[nH]nc(-c3cnn(CC4CCC4)c3)c2c(OC2CCOCC2)n1] |
| 132 | 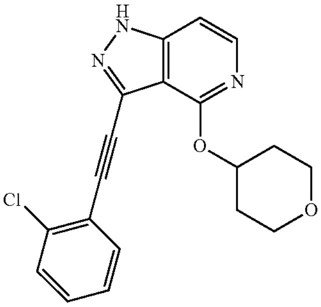 [SMILES: Clc1ccccc1C#Cc1n[nH]c2ccnc(OC3CCOCC3)c12] |
| 133 | 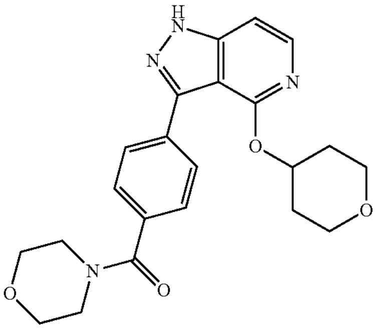 [SMILES: O=C(c1ccc(-c2n[nH]c3ccnc(OC4CCOCC4)c23)cc1)N1CCOCC1] |

-continued
| No. | Structure |
|---|---|
| 134 | 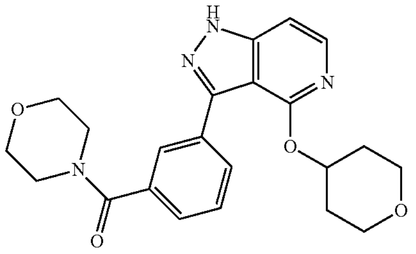 [SMILES: O=C(c1cccc(-c2n[nH]c3ccnc(OC4CCOCC4)c23)c1)N1CCOCC1] |
| 135 | 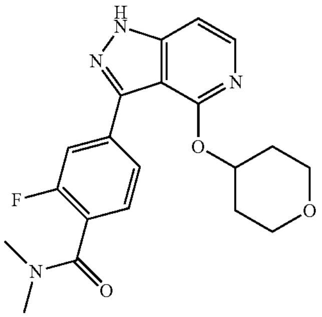 [SMILES: CN(C)C(=O)c1ccc(-c2n[nH]c3ccnc(OC4CCOCC4)c23)cc1F] |
| 136 | 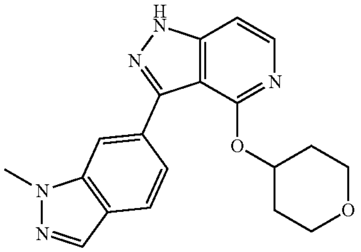 [SMILES: Cn1ncc2ccc(-c3n[nH]c4ccnc(OC5CCOCC5)c34)cc21] |
| 137 | 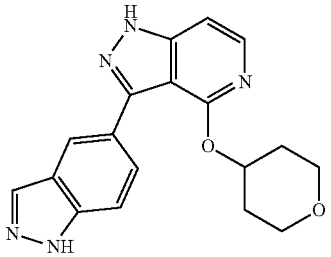 [SMILES: c1cc2[nH]nc(-c3ccc4[nH]ncc4c3)c2c(OC2CCOCC2)n1] |
| 138 | 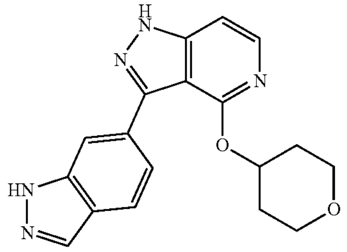 [SMILES: c1cc2[nH]nc(-c3ccc4cn[nH]c4c3)c2c(OC2CCOCC2)n1] |
-continued
| No. | Structure |
|---|---|
| 139 | 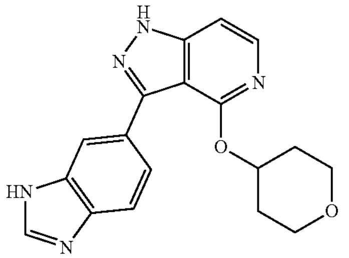 [SMILES: c1cc2[nH]nc(-c3ccc4nc[nH]c4c3)c2c(OC2CCOCC2)n1] |
| 140 | 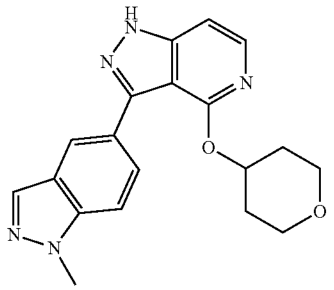 [SMILES: Cn1ncc2cc(-c3n[nH]c4ccnc(OC5CCOCC5)c34)ccc21] |
| 141 | 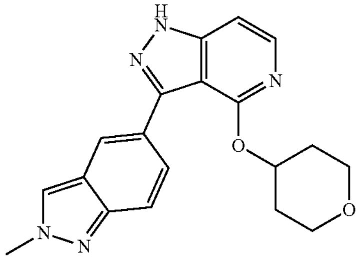 [SMILES: Cn1cc2cc(-c3n[nH]c4ccnc(OC5CCOCC5)c34)ccc2n1] |
| 142 | 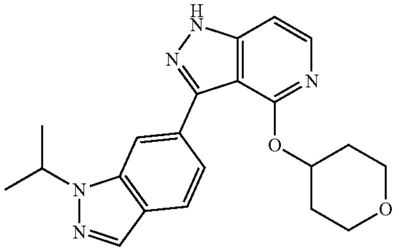 [SMILES: CC(C)n1ncc2ccc(-c3n[nH]c4ccnc(OC5CCOCC5)c34)cc21] |
| 143 | 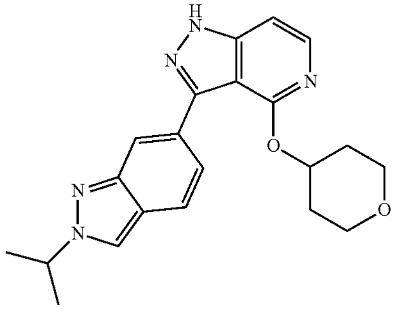 [SMILES: CC(C)n1cc2ccc(-c3n[nH]c4ccnc(OC5CCOCC5)c34)cc2n1] |

-continued
| No. | Structure |
|---|---|
| 144 | 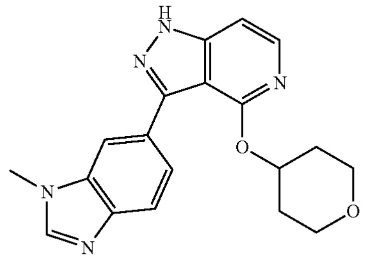 [SMILES: Cn1cnc2ccc(-c3n[nH]c4ccnc(OC5CCOCC5)c34)cc21] |
| 145 | 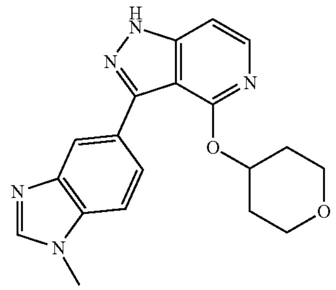 [SMILES: Cn1cnc2cc(-c3n[nH]c4ccnc(OC5CCOCC5)c34)ccc21] |
| 146 | 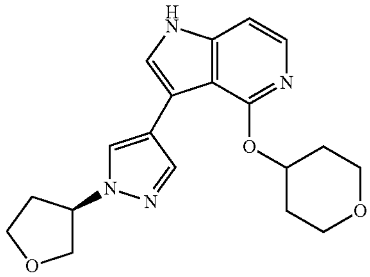 [SMILES: c1cc2[nH]cc(-c3cnn([C@@H]4CCOC4)c3)c2c(OC2CCOCC2)n1] |
| 147 | 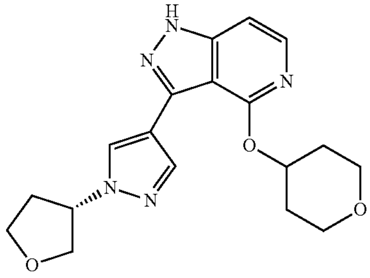 [SMILES: c1cc2[nH]nc(-c3cnn([C@H]4CCOC4)c3)c2c(OC2CCOCC2)n1] |
| 148 | 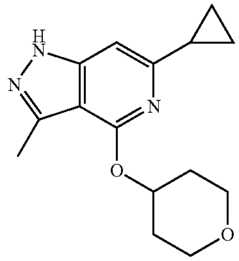 [SMILES: Cc1n[nH]c2cc(C3CC3)nc(OC3CCOCC3)c12] |
-continued
| No. | Structure |
|---|---|
| 149 | 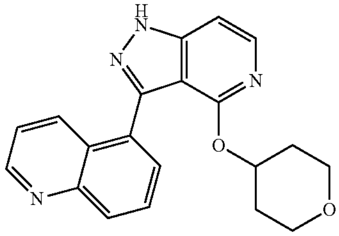 [SMILES: c1cc(-c2n[nH]c3ccnc(OC4CCOCC4)c23)c2cccnc2c1] |
| 150 | 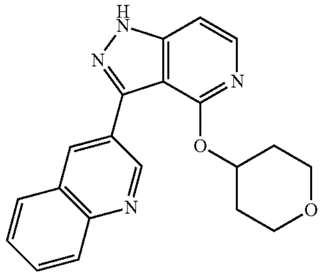 [SMILES: c1ccc2ncc(-c3n[nH]c4ccnc(OC5CCOCC5)c34)cc2c1] |
| 151 | 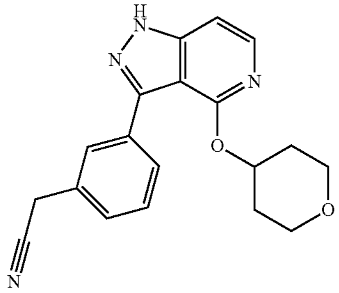 [SMILES: N#CCc1cccc(-c2n[nH]c3ccnc(OC4CCOCC4)c23)c1] |
| 152 | 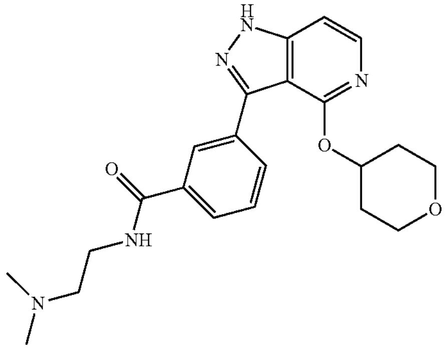 [SMILES: CN(C)CCNC(=O)c1cccc(-c2n[nH]c3ccnc(OC4CCOCC4)c23)c1] |
| 153 | 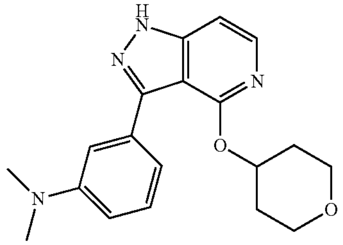 [SMILES: CN(C)c1cccc(-c2n[nH]c3ccnc(OC4CCOCC4)c23)c1] |

-continued
| No. | Structure |
|---|---|
| 154 | 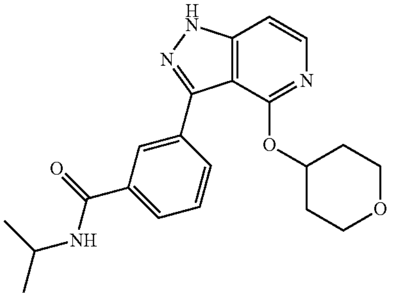 [SMILES: CC(C)NC(=O)c1cccc(-c2n[nH]c3ccnc(OC4CCOCC4)c23)c1] |
| 155 | 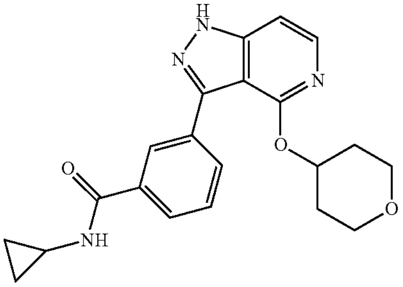 [SMILES: O=C(NC1CC1)c1cccc(-c2n[nH]c3ccnc(OC4CCOCC4)c23)c1] |
| 156 | 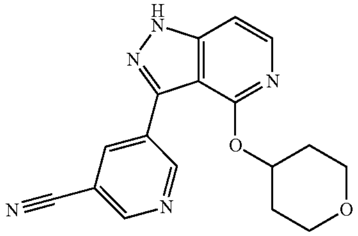 [SMILES: N#Cc1cncc(-c2n[nH]c3ccnc(OC4CCOCC4)c23)c1] |
| 157 | 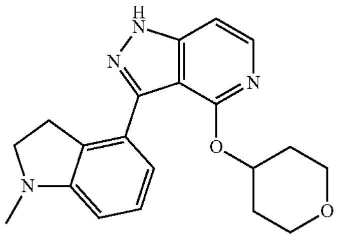 [SMILES: CN1CCc2c(-c3n[nH]c4ccnc(OC5CCOCC5)c34)cccc21] |
| 158 | 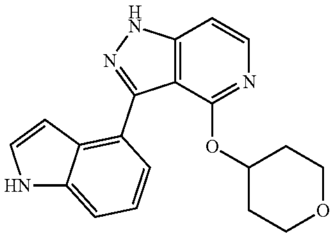 [SMILES: c1cc(-c2n[nH]c3ccnc(OC4CCOCC4)c23)c2cc[nH]c2c1] |
| 159 | 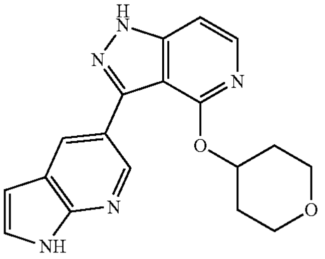 [SMILES: c1cc2[nH]nc(-c3cnc4[nH]ccc4c3)c2c(OC2CCOCC2)n1] |
-continued
| No. | Structure |
|---|---|
| 160 | 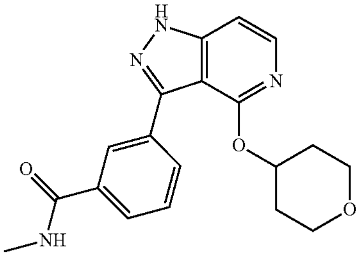 [SMILES: CNC(=O)c1cccc(-c2n[nH]c3ccnc(OC4CCOCC4)c23)c1] |
| 161 | 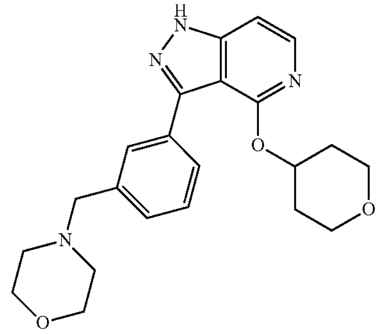 [SMILES: c1cc(CN2CCOCC2)cc(-c2n[nH]c3ccnc(OC4CCOCC4)c23)c1] |
| 162 | 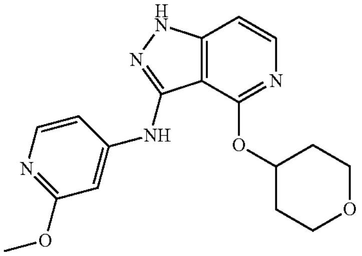 [SMILES: COc1cc(Nc2n[nH]c3ccnc(OC4CCOCC4)c23)ccn1] |
| 163 | 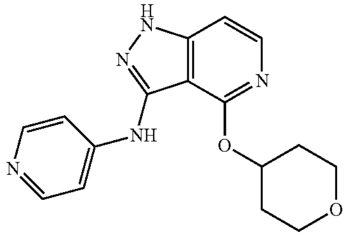 [SMILES: c1cc(Nc2n[nH]c3ccnc(OC4CCOCC4)c23)ccn1] |
| 164 | 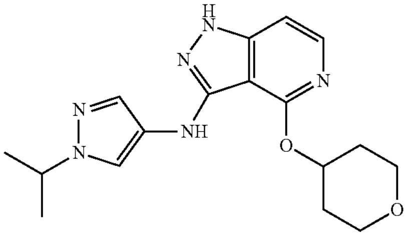 [SMILES: CC(C)n1cc(Nc2n[nH]c3ccnc(OC4CCOCC4)c23)cn1] |
| 165 | 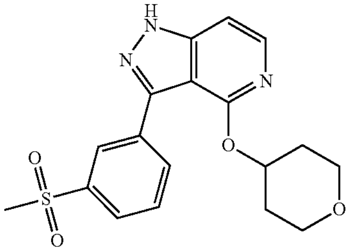 [SMILES: CS(=O)(=O)c1cccc(-c2n[nH]c3ccnc(OC4CCOCC4)c23)c1] |

-continued
| No. | Structure |
|---|---|
| 166 | 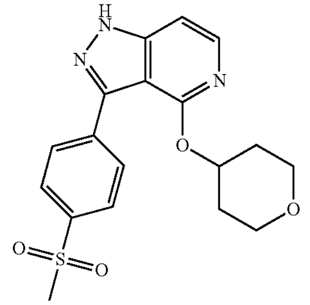 [SMILES: CS(=O)(=O)c1ccc(-c2n[nH]c3ccnc(OC4CCOCC4)c23)cc1] |
| 167 | 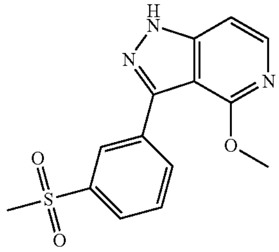 |
| 168 | 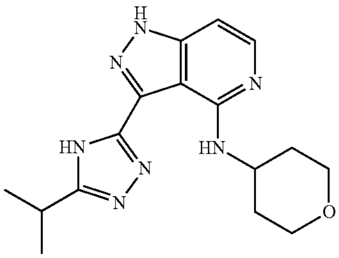 [SMILES: CC(C)c1nnc(-c2n[nH]c3ccnc(NC4CCOCC4)c23)[nH]1] |
| 169 | 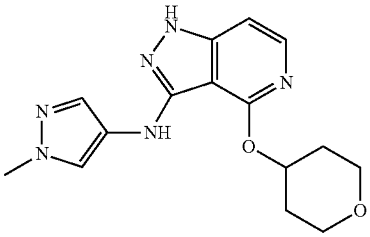 [SMILES: Cn1cc(Nc2n[nH]c3ccnc(OC4CCOCC4)c23)cn1] |
| 170 | 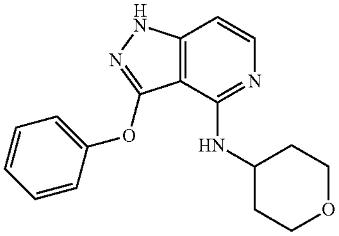 [SMILES: c1ccc(Oc2n[nH]c3ccnc(NC4CCOCC4)c23)cc1] |
| 171 | 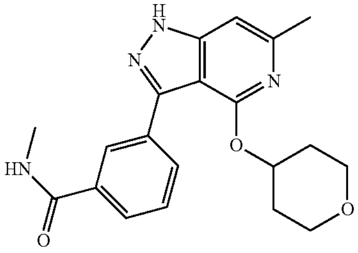 |
-continued
| No. | Structure |
|---|---|
| 172 | 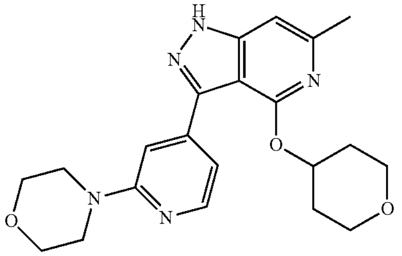 [SMILES: Cc1cc2[nH]nc(-c3ccnc(N4CCOCC4)c3)c2c(OC2CCOCC2)n1] |
| 173 | 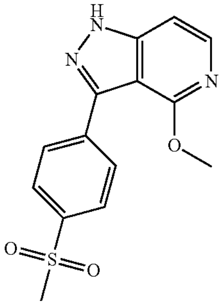 [SMILES: COc1nccc2[nH]nc(-c3ccc(S(C)(=O)=O)cc3)c12] |
| 174 | 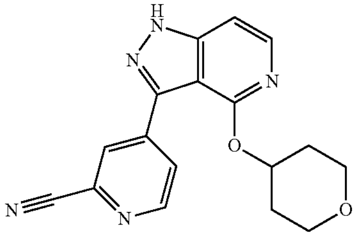 [SMILES: N#Cc1cc(-c2n[nH]c3ccnc(OC4CCOCC4)c23)ccn1] |
| 175 | 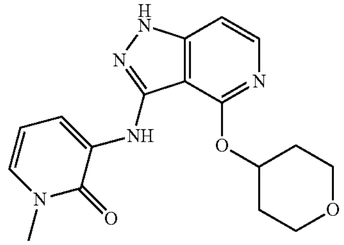 [SMILES: Cn1cccc(Nc2n[nH]c3ccnc(OC4CCOCC4)c23)c1=O] |
| 176 | 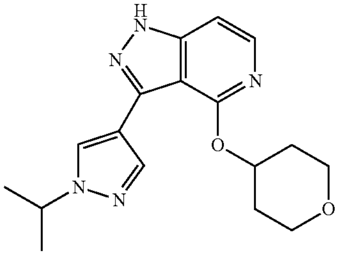 [SMILES: CC(C)n1cc(-c2n[nH]c3ccnc(OC4CCOCC4)c23)cn1] |
| 177 | 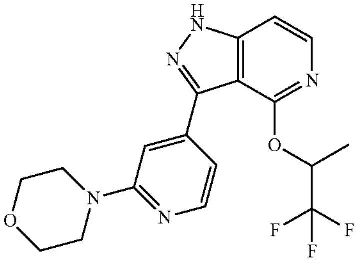 [SMILES: CC(Oc1nccc2[nH]nc(-c3ccnc(N4CCOCC4)c3)c12)C(F)(F)F] |

-continued
| No. | Structure |
| --- | --- |
| 178 | 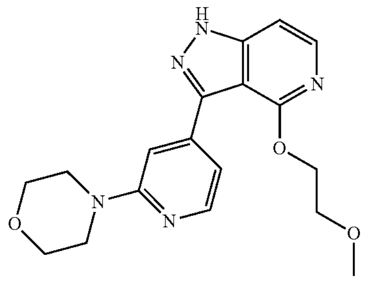 [SMILES: COCCOc1nccc2[nH]nc(-c3ccnc(N4CCOCC4)c3)c12] |
| 179 | 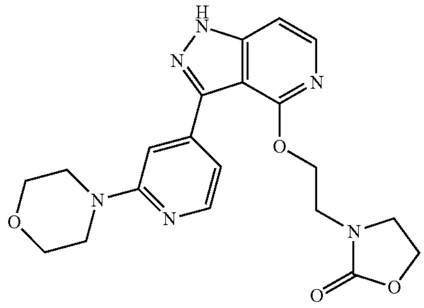 [SMILES: O=C1OCCN1CCOc1nccc2[nH]nc(-c3ccnc(N4CCOCC4)c3)c12] |
| 180 | 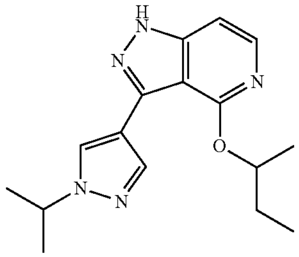 [SMILES: CCC(C)Oc1nccc2[nH]nc(-c3cnn(C(C)C)c3)c12] |
| 181 | 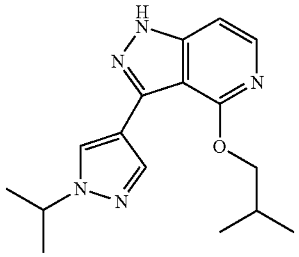 [SMILES: CC(C)COc1nccc2[nH]nc(-c3cnn(C(C)C)c3)c12] |
| 182 | 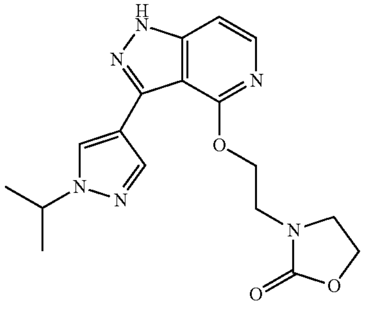 [SMILES: CC(C)n1cc(-c2n[nH]c3ccnc(OCCN4CCOC4=O)c23)cn1] |
-continued
| No. | Structure |
| --- | --- |
| 183 | 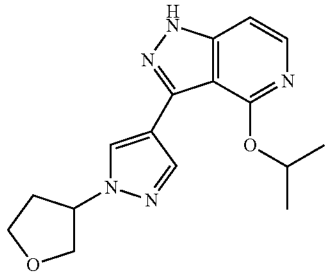 [SMILES: CC(C)Oc1nccc2[nH]nc(-c3cnn(C4CCOC4)c3)c12] |
| 184 | 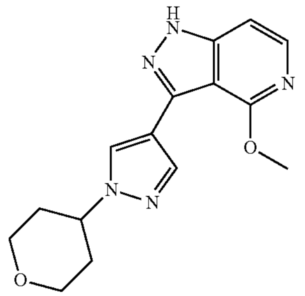 [SMILES: COc1nccc2[nH]nc(-c3cnn(C4CCOCC4)c3)c12] |
| 185 | 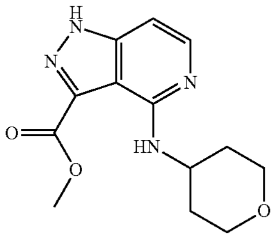 [SMILES: COC(=O)c1n[nH]c2ccnc(NC3CCOCC3)c12] |
| 186 | 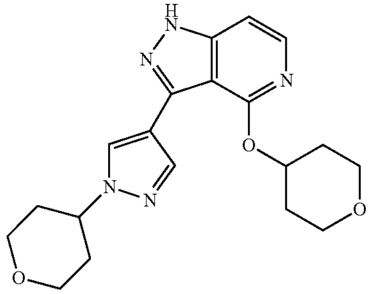 [SMILES: c1cc2[nH]nc(-c3cnn(C4CCOCC4)c3)c2c(OC2CCOCC2)n1] |
| 187 | 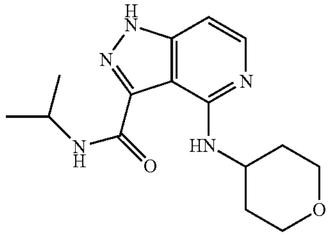 [SMILES: CC(C)NC(=O)c1n[nH]c2ccnc(NC3CCOCC3)c12] |
| 188 | 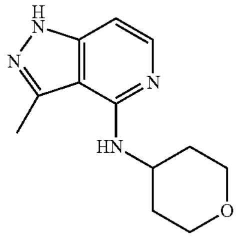 [SMILES: Cc1n[nH]c2ccnc(NC3CCOCC3)c12] |

-continued
| No. | Structure |
|---|---|
| 189 | 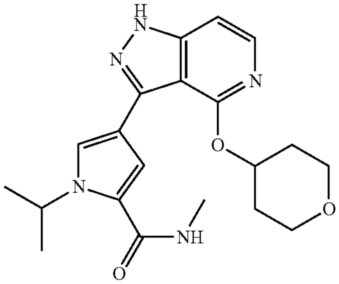 [SMILES: CNC(=O)c1cc(-c2n[nH]c3ccnc(OC4CCOCC4)c23)cn1C(C)C] |
| 190 | 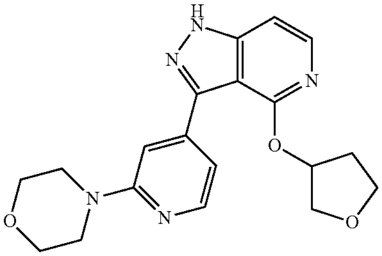 [SMILES: c1cc(-c2n[nH]c3ccnc(OC4CCOC4)c23)cc(N2CCOCC2)n1] |
| 191 | 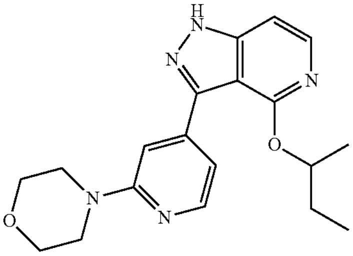 [SMILES: CCC(C)Oc1nccc2[nH]nc(-c3ccnc(N4CCOCC4)c3)c12] |
| 192 | 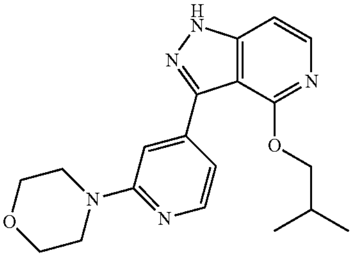 [SMILES: CC(C)COc1nccc2[nH]nc(-c3ccnc(N4CCOCC4)c3)c12] |
| 193 | 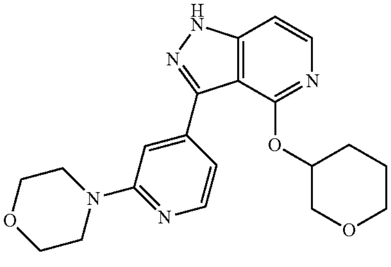 [SMILES: c1cc(-c2n[nH]c3ccnc(OC4CCCOC4)c23)cc(N2CCOCC2)n1] |
| 194 | 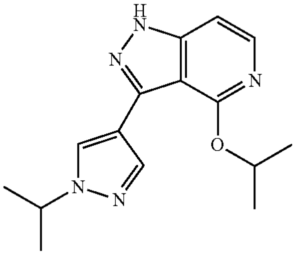 [SMILES: CC(C)Oc1nccc2[nH]nc(-c3cnn(C(C)C)c3)c12] |
-continued
| No. | Structure |
|---|---|
| 195 | 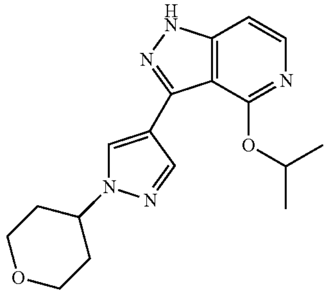 [SMILES: CC(C)Oc1nccc2[nH]nc(-c3cnn(C4CCOCC4)c3)c12] |
| 196 | 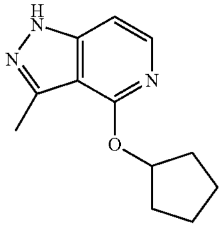 [SMILES: Cc1n[nH]c2ccnc(OC3CCCC3)c12] |
| 197 | 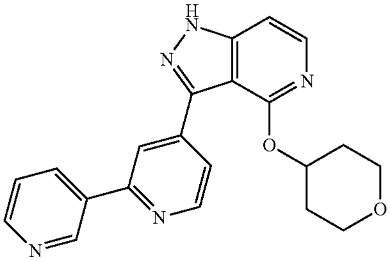 [SMILES: c1cncc(-c2cc(-c3n[nH]c4ccnc(OC5CCOCC5)c34)ccn2)c1] |
| 198 | 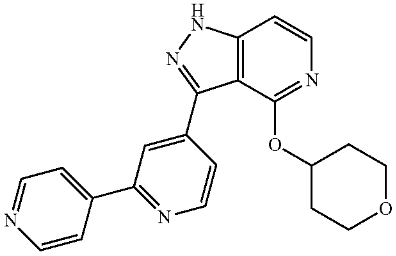 [SMILES: c1cc(-c2cc(-c3n[nH]c4ccnc(OC5CCOCC5)c34)ccn2)ccn1] |
| 199 | 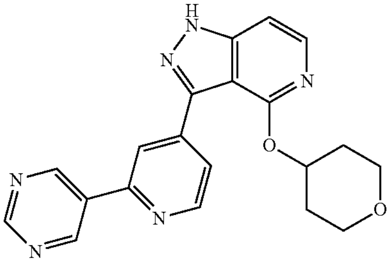 [SMILES: c1ncc(-c2cc(-c3n[nH]c4ccnc(OC5CCOCC5)c34)ccn2)cn1] |
| 200 | 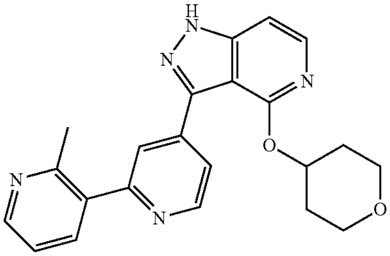 [SMILES: Cc1ncccc1-c1cc(-c2n[nH]c3ccnc(OC4CCOCC4)c23)ccn1] |

-continued
| No. | Structure |
| --- | --- |
| 201 | 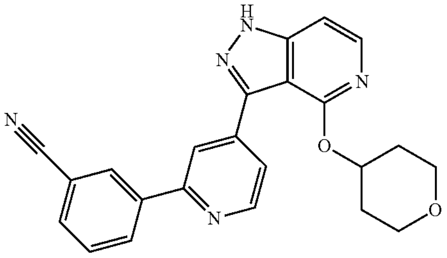 [SMILES: N#Cc1cccc(-c2cc(-c3n[nH]c4ccnc(OC5CCOCC5)c34)ccn2)c1] |
| 202 | 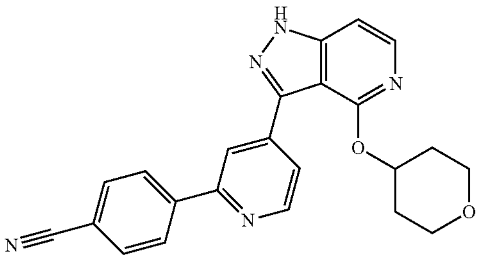 [SMILES: N#Cc1ccc(-c2cc(-c3n[nH]c4ccnc(OC5CCOCC5)c34)ccn2)cc1] |
| 203 | 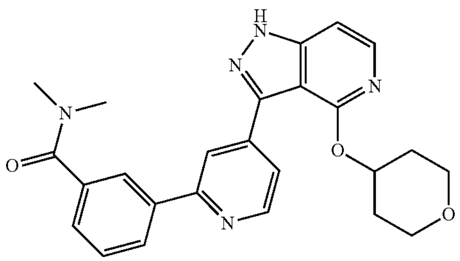 [SMILES: CN(C)C(=O)c1cccc(-c2cc(-c3n[nH]c4ccnc(OC5CCOCC5)c34)ccn2)c1] |
| 204 | 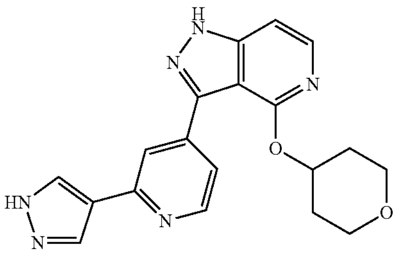 [SMILES: c1cc(-c2n[nH]c3ccnc(OC4CCOCC4)c23)cc(-c2cn[nH]c2)n1] |
| 205 | 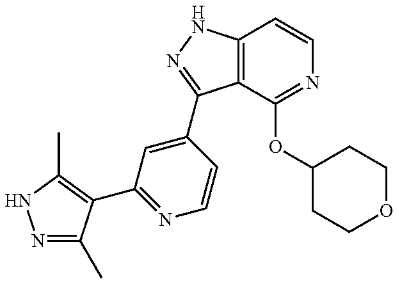 [SMILES: Cc1n[nH]c(C)c1-c1cc(-c2n[nH]c3ccnc(OC4CCOCC4)c23)ccn1] |
| 206 | 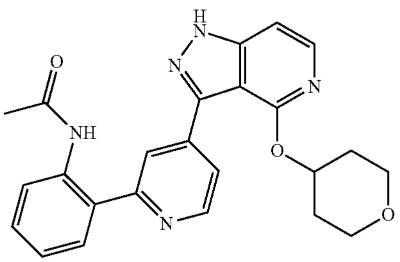 [SMILES: CC(=O)Nc1ccccc1-c1cc(-c2n[nH]c3ccnc(OC4CCOCC4)c23)ccn1] |
-continued
| No. | Structure |
| --- | --- |
| 207 | 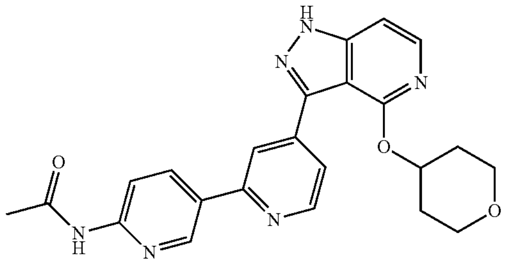 [SMILES: CC(=O)Nc1ccc(-c2cc(-c3n[nH]c4ccnc(OC5CCOCC5)c34)ccn2)cn1] |
| 208 | 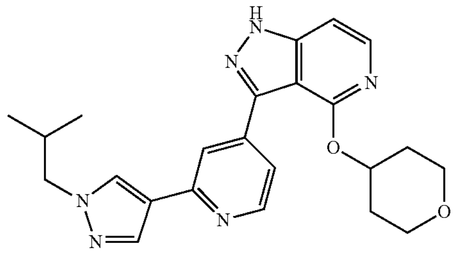 [SMILES: CC(C)Cn1cc(-c2cc(-c3n[nH]c4ccnc(OC5CCOCC5)c34)ccn2)cn1] |
| 209 | 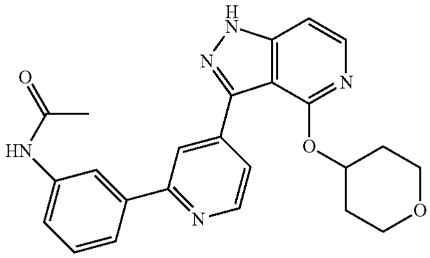 [SMILES: CC(=O)Nc1cccc(-c2cc(-c3n[nH]c4ccnc(OC5CCOCC5)c34)ccn2)c1] |
| 210 | 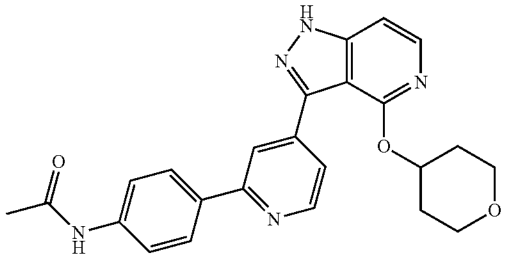 [SMILES: CC(=O)Nc1ccc(-c2cc(-c3n[nH]c4ccnc(OC5CCOCC5)c34)ccn2)cc1] |
| 211 | 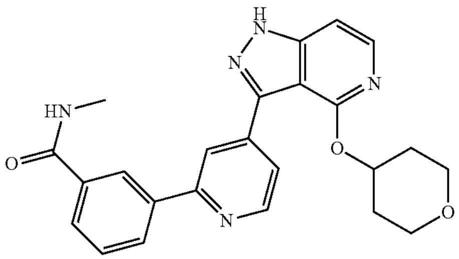 [SMILES: CNC(=O)c1cccc(-c2cc(-c3n[nH]c4ccnc(OC5CCOCC5)c34)ccn2)c1] |
| 212 | 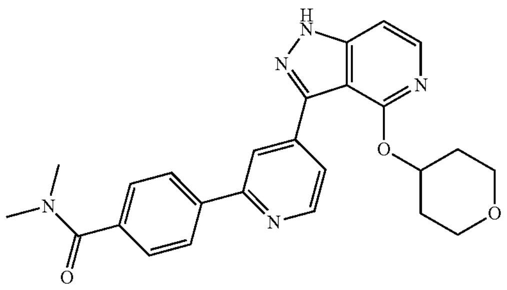 [SMILES: CN(C)C(=O)c1ccc(-c2cc(-c3n[nH]c4ccnc(OC5CCOCC5)c34)ccn2)cc1] |

-continued
| No. | Structure |
|---|---|
| 213 | 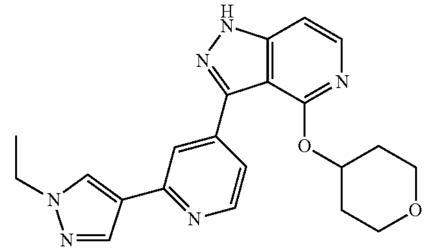 [SMILES: CCn1cc(-c2cc(-c3n[nH]c4ccnc(OC5CCOCC5)c34)ccn2)cn1] |
| 214 | 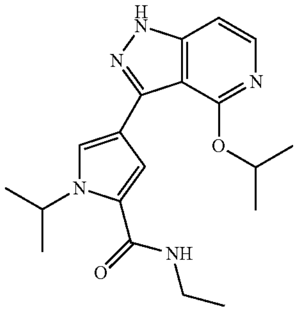 [SMILES: CCNC(=O)c1cc(-c2n[nH]c3ccnc(OC(C)C)c23)cn1C(C)C] |
| 215 | 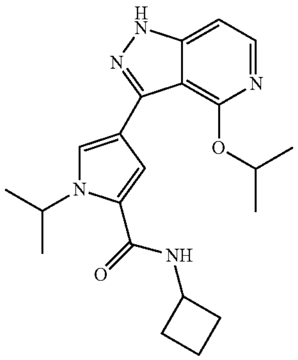 [SMILES: CC(C)Oc1nccc2[nH]nc(-c3cc(C(=O)NC4CCC4)n(C(C)C)c3)c12] |
| 216 | 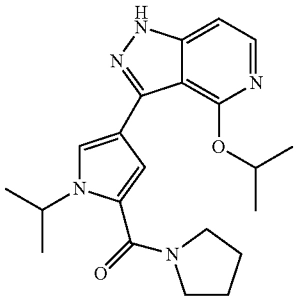 [SMILES: CC(C)Oc1nccc2[nH]nc(-c3cc(C(=O)N4CCCC4)n(C(C)C)c3)c12] |
| 217 | 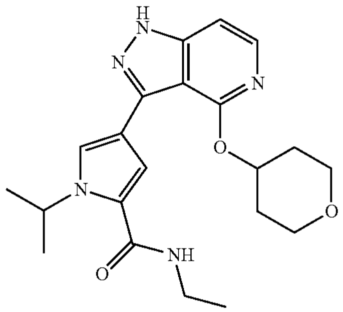 [SMILES: CCNC(=O)c1cc(-c2n[nH]c3ccnc(OC4CCOCC4)c23)cn1C(C)C] |
-continued
| No. | Structure |
|---|---|
| 218 | 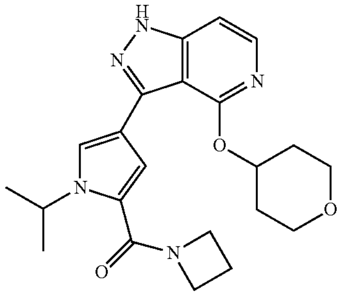 [SMILES: CC(C)n1cc(-c2n[nH]c3ccnc(OC4CCOCC4)c23)cc1C(=O)N1CCC1] |
| 219 | 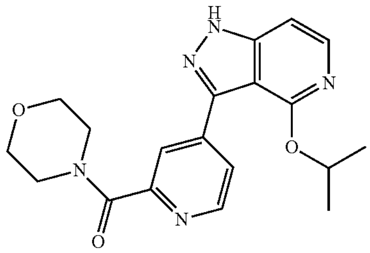 [SMILES: CC(C)Oc1nccc2[nH]nc(-c3ccnc(C(=O)N4CCOCC4)c3)c12] |
| 220 | 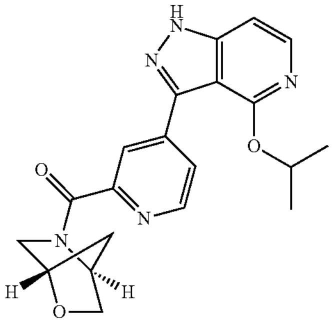 [SMILES: CC(C)Oc1nccc2[nH]nc(-c3ccnc(C(=O)N4C[C@@H]5C[C@H]4CO5)c3)c12] |
| 221 | 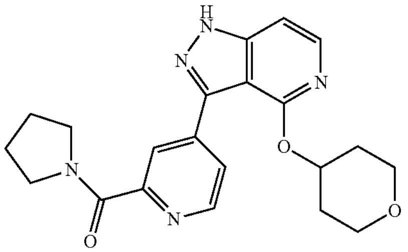 [SMILES: O=C(c1cc(-c2n[nH]c3ccnc(OC4CCOCC4)c23)ccn1)N1CCCC1] |
| 222 | 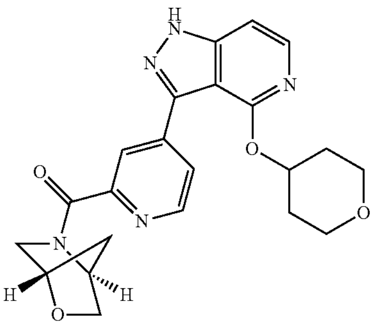 [SMILES: O=C(c1cc(-c2n[nH]c3ccnc(OC4CCOCC4)c23)ccn1)N1C[C@@H]2C[C@H]1CO2] |

-continued
| No. | Structure |
| --- | --- |
| 223 | 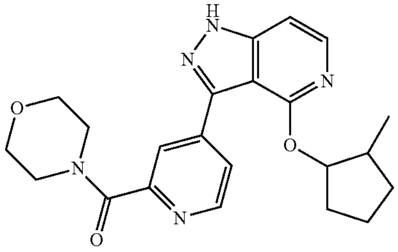 [SMILES: CC1CCCC1Oc1nccc2[nH]nc(-c3ccnc(C(=O)N4CCOCC4)c3)c12] |
| 224 | 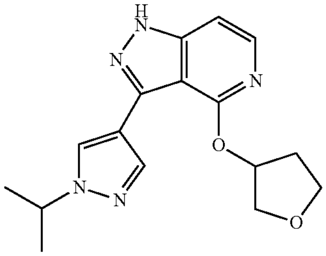 [SMILES: CC(C)n1cc(-c2n[nH]c3ccnc(OC4CCOC4)c23)cn1] |
| 225 | 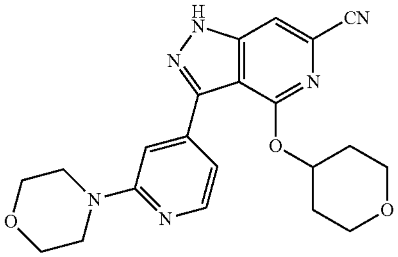 [SMILES: N#Cc1cc2[nH]nc(-c3ccnc(N4CCOCC4)c3)c2c(OC2CCOCC2)n1] |
| 226 | 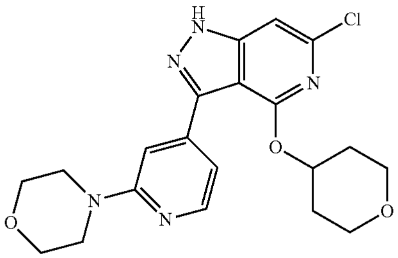 [SMILES: Clc1cc2[nH]nc(-c3ccnc(N4CCOCC4)c3)c2c(OC2CCOCC2)n1] |
| 227 | 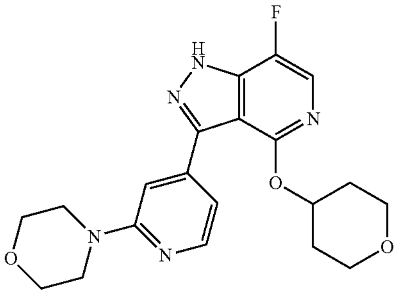 [SMILES: Fc1cnc(OC2CCOCC2)c2c(-c3ccnc(N4CCOCC4)c3)n[nH]c12] |
| 228 | 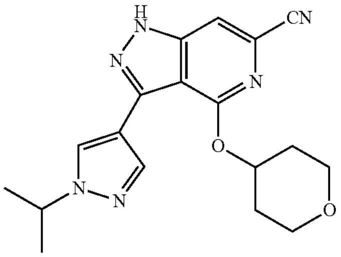 [SMILES: CC(C)n1cc(-c2n[nH]c3cc(C#N)nc(OC4CCOCC4)c23)cn1] |
-continued
| No. | Structure |
| --- | --- |
| 229 | 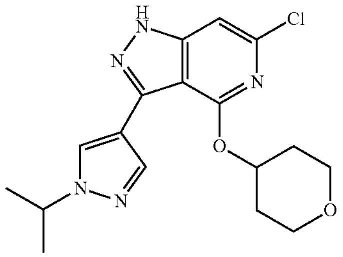 [SMILES: CC(C)n1cc(-c2n[nH]c3cc(Cl)nc(OC4CCOCC4)c23)cn1] |
| 230 | 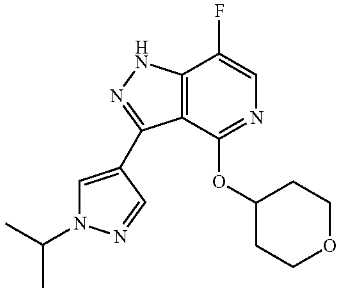 [SMILES: CC(C)n1cc(-c2n[nH]c3c(F)cnc(OC4CCOCC4)c23)cn1] |
| 231 | 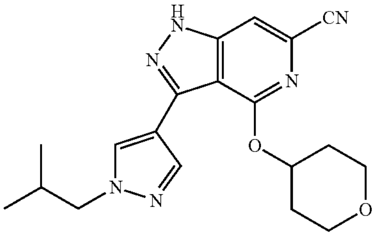 [SMILES: CC(C)Cn1cc(-c2n[nH]c3cc(C#N)nc(OC4CCOCC4)c23)cn1] |
| 232 | 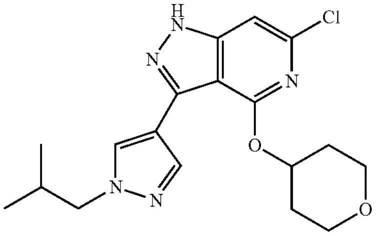 [SMILES: CC(C)Cn1cc(-c2n[nH]c3cc(Cl)nc(OC4CCOCC4)c23)cn1] |
| 233 | 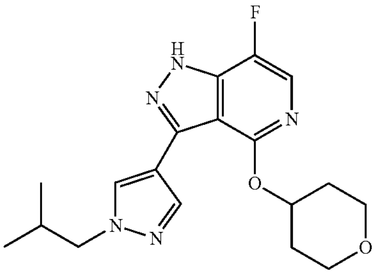 [SMILES: CC(C)Cn1cc(-c2n[nH]c3c(F)cnc(OC4CCOCC4)c23)cn1] |
| 234 | 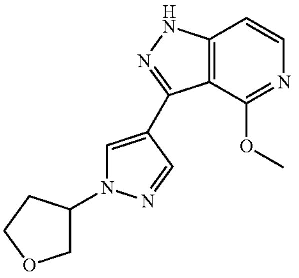 [SMILES: COc1nccc2[nH]nc(-c3cnn(C4CCOC4)c3)c12] |

-continued

| No. | Structure |
|---|---|
| 235 | 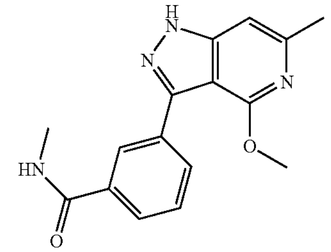 [SMILES: CNC(=O)c1cccc(-c2n[nH]c3cc(C)nc(OC)c23)c1] |
| 236 | 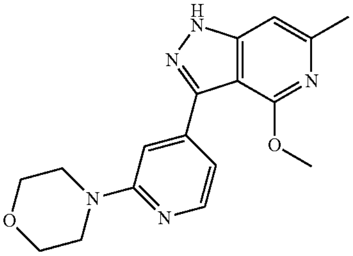 [SMILES: COc1nc(C)cc2[nH]nc(-c3ccnc(N4CCOCC4)c3)c12] |
| 237 | 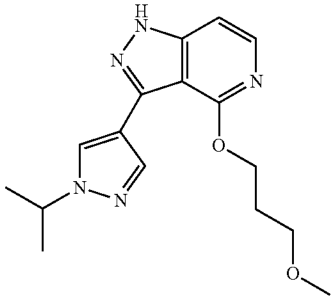 [SMILES: COCCCOc1nccc2[nH]nc(-c3cnn(C(C)C)c3)c12] |
| 238 | 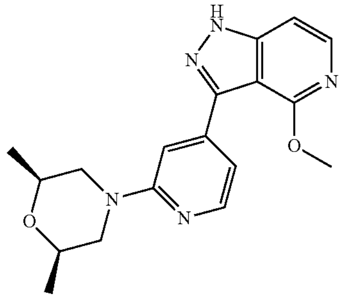 |
| 239 | 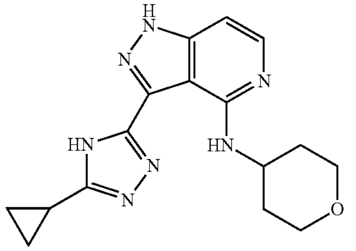 [SMILES: c1cc2[nH]nc(-c3nnc(C4CC4)[nH]3)c2c(NC2CCOCC2)n1] |

or a pharmaceutically acceptable salt or ester thereof.

2. A pharmaceutical composition comprising a compound according to claim 1 and a pharmaceutically acceptable carrier, diluent or excipient.

3. A method of treating a neurodegenerative disease, wherein the method comprises administering to a subject in need thereof, a therapeutically effective amount of a compound according to claim 1, thereby treating said neurodegenerative disease.

4. A method of treating a disease alleviated by the inhibition of LRRK2, wherein the method comprises administering to a mammal in need thereof a therapeutically effective amount of a compound according to claim 1, thereby treating said disease.

5. A method for identifying a compound capable of inhibiting LRRK, the method comprising the steps of:

contacting a LRRK with a candidate compound in the presence of a compound according to claim 1; and detecting interaction between LRRK and the compound according to claim 1, wherein a change in the interaction indicates that the candidate compound is an inhibitor of the LRRK.

6. A combination comprising a compound according to claim 1 and a further therapeutic agent.

7. A pharmaceutical composition according to claim 6 which further comprises a second therapeutic agent.

8. The method according to claim 3, wherein the neurodegenerative disease is Parkinson's Disease.

9. The method according to claim 5, wherein the LRRK is LRRK2.

* * * * *